United States Patent
Cheng et al.

(10) Patent No.: US 12,263,227 B2
(45) Date of Patent: Apr. 1, 2025

(54) OPTIMIZED mRNA ENCODING CAS9 FOR USE IN LNPs

(71) Applicants: CRISPR THERAPEUTICS AG, Zug (CH); BAYER HEALTHCARE LLC, Whippany, NJ (US)

(72) Inventors: Christopher J. Cheng, San Francisco, CA (US); Andrew Scharenberg, San Francisco, CA (US); Kui Wang, San Francisco, CA (US); Shailendra Sane, San Francisco, CA (US)

(73) Assignees: CRISPR THERAPEUTICS AG, Zug (CH); BAYER HEALTHCARE LLC, Whippany, NJ (US)

( * ) Notice: Subject to any disclaimer, the term of this patent is extended or adjusted under 35 U.S.C. 154(b) by 826 days.

(21) Appl. No.: 17/298,114

(22) PCT Filed: Nov. 26, 2019

(86) PCT No.: PCT/US2019/063456
§ 371 (c)(1),
(2) Date: May 28, 2021

(87) PCT Pub. No.: WO2020/112908
PCT Pub. Date: Jun. 4, 2020

(65) Prior Publication Data
US 2022/0047723 A1 Feb. 17, 2022

Related U.S. Application Data

(60) Provisional application No. 62/772,278, filed on Nov. 28, 2018.

(51) Int. Cl.
*A61K 48/00* (2006.01)
*C12N 9/22* (2006.01)
(Continued)

(52) U.S. Cl.
CPC .......... *A61K 48/0025* (2013.01); *C12N 9/22* (2013.01); *C12N 15/111* (2013.01); *C12N 15/88* (2013.01);
(Continued)

(58) Field of Classification Search
CPC .... A61K 48/0025; A61K 9/1271; C12N 9/22; C12N 15/111; C12N 15/88; C12N 2310/20; C12N 2320/32
See application file for complete search history.

(56) References Cited

U.S. PATENT DOCUMENTS

| 3,687,808 A | 8/1972 | Merigan et al. |
| 4,469,863 A | 9/1984 | Ts et al. |

(Continued)

FOREIGN PATENT DOCUMENTS

| CN | 105899658 | 8/2016 |
| WO | WO1993/003769 | 3/1993 |

(Continued)

OTHER PUBLICATIONS

GenPept Accession # WP_002460848.1 (Year: 2015).*
GenPept Accession # WP_023374365.1 (Year: 2015).*
(Continued)

*Primary Examiner* — Ram R Shukla
*Assistant Examiner* — Shabana S Meyering
(74) *Attorney, Agent, or Firm* — Casimir Jones, S.C.; J. Mitchell Jones

(57) ABSTRACT

The present disclosure relates generally to novel lipid nanoparticle (LNP)-based compositions useful for, e.g., the delivery of a site-specific endonuclease or a nucleic acid molecule encoding same, into a target cell. Some embodiments of the disclosure relate to compositions and methods for editing the genome of a cell, which involve contacting the cell with an LNP composition as described herein.

18 Claims, 12 Drawing Sheets

Specification includes a Sequence Listing.

(51) Int. Cl.
*C12N 15/11* (2006.01)
*C12N 15/88* (2006.01)

(52) U.S. Cl.
CPC ...... *C12N 2310/20* (2017.05); *C12N 2320/32* (2013.01)

(56) References Cited

U.S. PATENT DOCUMENTS

| | | |
|---|---|---|
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,222,982 A | 6/1993 | Ommaya |
| 5,235,033 A | 8/1993 | Summerton et al. |
| 5,245,022 A | 9/1993 | Weis et al. |
| 5,254,469 A | 10/1993 | Warren et al. |
| 5,258,506 A | 11/1993 | Urdea et al. |
| 5,262,536 A | 11/1993 | Hobbs |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,385,582 A | 1/1995 | Ommaya |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,451,513 A | 9/1995 | Maliga et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,545,817 A | 8/1996 | Mcbride et al. |
| 5,545,818 A | 8/1996 | Mcbride et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,576,198 A | 11/1996 | Mcbride et al. |
| 5,578,717 A | 11/1996 | Urdea et al. |
| 5,578,718 A | 11/1996 | Cook et al. |
| 5,580,731 A | 12/1996 | Chang et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,786,211 A | 7/1998 | Johnson |
| 5,830,653 A | 11/1998 | Froehler et al. |
| 5,843,780 A | 12/1998 | Thomson |
| 5,871,982 A | 2/1999 | Wilson et al. |
| 6,005,096 A | 12/1999 | Matteucci et al. |
| 6,200,806 B1 | 3/2001 | Thomson |
| 6,258,595 B1 | 7/2001 | Gao et al. |
| 6,287,860 B1 | 9/2001 | Monia et al. |
| 7,029,913 B2 | 4/2006 | Thomson |
| 7,078,387 B1 | 7/2006 | Leiden et al. |
| 7,153,684 B1 | 12/2006 | Hogan |
| 7,169,874 B2 | 1/2007 | Salamone et al. |
| 8,158,601 B2 | 4/2012 | Chen et al. |
| 2003/0022831 A1 | 1/2003 | Rothbard et al. |
| 2003/0032593 A1 | 2/2003 | Wender et al. |
| 2003/0083256 A1 | 5/2003 | Rothbard et al. |
| 2003/0158403 A1 | 8/2003 | Manoharan et al. |

(56) References Cited

U.S. PATENT DOCUMENTS

| | | | |
|---|---|---|---|
| 2003/0220334 | A1 | 11/2003 | Wender et al. |
| 2004/0142025 | A1 | 7/2004 | MacLachlan et al. |
| 2007/0042031 | A1 | 2/2007 | MacLachlan et al. |
| 2007/0254842 | A1 | 11/2007 | Bankiewicz |
| 2008/0081064 | A1 | 4/2008 | Jelle et al. |
| 2009/0047263 | A1 | 2/2009 | Yamanaka et al. |
| 2009/0068742 | A1 | 3/2009 | Yamanaka et al. |
| 2009/0191159 | A1 | 7/2009 | Sakurada et al. |
| 2009/0196903 | A1 | 8/2009 | Kliman |
| 2009/0227032 | A1 | 9/2009 | Yamanaka et al. |
| 2009/0246875 | A1 | 10/2009 | Yamanaka et al. |
| 2009/0304646 | A1 | 12/2009 | Sakurada et al. |
| 2018/0127786 | A1* | 5/2018 | Bouchon ............... C12N 9/22 |

FOREIGN PATENT DOCUMENTS

| | | | |
|---|---|---|---|
| WO | WO1993/007883 | | 4/1993 |
| WO | WO1993/009239 | | 5/1993 |
| WO | WO1993/019191 | | 9/1993 |
| WO | WO1994/012649 | | 6/1994 |
| WO | WO1994/028938 | | 12/1994 |
| WO | WO1995/000655 | | 1/1995 |
| WO | WO1995/011984 | | 5/1995 |
| WO | WO1995/013365 | | 5/1995 |
| WO | WO1995/013392 | | 5/1995 |
| WO | WO1995/016783 | | 6/1995 |
| WO | WO1996/017947 | | 6/1996 |
| WO | WO1997/006243 | | 2/1997 |
| WO | WO1997/008298 | | 3/1997 |
| WO | WO1997/009441 | | 3/1997 |
| WO | WO1997/021825 | | 6/1997 |
| WO | WO1998/039352 | | 9/1998 |
| WO | WO1999/011764 | | 1/1999 |
| WO | WO1999/014226 | | 3/1999 |
| WO | WO1999/020741 | | 4/1999 |
| WO | WO2001/018048 | | 3/2001 |
| WO | WO2001/051616 | | 7/2001 |
| WO | WO2001/083692 | | 11/2001 |
| WO | WO2003/020920 | | 3/2003 |
| WO | 2013/138339 | | 9/2013 |
| WO | WO2013/176722 | | 11/2013 |
| WO | WO2013176772 | | 11/2013 |
| WO | WO2014/008334 | | 1/2014 |
| WO | WO2015/077318 | | 5/2015 |
| WO | 2015/089419 | A2 | 6/2015 |
| WO | 2015/089465 | | 6/2015 |
| WO | WO2015/095340 | | 6/2015 |
| WO | WO2015/103153 | | 7/2015 |
| WO | WO2015/130584 | | 9/2015 |
| WO | WO2015/153780 | | 10/2015 |
| WO | WO/2016/186953 | | 11/2016 |
| WO | 2016/205759 | | 12/2016 |
| WO | WO2016/205613 | | 12/2016 |
| WO | WO2017/048969 | | 3/2017 |
| WO | WO2017/070622 | | 4/2017 |
| WO | WO2017/070632 | | 4/2017 |
| WO | WO2017/099823 | | 6/2017 |
| WO | 2017/144630 | A1 | 8/2017 |
| WO | WO2017/173054 | | 10/2017 |
| WO | WO2018/002719 | | 1/2018 |
| WO | WO2018/002812 | | 1/2018 |
| WO | 2018/058064 | A1 | 3/2018 |
| WO | WO2018/039145 | | 3/2018 |
| WO | WO2018/081480 | | 5/2018 |
| WO | 2018/107026 | A1 | 6/2018 |
| WO | WO-2018172556 | A1 * | 9/2018 ......... A61K 31/7088 |
| WO | 2019/183150 | A1 | 9/2019 |
| WO | 2020/112908 | A2 | 6/2020 |

OTHER PUBLICATIONS

Aguilera et al., "Systemic in vivo distribution of activatable cell penetrating peptides is superior to that of cell penetrating peptides," Integrative Biology 2009, 1(5-6), 371-381.

Akyürek et al., "SM22 α Promoter Targets Gene Expression to Vascular Smooth Muscle Cells In Vitro and In Vivo," Molecular Medicine 2000, 6, 983-991.

Ali et al., "Adeno-associated virus gene transfer to mouse retina," Human Gene Therapy 1998, 9(1), 81-86.

Ali et al., "Gene transfer into the mouse retina mediated by an adeno-associated viral vector," Human Molecular Genetics 1996, 5(5), 591-594.

Altschul et al., "Basic local alignment search tool," Journal of Molecular Biology 1990, 215(3), 403-410.

Anders & Jinek, "In vitro enzymology of Cas9," Methods in Enzymology 2014, 546, 1-20.

Angart et al., "Design of siRNA therapeutics from the molecular scale," Pharmaceuticals 2013, 6(4), 440-468.

Angel & Yanik, "Innate immune suppression enables frequent transfection with RNA encoding reprogramming proteins," PloS One 2010, 5(7), in 7 pages.

Baetge et al., "Transgenic mice express the human phenylethanolamine N-methyltransferase gene in adrenal medulla and retina," Proceedings of the National Academy of Sciences 1988, 85(10), 3648-3652.

Barbour et al., "Characterization of the bipartite degron that regulates ubiquitin-independent degradation of thymidylate synthase," Bioscience Reports 2013, 33(1), in 19 pages.

Behlke, "Chemical modification of siRNAs for in vivo use," Oligonucleotides 2008, 18(4), 305-320.

Bennett et al., "Real-time, noninvasive in vivo assessment of adeno-associated virus-mediated retinal transduction," Investigative Ophthalmology & Visual Science 1997, 38(13), 2857-2863.

Beumer et al., "Efficient gene targeting in Drosophila by direct embryo injection with zinc-finger nucleases," Proceedings of the National Academy of Sciences 2008, 105(50), 19821-19826.

Bevan, "Binary Agrobacterium vectors for plant transformation," Nucleic Acids Research 1984, 12(22), 8711-8721.

Bitter et al., "[33] Expression and secretion vectors for yeast," Methods in Enzymology 1987, 153, 516-544.

Bolukbasi et al., "Creating and evaluating accurate CRISPR-Cas9 scalpels for genomic surgery," Nature Methods 2016, 13(1), 41-50.

Borrás et al., "Adenoviral reporter gene transfer to the human trabecular meshwork does not alter aqueous humor outflow. Relevance for potential gene therapy of glaucoma," Gene Therapy 1999, 6(4), 515-524.

Boundy et al., "Regulation of tyrosine hydroxylase promoter activity by chronic morphine in TH9. 0-LacZ transgenic mice," Journal of Neuroscience 1998, 18(23), 9989-9995.

Boynton & Gillham, "[37] Chloroplast transformation in Chlamydomonas," Methods in Enzymology 1993, 217, 510-536.

Braasch et al., "Novel antisense and peptide nucleic acid strategies for controlling gene expression," Biochemistry 2002, 41(14), 4503-4510.

Bramsen & Kjems, "Development of therapeutic-grade small interfering RNAs by chemical engineering," Frontiers in Genetics 2012, 3, in 22 pages.

Brinkman et al., "Easy quantitative assessment of genome editing by sequence trace decomposition," Nucleic Acids Research 2014, 42(22), in 8 pages.

Burnett et al., "Current progress of siRNA/shRNA therapeutics in clinical trials," Biotechnology Journal 2011, 6(9), 1130-1146.

Carter, "Adeno-associated virus vectors," Current Opinion in Biotechnology 1992, 3(5), 533-539.

Casanova et al., "A CamKIIα iCre BAC allows brain-specific gene inactivation," Genesis 2001, 31(1), 37-42.

Ceccaldi et al., "Homologous-recombination-deficient tumours are dependent on Pole-mediated repair," Nature 2015, 518 (7538), 258-262.

Cekaite et al., "Gene expression analysis in blood cells in response to unmodified and 2'-modified siRNAs reveals TLR-dependent and independent effects," Journal of Molecular Biology 2007, 365(1), 90-108.

Chakrabarti, "Promoting adipose specificity: the adiponectin promoter," Endocrinology 2010, 151(6), 2408-2410.

(56) References Cited

OTHER PUBLICATIONS

Chang & Wilson, "Modification of DNA ends can decrease end joining relative to homologous recombination in mammalian cells," Proceedings of the National Academy of Sciences 1987, 84(14), 4959-4963.
Chen et al., "A lymphoproliferative abnormality associated with inappropriate expression of the Thy-1 antigen in transgenic mice," Cell 1987, 51(1), 7-19.
Chen et al., "Analysis of a 762-bp proximal leptin promoter to drive and control regulation of transgene expression of growth hormone receptor in mice," Biochemical and Biophysical Research Communications 1999, 262(1), 187-192.
Chernolovskaya & Zenkova, "Chemical modification of siRNA," Current Opinion in Molecular Therapeutics 2010, 12(2), 158-167.
Cho & Greenberg, "Familiar ends with alternative endings," Nature 2015, 518(7538), 174-175.
Cho et al., "Generation of transgenic mice," Current Protocols in Cell Biology 2009, 42(1), 19-11.
Christou et al., "Production of transgenic rice (Oryza sativa L.) plants from agronomically important indica and japonica varieties via electric discharge particle acceleration of exogenous DNA into immature zygotic embryos," Bio/technology 1991, 9(10), 957-962.
Chu et al., "Recent progress with FKBP-derived destabilizing domains," Bioorganic & Medicinal Chemistry Letters 2008, 18(22), 5941-5944.
Citartan et al., "Assays for aptamer-based platforms," Biosensors and Bioelectronics 2012, 34(1), in 11 pages.
Clark et al., "A stable cell line carrying adenovirus-inducible rep and cap genes allows for infectivity titration of adeno-associated virus vectors," Gene Therapy 1996, 3(12), 1124-1132.
Comb et al., "Proteins bound at adjacent DNA elements act synergistically to regulate human proenkephalin cAMP inducible transcription," The EMBO Journal 1988, 7(12), 3793-3805.
Cox et al., "Therapeutic genome editing: prospects and challenges," Nature Medicine 2015, 21(2), 121-131.
Crooke et al., "Pharmacokinetic properties of several novel oligonucleotide analogs in mice," Journal of Pharmacology and Experimental Therapeutics 1996, 277(2), 923-937.
Daniell et al., "Containment of herbicide resistance through genetic engineering of the chloroplast genome," Nature Biotechnology 1998, 16(4), 345-348.
De Mesmaeker et al., "Antisense oligonucleotides," Accounts of Chemical Research 1995, 28(9), 366-374.
Deleavey et al., "Chemical modification of siRNA," Current Protocols in Nucleic Acid Chemistry 2009, 39(1), in 22 pages.
Derossi et al., "Cell internalization of the third helix of the Antennapedia homeodomain is receptor-independent," Journal of Biological Chemistry 1996, 271(30), 18188-18193.
Devereux et al., "A comprehensive set of sequence analysis programs for the VAX," Nucleic Acids Research 1984, 12(1), 387-395.
Dohmen et al., "Heat-inducible degron: a method for constructing temperature-sensitive mutants," Science 1994, 263(5151), 1273-1276.
Englisch & Gauss, "Chemically modified oligonucleotides as probes and inhibitors," Angewandte Chemie International Edition in English 1991, 30(6), 613-629.
European Nucleotide Archive, "Sequence: X51956.1 Human ENO2 gene for neuron specific (gamma) enolase," nih.gov 2023, in 2 page2.
Feng et al., "High-level expression and mutagenesis of recombinant human phosphatidylcholine transfer protein using a synthetic gene: evidence for a C-terminal membrane binding domain," Biochemistry 2000, 39(50), 15399-15409.
First Office Action dated Oct. 8, 2023 in Chinese Patent Application No. 201980090537.2.
Flannery et al., "Efficient photoreceptor-targeted gene expression in vivo by recombinant adeno-associated virus," Proceedings of the National Academy of Sciences 1997, 94(13), 6916-6921.
Flotte et al., "Stable in vivo expression of the cystic fibrosis transmembrane conductance regulator with an adeno-associated virus vector," Proceedings of the National Academy of Sciences 1993, 90(22), 10613-10617.
Franz et al., "Analysis of tissue-specific gene delivery by recombinant adenoviruses containing cardiac-specific promoters," Cardiovascular Research 1997, 35(3), 560-566.
Fucini et al., "Adenosine modification may be preferred for reducing siRNA immune stimulation," Nucleic Acid Therapeutics 2012, 22(3), 205-210.
Futaki et al., "Structural variety of membrane permeable peptides," Current Protein and Peptide Science 2003, 4(2), 87-96.
Gaglione & Messere, "Recent progress in chemically modified siRNAs," Mini Reviews in Medicinal Chemistry 2010, 10(7), 578-595.
Gama Sosa et al., "Animal transgenesis: an overview," Brain Structure and Function 2010, 214, 91-109.
Gaudelli et al., "Programmable base editing of A• T to G• C in genomic DNA without DNA cleavage," Nature 2017, 551(7681), 464-471.
Gebeyehu et al., "Novel biotinylated nucleotide-analogs for labeling and colorimetric detection of DNA," Nucleic Acids Research 1987, 15(11), 4513-4534.
Gibbs et al., "Degenerate oligonucleotide gene shuffling (DOGS): a method for enhancing the frequency of recombination with family shuffling," Gene 2001, 271(1), 13-20.
Glaser et al., "GFP to BFP conversion: a versatile assay for the quantification of CRISPR/Cas9-mediated genome editing," Molecular Therapy—Nucleic Acids 2016, 5, in 4 pages.
Gordon-Kamm et al., "Transformation of maize cells and regeneration of fertile transgenic plants," The Plant Cell 1990, 2(7), 603-618.
Greussing et al., "Monitoring of ubiquitin-proteasome activity in living cells using a Degron (dgn)-destabilized green fluorescent protein (GFP)-based reporter protein," JoVE (Journal of Visualized Experiments) 2012, 69, in 8 pages.
Harayama, "Artificial evolution by DNA shuffling," Trends in Biotechnology 1998, 16(2), 76-82.
Heasman, "Morpholino oligos: making sense of antisense?," Developmental Biology 2002, 243(2), 209-214.
Hermonat & Muzyczka, "Use of adeno-associated virus as a mammalian DNA cloning vector: transduction of neomycin resistance into mammalian tissue culture cells," Proceedings of the National Academy of Sciences 1984, 81(20), 6466-6470.
Herrera-Estrella et al., "Expression of chimaeric genes transferred into plant cells using a Ti-plasmid-derived vector," Nature 1983, 303(5914), 209-213.
Hu et al., "Physiological roles of asialoglycoprotein receptors (ASGPRs) variants and recent advances in hepatic-targeted delivery of therapeutic molecules via ASGPRs," Protein and Peptide Letters 2014, 21(10), 1025-1030.
Hunter et al., "Targeting gene expression to specific cardiovascular cell types in transgenic mice," Hypertension 1993, 22(4), 608-617.
Husaini et al., "Approaches for gene targeting and targeted gene expression in plants," GM Crops 2011, 2(3), 150-162.
International Preliminary Report on Patentability dated Sep. 22, 2020 in International Application No. PCT/US2019/023044.
International Search Report and Written Opinion dated Jul. 5, 2019 in International Application No. PCT/US2019/023044.
Ishida et al., "High efficiency transformation of maize (Zea mays L.) mediated by Agrobacterium tumefaciens," Nature Biotechnology 1996, 14(6), 745-750.
Joern, "DNA shuffling," Directed Evolution Library Creation: Methods and Protocols 2003, 231, 85-89.
Jomary et al., "Rescue of photoreceptor function by AAV-mediated gene transfer in a mouse model of inherited retinal degeneration," Gene Therapy 1997, 4(7), 683-690.
Judge & MacLachlan, "Overcoming the innate immune response to small interfering RNA," Human Gene Therapy 2008, 19(2), 111-124.
Judge et al., "Design of noninflammatory synthetic siRNA mediating potent gene silencing in vivo," Molecular Therapy 2006, 13(3), 494-505.

(56) References Cited

OTHER PUBLICATIONS

Kabanov et al., "A new class of antivirals: antisense oligonucleotides combined with a hydrophobic substituent effectively inhibit influenza virus reproduction and synthesis of virus-specific proteins in MDCK cells," FEBS letters 1990, 259(2), 327-330.

Kanasty et al., "Action and reaction: the biological response to siRNA and its delivery vehicles," Molecular Therapy 2012, 20(3), 513-524.

Kaneda et al., "Tissue-specific and high-level expression of the human tyrosine hydroxylase gene in transgenic mice," Neuron 1991, 6(4), 583-594.

Kanemaki, "Frontiers of protein expression control with conditional degrons," Pflügers Archiv—European Journal of Physiology 2013, 465, 419-425.

Karikó et al., "Suppression of RNA recognition by Toll-like receptors: the impact of nucleoside modification and the evolutionary origin of RNA," Immunity 2005, 23(2), 165-175.

Kawai et al., "Transformation of *Saccharomyces cerevisiae* and other fungi: methods and possible underlying mechanism," Bioengineered Bugs 2010, 1(6), 395-403.

Kazutaka Katoh, "Mafft version 7," mafft.cbrc.jp 2023, in 2 pages.

Kent et al., "Mechanism of microhomology-mediated end-joining promoted by human DNA polymerase θ," Nature Structural & Molecular Biology 2015, 22(3), 230-237.

Kim et al. "A serum response factor-dependent transcriptional regulatory program identifies distinct smooth muscle cell sublineages." Molecular and Cellular Biology 1997, 17(4), 2266-2278.

Kim et al., "Increasing the genome-targeting scope and precision of base editing with engineered Cas9-cytidine deaminase fusions," Nature Biotechnology 2017, 35(4), 371-376.

Kita et al., "Identification of the promoter region required for human adiponectin gene transcription: association with CCAAT/enhancer binding protein-β and tumor necrosis factor-α," Biochemical and Biophysical Research Communications 2005, 331(2), 484-490.

Klee et al., "Vectors for transformation of higher plants," Bio/technology 1985, 3(7), 637-642.

Klein et al., "High-velocity microprojectiles for delivering nucleic acids into living cells," Nature 1987, 327(6117), 70-73.

Knight et al., "Regulation of the human GLUT4 gene promoter: interaction between a transcriptional activator and myocyte enhancer factor 2A," Proceedings of the National Academy of Sciences 2003, 100(25), 14725-14730.

Knoblauch et al., "A galinstan expansion femtosyringe for microinjection of eukaryotic organelles and prokaryotes," Nature Biotechnology 1999, 17(9), 906-909.

Kole et al., "RNA therapeutics: beyond RNA interference and antisense oligonucleotides," Nature Reviews Drug Discovery 2012, 11(2), 125-140.

Komor et al., "Improved base excision repair inhibition and bacteriophage Mu Gam protein yields C: G-to-T: A base editors with higher efficiency and product purity," Science Advances 2017, 3(8), in 10 pages.

Komor et al., "Programmable editing of a target base in genomic DNA without double-stranded DNA cleavage," Nature 2016, 533(7603), 420-424.

Kormann et al., "Expression of therapeutic proteins after delivery of chemically modified mRNA in mice," Nature biotechnology 2011, 29(2), 154-157.

Koshimizu et al., "Functional requirement of gp130-mediated signaling for growth and survival of mouse primordial germ cells in vitro and derivation of embryonic germ (EG) cells," Development 1996, 122(4), 1235-1242.

Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron 1998, 54(14), 3607-3630.

Krishnan et al., "CRISPR deletion of the C9ORF72 promoter in ALS/FTD patient motor neurons abolishes production of dipeptide repeat proteins and rescues neurodegeneration," Acta Neuropathologica 2020, 140, 81-84.

Kuriki et al., "Structural and functional analysis of a new upstream promoter of the human FAT/CD36 gene," Biological and Pharmaceutical Bulletin 2002, 25(11), 1476-1478.

Lacerra et al., "Restoration of hemoglobin A synthesis in erythroid cells from peripheral blood of thalassemic patients," Proceedings of the National Academy of Sciences 2000, 97(17), 9591-9596.

Langer, "New methods of drug delivery," Science 1990, 249(4976), 1527-1533.

Laughlin et al., "Cloning of infectious adeno-associated virus genomes in bacterial plasmids," Gene 1983, 23(1), 65-73.

Lebkowski et al. "Adeno-associated virus: a vector system for efficient introduction and integration of DNA into a variety of mammalian cell types," Molecular and Cellular Biology 1988, 8(10), 3988-3996.

Letsinger et al., "Cholesteryl-conjugated oligonucleotides: synthesis, properties, and activity as inhibitors of replication of human immunodeficiency virus in cell culture," Proceedings of the National Academy of Sciences 1989, 86(17), 6553-6556.

Li & Davidson, "Phenotype correction in retinal pigment epithelium in murine mucopolysaccharidosis VII by adenovirus-mediated gene transfer," Proceedings of the National Academy of Sciences 1995, 92(17), 7700-7704.

Li et al., "Expression of the SM22alpha promoter in transgenic mice provides evidence for distinct transcriptional regulatory programs in vascular and visceral smooth muscle cells," The Journal of Cell Biology 1996, 132(5), 849-859.

Li et al., "In vivo transfer of a reporter gene to the retina mediated by an adenoviral vector," Investigative Ophthalmology & Visual Science 1994, 35(5), 2543-2549.

Liberman & Wedekind, "Riboswitch structure in the ligand-free state," Wiley Interdisciplinary Reviews: RNA 2012, 3(3), 369-384.

Linn et al., "Conservation of an AE3 Cl-/HCO3-exchanger cardiac-specific exon and promoter region and AE3 mRNA expression patterns in murine and human hearts," Circulation Research 1995, 76(4), 584-591.

Liu et al., "CMV enhancer/human PDGF-β promoter for neuron-specific transgene expression," Gene Therapy 2004, 11(1), 52-60.

Llewellyn et al., "Orderly recruitment of motor units under optical control in vivo," Nature Medicine 2010, 16(10), 1161-1165.

Loakes & Brown, "5-Nitroindole as an universal base analogue," Nucleic Acids Research 1994, 22(20), 4039-4043.

Ma et al., "Pol III promoters to express small RNAs: delineation of transcription initiation," Molecular Therapy—Nucleic Acids 2014, 3, in 11 pages.

Mae et al., "Chemically modified cell-penetrating peptides for the delivery of nucleic acids," Expert Opinion on Drug Delivery 2009, 6(11), 1195-1205.

Makrides, "Gene transfer and expression in mammalian cells," Gulf Professional Publishing, 2003, in 680 pages.

Manoharan et al., "Chemical modifications to improve uptake and bioavailability of antisense oligonucleotides," Annals of the New York Academy of Sciences 1992, 660(1), 306-309.

Manoharan et al., "Cholic acid-oligonucleotide conjugates for antisense applications," Bioorganic & Medicinal Chemistry Letters 1994, 4(8), 1053-1060.

Manoharan et al., "Introduction of a lipophilic thioether tether in the minor groove of nucleic acids for antisense applications," Bioorganic & Medicinal Chemistry Letters 1993, 3(12), 2765-2770.

Manoharan et al., "Lipidic nucleic acids," Tetrahedron Letters 1995, 36(21), 3651-3654.

Manoharan et al., "Oligonucleotide conjugates: alteration of the pharmacokinetic properties of antisense agents," Nucleosides, Nucleotides & Nucleic Acids 1995, 14(3-5), 969-973.

Martin, "Ein neuer Zugang zu 2'-O-Alkylribonucleosiden und Eigenschaflen deren Oligonucleotide," Helv. Chim. Acta 1995, 78(2), 486-504.

Mason et al., "Regulation of leptin promoter function by Sp1, C/EBP, and a novel factor," Endocrinology 1998, 139(3), 1013-1022.

Mateos-Gomez et al., "Mammalian polymerase θ promotes alternative NHEJ and suppresses recombination," Nature 2015, 518(7538), 254-257.

(56) References Cited

OTHER PUBLICATIONS

Matsui et al., "Derivation of pluripotential embryonic stem cells from murine primordial germ cells in culture," Cell 1992, 70(5), 841-847.
Mayford et al., "The 3'-untranslated region of CaMKIIα is a cis-acting signal for the localization and translation of mRNA in dendrites," Proceedings of the National Academy of Sciences 1996, 93(23), 13250-13255.
McBride et al., "Controlled expression of plastid transgenes in plants based on a nuclear DNA-encoded and plastid-targeted T7 RNA polymerase," Proceedings of the National Academy of Sciences 1994, 91(15), 7301-7305.
McLaughlin et al., "Adeno-associated virus general transduction vectors: analysis of proviral structures," Journal of Virology 1988, 62(6), 1963-1973.
Mendelson et al., "Expression and rescue of a nonselected marker from an integrated AAV vector," Virology 1988, 166(1), 154-165.
Mishra et al., "Improved leishmanicidal effect of phosphorotioate antisense oligonucleotides by LDL-mediated delivery," Biochimica et Biophysica Acta (BBA)-Gene Structure and Expression 1995, 1264(2), 229-237.
Miyagishi & Taira, "U6 promoter-driven siRNAs with four uridine 3' overhangs efficiently suppress targeted gene expression in mammalian cells," Nature Biotechnology 2002, 20(5), 497-500.
Miyoshi et al., "Stable and efficient gene transfer into the retina using an HIV-based lentiviral vector," Proceedings of the National Academy of Sciences 1997, 94(19), 10319-10323.
Moessler et al., "The SM 22 promoter directs tissue-specific expression in arterial but not in venous or visceral smooth muscle cells in transgenic mice," Development 1996, 122(8), 2415-2425.
Morrison et al., "Regulatory mechanisms in stem cell biology," Cell 1997, 88(3), 287-298.
Mullis, "The polymerase chain reaction," Springer Science & Business Media 1994, 41(5), in 458 pages.
Muzyczka, "Use of adeno-associated virus as a general transduction vector for mammalian cells," Viral Expression Vectors 1992, 97-129.
Nakamura et al., "RNA plasticity and selectivity applicable to therapeutics and novel biosensor development," Genes to Cells 2012, 17(5), 344-364.
Nasevicius & Ekker, "Effective targeted gene 'knockdown' in zebrafish," Nature Genetics 2000, 26(2), 216-220.
National Library of Medicine, "5-HT1C serotonin receptor {promoter region} [mice, Genomic, 1859 nt] GenBank: S62283.1," nih.gov 2023, in 1 page.
National Library of Medicine, "Adeno-associated virus-1, complete genome NCBI Reference Sequence: NC_002077.1," nih.gov 2023, in 3 pages.
National Library of Medicine, "Adeno-associated virus-2, complete genome NCBI Reference Sequence: NC_001401.2," nih.gov 2023, in 5 pages.
National Library of Medicine, "Adeno-associated virus-3, complete genome NCBI Reference Sequence: NC_001729.1," nih.gov 2023, in 3 pages.
National Library of Medicine, "Adeno-associated virus-4, complete genome NCBI Reference Sequence: NC_001829.1," nih.gov 2023, in 3 pages.
National Library of Medicine, "type II CRISPR RNA-guided endonuclease Cas9 [Listeria innocua] NCBI Reference Sequence: WP_033838504.1," nih.gov 2023, in 2 pages.
National Library of Medicine, "Adeno-associated virus-7, complete genome NCBI Reference Sequence: NC_006260.1," nih.gov 2023, in 3 pages.
National Library of Medicine, "Adeno-associated virus-8, complete genome NCBI Reference Sequence: NC_006261.1," nih.gov 2023, in 3 pages.
National Library of Medicine, "Adeno-associated virus 10 nonstructural protein and capsid protein genes, complete cds GenBank: AY631965.1," nih.gov 2023, in 2 pages.
National Library of Medicine, "Adeno-associated virus 11 nonstructural protein and capsid protein genes, complete cds GenBank: AY631966.1," nih.gov 2023, in 2 pages.
National Library of Medicine, "Adeno-associated virus 12 Rep78 and VP1 genes, complete cds GenBank: DQ813647.1," nih.gov 2023, in 2 pages.
National Library of Medicine, "Adeno-associated virus 13 nonstructural protein and capsid protein genes, complete cds GenBank: EU285562.1," nih.gov 2023, in 2 pages.
National Library of Medicine, "Adeno-associated virus 3B, complete genome GenBank: AF028705.1," nih.gov 2023, in 2 pages.
National Library of Medicine, "Adeno-associated virus 5, complete genome NCBI Reference Sequence: NC_006152.1," nih.gov 2023, in 3 pages.
National Library of Medicine, "Adeno-associated virus 6, complete genome GenBank: AF028704.1," nih.gov 2023, in 2 pages.
National Library of Medicine, "CRISPR-associated protein Cas9, partial [*Staphylococcus coagulans*] NCBI Reference Sequence: WP_103356723.1," nih.gov 2023, in 1 page.
National Library of Medicine, "HNH endonuclease domain-containing protein, partial [*Staphylococcus simulans*] NCBI Reference Sequence: WP_107604002.1," nih.gov 2023, in 1 page.
National Library of Medicine, "HNH endonuclease domain-containing protein [*Staphylococcus schleiferi*] NCBI Reference Sequence: WP_016424981.1," nih.gov 2023, in 1 page.
National Library of Medicine, "HNH endonuclease domain-containing protein [Chryseomicrobium excrementi] NCBI Reference Sequence: WP_100353964.1," nih.gov 2023, in 1 page.
National Library of Medicine, "HNH endonuclease domain-containing protein [*Bacillus* sp. SA1-12] NCBI Reference Sequence: WP_046517046.1," nih.gov 2023, in 1 page.
National Library of Medicine, "Human neurofilament light chain (NEFL) gene, promoter region GenBank: L04147.1," nih.gov 2023, in 2 pages.
National Library of Medicine, "Human synapsin I gene, 5' end GenBank: M55301.1," nih.gov 2023, in 2 pages.
National Library of Medicine, "hypothetical protein [Alkalibacillus haloalkaliphilus] NCBI Reference Sequence: WP_050980543.1," nih.gov 2023, in 1 page.
National Library of Medicine, "hypothetical protein [*Anoxybacillus* sp. KU2-6(11)] NCBI Reference Sequence: WP_052025682.1," nih.gov 2023, in 1 page.
National Library of Medicine, "hypothetical protein [Heyndrickxia sporothermodurans] NCBI Reference Sequence: WP_066230975.1," nih.gov 2023, in 1 page.
National Library of Medicine, "hypothetical protein [Listeria fleischmannii] NCBI Reference Sequence: WP_077914265.1," nih.gov 2023, in 1 page.
National Library of Medicine, "hypothetical protein [Listeria fleischmannii] NCBI Reference Sequence: WP_077914264.1," nih.gov 2023, in 1 page.
National Library of Medicine, "hypothetical protein [Mammaliicoccus sciuri] NCBI Reference Sequence: WP_103361956.1," nih.gov 2023, in 1 page.
National Library of Medicine, "hypothetical protein [Salinicoccus sediminis] NCBI Reference Sequence: WP_046580811.1," nih.gov 2023, in 1 page.
National Library of Medicine, "hypothetical protein [*Staphylococcus simulans*] NCBI Reference Sequence: WP_107593719.1," nih.gov 2023, in 1 page.
National Library of Medicine, "hypothetical protein [*Staphylococcus agnetis*] NCBI Reference Sequence: WP_107371387.1," nih.gov 2023, in 1 page.
National Library of Medicine, "hypothetical protein [*Staphylococcus* sp. HMSC065D05] NCBI Reference Sequence: WP_070592992.1," nih.gov 2023, in 1 page.
National Library of Medicine, "hypothetical protein [*Staphylococcus warneri*] NCBI Reference Sequence: WP_107536245.1," nih.gov 2023, in 1 page.
National Library of Medicine, "hypothetical protein [*Staphylococcus agnetis*] NCBI Reference Sequence: WP_107368971.1," nih.gov 2023, in 1 page.

(56) References Cited

OTHER PUBLICATIONS

National Library of Medicine, "Multispecies: ABC transporter permease [Mammaliicoccus] NCBI Reference Sequence: WP_017000597.1," nih.gov 2023, in 1 page.
National Library of Medicine, "Multispecies: hypothetical protein [*Staphylococcus*] NCBI Reference Sequence: WP_060803559.1," nih.gov 2023, in 1 page.
National Library of Medicine, "Multispecies: type II CRISPR RNA-guided endonuclease Cas9 [*Staphylococcus*] NCBI Reference Sequence: WP_082709447.1," nih.gov 2023, in 2 pages.
National Library of Medicine, "Multispecies: type II CRISPR RNA-guided endonuclease Cas9 [*Staphylococcus*] NCBI Reference Sequence: WP_083326835.1," nih.gov 2023, in 2 pages.
National Library of Medicine, "Multispecies: type II CRISPR RNA-guided endonuclease Cas9 [*Staphylococcus*] NCBI Reference Sequence: WP_104681501.1," nih.gov 2023, in 2 pages.
National Library of Medicine, "Multispecies: type II CRISPR RNA-guided endonuclease Cas9 [*Staphylococcus*] NCBI Reference Sequence: WP_016424980.1," nih.gov 2023, in 2 pages.
National Library of Medicine, "Multispecies: type II CRISPR RNA-guided endonuclease Cas9 [*Staphylococcus*] NCBI Reference Sequence: WP_060803934.1," nih.gov 2023, in 2 pages.
National Library of Medicine, "Multispecies: type II CRISPR RNA-guided endonuclease Cas9 [*Staphylococcus*] NCBI Reference Sequence: WP_107376447.1," nih.gov 2023, in 2 pages.
National Library of Medicine, "Multispecies: type II CRISPR RNA-guided endonuclease Cas9 [unclassified *Staphylococcus*] NCBI Reference Sequence: WP_070848771.1," nih.gov 2023, in 2 pages.
National Library of Medicine, "Multispecies: type II CRISPR RNA-guided endonuclease Cas9 [Listeria] NCBI Reference Sequence: WP_088825434.1," nih.gov 2023, in 2 pages.
National Library of Medicine, "Multispecies: type II CRISPR RNA-guided endonuclease Cas9 [*Staphylococcus*] NCBI Reference Sequence: WP_075777761.1," nih.gov 2023, in 2 pages.
National Library of Medicine, "Multispecies: type II CRISPR RNA-guided endonuclease Cas9 [Listeria] NCBI Reference Sequence: WP_088816271.1," nih.gov 2023, in 2 pages.
National Library of Medicine, "Multispecies: type II CRISPR RNA-guided endonuclease Cas9 [Bacillus cereus group] NCBI Reference Sequence: WP_048723014.1," nih.gov 2023, in 2 pages.
National Library of Medicine, "Multispecies: type II CRISPR RNA-guided endonuclease Cas9 [Geobacillus] NCBI Reference Sequence: WP_064213580.1," nih.gov 2023, in 2 pages.
National Library of Medicine, "Multispecies: type II CRISPR RNA-guided endonuclease Cas9 [Geobacillus] NCBI Reference Sequence: WP_033018780.1," nih.gov 2023, in 2 pages.
National Library of Medicine, "Multispecies: type II CRISPR RNA-guided endonuclease Cas9 [Bacillus cereus group] NCBI Reference Sequence: WP_088027793.1," nih.gov 2023, in 2 pages.
National Library of Medicine, "Multispecies: type II CRISPR RNA-guided endonuclease Cas9 [Bacillus cereus group] NCBI Reference Sequence: WP_048539452.1," nih.gov 2023, in 2 pages.
National Library of Medicine, "RNA-guided endonuclease IscB [Alicyclobacillus acidocaldarius] NCBI Reference Sequence: WP_008341324.1," nih.gov 2023, in 1 page.
National Library of Medicine, "Sequence 5 from Patent EP1310571 GenBank: AX753250.1," nih.gov 2023, in 2 pages.
National Library of Medicine, "type II CRISPR RNA-guided endonuclease Cas9 [*Staphylococcus pasteuri*] NCBI Reference Sequence: WP_023374365.1," nih.gov 2023, in 2 pages.
National Library of Medicine, "type II CRISPR RNA-guided endonuclease Cas9 [*Staphylococcus pasteuri*] NCBI Reference Sequence: WP_048803085.1," nih.gov 2023, in 2 pages.
National Library of Medicine, "type II CRISPR RNA-guided endonuclease Cas9 [*Staphylococcus haemolyticus*] NCBI Reference Sequence: WP_053019794.1," nih.gov 2023, in 2 pages.
National Library of Medicine, "type II CRISPR RNA-guided endonuclease Cas9 [*Staphylococcus hominis*] NCBI Reference Sequence: WP_071859985.1," nih.gov 2023, in 2 pages.
National Library of Medicine, "type II CRISPR RNA-guided endonuclease Cas9 [*Staphylococcus hominis*] NCBI Reference Sequence: WP_049437627.1," nih.gov 2023, in 2 pages.
National Library of Medicine, "type II CRISPR RNA-guided endonuclease Cas9 [*Staphylococcus equorum*] NCBI Reference Sequence: WP_081329738.1," nih.gov 2023, in 2 pages.
National Library of Medicine, "type II CRISPR RNA-guided endonuclease Cas9 [*Staphylococcus equorum*] NCBI Reference Sequence: WP_081330634.1," nih.gov 2023, in 2 pages.
National Library of Medicine, "type II CRISPR RNA-guided endonuclease Cas9 [*Staphylococcus epidermidis*] NCBI Reference Sequence: WP_088922804.1," nih.gov 2023, in 2 pages.
National Library of Medicine, "type II CRISPR RNA-guided endonuclease Cas9 [*Staphylococcus kloosii*] NCBI Reference Sequence: WP_061854099.1," nih.gov 2023, in 2 pages.
National Library of Medicine, "type II CRISPR RNA-guided endonuclease Cas9 [Mammaliicoccus sciuri] NCBI Reference Sequence: WP_096792116.1," nih.gov 2023, in 2 pages.
National Library of Medicine, "type II CRISPR RNA-guided endonuclease Cas9 [*Staphylococcus simulans*] NCBI Reference Sequence: WP_107588422.1," nih.gov 2023, in 2 pages.
National Library of Medicine, "type II CRISPR RNA-guided endonuclease Cas9 [*Staphylococcus simulans*] NCBI Reference Sequence: WP_107543406.1," nih.gov 2023, in 2 pages.
National Library of Medicine, "type II CRISPR RNA-guided endonuclease Cas9 [*Staphylococcus simulans*] NCBI Reference Sequence: WP_105966910.1," nih.gov 2023, in 2 pages.
National Library of Medicine, "type II CRISPR RNA-guided endonuclease Cas9 [*Staphylococcus simulans*] NCBI Reference Sequence: WP_107597066.1," nih.gov 2023, in 2 pages.
National Library of Medicine, "type II CRISPR RNA-guided endonuclease Cas9 [*Staphylococcus simulans*] NCBI Reference Sequence: WP_096754380.1," nih.gov 2023, in 2 pages.
National Library of Medicine, "type II CRISPR RNA-guided endonuclease Cas9 [*Staphylococcus simulans*] NCBI Reference Sequence: WP_082732265.1," nih.gov 2023, in 2 pages.
National Library of Medicine, "type II CRISPR RNA-guided endonuclease Cas9 [*Staphylococcus* sp. HMSC061G12] NCBI Reference Sequence: WP_083326931.1," nih.gov 2023, in 2 pages.
National Library of Medicine, "type II CRISPR RNA-guided endonuclease Cas9 [*Staphylococcus simulans*] NCBI Reference Sequence: WP_105980293.1," nih.gov 2023, in 2 pages.
National Library of Medicine, "type II CRISPR RNA-guided endonuclease Cas9, partial [*Staphylococcus simulans*] NCBI Reference Sequence: WP_107580550.1," nih.gov 2023, in 2 pages.
National Library of Medicine, "type II CRISPR RNA-guided endonuclease Cas9 [*Staphylococcus* sp. HMSC065D05] NCBI Reference Sequence: WP_083310250.1," nih.gov 2023, in 2 pages.
National Library of Medicine, "type II CRISPR RNA-guided endonuclease Cas9 [*Staphylococcus simulans*] NCBI Reference Sequence: WP_105977729.1," nih.gov 2023, in 2 pages.
National Library of Medicine, "type II CRISPR RNA-guided endonuclease Cas9 [*Staphylococcus simulans*] NCBI Reference Sequence: WP_105978400.1," nih.gov 2023, in 2 pages.
National Library of Medicine, "type II CRISPR RNA-guided endonuclease Cas9, partial [*Staphylococcus simulans*] NCBI Reference Sequence: WP_107530431.1," nih.gov 2023, in 2 pages.
National Library of Medicine, "type II CRISPR RNA-guided endonuclease Cas9 [*Staphylococcus simulans*] NCBI Reference Sequence: WP_107578657.1," nih.gov 2023, in 2 pages.
National Library of Medicine, "type II CRISPR RNA-guided endonuclease Cas9 [*Staphylococcus simulans*] NCBI Reference Sequence: WP_107539784.1," nih.gov 2023, in 2 pages.
National Library of Medicine, "type II CRISPR RNA-guided endonuclease Cas9 [*Staphylococcus simulans*] NCBI Reference Sequence: WP_107597643.1," nih.gov 2023, in 2 pages.
National Library of Medicine, "type II CRISPR RNA-guided endonuclease Cas9 [*Staphylococcus simulans*] NCBI Reference Sequence: WP_105994700.1," nih.gov 2023, in 2 pages.
National Library of Medicine, "type II CRISPR RNA-guided endonuclease Cas9 [*Staphylococcus simulans*] NCBI Reference Sequence: WP_107533955.1," nih.gov 2023, in 2 pages.

(56) References Cited

OTHER PUBLICATIONS

National Library of Medicine, "type II CRISPR RNA-guided endonuclease Cas9 [*Staphylococcus simulans*] NCBI Reference Sequence: WP_107596301.1," nih.gov 2023, in 2 pages.
National Library of Medicine, "type II CRISPR RNA-guided endonuclease Cas9, partial [*Staphylococcus simulans*] NCBI Reference Sequence: WP_107568091.1," nih.gov 2023, in 2 pages.
National Library of Medicine, "type II CRISPR RNA-guided endonuclease Cas9, partial [*Staphylococcus simulans*] NCBI Reference Sequence: WP_107544007.1," nih.gov 2023, in 2 pages.
National Library of Medicine, "type II CRISPR RNA-guided endonuclease Cas9 [*Staphylococcus simulans*] NCBI Reference Sequence: WP_107593728.1," nih.gov 2023, in 2 pages.
National Library of Medicine, "type II CRISPR RNA-guided endonuclease Cas9 [*Staphylococcus coagulans*] NCBI Reference Sequence: WP_050345681.1," nih.gov 2023, in 2 pages.
National Library of Medicine, "type II CRISPR RNA-guided endonuclease Cas9 [*Staphylococcus haemolyticus*] NCBI Reference Sequence: WP_107641154.1," nih.gov 2023, in 2 pages.
National Library of Medicine, "type II CRISPR RNA-guided endonuclease Cas9 [*Staphylococcus agnetis*] NCBI Reference Sequence: WP_107378676.1," nih.gov 2023, in 2 pages.
National Library of Medicine, "type II CRISPR RNA-guided endonuclease Cas9 [*Staphylococcus pseudintermedius*] NCBI Reference Sequence: WP_104039168.1," nih.gov 2023, in 2 pages.
National Library of Medicine, "type II CRISPR RNA-guided endonuclease Cas9, partial [*Staphylococcus chromogenes*] NCBI Reference Sequence: WP_107366415.1," nih.gov 2023, in 2 pages.
National Library of Medicine, "type II CRISPR RNA-guided endonuclease Cas9 [*Staphylococcus agnetis*] NCBI Reference Sequence: WP_107371508.1," nih.gov 2023, in 2 pages.
National Library of Medicine, "type II CRISPR RNA-guided endonuclease Cas9, partial [*Staphylococcus simulans*] NCBI Reference Sequence: WP_107547877.1," nih.gov 2023, in 2 pages.
National Library of Medicine, "type II CRISPR RNA-guided endonuclease Cas9, partial [*Staphylococcus haemolyticus*] NCBI Reference Sequence: WP_107642811.1," nih.gov 2023, in 2 pages.
National Library of Medicine, "type II CRISPR RNA-guided endonuclease Cas9 [*Staphylococcus warneri*] NCBI Reference Sequence: WP_107560076.1," nih.gov 2023, in 2 pages.
National Library of Medicine, "type II CRISPR RNA-guided endonuclease Cas9 [*Staphylococcus pseudintermedius*] NCBI Reference Sequence: WP_101457463.1," nih.gov 2023, in 2 pages.
National Library of Medicine, "type II CRISPR RNA-guided endonuclease Cas9 [*Staphylococcus pseudintermedius*] NCBI Reference Sequence: WP_063278948.1," nih.gov 2023, in 2 pages.
National Library of Medicine, "type II CRISPR RNA-guided endonuclease Cas9 [*Staphylococcus cornubiensis*] NCBI Reference Sequence: WP_086428210.1," nih.gov 2023, in 2 pages.
National Library of Medicine, "type II CRISPR RNA-guided endonuclease Cas9, partial [*Staphylococcus simulans*] NCBI Reference Sequence: WP_107544006.1," nih.gov 2023, in 2 pages.
National Library of Medicine, "type II CRISPR RNA-guided endonuclease Cas9 [*Staphylococcus simulans*] NCBI Reference Sequence: WP_105966809.1," nih.gov 2023, in 2 pages.
National Library of Medicine, "type II CRISPR RNA-guided endonuclease Cas9 [*Staphylococcus simulans*] NCBI Reference Sequence: WP_105978348.1," nih.gov 2023, in 2 pages.
National Library of Medicine, "type II CRISPR RNA-guided endonuclease Cas9 [*Staphylococcus simulans*] NCBI Reference Sequence: WP_107567989.1," nih.gov 2023, in 2 pages.
National Library of Medicine, "type II CRISPR RNA-guided endonuclease Cas9, partial [*Staphylococcus simulans*] NCBI Reference Sequence: WP_107580472.1," nih.gov 2023, in 2 pages.
National Library of Medicine, "type II CRISPR RNA-guided endonuclease Cas9 [*Paraliobacillus ryukyuensis*] NCBI Reference Sequence: WP_079708828.1," nih.gov 2023, in 2 pages.
National Library of Medicine, "typeII CRISPR RNA-guided endonuclease Cas9 [*Salinicoccus sediminis*] NCBI Reference Sequence: WP_082099322.1," nih.gov 2023, in 1 page.
National Library of Medicine, "type II CRISPR RNA-guided endonuclease Cas9 [*Bacillus niameyensis*] NCBI Reference Sequence: WP_084781893.1," nih.gov 2023, in 2 pages.
National Library of Medicine, "type II CRISPR RNA-guided endonuclease Cas9 [*Listeria fleischmannii*] NCBI Reference Sequence: WP_007547525.1," nih.gov 2023, in 2 pages.
National Library of Medicine, "type II CRISPR RNA-guided endonuclease Cas9 [*Alicyclobacillus tengchongensis*] NCBI Reference Sequence: WP_058095017.1," nih.gov 2023, in 2 pages.
National Library of Medicine, "type II CRISPR RNA-guided endonuclease Cas9 [*Bacillus cereus*] NCBI Reference Sequence: WP_001271092.1," nih.gov 2023, in 2 pages.
National Library of Medicine, "type II CRISPR RNA-guided endonuclease Cas9 [*Bacillus thuringiensis*] NCBI Reference Sequence: WP_088031364.1," nih.gov 2023, in 2 pages.
National Library of Medicine, "type II CRISPR RNA-guided endonuclease Cas9 [*Bacillus smithii*] NCBI Reference Sequence: WP_003354196.1," nih.gov 2023, in 2 pages.
National Library of Medicine, "type II CRISPR RNA-guided endonuclease Cas9 [*Mammaliicoccus sciuri*] NCBI Reference Sequence: WP_103361957.1," nih.gov 2023, in 2 pages.
National Library of Medicine, "type II CRISPR RNA-guided endonuclease Cas9 [*Staphylococcus devriesei*] NCBI Reference Sequence: WP_103167028.1," nih.gov 2023, in 2 pages.
National Library of Medicine, "type II CRISPR RNA-guided endonuclease Cas9 [*Staphylococcus warneri*] NCBI Reference Sequence: WP_107546539.1," nih.gov 2023, in 2 pages.
National Library of Medicine, "type II CRISPR RNA-guided endonuclease Cas9 [*Staphylococcus haemolyticus*] NCBI Reference Sequence: WP_053017934.1," nih.gov 2023, in 2 pages.
National Library of Medicine, "type II CRISPR RNA-guided endonuclease Cas9 [*Staphylococcus auricularis*] NCBI Reference Sequence: WP_107392933.1," nih.gov 2023, in 2 pages.
National Library of Medicine, "type II CRISPR RNA-guided endonuclease Cas9 [*Staphylococcus agnetis*] NCBI Reference Sequence: WP_060552032.1," nih.gov 2023, in 2 pages.
National Library of Medicine, "type II CRISPR RNA-guided endonuclease Cas9 [*Staphylococcus pseudintermedius*] NCBI Reference Sequence: WP_104052030.1," nih.gov 2023, in 2 pages.
National Library of Medicine, "type II CRISPR RNA-guided endonuclease Cas9, partial [*Staphylococcus agnetis*] NCBI Reference Sequence: WP_107393309.1," nih.gov 2023, in 2 pages.
National Library of Medicine, "type II CRISPR RNA-guided endonuclease Cas9, partial [*Staphylococcus simulans*] NCBI Reference Sequence: WP_107538271.1," nih.gov 2023, in 2 pages.
National Library of Medicine, "type II CRISPR RNA-guided endonuclease Cas9, partial [*Staphylococcus haemolyticus*] NCBI Reference Sequence: WP_107634675.1," nih.gov 2023, in 2 pages.
National Library of Medicine, "type II CRISPR RNA-guided endonuclease Cas9, partial [*Staphylococcus petrasii*] NCBI Reference Sequence: WP_103298901.1," nih.gov 2023, in 2 pages.
National Library of Medicine, "type II CRISPR RNA-guided endonuclease Cas9, partial [*Staphylococcus agnetis*] NCBI Reference Sequence: WP_107368542.1," nih.gov 2023, in 2 pages.
National Library of Medicine, "type II CRISPR RNA-guided endonuclease Cas9 [*Staphylococcus massiliensis*] NCBI Reference Sequence: WP_009382362.1," nih.gov 2023, in 2 pages.
National Library of Medicine, "type II CRISPR RNA-guided endonuclease Cas9, partial [*Staphylococcus haemolyticus*] NCBI Reference Sequence: WP_107637979.1," nih.gov 2023, in 1 page.
National Library of Medicine, "type II CRISPR RNA-guided endonuclease Cas9 [*Staphylococcus pseudintermedius*] NCBI Reference Sequence: WP_105503156.1," nih.gov 2023, in 2 pages.
National Library of Medicine, "type II CRISPR RNA-guided endonuclease Cas9 [*Staphylococcus intermedius*] NCBI Reference Sequence: WP_096601671.1," nih.gov 2023, in 2 pages.
National Library of Medicine, "type II CRISPR RNA-guided endonuclease Cas9 [*Staphylococcus delphini*] NCBI Reference Sequence: WP_096665615.1," nih.gov 2023, in 2 pages.
National Library of Medicine, "type II CRISPR RNA-guided endonuclease Cas9, partial [*Staphylococcus simulans*] NCBI Reference Sequence: WP_107538330.1," nih.gov 2023, in 2 pages.

(56) References Cited

OTHER PUBLICATIONS

National Library of Medicine, "type II CRISPR RNA-guided endonuclease Cas9 [*Staphylococcus* sp. HMSC12H08] NCBI Reference Sequence: WP_070469119.1," nih.gov 2023, in 2 pages.
National Library of Medicine, "type II CRISPR RNA-guided endonuclease Cas9, partial [*Staphylococcus simulans*] NCBI Reference Sequence: WP_107549437.1," nih.gov 2023, in 2 pages.
National Library of Medicine, "type II CRISPR RNA-guided endonuclease Cas9 [*Staphylococcus delphini*] NCBI Reference Sequence: WP_096598476.1," nih.gov 2023, in 2 pages.
National Library of Medicine, "type II CRISPR RNA-guided endonuclease Cas9 [*Staphylococcus delphini*] NCBI Reference Sequence: WP_096544347.1," nih.gov 2023, in 2 pages.
National Library of Medicine, "type II CRISPR RNA-guided endonuclease Cas9, partial [*Staphylococcus simulans*] NCBI Reference Sequence: WP_107530433.1," nih.gov 2023, in 2 pages.
National Library of Medicine, "type II CRISPR RNA-guided endonuclease Cas9 [*Staphylococcus simulans*] NCBI Reference Sequence: WP_107571609.1," nih.gov 2023, in 2 pages.
National Library of Medicine, "type II CRISPR RNA-guided endonuclease Cas9 [Macrococcus caseolyticus] NCBI Reference Sequence: WP_101040307.1," nih.gov 2023, in 2 pages.
National Library of Medicine, "type II CRISPR RNA-guided endonuclease Cas9, partial [Alkalibacillus haloalkaliphilus] NCBI Reference Sequence: WP_017185731.1," nih.gov 2023, in 2 pages.
National Library of Medicine, "type II CRISPR RNA-guided endonuclease Cas9 [*Lentibacillus* sp. Marseille-P4043] NCBI Reference Sequence: WP_106494556.1," nih.gov 2023, in 2 pages.
National Library of Medicine, "type II CRISPR RNA-guided endonuclease Cas9 [Heyndrickxia sporothermodurans] NCBI Reference Sequence: WP_084347835.1," nih.gov 2023, in 2 pages.
National Library of Medicine, "type II CRISPR RNA-guided endonuclease Cas9 [Alicyclobacillus hesperidum] NCBI Reference Sequence: WP_006446566.1," nih.gov 2023, in 2 pages.
National Library of Medicine, "type II CRISPR RNA-guided endonuclease Cas9 [Bacillus thuringiensis] NCBI Reference Sequence: WP_087971021.1," nih.gov 2023, in 2 pages.
National Library of Medicine, "type II CRISPR RNA-guided endonuclease Cas9 [Bacillus mycoides] NCBI Reference Sequence: WP_088038716.1," nih.gov 2023, in 2 pages.
National Library of Medicine, "type II CRISPR RNA-guided endonuclease Cas9 [*Anoxybacillus* sp. P3H1B] NCBI Reference Sequence: WP_066148467.1," nih.gov 2023, in 2 pages.
National Library of Medicine, "type II CRISPR RNA-guided endonuclease Cas9 [*Staphylococcus aureus*] NCBI Reference Sequence: WP_001573634.1," nih.gov 2023, in 2 pages.
National Library of Medicine, "type II CRISPR RNA-guided endonuclease Cas9 [*Staphylococcus warneri*] NCBI Reference Sequence: WP_107532850.1," nih.gov 2023, in 2 pages.
National Library of Medicine, "type II CRISPR RNA-guided endonuclease Cas9 [*Staphylococcus warneri*] NCBI Reference Sequence: WP_058710220.1," nih.gov 2023, in 2 pages.
National Library of Medicine, "type II CRISPR RNA-guided endonuclease Cas9 [*Staphylococcus warneri*] NCBI Reference Sequence: WP_049415449.1," nih.gov 2023, in 2 pages.
National Library of Medicine, "type II CRISPR RNA-guided endonuclease Cas9 [*Staphylococcus chromogenes*] NCBI Reference Sequence: WP_107389582.1," nih.gov 2023, in 2 pages.
National Library of Medicine, "type II CRISPR RNA-guided endonuclease Cas9 [*Staphylococcus lutrae*] NCBI Reference Sequence: WP_085237539.1," nih.gov 2023, in 2 pages.
National Library of Medicine, "type II CRISPR RNA-guided endonuclease Cas9 [*Staphylococcus hyicus*] NCBI Reference Sequence: WP_107633689.1," nih.gov 2023, in 2 pages.
National Library of Medicine, "type II CRISPR RNA-guided endonuclease Cas9, partial [*Staphylococcus hyicus*] NCBI Reference Sequence: WP_107642914.1," nih.gov 2023, in 2 pages.
National Library of Medicine, "type II CRISPR RNA-guided endonuclease Cas9, partial [*Staphylococcus warneri*] NCBI Reference Sequence: WP_107532082.1," nih.gov 2023, in 2 pages.

National Library of Medicine, "type II CRISPR RNA-guided endonuclease Cas9, partial [*Staphylococcus haemolyticus*] NCBI Reference Sequence: WP_107611983.1," nih.gov 2023, in 2 pages.
National Library of Medicine, "type II CRISPR RNA-guided endonuclease Cas9 [*Staphylococcus massiliensis*] NCBI Reference Sequence: WP_081502240.1," nih.gov 2023, in 2 pages.
National Library of Medicine, "type II CRISPR RNA-guided endonuclease Cas9 [*Staphylococcus aureus*] NCBI Reference Sequence: WP_001573633.1," nih.gov 2023, in 2 pages.
National Library of Medicine, "type II CRISPR RNA-guided endonuclease Cas9, partial [*Staphylococcus haemolyticus*] NCBI Reference Sequence: WP_107612621.1," nih.gov 2023, in 1 page.
National Library of Medicine, "type II CRISPR RNA-guided endonuclease Cas9 [*Staphylococcus pseudintermedius*] NCBI Reference Sequence: WP_096548249.1," nih.gov 2023, in 2 pages.
National Library of Medicine, "type II CRISPR RNA-guided endonuclease Cas9 [*Staphylococcus pseudintermedius*] NCBI Reference Sequence: WP_103863320.1," nih.gov 2023, in 2 pages.
National Library of Medicine, "type II CRISPR RNA-guided endonuclease Cas9 [*Staphylococcus simulans*] NCBI Reference Sequence: WP_105976295.1," nih.gov 2023, in 2 pages.
National Library of Medicine, "type II CRISPR RNA-guided endonuclease Cas9 [*Staphylococcus delphini*] NCBI Reference Sequence: WP_096589032.1," nih.gov 2023, in 2 pages.
National Library of Medicine, "type II CRISPR RNA-guided endonuclease Cas9 [*Staphylococcus simulans*] NCBI Reference Sequence: WP_107579080.1," nih.gov 2023, in 2 pages.
National Library of Medicine, "type II CRISPR RNA-guided endonuclease Cas9 [*Staphylococcus simulans*] NCBI Reference Sequence: WP_107587102.1," nih.gov 2023, in 2 pages.
National Library of Medicine, "type II CRISPR RNA-guided endonuclease Cas9 [*Staphylococcus simulans*] NCBI Reference Sequence: WP_023015764.1," nih.gov 2023, in 2 pages.
National Library of Medicine, "type II CRISPR RNA-guided endonuclease Cas9, partial [*Staphylococcus simulans*] NCBI Reference Sequence: WP_107580731.1," nih.gov 2023, in 2 pages.
National Library of Medicine, "type II CRISPR RNA-guided endonuclease Cas9, partial [*Staphylococcus simulans*] NCBI Reference Sequence: WP_107559911.1," nih.gov 2023, in 2 pages.
National Library of Medicine, "type II CRISPR RNA-guided endonuclease Cas9 [Virgibacillus senegalensis] NCBI Reference Sequence: WP_053216997.1," nih.gov 2023, in 2 pages.
National Library of Medicine, "type II CRISPR RNA-guided endonuclease Cas9 [*Bacillus* sp. V3-13] NCBI Reference Sequence: WP_101662761.1," nih.gov 2023, in 2 pages.
National Library of Medicine, "type II CRISPR RNA-guided endonuclease Cas9 [*Nosocomiicoccus* sp. HMSC059G07] NCBI Reference Sequence: WP_070710475.1," nih.gov 2023, in 2 pages.
National Library of Medicine, "type II CRISPR RNA-guided endonuclease Cas9 [Alicyclobacillus hesperidum] NCBI Reference Sequence: WP_074693676.1," nih.gov 2023, in 2 pages.
National Library of Medicine, "type II CRISPR RNA-guided endonuclease Cas9 [Bacillus cereus] NCBI Reference Sequence: WP_061668060.1," nih.gov 2023, in 2 pages.
National Library of Medicine, "type II CRISPR RNA-guided endonuclease Cas9 [Listeria fleischmannii] NCBI Reference Sequence: WP_007476473.1," nih.gov 2023, in 1 page.
National Library of Medicine, "type II CRISPR RNA-guided endonuclease Cas9 [Acidibacillus ferrooxidans] NCBI Reference Sequence: WP_082806588.1," nih.gov 2023, in 2 pages.
National Library of Medicine, "type II CRISPR RNA-guided endonuclease Cas9, partial [*Staphylococcus simulans*] NCBI Reference Sequence: WP_107576310.1," nih.gov 2023, in 2 pages.
National Library of Medicine, "type II CRISPR RNA-guided endonuclease Cas9 [*Staphylococcus lugdunensis*] NCBI Reference Sequence: WP_002460848.1," nih.gov 2023, in 2 pages.
National Library of Medicine, "type II CRISPR RNA-guided endonuclease Cas9 [*Staphylococcus schleiferi*] NCBI Reference Sequence: WP_060829977.1," nih.gov 2023, in 2 pages.
National Library of Medicine, "type II CRISPR RNA-guided endonuclease Cas9 [*Staphylococcus agnetis*] NCBI Reference Sequence: WP_107390356.1," nih.gov 2023, in 2 pages.

(56) References Cited

OTHER PUBLICATIONS

National Library of Medicine, "type II CRISPR RNA-guided endonuclease Cas9 [*Staphylococcus hyicus*] NCBI Reference Sequence: WP_039643679.1," nih.gov 2023, in 2 pages.

National Library of Medicine, "type II CRISPR RNA-guided endonuclease Cas9 [*Staphylococcus rostri*] NCBI Reference Sequence: WP_103357343.1," nih.gov 2023, in 2 pages.

National Library of Medicine, "type II CRISPR RNA-guided endonuclease Cas9, partial [*Staphylococcus agnetis*] NCBI Reference Sequence: WP_107397003.1," nih.gov 2023, in 2 pages.

National Library of Medicine, "type II CRISPR RNA-guided endonuclease Cas9, partial [*Staphylococcus warneri*] NCBI Reference Sequence: WP_107536061.1," nih.gov 2023, in 2 pages.

National Library of Medicine, "type II CRISPR RNA-guided endonuclease Cas9, partial [*Staphylococcus simulans*] NCBI Reference Sequence: WP_107604007.1," nih.gov 2023, in 2 pages.

National Library of Medicine, "type II CRISPR RNA-guided endonuclease Cas9 [*Staphylococcus haemolyticus*] NCBI Reference Sequence: WP_107623815.1," nih.gov 2023, in 2 pages.

National Library of Medicine, "type II CRISPR RNA-guided endonuclease Cas9, partial [*Staphylococcus haemolyticus*] NCBI Reference Sequence: WP_107642817.1," nih.gov 2023, in 1 page.

National Library of Medicine, "type II CRISPR RNA-guided endonuclease Cas9 [*Staphylococcus felis*] NCBI Reference Sequence: WP_103209613.1," nih.gov 2023, in 2 pages.

National Library of Medicine, "type II CRISPR RNA-guided endonuclease Cas9 [*Staphylococcus pseudintermedius*] NCBI Reference Sequence: WP_096536567.1," nih.gov 2023, in 2 pages.

National Library of Medicine, "type II CRISPR RNA-guided endonuclease Cas9 [*Staphylococcus intermedius*] NCBI Reference Sequence: WP_096559644.1," nih.gov 2023, in 2 pages.

National Library of Medicine, "type II CRISPR RNA-guided endonuclease Cas9 [*Staphylococcus simulans*] NCBI Reference Sequence: WP_107576302.1," nih.gov 2023, in 2 pages.

National Library of Medicine, "type II CRISPR RNA-guided endonuclease Cas9 [*Staphylococcus delphini*] NCBI Reference Sequence: WP_096605716.1," nih.gov 2023, in 2 pages.

National Library of Medicine, "type II CRISPR RNA-guided endonuclease Cas9 [*Staphylococcus simulans*] NCBI Reference Sequence: WP_105996442.1," nih.gov 2023, in 2 pages.

National Library of Medicine, "type II CRISPR RNA-guided endonuclease Cas9 [*Staphylococcus simulans*] NCBI Reference Sequence: WP_107547813.1," nih.gov 2023, in 2 pages.

National Library of Medicine, "type II CRISPR RNA-guided endonuclease Cas9, partial [*Staphylococcus simulans*] NCBI Reference Sequence: WP_107533825.1," nih.gov 2023, in 2 pages.

National Library of Medicine, "type II CRISPR RNA-guided endonuclease Cas9, partial [*Staphylococcus lutrae*] NCBI Reference Sequence: WP_103322053.1," nih.gov 2023, in 2 pages.

National Library of Medicine, "type II CRISPR RNA-guided endonuclease Cas9, partial [*Staphylococcus simulans*] NCBI Reference Sequence: WP_107571610.1," nih.gov 2023, in 1 page.

National Library of Medicine, "type II CRISPR RNA-guided endonuclease Cas9 [Massilibacterium senegalense] NCBI Reference Sequence: WP_062197343.1," nih.gov 2023, in 2 pages.

National Library of Medicine, "type II CRISPR RNA-guided endonuclease Cas9 [Salsuginibacillus halophilus] NCBI Reference Sequence: WP_106588293.1," nih.gov 2023, in 2 pages.

National Library of Medicine, "type II CRISPR RNA-guided endonuclease Cas9 [Bacillus massilionigeriensis] NCBI Reference Sequence: WP_084780162.1," nih.gov 2023, in 2 pages.

National Library of Medicine, "type II CRISPR RNA-guided endonuclease Cas9 [Listeria fleischmannii] NCBI Reference Sequence: WP_077907981.1," nih.gov 2023, in 2 pages.

National Library of Medicine, "type II CRISPR RNA-guided endonuclease Cas9 [Bacillus cereus] NCBI Reference Sequence: WP_016119566.1," nih.gov 2023, in 2 pages.

National Library of Medicine, "type II CRISPR RNA-guided endonuclease Cas9 [Brevibacillus laterosporus] NCBI Reference Sequence: WP_003343632.1," nih.gov 2023, in 2 pages.

National Library of Medicine, "type II CRISPR RNA-guided endonuclease Cas9 [Bacillus cytotoxicus] NCBI Reference Sequence: WP_087094968.1," nih.gov 2023, in 2 pages.

National Library of Medicine, "type II CRISPR RNA-guided endonuclease Cas9, partial [*Staphylococcus simulans*] NCBI Reference Sequence: WP_107571611.1," nih.gov 2023, in 2 pages.

National Library of Medicine, "type II CRISPR RNA-guided endonuclease Cas9 [*Staphylococcus devriesei*] NCBI Reference Sequence: WP_107506206.1," nih.gov 2023, in 2 pages.

National Library of Medicine, "type II CRISPR RNA-guided endonuclease Cas9 [*Staphylococcus coagulans*] NCBI Reference Sequence: WP_050331073.1," nih.gov 2023, in 2 pages.

National Library of Medicine, "type II CRISPR RNA-guided endonuclease Cas9 [*Staphylococcus* sp. HMSC34C02] NCBI Reference Sequence: WP_070855141.1," nih.gov 2023, in 2 pages.

National Library of Medicine, "type II CRISPR RNA-guided endonuclease Cas9 [*Staphylococcus chromogenes*] NCBI Reference Sequence: WP_107378401.1," nih.gov 2023, in 2 pages.

National Library of Medicine, "type II CRISPR RNA-guided endonuclease Cas9 [*Staphylococcus pseudintermedius*] NCBI Reference Sequence: WP_101457364.1," nih.gov 2023, in 2 pages.

National Library of Medicine, "type II CRISPR RNA-guided endonuclease Cas9 [*Staphylococcus microti*] NCBI Reference Sequence: WP_044361501.1," nih.gov 2023, in 2 pages.

National Library of Medicine, "type II CRISPR RNA-guided endonuclease Cas9, partial [*Staphylococcus agnetis*] NCBI Reference Sequence: WP_107386954.1," nih.gov 2023, in 2 pages.

National Library of Medicine, "type II CRISPR RNA-guided endonuclease Cas9, partial [*Staphylococcus simulans*] NCBI Reference Sequence: WP_107605852.1," nih.gov 2023, in 2 pages.

National Library of Medicine, "type II CRISPR RNA-guided endonuclease Cas9, partial [*Staphylococcus coagulans*] NCBI Reference Sequence: WP_103356745.1," nih.gov 2023, in 2 pages.

National Library of Medicine, "type II CRISPR RNA-guided endonuclease Cas9, partial [*Staphylococcus devriesei*] NCBI Reference Sequence: WP_107522281.1," nih.gov 2023, in 2 pages.

National Library of Medicine, "type II CRISPR RNA-guided endonuclease Cas9 [*Staphylococcus chromogenes*] NCBI Reference Sequence: WP_107377516.1," nih.gov 2023, in 2 pages.

National Library of Medicine, "type II CRISPR RNA-guided endonuclease Cas9, partial [*Staphylococcus petrasii*] NCBI Reference Sequence: WP_103298687.1," nih.gov 2023, in 2 pages.

National Library of Medicine, "type II CRISPR RNA-guided endonuclease Cas9 [*Staphylococcus pseudintermedius*] NCBI Reference Sequence: WP_063284667.1," nih.gov 2023, in 2 pages.

National Library of Medicine, "type II CRISPR RNA-guided endonuclease Cas9 [*Staphylococcus pseudintermedius*] NCBI Reference Sequence: WP_014613259.1," nih.gov 2023, in 2 pages.

National Library of Medicine, "type II CRISPR RNA-guided endonuclease Cas9 [*Staphylococcus intermedius*] NCBI Reference Sequence: WP_019167918.1," nih.gov 2023, in 2 pages.

National Library of Medicine, "type II CRISPR RNA-guided endonuclease Cas9 [*Staphylococcus simulans*] NCBI Reference Sequence: WP_105977863.1," nih.gov 2023, in 2 pages.

National Library of Medicine, "type II CRISPR RNA-guided endonuclease Cas9 [*Staphylococcus piscifermentans*] NCBI Reference Sequence: WP_095105824.1," nih.gov 2023, in 2 pages.

National Library of Medicine, "type II CRISPR RNA-guided endonuclease Cas9 [*Staphylococcus simulans*] NCBI Reference Sequence: WP_107552556.1," nih.gov 2023, in 2 pages.

National Library of Medicine, "type II CRISPR RNA-guided endonuclease Cas9 [*Staphylococcus simulans*] NCBI Reference Sequence: WP_107591747.1," nih.gov 2023, in 2 pages.

National Library of Medicine, "type II CRISPR RNA-guided endonuclease Cas9, partial [*Staphylococcus simulans*] NCBI Reference Sequence: WP_107588308.1," nih.gov 2023, in 2 pages.

National Library of Medicine, "type II CRISPR RNA-guided endonuclease Cas9, partial [*Staphylococcus simulans*] NCBI Reference Sequence: WP_107559912.1," nih.gov 2023, in 2 pages.

National Library of Medicine, "type II CRISPR RNA-guided endonuclease Cas9, partial [*Staphylococcus simulans*] NCBI Reference Sequence: WP_107530436.1," nih.gov 2023, in 1 page.

(56) References Cited

OTHER PUBLICATIONS

National Library of Medicine, "type II CRISPR RNA-guided endonuclease Cas9 [Halalkalibacillus halophilus] NCBI Reference Sequence: WP_035512507.1," nih.gov 2023, in 2 pages.

National Library of Medicine, "type II CRISPR RNA-guided endonuclease Cas9 [Alkalicoccus saliphilus] NCBI Reference Sequence: WP_107585021.1," nih.gov 2023, in 2 pages.

National Library of Medicine, "type II CRISPR RNA-guided endonuclease Cas9 [Ureibacillus thermosphaericus] NCBI Reference Sequence: WP_016837331.1," nih.gov 2023, in 2 pages.

National Library of Medicine, "type II CRISPR RNA-guided endonuclease Cas9 [Listeria fleischmannii] NCBI Reference Sequence: WP_059140148.1," nih.gov 2023, in 2 pages.

National Library of Medicine, "type II CRISPR RNA-guided endonuclease Cas9 [Gracilibacillus boraciitolerans] NCBI Reference Sequence: WP_035723552.1," nih.gov 2023, in 1 page.

National Library of Medicine, "type II CRISPR RNA-guided endonuclease Cas9 [Bacillus toyonensis] NCBI Reference Sequence: WP_001271093.1," nih.gov 2023, in 2 pages.

National Library of Medicine, "type II CRISPR RNA-guided endonuclease Cas9 [Bacillus toyonensis] NCBI Reference Sequence: WP_016106885.1," nih.gov 2023, in 2 pages.

National Library of Medicine, "type II CRISPR RNA-guided endonuclease Cas9 [Virgibacillus dakarensis] NCBI Reference Sequence: WP_088049424.1," nih.gov 2023, in 2 pages.

National Library of Medicine, "type II CRISPR RNA-guided endonuclease Cas9 [Geobacillus subterraneus] NCBI Reference Sequence: WP_033844707.1," nih.gov 2023, in 2 pages.

National Library of Medicine, "type II CRISPR RNA-guided endonuclease Cas9 [*Bacillus* sp. FJAT-20673] NCBI Reference Sequence: WP_063577905.1," nih.gov 2023, in 2 pages.

National Library of Medicine, "type II CRISPR RNA-guided endonuclease Cas9 [Effusibacillus pohliae] NCBI Reference Sequence: WP_018130201.1," nih.gov 2023, in 2 pages.

National Library of Medicine, "type II CRISPR RNA-guided endonuclease Cas9 [Bacillus cereus] NCBI Reference Sequence: WP_001105082.1," nih.gov 2023, in 2 pages.

National Library of Medicine, "type II CRISPR RNA-guided endonuclease Cas9 [Listeria monocytogenes] NCBI Reference Sequence: WP_070034634.1," nih.gov 2023, in 2 pages.

National Library of Medicine, "type II CRISPR RNA-guided endonuclease Cas9 [Listeria seeligeri] NCBI Reference Sequence: WP_046323366.1," nih.gov 2023, in 2 pages.

National Library of Medicine, "type II CRISPR RNA-guided endonuclease Cas9, partial [Listeria seeligeri] NCBI Reference Sequence: WP_003749665.1," nih.gov 2023, in 2 pages.

National Library of Medicine, "type II CRISPR RNA-guided endonuclease Cas9 [Listeria monocytogenes] NCBI Reference Sequence: WP_085392451.1," nih.gov 2023, in 2 pages.

National Library of Medicine, "type II CRISPR RNA-guided endonuclease Cas9 [Macrococcus caseolyticus] NCBI Reference Sequence: WP_101143453.1," nih.gov 2023, in 2 pages.

National Library of Medicine, "type II CRISPR RNA-guided endonuclease Cas9 [Listeria monocytogenes] NCBI Reference Sequence: WP_085400884.1," nih.gov 2023, in 2 pages.

National Library of Medicine, "type II CRISPR RNA-guided endonuclease Cas9 [Listeria innocua] NCBI Reference Sequence: WP_010991369.1," nih.gov 2023, in 2 pages.

National Library of Medicine, "type II CRISPR RNA-guided endonuclease Cas9 [Listeria monocytogenes] NCBI Reference Sequence: WP_003733029.1," nih.gov 2023, in 2 pages.

National Library of Medicine, "type II CRISPR RNA-guided endonuclease Cas9 [Listeria monocytogenes] NCBI Reference Sequence: WP_070274575.1," nih.gov 2023, in 2 pages.

National Library of Medicine, "type II CRISPR RNA-guided endonuclease Cas9 [Listeria monocytogenes] NCBI Reference Sequence: WP_031665337.1," nih.gov 2023, in 2 pages.

National Library of Medicine, "type II CRISPR RNA-guided endonuclease Cas9 [Listeria monocytogenes] NCBI Reference Sequence: WP_070307355.1," nih.gov 2023, in 2 pages.

National Library of Medicine, "type II CRISPR RNA-guided endonuclease Cas9 [Listeria monocytogenes] NCBI Reference Sequence: WP_069009724.1," nih.gov 2023, in 2 pages.

National Library of Medicine, "type II CRISPR RNA-guided endonuclease Cas9 [Listeria monocytogenes] NCBI Reference Sequence: WP_060587936.1," nih.gov 2023, in 2 pages.

National Library of Medicine, "type II CRISPR RNA-guided endonuclease Cas9 [Listeria monocytogenes] NCBI Reference Sequence: WP_058876445.1," nih.gov 2023, in 2 pages.

National Library of Medicine, "type II CRISPR RNA-guided endonuclease Cas9, partial [Listeria monocytogenes] NCBI Reference Sequence: WP_080151624.1," nih.gov 2023, in 2 pages.

National Library of Medicine, "type II CRISPR RNA-guided endonuclease Cas9, partial [Listeria monocytogenes] NCBI Reference Sequence: WP_072240445.1," nih.gov 2023, in 1 page.

National Library of Medicine, "type II CRISPR RNA-guided endonuclease Cas9, partial [Listeria monocytogenes] NCBI Reference Sequence: WP_080151712.1," nih.gov 2023, in 1 page.

National Library of Medicine, "type II CRISPR RNA-guided endonuclease Cas9 [*Geobacillus* sp. Sah69] NCBI Reference Sequence: WP_055358891.1," nih.gov 2023, in 2 pages.

National Library of Medicine, "type II CRISPR RNA-guided endonuclease Cas9 [*Geobacillus* sp. 46C-IIa] NCBI Reference Sequence: WP_081209836.1," nih.gov 2023, in 2 pages.

National Library of Medicine, "type II CRISPR RNA-guided endonuclease Cas9 [*Geobacillus* sp. MAS1] NCBI Reference Sequence: WP_023633350.1," nih.gov 2023, in 2 pages.

National Library of Medicine, "type II CRISPR RNA-guided endonuclease Cas9 [*Geobacillus* sp. 47C-IIb] NCBI Reference Sequence: WP_081157433.1," nih.gov 2023, in 2 pages.

National Library of Medicine, "type II CRISPR RNA-guided endonuclease Cas9 [Geobacillus thermodenitrificans] NCBI Reference Sequence: WP_087959824.1," nih.gov 2023, in 2 pages.

National Library of Medicine, "type II CRISPR RNA-guided endonuclease Cas9 [*Geobacillus* genomosp. 3] NCBI Reference Sequence: WP_041267823.1," nih.gov 2023, in 2 pages.

National Library of Medicine, "type II CRISPR RNA-guided endonuclease Cas9 [Salsuginibacillus kocurii] NCBI Reference Sequence: WP_018922791.1," nih.gov 2023, in 2 pages.

National Library of Medicine, "type II CRISPR RNA-guided endonuclease Cas9 [Geobacillus jurassicus] NCBI Reference Sequence: WP_066227285.1," nih.gov 2023, in 2 pages.

National Library of Medicine, "type II CRISPR RNA-guided endonuclease Cas9 [Geobacillus kaustophilus] NCBI Reference Sequence: WP_044736072.1," nih.gov 2023, in 2 pages.

National Library of Medicine, "type II CRISPR RNA-guided endonuclease Cas9 [Geobacillus stearothermophilus] NCBI Reference Sequence: WP_033016936.1," nih.gov 2023, in 2 pages.

National Library of Medicine, "type II CRISPR RNA-guided endonuclease Cas9 [*Geobacillus* sp. WSUCF-018B] NCBI Reference Sequence: WP_100664518.1," nih.gov 2023, in 2 pages.

National Library of Medicine, "type II CRISPR RNA-guided endonuclease Cas9 [Geobacillus stearothermophilus] NCBI Reference Sequence: WP_053532223.1," nih.gov 2023, in 2 pages.

National Library of Medicine, "type II CRISPR RNA-guided endonuclease Cas9 [Oceanobacillus manasiensis] NCBI Reference Sequence: WP_042224718.1," nih.gov 2023, in 2 pages.

National Library of Medicine, "type II CRISPR RNA-guided endonuclease Cas9 [Alkalihalobacillus okhensis] NCBI Reference Sequence: WP_084138993.1," nih.gov 2023, in 2 pages.

National Library of Medicine, "type II CRISPR RNA-guided endonuclease Cas9 [Sporolactobacillus vineae] NCBI Reference Sequence: WP_010632729.1," nih.gov 2023, in 2 pages.

National Library of Medicine, "type II CRISPR RNA-guided endonuclease Cas9 [Bacillus thuringiensis] NCBI Reference Sequence: WP_065212529.1," nih.gov 2023, in 2 pages.

National Library of Medicine, "type II CRISPR RNA-guided endonuclease Cas9 [Bacillus paranthracis] NCBI Reference Sequence: WP_001105083.1," nih.gov 2023, in 2 pages.

National Library of Medicine, "type II CRISPR RNA-guided endonuclease Cas9 [Bacillus thuringiensis] NCBI Reference Sequence: WP_086397116.1," nih.gov 2023, in 2 pages.

(56) References Cited

OTHER PUBLICATIONS

National Library of Medicine, "type II CRISPR RNA-guided endonuclease Cas9 [Bacillus thuringiensis] NCBI Reference Sequence: WP_086390158.1," nih.gov 2023, in 2 pages.
National Library of Medicine, "type II CRISPR RNA-guided endonuclease Cas9 [Listeria monocytogenes] NCBI Reference Sequence: WP_070006567.1," nih.gov 2023, in 2 pages.
National Library of Medicine, "type II CRISPR RNA-guided endonuclease Cas9 [Listeria monocytogenes] NCBI Reference Sequence: WP_003739838.1," nih.gov 2023, in 2 pages.
National Library of Medicine, "type II CRISPR RNA-guided endonuclease Cas9 [Listeria seeligeri] NCBI Reference Sequence: WP_075702521.1," nih.gov 2023, in 2 pages.
National Library of Medicine, "type II CRISPR RNA-guided endonuclease Cas9 [Brochothrix thermosphacta] NCBI Reference Sequence: WP_029090905.1," nih.gov 2023, in 2 pages.
National Library of Medicine, "type II CRISPR RNA-guided endonuclease Cas9 [Listeria ivanovii] NCBI Reference Sequence: WP_038409211.1," nih.gov 2023, in 2 pages.
National Library of Medicine, "type II CRISPR RNA-guided endonuclease Cas9 [Brochothrix thermosphacta] NCBI Reference Sequence: WP_069125601.1," nih.gov 2023, in 2 pages.
National Library of Medicine, "type II CRISPR RNA-guided endonuclease Cas9 [Listeria monocytogenes] NCBI Reference Sequence: WP_069887401.1," nih.gov 2023, in 2 pages.
National Library of Medicine, "type II CRISPR RNA-guided endonuclease Cas9 [Brochothrix thermosphacta] NCBI Reference Sequence: WP_069134523.1," nih.gov 2023, in 2 pages.
National Library of Medicine, "type II CRISPR RNA-guided endonuclease Cas9 [Listeria monocytogenes] NCBI Reference Sequence: WP_061665472.1," nih.gov 2023, in 2 pages.
National Library of Medicine, "type II CRISPR RNA-guided endonuclease Cas9 [Listeria monocytogenes] NCBI Reference Sequence: WP_070294293.1," nih.gov 2023, in 2 pages.
National Library of Medicine, "type II CRISPR RNA-guided endonuclease Cas9 [Listeria monocytogenes] NCBI Reference Sequence: WP_070784981.1," nih.gov 2023, in 2 pages.
National Library of Medicine, "type II CRISPR RNA-guided endonuclease Cas9 [Listeria monocytogenes] NCBI Reference Sequence: WP_031669209.1," nih.gov 2023, in 2 pages.
National Library of Medicine, "type II CRISPR RNA-guided endonuclease Cas9 [Brochothrix thermosphacta] NCBI Reference Sequence: WP_106787163.1," nih.gov 2023, in 2 pages.
National Library of Medicine, "type II CRISPR RNA-guided endonuclease Cas9 [Listeria monocytogenes] NCBI Reference Sequence: WP_077287021.1," nih.gov 2023, in 2 pages.
National Library of Medicine, "type II CRISPR RNA-guided endonuclease Cas9 [Listeria monocytogenes] NCBI Reference Sequence: WP_023548323.1," nih.gov 2023, in 2 pages.
National Library of Medicine, "type II CRISPR RNA-guided endonuclease Cas9 [Listeria monocytogenes] NCBI Reference Sequence: WP_061108493.1," nih.gov 2023, in 2 pages.
National Library of Medicine, "type II CRISPR RNA-guided endonuclease Cas9 [Macrococcus caseolyticus] NCBI Reference Sequence: WP_101152964.1," nih.gov 2023, in 2 pages.
National Library of Medicine, "type II CRISPR RNA-guided endonuclease Cas9 [Macrococcus caseolyticus] NCBI Reference Sequence: WP_101143843.1," nih.gov 2023, in 2 pages.
National Library of Medicine, "type II CRISPR RNA-guided endonuclease Cas9 [Macrococcus caseolyticus] NCBI Reference Sequence: WP_101140817.1," nih.gov 2023, in 2 pages.
National Library of Medicine, "type II CRISPR RNA-guided endonuclease Cas9 [Caryophanon latum] NCBI Reference Sequence: WP_066465432.1," nih.gov 2023, in 2 pages.
National Library of Medicine, "type II CRISPR RNA-guided endonuclease Cas9 [Listeria monocytogenes] NCBI Reference Sequence: WP_033920898.1," nih.gov 2023, in 2 pages.
National Library of Medicine, "type II CRISPR RNA-guided endonuclease Cas9 [Listeria monocytogenes] NCBI Reference Sequence: WP_069001072.1," nih.gov 2023, in 2 pages.
National Library of Medicine, "type II CRISPR RNA-guided endonuclease Cas9 [Macrococcus caseolyticus] NCBI Reference Sequence: WP_101057368.1," nih.gov 2023, in 2 pages.
National Library of Medicine, "type II CRISPR RNA-guided endonuclease Cas9 [*Listeria* sp. ILCC792] NCBI Reference Sequence: WP_088838826.1," nih.gov 2023, in 2 pages.
National Library of Medicine, "type II CRISPR RNA-guided endonuclease Cas9, partial [Listeria monocytogenes] NCBI Reference Sequence: WP_072240946.1," nih.gov 2023, in 2 pages.
National Library of Medicine, "type II CRISPR RNA-guided endonuclease Cas9, partial [Listeria monocytogenes] NCBI Reference Sequence: WP_072218760.1," nih.gov 2023, in 2 pages.
National Library of Medicine, "type II CRISPR RNA-guided endonuclease Cas9 [Listeria innocua] NCBI Reference Sequence: WP_072238933.1," nih.gov 2023, in 2 pages.
National Library of Medicine, "type II CRISPR RNA-guided endonuclease Cas9 [Listeria monocytogenes] NCBI Reference Sequence: WP_070227966.1," nih.gov 2023, in 2 pages.
National Library of Medicine, "type II CRISPR RNA-guided endonuclease Cas9 [Listeria monocytogenes] NCBI Reference Sequence: WP_061663015.1," nih.gov 2023, in 2 pages.
National Library of Medicine, "type II CRISPR RNA-guided endonuclease Cas9 [Macrococcus caseolyticus] NCBI Reference Sequence: WP_101142252.1," nih.gov 2023, in 2 pages.
National Library of Medicine, "type II CRISPR RNA-guided endonuclease Cas9 [Listeria monocytogenes] NCBI Reference Sequence: WP_070031693.1," nih.gov 2023, in 2 pages.
National Library of Medicine, "type II CRISPR RNA-guided endonuclease Cas9 [Listeria monocytogenes] NCBI Reference Sequence: WP_070785826.1," nih.gov 2023, in 2 pages.
National Library of Medicine, "type II CRISPR RNA-guided endonuclease Cas9 [Listeria monocytogenes] NCBI Reference Sequence: WP_003730785.1," nih.gov 2023, in 2 pages.
National Library of Medicine, "type II CRISPR RNA-guided endonuclease Cas9 [Listeria monocytogenes] NCBI Reference Sequence: WP_003727705.1," nih.gov 2023, in 2 pages.
National Library of Medicine, "type II CRISPR RNA-guided endonuclease Cas9 [Listeria monocytogenes] NCBI Reference Sequence: WP_069890501.1," nih.gov 2023, in 2 pages.
National Library of Medicine, "type II CRISPR RNA-guided endonuclease Cas9 [Listeria monocytogenes] NCBI Reference Sequence: WP_070233243.1," nih.gov 2023, in 2 pages.
National Library of Medicine, "type II CRISPR RNA-guided endonuclease Cas9 [Listeria monocytogenes] NCBI Reference Sequence: WP_070039312.1," nih.gov 2023, in 2 pages.
National Library of Medicine, "type II CRISPR RNA-guided endonuclease Cas9 [Listeria monocytogenes] NCBI Reference Sequence: WP_070222802.1," nih.gov 2023, in 2 pages.
National Library of Medicine, "type II CRISPR RNA-guided endonuclease Cas9 [Listeria monocytogenes] NCBI Reference Sequence: WP_070264592.1," nih.gov 2023, in 2 pages.
National Library of Medicine, "type II CRISPR RNA-guided endonuclease Cas9 [Listeria monocytogenes] NCBI Reference Sequence: WP_103682188.1," nih.gov 2023, in 2 pages.
National Library of Medicine, "type II CRISPR RNA-guided endonuclease Cas9 [Listeria monocytogenes] NCBI Reference Sequence: WP_070299153.1," nih.gov 2023, in 2 pages.
National Library of Medicine, "type II CRISPR RNA-guided endonuclease Cas9 [Listeria monocytogenes] NCBI Reference Sequence: WP_061395959.1," nih.gov 2023, in 2 pages.
National Library of Medicine, "type II CRISPR RNA-guided endonuclease Cas9 [Listeria monocytogenes] NCBI Reference Sequence: WP_070764199.1," nih.gov 2023, in 2 pages.
National Library of Medicine, "type II CRISPR RNA-guided endonuclease Cas9 [Listeria monocytogenes] NCBI Reference Sequence: WP_061128889.1," nih.gov 2023, in 2 pages.
National Library of Medicine, "type II CRISPR RNA-guided endonuclease Cas9 [Listeria monocytogenes] NCBI Reference Sequence: WP_070283519.1," nih.gov 2023, in 2 pages.
National Library of Medicine, "type II CRISPR RNA-guided endonuclease Cas9 [Listeria monocytogenes] NCBI Reference Sequence: WP_070228842.1," nih.gov 2023, in 2 pages.

(56) References Cited

OTHER PUBLICATIONS

National Library of Medicine, "type II CRISPR RNA-guided endonuclease Cas9 [Listeria monocytogenes] NCBI Reference Sequence: WP_014601172.1," nih.gov 2023, in 2 pages.
National Library of Medicine, "type II CRISPR RNA-guided endonuclease Cas9 [Listeria monocytogenes] NCBI Reference Sequence: WP_103757671.1," nih.gov 2023, in 2 pages.
National Library of Medicine, "type II CRISPR RNA-guided endonuclease Cas9 [Listeria monocytogenes] NCBI Reference Sequence: WP_070293394.1," nih.gov 2023, in 2 pages.
National Library of Medicine, "type II CRISPR RNA-guided endonuclease Cas9 [Listeria monocytogenes] NCBI Reference Sequence: WP_070238603.1," nih.gov 2023, in 2 pages.
National Library of Medicine, "type II CRISPR RNA-guided endonuclease Cas9 [Listeria monocytogenes] NCBI Reference Sequence: WP_070215465.1," nih.gov 2023, in 2 pages.
National Library of Medicine, "type II CRISPR RNA-guided endonuclease Cas9 [Listeria monocytogenes] NCBI Reference Sequence: WP_003723650.1," nih.gov 2023, in 2 pages.
National Library of Medicine, "type II CRISPR RNA-guided endonuclease Cas9 [Listeria monocytogenes] NCBI Reference Sequence: WP_070214481.1," nih.gov 2023, in 2 pages.
National Library of Medicine, "type II CRISPR RNA-guided endonuclease Cas9 [Listeria monocytogenes] NCBI Reference Sequence: WP_060567941.1," nih.gov 2023, in 2 pages.
National Library of Medicine, "type II CRISPR RNA-guided endonuclease Cas9 [Kurthia huakuii] NCBI Reference Sequence: WP_029499861.1," nih.gov 2023, in 2 pages.
National Library of Medicine, "type II CRISPR RNA-guided endonuclease Cas9 [Gemella cuniculi] NCBI Reference Sequence: WP_027129613.1," nih.gov 2023, in 2 pages.
National Library of Medicine, "type II CRISPR RNA-guided endonuclease Cas9 [Gemella haemolysans] NCBI Reference Sequence: WP_003145379.1," nih.gov 2023, in 2 pages.
National Library of Medicine, "type II CRISPR RNA-guided endonuclease Cas9 [Gemella bergeri] NCBI Reference Sequence: WP_021752441.1," nih.gov 2023, in 2 pages.
National Library of Medicine, "type II CRISPR RNA-guided endonuclease Cas9 [Brochothrix thermosphacta] NCBI Reference Sequence: WP_069132012.1," nih.gov 2023, in 2 pages.
National Library of Medicine, "type II CRISPR RNA-guided endonuclease Cas9 [Brochothrix campestris] NCBI Reference Sequence: WP_084038511.1," nih.gov 2023, in 2 pages.
National Library of Medicine, "type II CRISPR RNA-guided endonuclease Cas9 [Gemella morbillorum] NCBI Reference Sequence: WP_004632196.1," nih.gov 2023, in 2 pages.
National Library of Medicine, "type II CRISPR RNA-guided endonuclease Cas9 [Gemella massiliensis] NCBI Reference Sequence: WP_072520207.1," nih.gov 2023, in 2 pages.
National Library of Medicine, "type II CRISPR RNA-guided endonuclease Cas9 [*Gemella* sp. oral taxon 928] NCBI Reference Sequence: WP_082729137.1," nih.gov 2023, in 2 pages.
National Library of Medicine, "type II CRISPR RNA-guided endonuclease Cas9, partial [Listeria monocytogenes] NCBI Reference Sequence: WP_080149038.1," nih.gov 2023, in 1 page.
National Library of Medicine, "type II CRISPR RNA-guided endonuclease Cas9, partial [Listeria monocytogenes] NCBI Reference Sequence: WP_072233091.1," nih.gov 2023, in 1 page.
National Library of Medicine, "type II CRISPR RNA-guided endonuclease Cas9, partial [Listeria monocytogenes] NCBI Reference Sequence: WP_072218465.1," nih.gov 2023, in 1 page.
National Library of Medicine, "type II CRISPR RNA-guided endonuclease Cas9, partial [Listeria monocytogenes] NCBI Reference Sequence: WP_072239624.1," nih.gov 2023, in 1 page.
National Library of Medicine, "type II CRISPR RNA-guided endonuclease Cas9, partial [Listeria monocytogenes] NCBI Reference Sequence: WP_080151670.1," nih.gov 2023, in 1 page.
Nehls et al., "Two genetically separable steps in the differentiation of thymic epithelium," Science 1996, 272(5263), 886-889.

Nichols et al., "A universal nucleoside for use at ambiguous sites in DNA primers," Nature 1994, 369(6480), 492-493.
Nicoud et al., "Development of photoreceptor-specific promoters and their utility to investigate EIAV lentiviral vector mediated gene transfer to photoreceptors," The Journal of Gene Medicine 2007, 9(12), 1015-1023.
Nielsen et al., "Sequence-selective recognition of DNA by strand displacement with a thymine-substituted polyamide," Science 1991, 254(5037), 1497-1500.
Nishimasu et al., "Crystal structure of *Staphylococcus aureus* Cas9," Cell 2015, 162(5), 1113-1126.
Noguchi et al., "PDX-1 protein containing its own antennapedia-like protein transduction domain can transduce pancreatic duct and islet cells," Diabetes 2003, 52(7), 1732-1737.
Notice of Reasons for Rejection dated Aug. 25, 2023 in Japanese Patent Application No. 2020-550714.
Notice of Reasons for Rejection dated Feb. 28, 2023 in Japanese Patent Application No. 2020-550714.
Notice of Reasons for Rejection dated Oct. 5, 2023 in Japanese Patent Application No. 2021-530251.
O'Neill et al., "Chloroplast transformation in plants: polyethylene glycol (PEG) treatment of protoplasts is an alternative to biolistic delivery systems," The Plant Journal 1993, 3(5), 729-738.
Oakes et al., "Protein engineering of Cas9 for enhanced function," Methods in Enzymology 2014, 546, 491-511.
Oberdick et al., "A promoter that drives transgene expression in cerebellar Purkinje and retinal bipolar neurons," Science 1990, 248(4952), 223-226.
Oberhauser & Wagner, "Effective incorporation of 2'-O-methyl-oligoribonucleotides into liposomes and enhanced cell association through modification with thiocholesterol," Nucleic Acids Research 1992, 20(3), 533-538.
Oh et al., "Expression of transgenes in midbrain dopamine neurons using the tyrosine hydroxylase promoter," Gene Therapy 2009, 16(3), 437-440.
Olson et al., "Preparation of liposomes of defined size distribution by extrusion through polycarbonate membranes," Biochimica et Biophysica Acta (BBA)-Biomembranes 1979, 557(1), 9-23.
Outchkourov et al., "Optimization of the expression of equistatin in Pichia pastoris," Protein Expression and Purification 2002, 24(1), 18-24.
Pajvani et al., "Fat apoptosis through targeted activation of caspase 8: a new mouse model of inducible and reversible lipoatrophy," Nature Medicine 2005, 11(7), 797-803.
Panyam & Labhasetwar, "Biodegradable nanoparticles for drug and gene delivery to cells and tissue," Advanced Drug Delivery Reviews 2012, 64(Suplement), 61-71.
Parmacek et al., "A novel myogenic regulatory circuit controls slow/cardiac troponin C gene transcription in skeletal muscle," Molecular and Cellular Biology 1994, 14(3), 1870-1885.
Paul et al., "Increased viral titer through concentration of viral harvests from retroviral packaging lines," Human Gene Therapy 1993, 4(5), 609-615.
Peer & Lieberman, "Special delivery: targeted therapy with small RNAs," Gene Therapy 2011, 18(12), 1127-1133.
Perrin et al., "An experimental rabies vaccine produced with a new BHK-21 suspension cell culture process: use of serum-free medium and perfusion-reactor system," Vaccine 1995, 13(13), 1244-1250.
Platt et al., "Obesity-linked regulation of the adipsin gene promoter in transgenic mice," Proceedings of the National Academy of Sciences 1989, 86(19), 7490-7494.
Podesta & Kostarelos, "Engineering cationic liposome: sirna complexes for in vitro and in vivo delivery," Methods in Enzymology 2009, 464, 343-354.
Radovick et al. "Migratory arrest of gonadotropin-releasing hormone neurons in transgenic mice," Proceedings of the National Academy of Sciences 1991, 88(8), 3402-3406.
Restriction Requirement dated Oct. 27, 2023 in U.S. Appl. No. 16/982,433.
Riaz, "Liposomes preparation methods," Pakistan Journal of Pharmaceutical Sciences 1996, 9(1), 65-77.

(56) References Cited

OTHER PUBLICATIONS

Robbins et al., "In vivo definition of a cardiac specific promoter and its potential utility in remodeling the heart," Annals of the New York Academy of Sciences 1995, 752(1), 492-505.
Rolling et al., "Evaluation of adeno-associated virus-mediated gene transfer into the rat retina by clinical fluorescence photography," Human Gene Therapy 1999, 10(4), 641-648.
Ross et al., "A fat-specific enhancer is the primary determinant of gene expression for adipocyte P2 in vivo," Proceedings of the National Academy of Sciences 1990, 87(24), 9590-9594.
Saison-Behmoaras et al., "Short modified antisense oligonucleotides directed against Ha-ras point mutation induce selective cleavage of the mRNA and inhibit T24 cells proliferation," The EMBO Journal 1991, 10(5), 1111-1118.
Sakamoto et al., "A vitrectomy improves the transfection efficiency of adenoviral vector-mediated gene transfer to Müller cells," Gene Therapy 1998, 5(8), 1088-1097.
Samulski et al., "Cloning of adeno-associated virus into pBR322: rescue of intact virus from the recombinant plasmid in human cells," Proceedings of the National Academy of Sciences 1982, 79(6), 2077-2081.
Samulski et al., "Helper-free stocks of recombinant adeno-associated viruses: normal integration does not require viral gene expression," Journal of Virology 1989, 63(9), 3822-3828.
Santos et al., "Mipomersen, an antisense oligonucleotide to apolipoprotein B-100, reduces lipoprotein (a) in various populations with hypercholesterolemia: results of 4 phase III trials," Arteriosclerosis, Thrombosis, and Vascular Biology 2015, 35(3), 689-699.
Sartorelli et al., "Myocardial activation of the human cardiac alpha-actin promoter by helix-loop-helix proteins," Proceedings of the National Academy of Sciences 1992, 89(9), 4047-4051.
Sasaoka et al., "Analysis of the human tyrosine hydroxylase promoter-chloramphenicol acetyltransferase chimeric gene expression in transgenic mice," Molecular Brain Research 1992, 16(3-4), 274-286.
Sato et al., "Dual promoter structure of mouse and human fatty acid translocase/CD36 genes and unique transcriptional activation by peroxisome proliferator-activated receptor α and γ ligands," Journal of Biological Chemistry 2002, 277(18), 15703-15711.
Schoeber et al., "Conditional fast expression and function of multimeric TRPV5 channels using Shield-1," American Journal of Physiology—Renal Physiology 2009, 296(1), F204-F211.
Search Report and Search Opinion dated Jun. 28, 2023 in European Patent Application No. 19712889.5.
Senapathy & Carter, "Molecular cloning of adeno-associated virus variant genomes and generation of infectious virus by recombination in mammalian cells," Journal of Biological Chemistry 1984, 259(7), 4661-4666.
Seo et al., "Functional characterization of the human resistin promoter with adipocyte determination- and differentiation-dependent factor 1/sterol regulatory element binding protein 1c and CCAAT enhancer binding protein-α," Molecular Endocrinology 2003, 17(8), 1522-1533.
Shamblott et al., "Derivation of pluripotent stem cells from cultured human primordial germ cells," Proceedings of the National Academy of Sciences 1998, 95(23), 13726-13731.
Shamblott et al., "Human embryonic germ cell derivatives express a broad range of developmentally distinct markers and proliferate extensively in vitro," Proceedings of the National Academy of Sciences 2001, 98(1), 113-118.
Shea et al., "Synthesis, hybridization properties and antiviral activity of lipid-oligodeoxynucleotide conjugates," Nucleic Acids Research 1990, 18(13), 3777-3783.
Singh et al., "LNA (locked nucleic acids): synthesis and high-affinity nucleic acid recognition," Chemical Communications 1998, 4, 455-456.
Smith & Waterman, "Comparison of biosequences," Advances in Applied Mathematics 1981, 2(4), 482-489.
Soutschek et al., "Therapeutic silencing of an endogenous gene by systemic administration of modified siRNAs," Nature 2004, 432(7014), 173-178.

Staub et al., "High-yield production of a human therapeutic protein in tobacco chloroplasts," Nature Biotechnology 2000, 18(3), 333-338.
Svab & Maliga, "High-frequency plastid transformation in tobacco by selection for a chimeric aadA gene," Proceedings of the National Academy of Sciences 1993, 90(3), 913-917.
Svinarchuk et al., "Inhibition of HIV proliferation in MT-4 cells by antisense oligonucleotide conjugated to lipophilic groups," Biochimie 1993, 75(1-2), 49-54.
Szoka et al., "Preparation of unilamellar liposomes of intermediate size (0.1-0.2 μm) by a combination of reverse phase evaporation and extrusion through polycarbonate membranes," Biochimica et Biophysica Acta (BBA)-Biomembranes 1980, 601, 559-571.
Tabor et al., "Identification of conserved cis-elements and transcription factors required for sterol-regulated transcription of stearoyl-CoA desaturase 1 and 2," Journal of Biological Chemistry 1999, 274(29), 20603-20610.
Takahashi et al., "Induction of pluripotent stem cells from adult human fibroblasts by defined factors," Cell 2007, 131(5), 861-872.
Takahashi et al., "Induction of pluripotent stem cells from fibroblast cultures," Nature Protocols 2007, 2(12), 3081-3089.
Takahashi et al., "Rescue from photoreceptor degeneration in the rd mouse by human immunodeficiency virus vector-mediated gene transfer," Journal of Virology 1999, 73(9), 7812-7816.
Tanaka et al., "Conformational variations in an infectious protein determine prion strain differences," Nature 2004, 428(6980), 323-328.
Thomson et al., "Blastocysts embryonic stem cell lines derived from human," Science 1998, 282(5391), 1145-1147.
Thomson et al., "Isolation of a primate embryonic stem cell line," Proceedings of the National Academy of Sciences 1995, 92(17), 7844-7848.
Thomson et al., "Pluripotent cell lines derived from common marmoset (*Callithrix jacchus*) blastocysts," Biology of Reproduction 1996, 55(2), 254-259.
Tozzo et al., "Amelioration of insulin resistance in streptozotocin diabetic mice by transgenic overexpression of GLUT4 driven by an adipose-specific promoter," Endocrinology 1997, 138(4), 1604-1611.
Tratschin et al., "A human parvovirus, adeno-associated virus, as a eucaryotic vector: transient expression and encapsidation of the procaryotic gene for chloramphenicol acetyltransferase," Molecular and Cellular Biology 1984, 4(10), 2072-2081.
Tratschin et al., "Adeno-associated virus vector for high-frequency integration, expression, and rescue of genes in mammalian cells," Molecular and Cellular Biology 1985, 5(11), 3251-3260.
Tréhin et al., "Cellular uptake but low permeation of human calcitonin-derived cell penetrating peptides and Tat (47-57) through well-differentiated epithelial models," Pharmaceutical Research 2004, 21, 1248-1256.
Uemura et al., "Short Polymers of Arginine Rapidly Translocate Into Vascular Cells Effects on Nitric Oxide Synthesis," Circulation Journal 2002, 66(12), 1155-1160.
Uniprot, "CRISPR-associated endonuclease Cas9," uniprot.org 2023, in 4 pages.
Vasil et al., "Rapid production of transgenic wheat plants by direct bombardment of cultured immature embryos," Bio/technology 1993, 11(12), 1553-1558.
Vavalle & Cohen, "The REG1 anticoagulation system: a novel actively controlled factor IX inhibitor using RNA aptamer technology for treatment of acute coronary syndrome," Future Cardiology 2012, 8(3), 371-382.
Vemuri & Rhodes, "Preparation and characterization of liposomes as therapeutic delivery systems: a review," Pharmaceutica Acta Helvetiae 1995, 70(2), 95-111.
Viney et al., "Antisense oligonucleotides targeting apolipoprotein (a) in people with raised lipoprotein (a): two randomised, double-blind, placebo-controlled, dose-ranging trials," The Lancet 2016, 388(10057), 2239-2253.
Volkov et al., "Selective protection of nuclease-sensitive sites in siRNA prolongs silencing effect," Oligonucleotides 2009, 19(2), 191-202.

(56) References Cited

OTHER PUBLICATIONS

Wahlestedt et al., "Potent and nontoxic antisense oligonucleotides containing locked nucleic acids," Proceedings of the National Academy of Sciences 2000, 97(10), 5633-5638.

Wan & Lemaux, "Generation of large Nos. of independently transformed fertile barley plants," Plant Physiology 1994, 104(1), 37-48.

Wang et al., "Cyclohexene Nucleic Acids (CeNA): Serum Stable Oligonucleotides that Activate RNase H and Increase Duplex Stability with Complementary RNA," J. Am. Chem. Soc. 2000, 122(36), 8595-8602.

Warren et al., "Highly efficient reprogramming to pluripotency and directed differentiation of human cells with synthetic modified mRNA," Cell Stem Cell 2010, 7(5), 618-630.

Watkins & Santalucia, "Nearest-neighbor thermodynamics of deoxyinosine pairs in DNA duplexes," Nucleic Acids Research 2005, 33(19), 6258-6267.

Watwe & Bellare, "Manufacture of liposomes: a review," Current Science 1995, 68 715-724.

Weeks et al., "Rapid production of multiple independent lines of fertile transgenic wheat (*Triticum aestivum*)," Plant Physiology 1993, 102(4), 1077-1084.

Wender et al., "The design, synthesis, and evaluation of molecules that enable or enhance cellular uptake: peptoid molecular transporters," Proceedings of the National Academy of Sciences 2000, 97(24), 13003-13008.

Whitehead et al., "Silencing or stimulation? siRNA delivery and the immune system," Annual Review of Chemical and Biomolecular Engineering 2011, 2, 77-96.

Winkler, "Oligonucleotide conjugates for therapeutic applications," Therapeutic Delivery 2013, 4(7), 791-809.

Xia et al., "An enhanced U6 promoter for synthesis of short hairpin RNA," Nucleic Acids Research 2003, 31(17), in 5 pages.

Yang & Bedford, "Titivated for destruction: the methyl degron," Molecular Cell 2012, 48(4), 487-488.

Yokoyama et al., "Photoreceptor-specific activity of the human interphotoreceptor retinoid-binding protein (IRBP) promoter in transgenic mice," Experimental Eye Research 1992, 55(2), 225-233.

Young et al., "A short, highly active photoreceptor-specific enhancer/promoter region upstream of the human rhodopsin kinase gene," Investigative Ophthalmology & Visual Science 2003, 44(9), 4076-4085.

Yu et al., "Induced pluripotent stem cell lines derived from human somatic cells," Science 2007, 318(5858), 1917-1920.

Zender et al., "VP22-mediated intercellular transport of p53 in hepatoma cells in vitro and in vivo," Cancer Gene Therapy 2002, 9(6), 489-496.

Zhang & Madden, "PowerBLAST: a new network BLAST application for interactive or automated sequence analysis and annotation," Genome Research 1997, 7(6), 649-656.

International Search Report and Written Opinion relating to International Application No. PCT/US2019/063456, dated Jul. 20, 2020; 21 pgs.

Finn et al., "A Single Administration of CRISPR/Cas9 Lipid Nanoparticles Achieves Robust and Persistent In Vivo Genome Editing", Cell Reports, 2018, pp. 2227-2235, and Supplemental Information, vol. 22, No. 9.

Hajj et al., "Tools for translation: non-viral materials for therapeutic mRNA delivery", Nature Reviews/Materials, 2017, pp. 1-17, vol. 2, No. 10.

Kim et al., "In vivo genome editing with a small Cas9 orthologue derived from Campylobacter jejuni", Nature Communications, 2017, pp. 1-12, vol. 8.

Miller et al., "An improved zinc-finger nuclease architecture for highly specific genome editing", Nature Biotechnology, 2007, pp. 778-785, vol. 25, No. 7.

Ran et al., "In vivo genome editing using *Staphylococcus aureus* Cas9", Nature, 2015, pp. 186-191, vol. 520.

Non-Final Office Action dated Apr. 10, 2024 in U.S. Appl. No. 16/982,433.

Notice of Reasons for Rejection dated Jan. 19, 2024 in Japanese Patent Application No. 2020-550714.

Notice of Reasons for Rejection dated Mar. 12, 2024 in Japanese Patent Application No. 2021-530251.

Kolkman Ja et al: "Directed Evolution of Protein by Exon Shuffling" Nature Biotechnology, Nature Publishing Group, vol. 19, May 2001, pp. 423-428.

E.H. Oliw: "CRISPR-associated endonuclease Cas9 from *Staphylococcus lugdunensis*" Jun. 8, 2016, XP055494049, Retrieved from the Internet: URL: https://rest.uniprot.org/unisave/A0A0U3QCR8?format=txt&versions=16.

Hafez M et al: "Homing endonucleases: DNA scissors on a mission" Genome, National Research Council Canada, Ottawa, CA, vol. 55, No. 8, Aug. 14, 2012, pp. 553-569.

Murovec Jana et al: "New variants of CRISPR RNA-guided genome editing enzymes" Plant Biotechnology Journal, vol. 15, No. 8, May 9, 2017, pp. 917-926.

Coco W M et al: "DNA Shuffling Method for Generating Highly Recombined Genes and Evolved Enzymes" Nature Biotechnology, Nature Publishing Group US, New York, vol. 19, Apr. 2001, pp. 354-359.

Schmidt Moritz J. et al: "Improved CRISPR genome editing using small highly active and specific using small highly active and specific engineered RNA-guided nucleases" Nature Communications, vol. 12, No. 1, Jul. 9, 2021, pp. 1-12.

K Singh, Raushan, et al. "Protein engineering approaches in the post-genomic era." Current Protein and Peptide Science 19.1 (2018): 5-15.

Office action dated Mar. 22, 2024 in Canadian Patent Application No. 3,121,191.

Office Action dated May 30, 2024 in Chinese Patent Application No. 201980090537.2.

Office Action dated Oct. 14, 2023 in Chinese Patent Application No. 201980033565.0.

Seffernick, Jennifer L., et al. "Melamine deaminase and atrazine chlorohydrolase: 98 percent identical but functionally different." Journal of bacteriology 183.8 (2001): 2405-2410.

Tang, Shuiquan, and Elizabeth A. Edwards. "Identification of Dehalobacter reductive dehalogenases that catalyse dechlorination of chloroform, 1, 1, 1-trichloroethane and 1, 1-dichloroethane." Philosophical Transactions of the Royal Society B: Biological Sciences 368.1616 (2013): 20120318.

Witkowski, Andrzej, et al. "Conversion of a β-ketoacyl synthase to a malonyl decarboxylase by replacement of the active-site cysteine with glutamine." Biochemistry 38.36 (1999): 11643-11650.

\* cited by examiner

SpCas9 Gib11-Spa3 mRNA (CM1 LNP)

200 nm

SpCas9 mRNA (CM1 LNP)

200 nm

OPTIMIZED mRNA ENCODING CAS9 FOR USE IN LNPs

CROSS-REFERENCE TO RELATED APPLICATIONS

This application is a national stage filing under 35 U.S.C. § 371 of International Application No. PCT/US2019/063456, filed Nov. 26, 2019, which claims the benefit of priority to U.S. Provisional Patent Application Ser. No. 62/772,278, filed on Nov. 28, 2018, which is herein expressly incorporated by reference in its entirety, including any drawings.

INCORPORATION OF THE SEQUENCE LISTING

The material in the accompanying Sequence Listing is hereby incorporated by reference into this application. The accompanying Sequence Listing text file, named 052984-536001WO_SequenceListing_ST25.txt, was created on Nov. 21, 2019, and is 229,434 bytes.

FIELD

The present disclosure relates to compositions and methods for delivering molecules, e.g., nucleic acids, to target cells. Such particles are useful for, e.g., delivery of components for genome editing. In particular, the application relates to RNA-lipid nanoparticle compositions.

BACKGROUND

Recent advances in genome sequencing techniques and analysis methods have significantly accelerated the ability to identify and map genetic elements associated with a diverse range of biological functions and diseases. Precise genome targeting technologies are needed to enable reverse engineering of causal genetic variations by allowing selective perturbation of individual genetic elements, as well as to advance synthetic biology, biotechnological, and medical applications. In recent years, targeted genome editing technologies using engineered nucleases have progressed from being niche technologies to advanced methods used by many biological researchers. This adoption has been largely fueled by the emergence of a new class of site-specific endonucleases, including designer zinc fingers, transcription activator-like effectors (TALEs), homing meganucleases, and the development of the clustered, regularly interspaced, short palindromic repeat (CRISPR) technology.

However, the delivery of large biologically active agents, such as site-specific endonucleases or nucleic acids encoding the same, to target cells or tissues is often hindered by difficulties in the agents reaching the target living cell or tissue. In particular, the trafficking of many biologically active agents into living cells can be restricted by the membrane systems of the cells. In fact, it has been widely reported that one class of biologically active agents that is particularly difficult to deliver to cells are large biomolecules including proteins, nucleic acid-based therapeutics, and derivatives thereof. Certain nucleic acids and proteins are stable for only a limited duration in cells or plasma, and sometimes are highly charged, which can complicate delivery across cell membranes.

Thus, there is a need for compositions and methods for delivering site-specific endonuclease to target living cells. In particular, there exists a need for compositions and methods that can improve stability and allow for efficient delivery of such biomolecules into living cells and tissues are of particular interest.

SUMMARY

This section provides a general summary of the disclosure and is not comprehensive of its full scope or all of its features.

The present disclosure relates to the invention of novel lipid nanoparticle (LNP)-based compositions comprising a nucleic acid molecule of about 3.8 kb or less in length (referred to hereinafter as "smLNP composition") that can be used for the delivery of a nucleic acid encoding a site-specific endonuclease into a target cell. In some embodiments, the disclosure provides methods for editing the genome of a cell, which involves contacting such cell with an LNP composition as described herein. In some embodiments, the disclosure provides methods for treating a disease using the compositions and/or methods described herein.

In one aspect, some embodiments of the present disclosure relate to a lipid-based nanoparticle (LNP) composition including: (a) a nucleic acid molecule including a nucleotide sequence encoding a site-specific endonuclease; and (b) one or more lipid moieties selected from the group consisting of amino lipids, ionizable lipids, neutral lipids, PEG lipids, helper lipids, and cholesterol or cholesterol derivatives; wherein the nucleic acid molecule is about 3.8 kb or less in length. Such LNP composition is referred to hereinafter as "smLNP composition."

Implementations of embodiments of the smLNP composition of the present disclosure can include one or more of the following features. In some embodiments, the nucleic acid molecule is about 3.7 kb or less in length. In some embodiments, the nucleic acid molecule is about 3.5 kb or less in length. In some embodiments, the nucleic acid molecule is a messenger RNA (mRNA). In some embodiments, the nucleotide sequence encoding the site-specific endonuclease is operably linked to at least one additional nucleotide sequence. In some embodiments, the at least one additional nucleotide sequence includes an untranslated terminal region (UTR), a consensus Kozak signal, a nucleotide sequence encoding a nuclear localization signal (NLS), a nucleotide sequence encoding a linker peptide, a nucleotide sequence encoding a tag peptide, or a combination of any thereof. In some embodiments, the nuclear localization signal (NLS) comprises a nucleoplasmin NLS or a SV40 NLS.

In some embodiments of the disclosure, the site-specific endonuclease is a Cas9 protein or a functional derivative thereof. In some embodiments, the site-specific endonuclease includes an amino acid sequence selected from the group consisting of SEQ ID NO: 1, SEQ ID NO: 2, SEQ ID NO: 3, SEQ ID NO: 4, SEQ ID NO 5, and SEQ ID NO: 6. In some embodiments, the nucleic acid molecule includes a nucleotide sequence selected from the group consisting of SEQ ID NO: 7, SEQ ID NO: 8, SEQ ID NO: 9, SEQ ID NO: 10, SEQ ID NO: 11, and SEQ ID NO: 12.

In some embodiments of the disclosure, the nucleotide sequence encoding the site-specific endonuclease is codon-optimized for expression in a host cell. In some embodiments, the host cell is a mammalian cell. In some embodiments, the mammalian cell is a human cell, a murine cell, or a non-human primate cell.

In some embodiments, the smLNP composition of the disclosure further includes one or more additional components of a CRISPR system. In some embodiments, the one or more additional components of the CRISPR system includes a guide RNA (gRNA) or a nucleic acid molecule encoding the gRNA.

In some embodiments, the smLNPs of an smLNP composition disclosed herein comprise an amino lipid. In some embodiments, the amino lipid includes C12-200.

In some embodiments, the smLNPs of an smLNP composition disclosed herein comprise a structural lipid. In some embodiments, the structural lipid includes cholesterol.

In some embodiments, the smLNPs of an smLNP composition disclosed herein comprise a helper lipid. In some embodiments, the helper lipid includes DOPE.

In some embodiments, the smLNPs of an smLNP composition disclosed herein comprise a PEG lipid. In some embodiments, the PEG lipid includes PEG-DMPE.

In some embodiments, the smLNPs of an smLNP composition disclosed herein comprise one or more of C12-200, cholesterol, DOPE, and PEG-DMPE. In some embodiments, the smLNPs comprise C12-200, cholesterol, DOPE, and PEG-DMPE.

In some embodiments, the smLNPs of the smLNP composition disclosed herein have a lower rate of change in a physicochemical property as compared to LNPs of a reference LNP composition including a nucleic acid molecule including a nucleotide sequence encoding a site-specific endonuclease, wherein the nucleic acid molecule is greater than about 4 kb. In some embodiments, the smLNPs of the smLNP composition have a rate of change in a physicochemical property that is at least about 5% less than the corresponding rate of the LNPs of the reference LNP composition. In some embodiments, the smLNP composition has a lower rate of decrease in functional performance as compared to that of a reference LNP composition comprising a nucleic acid molecule comprising a nucleotide sequence encoding a site-specific endonuclease, wherein the nucleic acid molecule is greater than about 4 kb. In some embodiments, the smLNP composition has a rate of decrease in functional performance that is at least about 5% less than the corresponding rate of the reference LNP composition.

In some embodiments, the smLNPs of the smLNP composition disclosed herein have an average particle diameter larger than that of LNPs of a reference LNP composition including a nucleic acid molecule including a nucleotide sequence encoding a site-specific endonuclease, wherein the nucleic acid molecule is greater than about 4.4 kb. In some embodiments, the smLNP of the smLNP composition have an average particle diameter that is at least about 10% (such as at least about any of 11%, 12%, 13%, 14%, 15%, 16%, 17%, 18%, 19%, 20%, 25%, 30%, or greater) larger than the average particle diameter of LNPs in the reference LNP composition. In some embodiments of the disclosure, the reference LNP composition includes a nucleic acid molecule of about 4.4 kb or more in length.

In one aspect, some embodiments of the present disclosure relate to a method for delivering a nucleic acid molecule into a cell, including contacting the cell with an smLNP composition as disclosed herein, wherein the smLNP composition includes the nucleic acid molecule.

In one aspect, some embodiments of the present disclosure relate to a method for editing a genome of a cell, including providing to the cell an smLNP composition as disclosed herein.

Implementations of embodiments of the methods of the disclosure can include one or more of the following features. In some embodiments, the editing efficiency of the smLNP composition is greater than that of a reference LNP composition including a nucleic acid molecule which includes a nucleotide sequence encoding a site-specific endonuclease, wherein the nucleic acid molecule is greater than about 4 kb. In some embodiments, the editing efficiency of the smLNP composition is at least 5% greater than that of the reference LNP composition. In some embodiments of the methods disclosed herein, the cell is a mammalian cell. In some embodiments, the mammalian cell is a human cell, a murine cell, or a non-human primate cell.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1A is a bar graph showing the particle size of the LNPs as assayed by dynamic light scattering (DLS). FIG. 1B is a bar graph showing the heterogeneity of mixed LNP populations as characterized by polydispersity index (PDI). FIG. 1C is a bar graph showing the size of the LNPs as determined by nanoparticle tracking analysis (NTA). FIG. 1D is a bar graph showing the mRNA encapsulation efficiency of the LNPs. FIG. 1E is a graph showing the distribution of the ratio of particles to RNA in relation with the particle size.

DETAILED DESCRIPTION OF THE DISCLOSURE

Figure 1A:
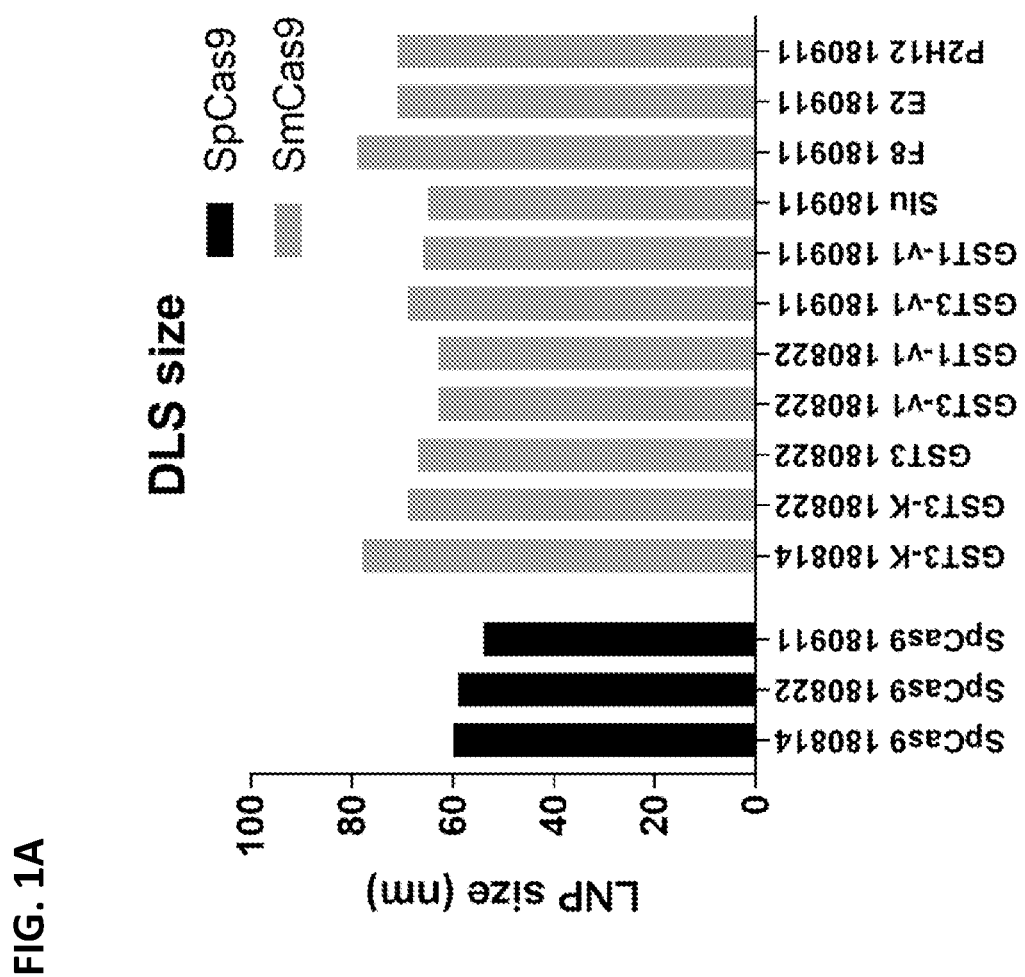
FIGS. 1A-1E graphically summarize the results of experiments performed to characterize lipid-based nanoparticles (LNPs), suggesting size differences between LNPs containing SpCas9 (i.e., referenced LNP) and smCas9s (i.e., smLNP).

Provided herein are novel lipid-based nanoparticle (LNP) compositions and methods for the delivery of CRISPR/Cas gene editing components to cells. Some embodiments of the disclosure provide compositions and methods for delivering genome editing components in vivo using LNPs that encapsulate mRNA encoding a site-specific endonuclease such as, for example, a small Cas9 (smCas9) endonuclease or a site-specific endonuclease derived from one or more smCas9s. Such an mRNA encoding an smCas9 or a site-specific endonuclease derived from one or more smCas9s is also referred to herein as an "smCas9 mRNA." Without being bound to any particular theory, the small size of the encapsulated mRNA, e.g., less than about 3.8 kb in length, is believed to confer a packaging advantage into smLNPs compared to a corresponding LNP composition comprising a nucleic acid molecule of greater than 4.0 kb in length. As described in greater detail below, the smLNPs in accordance with some embodiments of the disclosure have shown both improved genome editing performance and improved stability when compared to the corresponding LNPs.

The compositions and methods disclosed herein are expected to have significant commercial and/or clinical applicability since LNP delivery technology is a critical component for many in vivo gene editing approaches. Most LNP systems currently in commercial and/or clinical use carry siRNA payloads, which may be smaller, more stable, and/or safer than mRNA payloads. Development of stable LNPs to deliver a nucleic acid, such as an mRNA, encoding a site-specific endonuclease, such as Cas9, which is considered a large and complex payload, remains a challenge in the field.

Utilization of mRNA encoding smCas9s or site-specific endonucleases derived from one or more smCas9s as a payload for LNP delivery may enable LNP technology for delivering genome editing nucleases in vivo. Key advantages of the compositions and methods disclosed herein include, but are not limited to, (1) LNPs that deliver mRNA encoding an smCas9 mRNA or a site-specific endonuclease derived from one or more smCas9s have so far shown to be more potent than LNPs that deliver mRNA encoding SpCas9, and this improved performance may enable safer dosing in patients; (2) these LNPs are more stable than SpCas9 mRNA-loaded LNPs, so they is a more viable drug formulation; and (3) due to smaller size, the mRNAs encoding an smCas9 or a site-specific endonuclease derived from one or more smCas9s are easier to manufacture than SpCas9 mRNA.

As described in more detail below, LNP-based delivery systems can be engineered to target hepatocytes in the liver after systemic administration. Encapsulation of smCas9 mRNA into smLNPs is not expected to adversely affect hepatocyte targeting; indeed, smCas9 mRNA LNPs may have improved pharmacokinetics compared to SpCas9 mRNA LNPs due to enhanced LNP stability. Key attributes of LNP technology for delivering smCas9 mRNAs are the transient nature of endonuclease expression (with endonuclease levels expected to reach baseline 1 week post injection) and the ability to administer multiple LNP doses in order to titrate up to a target effect.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a," "an," and "the" include plural references unless the context clearly dictates otherwise. For example, the term "a cell" includes one or more cells, comprising mixtures thereof "A and/or B" is used herein to include all of the following alternatives: "A," "B," "A or B," and "A and B."

The term "about," as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

It is understood that aspects and embodiments of the disclosure described herein include "comprising," "consisting," and "consisting essentially of" aspects and embodiments.

As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a nucleic acid molecule by an LNP to a target tissue of interest (e.g., mammalian liver) compared to the level of delivery of a nucleic acid molecule by a control LNP to a target cell or tissue of interest. The level of delivery of an LNP to a tissue can be measured by (i) comparing the amount of protein produced in a cell or tissue to the weight of said cell or tissue; (ii) comparing the amount of nucleic acid molecule in a cell or tissue to the weight of said cell or tissue; (iii) comparing the amount of protein produced in a cell or tissue to the amount of total protein in said cell or tissue; (iv) or comparing the amount of polynucleotide in a cell or tissue to the amount of total nucleic acid molecule in said cell or tissue.

The terms "individual," "subject," "host," and "patient," are used interchangeably herein and refer to any mammalian subject, such as human (e.g., human subjects), non-human mammals and non-human primates, for whom diagnosis, treatment, or therapy is desired, particularly humans.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein. In some embodiments of the disclosure, the nucleic acid molecule of the smLNP composition disclosure herein is a messenger RNA (mRNA).

The term "recombinant" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence.

The term "operably linked," as used herein, denotes a physical or functional linkage between two or more elements, e.g., polypeptide sequences or polynucleotide sequences, which permits them to operate in their intended fashion. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements is contiguous or non-contiguous.

The term "recombination" as used herein refers to a process of exchange of genetic information between two polynucleotides. As used herein, "homology-directed repair (HDR)" refers to the specialized form DNA repair that takes place, for example, during repair of double-strand breaks in cells. This process requires nucleotide sequence homology, uses a "donor" molecule to template repair of a "target" molecule (e.g., the one that experienced the double-strand break), and leads to the transfer of genetic information from the donor to the target. Homology-directed repair may result in an alteration of the sequence of the target molecule (e.g., insertion, deletion, mutation), if the donor polynucleotide differs from the target molecule and part or all of the sequence of the donor polynucleotide is incorporated into the target DNA. In some embodiments, the donor polynucleotide, a portion of the donor polynucleotide, a copy of the donor polynucleotide, or a portion of a copy of the donor polynucleotide integrates into the target DNA.

The term "non-homologous end joining (NHEJ)" refers to the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

"Nuclease" and "endonuclease" are used interchangeably herein to mean an enzyme which possesses endonucleolytic catalytic activity for polynucleotide cleavage. The term includes site-specific endonucleases such as, designer zinc fingers, transcription activator-like effectors (TALEs), homing meganucleases, and site-specific endonucleases of clustered, regularly interspaced, short palindromic repeat (CRISPR) systems such as, e.g., Cas proteins.

The term "site-specific modifying enzyme" or "RNA-binding site-specific modifying enzyme" as used herein a polypeptide that binds RNA and is targeted to a specific DNA sequence, such as a Cas9 polypeptide. A site-specific modifying enzyme as described herein is targeted to a specific DNA sequence by the RNA molecule to which it is bound. The RNA molecule includes a sequence that binds, hybridizes to, or is complementary to a target sequence within the target DNA, thus targeting the bound polypeptide to a specific location within the target DNA (the target sequence).

By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In some embodiments, a complex comprising a guide RNA and a site-specific modifying enzyme is used for targeted double-stranded DNA cleavage.

By "cleavage domain" or "active domain" or "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

The terms "treatment," "treating," and the like are used herein to generally mean obtaining a desired pharmacologic and/or physiologic effect. The effect is prophylactic in terms of completely or partially preventing a disease or symptom thereof and/or is therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which is predisposed to acquiring the disease or symptom but has not yet been diagnosed as having it; (b) inhibiting the disease or symptom, e.g., arresting its development; or (c) relieving the disease, e.g., causing regression of the disease. The therapeutic agent is administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The therapy will desirably be administered during the symptomatic stage of the disease, and in some cases after the symptomatic stage of the disease.

Headings, e.g., (a), (b), (i) etc., are presented merely for ease of reading the specification and claims. The use of headings in the specification or claims does not require the steps or elements be performed in alphabetical or numerical order or the order in which they are presented.

Lipid-Based Nanoparticle Compositions of the Disclosure

In one aspect, provided herein is a lipid-based nanoparticle (LNP) composition including: (a) a nucleic acid molecule including a nucleotide sequence encoding a site-specific endonuclease; and (b) one or more lipid moieties selected from the group consisting of amino lipids, ionizable lipids, neutral lipids, PEG lipids, helper lipids, and cholesterol or cholesterol derivatives; wherein the nucleic acid molecule is about 3.8 kb or less in length (smLNP). In some embodiments, the nucleotide sequence encoding the site-specific endonuclease is operably linked to at least one additional nucleotide sequence. In some embodiments of the disclosure, the site-specific endonuclease is a Cas9 protein or a functional derivative thereof. In some embodiments of the disclosure, the nucleotide sequence encoding the site-specific endonuclease is codon-optimized for expression in a host cell. In some embodiments, the smLNP composition of the disclosure further includes one or more additional components of a CRISPR system. In some embodiments, the one or more additional components of the CRISPR system includes a guide RNA (gRNA) or a nucleic acid molecule encoding the gRNA.

Nucleic Acid Molecule

The nucleic acid molecule in accordance to some embodiments of an smLNP composition of the disclosure is about 3.8 kb, about 3.7 kb, about 3.6 kb, about 3.5 kb, about 3.4 kb, about 3.3 kb, about 3.2 kb, about 3.1 kb, or about 3.0 kb in length, including any ranges between these values. In some embodiments, the nucleic acid molecule is about 2.9 kb, about 2.8 kb, about 2.7 kb, about 2.6 kb, about 2.5 kb, about 2.4 kb, about 2.3 kb, about 2.2 kb, about 2.1 kb, or about 2.0 kb in length, including any ranges between these values. In some embodiments, the nucleic acid molecule is less than about 3.8 kb, less than about 3.7 kb, less than about 3.6 kb, less than about 3.5 kb, less than about 3.4 kb, less than about 3.3 kb, less than about 3.2 kb, less than about 3.1 kb, or less than about 3.0 kb in length. In some embodiments, the nucleic acid molecule is less than about 2.9 kb, less than about 2.8 kb, less than about 2.7 kb, less than about 2.6 kb, less than about 2.5 kb, less than about 2.4 kb, less than about 2.3 kb, less than about 2.2 kb, less than about 2.1 kb, or less than about 2.0 kb in length. In some embodiments, the nucleic acid molecule of the smLNP composition is between about 3.8 kb and about 2.0 kb, for example between about 3.7 kb and about 2.5 kb, between about 3.5 kb and about 2.6 kb, between about 3.2 kb and about 2.4 kb, or between about 3.0 kb and about 2.0 kb, for example between about 2.9 kb to 2.2 kb, between about 2.8 kb and about 2.3 kb, between about 2.7 kb and about 2.4 kb, between about 2.6 kb and about 2.5 kb, or between about 3.0 kb and about 2.5 kb in length. In some embodiments, the nucleic acid molecule of the smLNP composition is about 3.5 kb in length.

In some embodiments, according to any of the smLNP compositions described herein, the nucleotide sequence encoding the site-specific endonuclease is operably linked to at least one additional nucleotide sequence. In some embodiments, at least one additional nucleotide sequence comprises an untranslated terminal region (UTR), a consensus Kozak signal, a nucleotide sequence encoding a nuclear localization signal (NLS), a nucleotide sequence encoding a linker peptide, a nucleotide sequence encoding a tag peptide, or a combination of any thereof. In some embodiments, the consensus Kozak signal facilitates the initial binding of mRNA to ribosomes, thereby enhances its translation into a polypeptide product.

In some embodiments, according to any of the smLNP compositions described herein, the nucleic acid molecule of the smLNP composition further includes a 3' and/or 5' untranslated region (UTR). In some embodiments, the 3' or 5' UTR is derived from a human gene sequence. Non-limiting exemplary 3' and 5' UTRs include α- and β-globin, albumin, HSD17B4, and eukaryotic elongation factor 1a. In addition, viral-derived 5' and 3' UTRs can also be used and include orthopoxvirus and cytomegalovirus UTR sequences. In some embodiments, the 5' UTR comprises the polynucleotide sequence of SEQ ID NO: 20. In some embodiments, the 3' UTR comprises the polynucleotide sequence of SEQ ID NO: 21. In some embodiments, the mRNA includes a 5' cap, such as m7G(5')ppp(5')N. In addition, this cap is a cap-0 where nucleotide N does not contain 2'OMe, or cap-1 where nucleotide N contains 2'OMe, or cap-2 where nucleotides N and N+1 contain 2'OMe. This cap may also be of the structure m2 7'3 "G(5')N as incorporated by the anti-reverse-cap analog (ARCA), and may also include similar cap-0, cap-1, and cap-2, etc., structures. In some embodiments, the 5' cap may regulate nuclear export; prevent degradation by exonucleases; promote translation; and promote 5' proximal intron excision. Stabilizing elements for caps include phosphorothioate linkages, boranophosphate modifications, and methylene bridges. In addition, caps may also contain a non-nucleic acid entity that acts as the binding element for eukaryotic translation initiation factor 4E, eIF4E. In some embodiments, the mRNA includes a poly(A) tail. This tail can be about 40 to about 300 nucleotides in length. In some embodiments, the tail is about 40 to about 100 nucleotides in length. In some embodiments, the tail is about 100 to about 300 nucleotides in length. In some embodiments, the tail is about 100 to about 200 nucleotides in length. In some embodiments, the tail is about 50 to about 200 nucleotides in length. In some embodiments, the tail is about 50 to about 250 nucleotides in length. In some embodiments, the tail is about 100, 150, or 200 nucleotides in length. The poly(A) tail may contain modifications to prevent exonuclease degradation including phosphorothioate linkages and modifications to the nucleobase. In addition, the poly(A) tail may contain a 3' "cap" which could include modified or non-natural nucleobases or other synthetic moieties.

In some embodiments, according to any of the smLNP compositions described herein, the nucleic acid molecule of the smLNP composition includes a nucleotide sequence encoding a nuclear localization signal (NLS). In some embodiments, the NLS comprises a nucleoplasmin NLS or a SV40 NLS. In some embodiments, the nucleoplasmin NLS comprises the amino acid sequence of SEQ ID NO: 23. In some embodiments, the nucleoplasmin NLS is encoded by the polynucleotide sequence of SEQ ID NO: 22. In some embodiments, the SV40 NLS comprises the amino acid sequence of SEQ ID NO: 25. In some embodiments, the SV40 NLS is encoded by the polynucleotide sequence of SEQ ID NO: 24. In some embodiments, the nucleic acid molecule comprises a nucleotide sequence encoding a nucleoplasmin NLS and a nucleotide sequence encoding an SV40 NLS.

As used herein, the term "site-directed endonuclease" refers to a nuclease used in genome editing to cleave genomic DNA.

In some embodiments, according to any of the smLNP compositions described herein, the nucleic acid molecule (e.g., an RNA, such as an mRNA) of the smLNP composition includes a nucleotide sequence encoding a site-specific endonuclease which is a Cas protein (such as Cas9) or a functional derivative thereof. In some embodiments, the Cas protein is a "functional derivative" of a naturally occurring Cas protein. The term "functional derivative" of a native sequence polypeptide refers to a compound having a qualitative biological property in common with a native sequence polypeptide. As used herein, "functional derivatives" include, but are not limited to, fragments of a native sequence and derivatives of a native sequence polypeptide and its fragments, provided that they have a biological activity in common with a corresponding native sequence polypeptide. A non-limiting exemplary biological activity contemplated herein is the ability of the functional derivative to hydrolyze a DNA substrate into fragments. The term "derivative" encompasses both amino acid sequence variants of polypeptide, covalent modifications, and fusions thereof.

In some embodiments, according to any of the smLNP compositions described herein, the nucleic acid molecule component (e.g., an RNA, such as an mRNA) of an smLNP composition disclosed herein includes a nucleotide sequence encoding a site-specific endonuclease that is derived from one or more smCas9s. Gib11Spa1 endonuclease comprising the amino acid sequence of SEQ ID NO: 1 or a variant thereof having at least 90% sequence identity to SEQ ID NO: 1. In some embodiments, the site-specific endonuclease is a Gib11Spa3 endonuclease comprising the amino acid sequence of SEQ ID NO: 2 or a variant thereof having at least 90% sequence identity to SEQ ID NO: 2. In some embodiments, the site-specific endonuclease is a E2Cas9 endonuclease comprising the amino acid sequence of SEQ ID NO: 3 or a variant thereof having at least 90% sequence identity to SEQ ID NO: 3. In some embodiments, the site-specific endonuclease is a F8Cas9 endonuclease comprising the amino acid sequence of SEQ ID NO: 4 or a variant thereof having at least 90% sequence identity to SEQ ID NO: 4. In some embodiments, the site-specific endonuclease is a P2H12Cas9 endonuclease comprising the amino acid sequence of SEQ ID NO: 5 or a variant thereof having at least 90% sequence identity to SEQ ID NO: 5. In some embodiments, the site-specific endonuclease is a SluCas9 endonuclease comprising the amino acid sequence of SEQ ID NO: 6 or a variant thereof having at least 90% sequence identity to SEQ ID NO: 6.

In some embodiments, according to any of the smLNP compositions described herein, the nucleic acid molecule of the smLNP composition is an mRNA encoding a Cas nuclease, which is also referred herein as a Cas nuclease mRNA. The mRNA can be modified for improved stability and/or immunogenicity properties. The modifications can be made to one or more nucleosides within the mRNA. Examples of chemical modifications to mRNA nucleobases include pseudouridine, 1-methyl-pseudouridine (or N1-methylpseudouridine), 5-methoxyuridine, and 5-methylcytidine. In some embodiments, the mRNA contains N1-methylpseudouridine base modification. In some embodiments, the mRNA contains pseudouridine base modification. Additional known modifications to improve stability, expression, and immunogenicity are contemplated. The mRNA encoding a Cas nuclease can be codon optimized for expression in a particular cell type, such as a eukaryotic cell, a mammalian cell, or more specifically, a human cell. In some embodiments, the mRNA encodes a human codon optimized Cas9 nuclease. In some embodiments, the mRNA is further modified by uridine depletion. In some embodiments, the mRNA is modified by both uridine depletion and codon optimization (e.g., using Geneious® software platform). In some embodiments, the mRNA is purified. In some embodiments, the mRNA is purified using a precipitation method. In some embodiments, the mRNA is purified using a chromatography-based method, such as an HPLC-based method or an equivalent method. In some embodiments, the mRNA is purified using both a precipitation method and an HPLC-based method.

In some embodiments, according to any of the smLNP compositions described herein, the site-specific endonuclease comprises an amino acid sequence having at least 95% identity to a site-specific endonuclease having an amino acid sequence selected from the group consisting of SEQ ID NO: 1, SEQ ID NO: 2, SEQ ID NO: 3, SEQ ID NO: 4, SEQ ID NO 5, and SEQ ID NO: 6. The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or is applied to, the complement of a test sequence. This definition also includes sequences that have deletions and/or additions, as well as those that have substitutions. Sequence identity typically exists over a region that is at least about 20 amino acids or nucleotides in length, or over a region that is 10-100 amino acids or nucleotides in length, or over the entire length of a given sequence.

If necessary, sequence identity can be calculated using published techniques and widely available computer programs, such as the GCS program package (Devereux et al, Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

In some embodiments, according to any of the smLNP compositions described herein, the site-specific endonuclease comprises an amino acid sequence having at least 95%, at least 96%, at least 97%, at least 98, or at least 99% identity to an amino acid sequence selected from the group consisting of SEQ ID NO: 1, SEQ ID NO: 2, SEQ ID NO: 3, SEQ ID NO: 4, SEQ ID NO 5, and SEQ ID NO: 6. In some embodiments, the site-specific endonuclease comprises an amino acid sequence having 100% identity to an amino acid sequence selected from the group consisting of SEQ ID NO: 1, SEQ ID NO: 2, SEQ ID NO: 3, SEQ ID NO: 4, SEQ ID NO 5, and SEQ ID NO: 6.

In some embodiments, according to any of the smLNP compositions described herein, the nucleic acid molecule of the smLNP composition includes a nucleotide sequence having at least 95% identity to a nucleotide sequence selected from the group consisting of SEQ ID NO: 7, SEQ ID NO: 8, SEQ ID NO: 9, SEQ ID NO: 10, SEQ ID NO: 11, and SEQ ID NO: 12. In some embodiments, the nucleic acid molecule of the smLNP composition disclosed herein includes a nucleotide sequence having at least 95%, at least 96%, at least 97%, at least 98, or at least 99% identity to a nucleotide sequence selected from the group consisting of SEQ ID NO: 7, SEQ ID NO: 8, SEQ ID NO: 9, SEQ ID NO: 10, SEQ ID NO: 11, and SEQ ID NO: 12. In some embodiments, the nucleic acid molecule of the smLNP composition disclosed herein includes a nucleotide sequence having 100% identity to a nucleotide sequence selected from the group consisting of SEQ ID NO: 7, SEQ ID NO: 8, SEQ ID NO: 9, SEQ ID NO: 10, SEQ ID NO: 11, and SEQ ID NO: 12.

In some embodiments, according to any of the smLNP compositions described herein, the nucleic acid molecule of the smLNP composition encodes a polypeptide including the amino acid sequence of any one of SEQ ID NOs: 35, 37, 39, 41, 43, 45, 47, and 49.

In some embodiments, according to any of the smLNP compositions described herein, the nucleic acid molecule of the smLNP composition includes the polynucleotide sequence of any one of SEQ ID NOs: 34, 36, 38, 40, 42, 44, 46, and 48.

Sequence Optimization of Nucleotide Sequences

In some embodiments, according to any of the smLNP compositions described herein, the nucleic acid molecule (e.g., an RNA, such as an mRNA) of the smLNP composition includes a nucleotide sequence that is sequence optimized. In some embodiments, the nucleic acid molecule of the smLNP composition disclosed herein includes a nucleotide sequence encoding a site-specific endonuclease that is sequence optimized for expression in a target cell. A sequence-optimized nucleotide sequence, e.g., a codon-optimized mRNA sequence encoding a site-specific endonuclease, typically is a sequence comprising at least one synonymous nucleobase substitution with respect to a reference sequence (e.g., a wild type nucleotide sequence encoding a site-specific endonuclease). A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon, T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical. Some sequence optimization (also sometimes referred to as codon optimization) methods are known in the art and can be useful to achieve one or more desired results. These results can include, e.g., matching codon frequencies in certain tissue targets and/or host organisms to ensure proper folding; uridine depletion; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide.

Sequence optimization tools, algorithms and services are known in the art. Non-limiting examples include services from GeneArt (Life Technologies), DNA2.0 (Menlo Park CA), Geneious®, and/or proprietary methods. In some embodiments, the nucleic acid molecule (e.g., an RNA, such as an mRNA) of the smLNP composition disclosed herein includes a sequence-optimized nucleotide sequence (e.g., an ORF) encoding a site-specific endonuclease or a functional derivative thereof, wherein the site-specific endonuclease or a functional derivative thereof encoded by the sequence-optimized nucleotide sequence has improved properties (e.g., compared to a site-specific endonuclease or a functional derivative thereof encoded by a reference nucleotide sequence that is not sequence optimized), e.g., improved properties related to expression efficacy after administration in vivo. Such properties may include, but are not limited to, one or more of improving nucleic acid stability (e.g., mRNA stability), increasing translation efficacy in the target tissue, reducing the number of truncated proteins expressed, improving folding or prevent misfolding of the expressed proteins, reducing toxicity of the expressed products, reducing cell death caused by the expressed products, and increasing and/or decreasing protein aggregation. In some embodiments, the sequence-optimized nucleotide sequence is codon optimized for expression in human subjects, having structural and/or chemical features that avoid or reduce one or more of the problems known in the art, for example, features that are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways. In some embodiments, the sequence-optimized nucleotide sequence is uridine depleted. In some embodiments, the sequence-optimized nucleotide sequence is codon optimized and uridine depleted.

In some embodiments, according to any of the smLNP compositions described herein, the nucleic acid molecule (e.g., an RNA, such as an mRNA) of the smLNP composition includes an optimized sequence selected from the group consisting of SEQ ID NO: 13, SEQ ID NO: 14, SEQ ID NO: 15, SEQ ID NO: 16, SEQ ID NO: 17, SEQ ID NO: 18, and SEQ ID NO: 19.

In some embodiments, according to any of the smLNP compositions described herein, the nucleic acid molecule (e.g., an RNA, such as an mRNA) of the smLNP composition includes a nucleotide sequence that is codon-optimized for expression in a mammalian cell. In some embodiments, the mammalian cell is a human cell, a murine cell, or a non-human primate (NHP) cell.

Additional Components of CRISPR/Cas System

In some embodiments, according to any of the smLNP compositions described herein, the smLNP composition further includes one or more additional components of a CRISPR/Cas system. In principle, there are no specific limitations concerning the one or more additional components of a CRISPR/Cas system, which therefore can be selected from any known components of a CRISPR system. In some embodiments, the one or more additional components of the CRISPR system includes a guide RNA (gRNA). In some embodiments, the one or more additional components of the CRISPR system includes a nucleic acid molecule encoding a gRNA.

A gRNA has at least a spacer sequence that hybridizes to a target nucleic acid sequence of interest and a CRISPR repeat sequence (such a CRISPR repeat sequence is also referred to as a "tracr mate sequence"). In Type II systems, the gRNA also has a second RNA called the tracrRNA sequence. In the Type II guide RNA (gRNA), the CRISPR repeat sequence and tracrRNA sequence hybridize to each other to form a duplex. The duplex binds a site-specific polypeptide such that the guide RNA and site-specific endonuclease form a complex. In this case, a guide RNA and the site-specific endonuclease may form a ribonucleoprotein complex (e.g., bind via non-covalent interactions). The guide RNA of the complex provides target specificity to the complex by comprising a nucleotide sequence that is complementary to a sequence of a target DNA, and the site-specific endonuclease of the complex provides the endonuclease activity. In other words, the site-specific endonuclease is guided to a target DNA sequence (e.g., a target sequence in a chromosomal nucleic acid; a target sequence in an extrachromosomal nucleic acid, e.g., an episomal nucleic acid, a minicircle, etc.; a target sequence in a mitochondrial nucleic acid; a target sequence in a chloroplast nucleic acid; a target sequence in a plasmid; etc.) by virtue of its association with the protein-binding segment of the guide RNA.

Guide RNA can be a single-molecule guide RNA as also referred herein as a single guide RNA (sgRNA). In some embodiments, the guide RNA can include two RNA molecules and is referred to as a "dual guide RNA" or "dgRNA." In some embodiments, the dgRNA can include a first RNA molecule comprising a CRISPR RNA (crRNA) and a second RNA molecule comprising a tracr RNA. The first and second RNA molecules may form an RNA duplex via the base pairing between the flagpole on the crRNA and the tracr RNA. A double-molecule guide RNA has two strands of RNA. The first strand has in the 5' to 3' direction, an optional spacer extension sequence, a spacer sequence and a minimum CRISPR repeat sequence. The second strand has a minimum tracrRNA sequence (complementary to the minimum CRISPR repeat sequence), a 3' tracrRNA sequence and an optional tracrRNA extension sequence.

In some embodiments, according to any of the smLNP compositions described herein, the guide RNA includes a single RNA molecule and is referred to as a "single guide RNA" or "sgRNA." In some embodiments, the sgRNA includes a crRNA covalently linked to a tracr RNA. In some embodiments, the crRNA and the tracr RNA are covalently linked via a linker. In some embodiments, the single-molecule guide RNA includes a stem-loop structure via the base pairing between the flagpole on the crRNA and the tracr RNA.

A single-molecule guide RNA (sgRNA) in a Type II system has, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may have elements that contribute additional functionality (e.g., stability) to the guide RNA. The single-molecule guide linker links the minimum CRISPR repeat and the minimum tracrRNA sequence to form a hairpin structure. The optional tracrRNA extension has one or more hairpins.

In some embodiments, according to any of the smLNP compositions described herein, the nucleic acid molecule of the smLNP composition as disclosed herein is an mRNA encoding a Cas nuclease, which is also referred herein as a Cas nuclease mRNA. The mRNA can be modified for improved stability and/or immunogenicity properties. The modifications can be made to one or more nucleosides within the mRNA. Examples of chemical modifications to mRNA nucleobases include pseudouridine, 1-methyl-pseudouridine (or N1-methylpseudouridine), 5-methoxyuridine, and 5-methyl-cytidine. In some embodiments, the mRNA contains N1-methylpseudouridine base modification. In some embodiments, the mRNA contains pseudouridine base modification. Additional known modifications to improve stability, expression, and immunogenicity are contemplated. The mRNA encoding a Cas nuclease can be codon optimized for expression in a particular cell type, such as a eukaryotic cell, a mammalian cell, or more specifically, a human cell. In some embodiments, the mRNA encodes a human codon optimized Cas9 nuclease. In some embodiments, the mRNA is further modified by uridine depletion. In some embodiments, the mRNA is modified by both uridine depletion and codon optimization (e.g., using Geneious® software platform). In some embodiments, the mRNA is purified. In some embodiments, the mRNA is purified using a precipitation method (e.g., LiCl precipitation, alcohol precipitation, or an equivalent method, e.g., as described herein). In some embodiments, the mRNA is purified using a chromatography-based method, such as an HPLC-based method or an equivalent method (e.g., as described herein). In some embodiments, the mRNA is purified using both a precipitation method (e.g., LiCl precipitation) and an HPLC-based method.

Amino Lipids

In some embodiments, the smLNP composition disclosed herein can include one or more amino lipids. The terms "amino lipid" and "cationic lipid" are used interchangeably herein to include those lipids and salts thereof having one, two, three, or more fatty acid or fatty alkyl chains and a pH-titratable amino head group (e.g., an alkylamino or dialkylamino head group). In principle, there are no specific limitations concerning the amino lipids of the smLNP compositions disclosed herein. The cationic lipid is typically protonated (i.e., positively charged) at a pH below the pKa of the cationic lipid and is substantially neutral at a pH above the pKa. The cationic lipids of the disclosure can also be termed titratable cationic lipids. In some embodiments, the one or more cationic lipids include: a protonatable tertiary amine (e.g., pH-titratable) head group; alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DOTMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, y-DLen-C2-DMA, C12-200, cKK-E12, cKK-A12, cKK-O12, DLin-MC2-DMA (also known as MC2), and DLin-MC3-DMA (also known as MC3).

Helper Lipids

In some embodiments, the smLNP composition disclosed herein includes one or more one or more helper lipids. The term "helper lipid" as used herein refers to lipids that enhance transfection (e.g., transfection of the nanoparticle including the nucleic acid molecule comprising a nucleotide sequence that encodes a site-specific endonuclease). In principle, there are no specific limitations concerning the helper lipids of the smLNP compositions disclosed herein. Without being bound to any particular theory, it is believed that the mechanism by which the helper lipid enhances transfection includes enhancing particle stability. In some embodiments, the helper lipid enhances membrane fusogenicity. Generally, the helper lipid of the smLNP compositions disclosure herein can be any helper lipid known in the art. Non-limiting examples of helper lipids suitable for the compositions and methods of the disclosure include steroids, sterols, and alkyl resorcinols. Particularly helper lipids suitable for use in the present disclosure include, but are not limited to, saturated phosphatidylcholine (PC) such as distearoyl-PC (DSPC) and dipalymitoyl-PC (DPPC), dioleoylphosphatidylethanolamine (DOPE), 1,2-dilinoleoyl-sn-glycero-3-phosphocholine (DLPC), cholesterol, 5-heptadecylresorcinol, and cholesterol hemisuccinate. In some embodiments, the helper lipid of the smLNP composition includes cholesterol.

Structural Lipids

In some embodiments, the smLNP composition disclosed herein can include one or more structural lipids. As used herein, the term "structural lipid" refers to sterols and also to lipids containing sterol moieties. Without being bound to any particular theory, it is believed that the incorporation of structural lipids in the smLNP of the disclosure may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is cholesterol.

In some embodiments, the amount of the structural lipid (e.g., n sterol such as cholesterol) in the smLNP composition disclosed herein ranges from about 10 mol % to about 80 mol %, from about 20 mol % to about 70 mol %, from about 30 mol % to about 60 mol %, or from about 40 mol % to about 50 mol %. In some embodiments, the amount of the structural lipid in the smLNP composition disclosed herein ranges from about 25 mol % to about 30 mol %, from about 30 mol % to about 35 mol %, or from about 35 mol % to about 40 mol %. In some embodiments, the amount of the structural lipid (e.g., a sterol such as cholesterol) in the lipid composition disclosed herein is about 24 mol %, about 29 mol %, about 34 mol %, or about 39 mol %. In some embodiments, the amount of the structural lipid in the smLNP composition disclosed herein is at least about 10, 20, 25, 30, 35, 40, 45, 50, 55, 60, 65, 70, 75, or 80 mol %.

Phospholipids

In some embodiments, the smLNP composition disclosed herein includes one or more phospholipids. In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof Ionizable Lipids In some embodiments, the smLNP composition disclosed herein includes one or more one or more ionizable lipids. In principle, there are no specific limitations concerning the ionizable lipids of the smLNP compositions disclosed herein. In some embodiments, the one or more ionizable lipids are selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3 ü )-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3 ü )-cholest-5-en-3-yloxy]octyl}oxy)-N,N-dimethyl-3-[(9Z, 12Z)-octadeca-9,12-dien-1-yloxy]propan-1-amine (Octyl-CLinDMA (2R)), and (2S)-2-({8-[(3 ü )-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)).

PEG-Lipids

In some embodiments, the smLNP composition disclosed herein includes one or more polyethylene glycol (PEG) lipid. The term "PEG-lipid" refers to polyethylene glycol (PEG)-modified lipids. Such lipids are also referred to as PEGylated lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. For example, a PEG lipid can be PEG-c-DOMG, PEG-DMG, PEG-DLPE, PEG-DMPE, PEG-DPPC, or a PEG-DSPE lipid. In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In some embodiment, the PEG-lipid is PEG2k-DMG. In some embodiments, the one or more PEG lipids of the smLNP composition includes PEG-DMPE. In some embodiments, the one or more PEG lipids of the smLNP composition includes PEG-DMG.

In some embodiments, the amount of PEG-lipid in the smLNP composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %. In some embodiments, the amount of PEG-lipid in the lipid composition disclosed herein is about 2 mol %. In some embodiments, the amount of PEG-lipid in the lipid composition disclosed herein is about 1.5 mol %.

In some embodiments, the amount of PEG-lipid in the smLNP composition disclosed herein is at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6 mol %. PEG-lipids are known in the art, for which additional information can be found in, for example, U.S. Pat. No. 8,158,601 and International Publ. No. WO 2015/130584 A2.

In some particular embodiments, the smLNP compositions described herein include the following lipids: a C12-200 amino lipid; a 1,2-dioleoyl-sn-glycero-3-phosphoethanolamine (DOPE); a cholesterol; and a PEG-DMPE. In some embodiments, the LNP compositions described herein include the following lipids: DLin-M-C3-DMA (also known as MC3), 1,2-dimyristoyl-sn-glycerol methoxypolyethylene glycol (PEG-DMG), and/or 1,2-distearoyl-sn-glycero-3-phosphocholine (DSPC).

The ratio between the lipid components and the nucleic acid molecule encoding a site-specific endonuclease of the smLNP compositions disclosed herein can range from about 10:1 to about 100:1 (wt/wt), such as for example from 10:1 to about 90:1, from 20:1 to about 80:1, from 30:1 to about 70:1, from 40:1 to about 60:1, or from 10:1 to about 50:1, such as for example from 10:1 to about 45:1, from 15:1 to about 40:1, from 20:1 to about 35:1, from 25:1 to about 30:1, or from 10:1 to about 40:1, from 15:1 to about 50:1, from 20:1 to about 30:1, or from 10:1 to about 30:1. In some embodiments, the ratio between the lipid components and the nucleic acid molecule encoding a site-specific endonuclease is about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1. In some embodiments, the wt/wt ratio of the lipid components and the nucleic acid molecule encoding a site-specific endonuclease is about 20:1 or about 15:1.

In some embodiments, the smLNP composition disclosed herein can contain more than one nucleic acid molecules each encoding a site-specific endonuclease. For example, a pharmaceutical composition disclosed herein can contain two or more nucleic acid molecules (e.g., RNA, e.g., mRNA) each encoding a site-specific endonuclease. In some embodiments, the smLNP compositions described herein can include nucleic acid molecules (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In some embodiments, the lipid nanoparticles described herein include the nucleic acid molecule in a concentration from approximately 0.1 mg/mL to 2 mg/mL such as, but not limited to, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL or greater than 2.0 mg/mL.

Preparation of LNPs

The lipid nanoparticles of the present disclosure, in which a nucleic acid molecule (e.g., a mRNA) is entrapped within the lipid portion of the particle and is protected from degradation, can be formed by any method known in the art including, but not limited to, a continuous mixing method, a direct dilution process, and an in-line dilution process. Additional techniques and methods suitable for the preparation of the lipid nanoparticles described herein include coacervation, microemulsions, supercritical fluid technologies, phase-inversion temperature (PIT) techniques.

In some embodiments, the smLNPs of the present disclosure are produced via a continuous mixing method, e.g., a process that includes providing an aqueous solution comprising a nucleic acid molecule (e.g., a mRNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid molecule within the lipid vesicle. This process and the apparatus for carrying out this process are known in the art. More information in this regard can be found in, for example, U.S. Patent Publication No. 20040142025, the disclosure of which is herein incorporated by reference. The action of continuously introducing lipid and buffer solutions into a mixing environment, such as in a mixing chamber, causes a continuous dilution of the lipid solution with the buffer solution, thereby producing a lipid vesicle substantially instantaneously upon mixing. By mixing the aqueous solution comprising a nucleic acid molecule with the organic lipid solution, the organic lipid solution undergoes a continuous stepwise dilution in the presence of the buffer solution (e.g., aqueous solution) to produce a nucleic acid-lipid particle.

In some embodiments, the smLNPs of the present disclosure are produced via a direct dilution process that includes forming a lipid vesicle (e.g., liposome) solution and immediately and directly introducing the lipid vesicle solution into a collection vessel containing a controlled amount of dilution buffer. In some embodiments, the collection vessel includes one or more elements configured to stir the contents of the collection vessel to facilitate dilution. In some embodiments, the amount of dilution buffer present in the collection vessel is substantially equal to the volume of lipid vesicle solution introduced thereto.

In some embodiments, the smLNPs of the present disclosure are produced via an in-line dilution process in which a third reservoir containing dilution buffer is fluidly coupled to a second mixing region. In these embodiments, the lipid vesicle (e.g., liposome) solution formed in a first mixing region is immediately and directly mixed with dilution buffer in the second mixing region. These processes and the apparatuses for carrying out direct dilution and in-line dilution processes are known in the art. More information in this regard can be found in, for example, U.S. Patent Publication No. 20070042031, the disclosure of which is herein incorporated by reference.

Physicochemical Properties of the smLNPs of the Disclosure

In some embodiments, the smLNPs of the smLNP composition disclosed herein have a lower rate of change in a physicochemical property as compared to LNPs of a reference LNP composition comprising a nucleic acid molecule comprising a nucleotide sequence encoding a site-specific endonuclease, wherein the nucleic acid molecule is greater than about 4 kb. In some embodiments, the rate of change in the physicochemical property of the smLNPs of the smLNP composition as disclosed herein is at least about 5% less than the corresponding rate of the LNPs of the reference LNP composition. In some embodiments, the rate of change in the physicochemical property of the smLNPs of the smLNP composition as disclosed herein is at least about 5% less, at least about 10%, at least about 20%, at least about 30%, at least about 40%, at least about 50%, at least about 60%, at least about 70%, at least about 80%, at least about 90%, or at least about 100% less than the corresponding rate of the LNPs of the reference LNP composition. In some embodiments, the change in a physicochemical property is a rate of degradation of the smLNPs of the smLNP composition as determined by the concentration and/or size of the smLNPs in the smLNP composition over time. In some embodiments, the rate of degradation of the smLNPs of the smLNP composition as disclosed herein is at least about 5% less than the corresponding rate of the LNPs of the reference LNP composition. In some embodiments, the rate of degradation of the smLNPs of the smLNP composition as disclosed herein is at least about 5% less, at least about 10%, at least about 20%, at least about 30%, at least about 40%, at least about 50%, at least about 60%, at least about 70%, at least about 80%, at least about 90%, or at least about 100% less than the corresponding rate of the LNPs of the reference LNP composition.

Functional Performance of the LNPs of the Disclosure

In some embodiments, the smLNPs of the smLNP composition disclosed herein have a lower rate of decrease in functional performance as compared to that of a reference LNP composition comprising a nucleic acid molecule comprising a nucleotide sequence encoding a site-specific endonuclease, wherein the nucleic acid molecule is greater than about 4 kb. In some embodiments, the rate of decrease in functional performance of the smLNPs of the smLNP composition as disclosed herein is at least about 5% less than the corresponding rate of the LNPs of the reference LNP composition. In some embodiments, the rate of decrease in functional performance of the smLNPs of the smLNP composition as disclosed herein is at least about 5% less, at least about 10%, at least about 20%, at least about 30%, at least about 40%, at least about 50%, at least about 60%, at least about 70%, at least about 80%, at least about 90%, or at least about 100% less than the corresponding rate of the LNPs of the reference LNP composition.

In some embodiments, the rate of decrease in functional performance is determined by the genome editing efficiency of the smLNPs containing the site-specific endonuclease. In some embodiments, the editing efficiency of the smLNPs of the smLNP composition as disclosed herein is at least about 5% less than the corresponding efficiency of the LNPs of the reference LNP composition. In some embodiments, the editing efficiency of the smLNPs of the smLNP composition as disclosed herein is at least about 5% less, at least about 10%, at least about 20%, at least about 30%, at least about 40%, at least about 50%, at least about 60%, at least about 70%, at least about 80%, at least about 90%, or at least about 100% less than the corresponding efficiency of the LNPs of the reference LNP composition.

In some embodiments, the smLNPs of the smLNP composition disclosed herein have an average particle diameter larger than that of LNPs of a reference LNP composition comprising a nucleic acid molecule comprising a nucleotide sequence encoding a site-specific endonuclease, wherein the nucleic acid molecule is greater than about 4.0 kb. In some embodiments, the smLNPs of the smLNP composition disclosed herein have an average particle diameter that is at least about 10%, at least about 15%, at least about 20%, at least about 25%, at least about 30%, at least about 40%, at least about 50%, at least about 60%, at least about 70%, at least about 80%, or at least about 90% larger than the average particle diameter of LNPs in the reference LNP composition.

Pharmaceutical Compositions

In one aspect, an smLNP as described herein is incorporated into a composition, for example, a pharmaceutical composition. Such compositions typically include an smLNP and a pharmaceutically acceptable carrier. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., anticancer agents) can also be incorporated into the compositions. Accordingly, some embodiments of the disclosure relate to a pharmaceutical composition comprising an smLNP composition described herein and a pharmaceutically acceptable carrier.

Some embodiments of the disclosure relate to a pharmaceutical composition comprising an smLNP composition described herein for use in delivering a biomolecule, such as a site-specific endonuclease or a nucleic acid molecule encoding same, into a target cell. In a related aspect, some embodiments of the disclosure relate to a pharmaceutical composition comprising an smLNP composition described herein for use in editing the genome of a cell. In yet a related aspect, some embodiments of the disclosure provide an smLNP or a composition, e.g., a pharmaceutical composition, for use in treating a health condition or disease in a mammal, e.g., a human.

Methods of the Disclosure

Once formed, the smLNPs of the disclosure are particularly useful for the introduction of a nucleic acid molecule comprising, for example, a nucleotide sequence encoding a site-specific endonuclease into a cell or cells in a subject or organism. Accordingly, some embodiments of the present disclosure relate to a method for delivering a nucleic acid molecule into a cell, the method including contacting the cell with an smLNP composition or a pharmaceutical composition as disclosed herein, wherein the LNP composition includes the nucleic acid molecule. The method can be carried out in vitro or in vivo by first forming the smLNPs as described above and then contacting the smLNPs with the cells for a period of time sufficient for delivery of nucleic acid molecule to the cells to occur.

In some embodiments, the method includes administering an smLNP or a pharmaceutical composition disclosed herein under conditions suitable for delivery of the biologically active molecule component, e.g., nucleic acid molecule, to the cell or cells of the subject or organism. In some embodiments, the smLNP or pharmaceutical composition is contacted with the cell or cells of the subject or organism as is generally known in the art, such as via parental administration (e.g., intravenous, intramuscular, subcutaneous administration) of the formulated molecular composition with or without excipients to facilitate the administration.

In another aspect, some embodiments of the present disclosure relate to a method for editing a genome of a cell, the method including providing to the cell an smLNP composition or a pharmaceutical composition as disclosed herein. In some embodiments, the smLNPs or compositions disclosed herein improves gene editing efficiency in the host cell or organism. In some embodiments, the LNP composition of the disclosure confers a gene editing efficiency that is greater than that of a reference LNP composition including a nucleic acid molecule which includes a nucleotide sequence encoding a site-specific endonuclease, wherein the nucleic acid molecule is greater than about 4 kb. In some embodiments, the editing efficiency of the smLNP composition is at least about 5% greater than that of the reference LNP composition. In some embodiments, the editing efficiency of the smLNP composition is at least about 5%, at least about 10%, at least about 20%, at least about 30%, at least about 40%, at least about 50%, at least about 60%, at least about 70%, at least about 80%, at least about 90%, or at least about 100% greater than that of the reference LNP composition. In some embodiments, the editing efficiency of the smLNP composition is at least two-fold, at least three-fold, at least four-fold, at least five-fold, at least six-fold, or at least seven-fold greater than that of the reference LNP composition. In some embodiments, the editing efficiency of the smLNP composition is at least eight-fold, at least nine-fold, or at least ten-fold greater than that of the reference LNP composition.

The methods of the present disclosure can be practiced in a variety of host cells and organisms. Suitable hosts include animal species, including mammalian species, such as primates (e.g., humans and chimpanzees as well as other nonhuman primates), canines, felines, equines, bovines, bovines, rodents (e.g., rats and mice), lagomorphs, and swine. In some embodiments of the methods disclosed herein, the host cell is a mammalian cell. In some embodiments, the mammalian cell is a human cell, a murine cell, or a non-human primate cell.

Methods of Treatment

In one aspect, some embodiments of the disclosure relate to methods for treating, preventing, reducing the risk or likelihood of developing (e.g., reducing the susceptibility to), delaying the onset of, and/or ameliorating one or more symptoms associated with a health condition or a disease in a mammal (e.g., human) in need thereof, the method including administering to the mammal a therapeutically effective amount of an smLNP composition comprising a nucleic acid molecule encoding a site-specific endonuclease as described herein that target a gene of interest.

The terms "administration" and "administering," as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof. The term includes, but is not limited to, administering by a medical professional and self-administering.

In some embodiments, the health condition or a disease is hemophilia A. In some embodiments, the health condition or a disease is a cardiovascular disease.

Hemophilia A

Some embodiments of the disclosure relate to methods for treating, preventing, reducing the risk or likelihood of developing, delaying the onset of, and/or ameliorating one or more symptoms associated with a health condition or a disease in a mammal (e.g., human) in need thereof, wherein the health condition or a disease is hemophilia A.

Hemophilia A (HemA) is caused by a genetic defect in the Factor VIII (FVIII) gene that results in low or undetectable levels of FVIII protein in the blood. This results in ineffective clot formation at sites of tissue injury frequently leading to joint damage and hemarthropathy over time. Other potentially severe bleeding issues include intercranial hemorrhage and potentially uncontrolled bleeding which can be fatal if not treated.

The FVIII gene is expressed primarily in sinusoidal endothelial cells that are present in the liver as well as other sites in the body. Exogenous FVIII can be expressed in and secreted from the hepatocytes of the liver generating FVIII in the circulation and thus affecting a cure of the disease.

Rationale for Addressing Hemophilia A Disease by Genome Editing

Although a number of gene therapy approaches are currently in development or the clinic, they have undesirable features. Virus-based gene therapy using Adeno Associated Virus (AAV) has shown promise in pre-clinical animal models and in patients, it has a number of disadvantages. AAV-based gene therapy uses a FVIII gene driven by a liver specific promoter that is encapsulated inside an AAV virus capsid (typically using the serotypes AAV5, AAV8, AAV9, or AAVrh10, among others). All AAV viruses used for gene therapy deliver the packaged gene cassette into the nucleus of the transduced cells where the gene cassette remains almost exclusively episomal and it is the episomal copies of the therapeutic gene that give rise to the therapeutic protein. AAV does not have a mechanism to integrate its encapsulated DNA into the genome of the host cells but instead is maintained as an episome that is therefore not replicated when the host cell divides. Episomal DNA can also be subject to degradation over time. It has been demonstrated that when liver cells containing AAV episomes are induced to divide, the AAV genome is not replicated but is instead diluted. As a result, AAV based gene therapy is not expected to be effective when given to children whose livers have not yet achieved adult size. In addition, it is currently unknown how long a AAV based gene therapy will persist when given to adult humans, although animal data have demonstrated only small losses in therapeutic effect over periods as long as 10 years. A permanent cure for HemA is highly desirable, especially if FVIII levels within the normal range can be achieved. However, currently available treatments for HemA have a number of limitations. For example, replacement of the missing FM protein is an effective treatment for HemA patients and is the current standard of care. However, protein replacement therapy requires frequent intravenous injection of FVIII protein which is inconvenient in adults, problematic in children, cost prohibitive, and can result in break through bleeding events if the treatment regimen is not closely followed. In another example, a novel bi-specific antibody Hemlibra® has recently been approved and represents the first antibody based therapeutic to treat HemA. This molecule functions as a FVIIIa mimic and can be delivered subcutaneously with a potential treatment duration of 1 month. During the clinical trial there were fatalities when Hemlibra® was combined with FEIBA bypassing agents to treat breakthrough bleeds. Additionally there has been a recent report of anti-drug antibodies in one patient.

Therefore, there is a critical need for developing new effective and permanent treatments for HemA, which can be achieved through genome editing. Applicant contemplates performing experiments to target genome editing at the human albumin locus. Human Albumin intron 1-Albumin, which is located on chromosome 4q13.3, is an abundant liver protein expressed from hepatocytes and is the most highly expressed protein found in plasma. Without being bound to any particular theory, it is believed that targeted integration into 1% of albumin genes would not impact albumin expression levels while providing enough expression of FVIII to normalize activity.

In some embodiments, the smLNP compositions in accordance with some embodiments of the disclosure is deployed for the insertion of FVIII gene in liver hepatocytes. In these instances, the smLNP compositions are preferentially taken up by liver cells (e.g., hepatocytes). In some embodiments, the smLNP compositions used in a method of treating hemophilia A are biodegradable, in that they do not accumulate to cytotoxic levels in vivo at a therapeutically effective dose. In some embodiments, the smLNP compositions used in a method of treating hemophilia A do not cause an innate immune response that leads to substantial adverse effects at a therapeutic dose level. In some embodiments, the smLNP compositions do not cause toxicity at a therapeutic dose level. In some embodiments, the smLNP compositions disclosed herein specifically bind to apolipoproteins such as apolipoprotein E (ApoE) in the blood. Apolipoproteins are proteins circulating in plasma that are key in regulating lipid transport. ApoE represents one class of apolipoproteins which interacts with cell surface heparin sulfate proteoglycans in the liver during the uptake of lipoprotein.

Cardiovascular Disease

Some embodiments of the disclosure relate to methods for treating, preventing, reducing the risk or likelihood of developing, delaying the onset of, and/or ameliorating one or more symptoms associated with a health condition or a disease in a mammal (e.g., human) in need thereof, wherein the health condition or a disease is a cardiovascular disease.

High levels of the lipoprotein particle, Lp(a), are associated with the cardiovascular disease, or risk of developing a cardiovascular disease. For example, high plasma level of Lp(a) is an independent risk factor for calcific aortic valve disease, coronary heart disease, atherosclerosis, thrombosis, and stroke. Of interest is the range of plasma Lp(a) levels in humans, which vary by 1000-fold between individuals. This broad range suggests that it may not be detrimental to significant reduce plasma Lp(a) and therefore potential anti-Lp(a) drugs may have a wide therapeutic window.

Due to the scarcity of treatments to reliably and stably lower Lp(a) levels, a therapy that permanently lowers Lp(a) levels is highly desirable. As hepatocytes are the main source of apo(a), a gene editing approach directed at the liver for "targeted knockout" of apo(a) would be an attractive approach.

Unlike LDL, Lp(a) levels cannot be modulated by environment, diet, or existing lipid lower drugs like statins, making it a strictly genetically-driven disease risk factor. Antisense oligonucleotides against apo(B) were able to reduce Lp(a) by 25% (Santos et al., Arterioscler Thromb Vasc Biol. 2015 March; 35(3): 689-699). Subsequently, an antisense therapy specifically against the apo(a) mRNA has been tested in clinical trials and was shown to significantly decrease plasma Lp(a) levels by over 80% (Viney et al., Lancet 2016; 388: 2239-53). Unfortunately, antisense therapies require frequent dosing to be efficacious.

Therefore, there is a critical need for developing new effective and permanent treatments for cardiovascular disease, which is able to be achieved through genome editing. In some embodiments of the disclosure, Applicant contemplates performing experiments to target genome editing at the human Lipoprotein(a) (LPA) locus, which is located on chromosome 6q25.3-q26. Lipoprotein(a) is an atherogenic lipoprotein consisting of the protein apolipoprotein(a) [apo (a)] covalently bound to the apolipoprotein B-100 (apoB) component of a low-density lipoprotein (LDL) particle. The apo(a) protein is encoded by the LPA gene, made in hepatocytes and gets secreted into circulation. The pathogenic mechanisms of Lp(a) are mediated through its pro-atherogenic, proinflammatory, and pro-thrombogenic properties. The combination of apo(a) and the LDL components of Lp(a) result in compounding effects on the cardiovascular system. LDL alone can cause immune and inflammatory responses that characterize atherosclerosis through the entry of LDL into vessel walls where the phospholipids become oxidized. Lp(a) circulates and binds to oxidized phospholipids in the plasma, which causes proinflammatory responses. Apo(a) itself contains sites that can bind to exposed surfaces on damaged vessel walls, mediating its entry and accumulation at those locations. Small isoforms of apo(a) have been shown to promote thrombosis by inhibiting fibrinolysis. In some embodiments, LNP compositions in accordance with some embodiments of the disclosure is designed for the deletion of LPA gene in liver hepatocytes.

Implementations of embodiments of the methods of the disclosure can include one or more of the following features.

"Administration" and "administering," as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof. The term includes, but is not limited to, administering by a medical professional and self-administering. Accordingly, in some embodiments of the methods disclosed herein, the LNPs or compositions (e.g., a pharmaceutical composition) described herein are administered by one of the following routes of administration: oral, intranasal, intravenous, intraperitoneal, intramuscular, intra-articular, intralesional, intratracheal, subcutaneous, and intradermal. In some embodiments, the LNPs or compositions disclosed herein are administered systemically, e.g., via enteral or parenteral routes of administration.

The smLNPs or compositions disclosed herein are typically formulated to be compatible with its intended route of administration. The smLNPs and compositions of the disclosure is given orally or by inhalation, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Dosage, toxicity and therapeutic efficacy of such subject smLNPs or compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects is used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the disclosure, the therapeutically effective dose can be estimated initially from cell culture assays. A dose is formulated in animal models to achieve a circulating plasma concentration range that includes the $IC_{50}$ (e.g, the concentration of the test compound which achieves a half-maximal inhibition of symptoms) as determined in cell culture. Such information can be used to more accurately determine useful doses in humans. Levels in plasma is measured, for example, by high performance liquid chromatography.

As defined herein, a "therapeutically effective amount" of a subject smLNP or composition of the disclosure (e.g, an effective dosage) depends on the LNP or composition selected. For instance, single dose amounts in the range of approximately 0.001 to 0.1 mg/kg of patient body weight can be administered; in some embodiments, about 0.005, 0.01, 0.05 mg/kg is administered. In some embodiments, 600,000 IU/kg is administered (IU can be determined by a lymphocyte proliferation bioassay and is expressed in International Units (IU) as established by the World Health Organization 1st International Standard for Interleukin-2 (human)). The smLNPs or compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the subject smLNPs or compositions of the disclosure can include a single treatment or, can include a series of treatments. In some embodiments, the compositions are administered every 8 hours for five days, followed by a rest period of 2 to 14 days, e.g., 9 days, followed by an additional five days of administration every 8 hours.

In some embodiments, the smLNP composition is formulated for in vivo delivery. In some embodiments, the smLNP composition is formulated for ex vivo delivery. The LNPs of the disclosure can be adsorbed to almost any cell type with which they are mixed or contacted. Once adsorbed, the smLNPs can be endocytosed by a portion of the cells, exchange lipids with cell membranes, or fuse with the cells. Transfer or incorporation of the nucleic acid molecule portion of the particle can take place via any one of these pathways. In particular, when fusion takes place, the particle membrane is integrated into the cell membrane and the contents of the particle combine with the intracellular fluid.

In Vivo Administration

Systemic delivery for in vivo delivery of a nucleic acid molecule encoding a site-specific nuclease as described herein, to a distal target cell via body systems such as the circulation, can be achieved using smLNP compositions disclosed herein. Additionally, one or more nucleic acid molecules can be administered alone in the smLNP compositions of the disclosure, or in combination (e.g., co-administered) with one or more additional smLNP compositions comprising peptides, polypeptides, or small molecules such as conventional drugs.

For in vivo administration, administration can be in any manner known in the art, e.g., by injection, oral administration, inhalation (e.g., intranasal or intratracheal), transdermal application, or rectal administration. In vivo administration can be accomplished via single or divided doses. The smLNP compositions can be administered parenterally, i.e., intraarticularly, intravenously, intraperitoneally, subcutaneously, or intramuscularly. In some embodiments, the smLNP composition is administered intravenously or intraperitoneally by a bolus injection. In some embodiments, the smLNP compositions of the disclosure are administered parenterally or intraperitoneally. In addition or alternatively, the smLNP compositions of the present disclosure, either alone or in combination with other suitable components, can be made into aerosol formulations (i.e., they can be "nebulized") to be administered via inhalation (e.g., intranasally or intratracheally). Aerosol formulations can be placed into pressurized acceptable propellants, such as dichlorodifluoromethane, propane, nitrogen, and the like.

One skilled in the art will appreciate that the amount of particles administered will depend upon the ratio of nucleic acid molecules to lipid, the particular nucleic acid molecule used, but will generally be between about 0.01 and about 50 mg per kilogram of body weight, preferably between about 0.1 and about 5 mg/kg of body weight, or about 10-10 particles per administration (e.g., injection).

Ex Vivo Administration

For ex vivo applications, the delivery of smLNP compositions of the present disclosure can be administered to any cell grown in culture. In some embodiments, the cells are animal cells, more preferably mammalian cells, and most preferably human cells. Contact between the cells and the smLNPs, when carried out ex vivo, takes place in a biologically compatible medium. The concentration of smLNPs in the smLNP compositions varies depending on the particular application, but is generally between about 1 µmol and about 10 mmol. Treatment of the cells with the smLNPs can be generally carried out at physiological temperatures (about 37° C.) for periods of time of from about 1 to 72 hours, preferably of from about 2 to about 5 hours, from about 2 to about 4 hours, for from about 1 to about 3 hours.

Gene-Shuffled Site-Specific Endonucleases

Gib11SpaCas9 is a synthetic RNA-guided endonuclease (RGEN) generated using homology-based gene family shuffling of sequence fragments of CRISPR-Cas9 endonucleases of four different *Staphylococcus* species (*Staphylococcus lugdunensis, Staphylococcus pasteuri, Staphylococcus microti,* and *Staphylococcus hyicus*). Briefly, the sequences of all four Cas9 endonucleases were compared to identify regions with high homology to serve as anchor points, breaking each of the Cas9 endonucleases up into 8 corresponding mini-domains. A library of gene family shuffled synthetic Cas9 endonucleases was prepared by randomly assigning each mini-domain to be derived from one of the four original Cas9 endonucleases, except for the C-terminal mini-domain, which was selected as the PAM-interacting (PI) domain from *Staphylococcus lugdunensis* Cas9. The resulting library had a theoretical complexity of 8192. The library was initially screened for Cas9 endonuclease activity using a bacterial live/dead assay, and candidate synthetic Cas9 endonucleases were further screened using a BFP disruption assay in HEK cells. This resulted in the identification of Gib11Cas9 as a candidate synthetic Cas9 endonuclease having high Cas9 endonuclease activity. Gib11SpaCas9 was generated by replacing a C-terminal portion of Gib11Cas9 comprising the PI domain with a polypeptide comprising the PI domain from *Staphylococcus pasteuri*.

F8Cas9 is a synthetic RNA-guided endonuclease (RGEN) generated using homology-based gene family shuffling of sequence fragments of CRISPR-Cas9 endonucleases of four different *Staphylococcus* species (*Staphylococcus lugdunensis, Staphylococcus pasteuri, Staphylococcus microti,* and *Staphylococcus hyicus*). Briefly, the sequences of all four Cas9 endonucleases were compared to identify regions with high homology to serve as anchor points, breaking each of the Cas9 endonucleases up into 12 corresponding mini-domains. A library of gene family shuffled synthetic Cas9 endonucleases was prepared by randomly assigning each mini-domain to be derived from one of the four original Cas9 endonucleases, except for the C-terminal mini-domain, which was selected as the PAM-interacting (PI) domain from *Staphylococcus lugdunensis* Cas9. The resulting library had a theoretical complexity of $1.3 \times 10^5$. The library was initially screened for Cas9 endonuclease activity using a bacterial live/dead assay, and candidate synthetic Cas9 endonucleases were further screened using a BFP disruption assay in HEK cells. This resulted in the identification of F8Cas9 as a candidate synthetic Cas9 endonuclease having high Cas9 endonuclease activity.

E2Cas9 is a synthetic RNA-guided endonuclease (RGEN) generated using homology-based gene family shuffling of sequence fragments of CRISPR-Cas9 endonucleases of four different *Staphylococcus* species (*Staphylococcus lugdunensis, Staphylococcus pasteuri, Staphylococcus microti,* and *Staphylococcus hyicus*). Briefly, the sequences of all four Cas9 endonucleases were compared to identify regions with high homology to serve as anchor points, breaking each of the Cas9 endonucleases up into 8 corresponding mini-domains. A library of gene family shuffled synthetic Cas9 endonucleases was prepared by randomly assigning each mini-domain to be derived from one of the four original Cas9 endonucleases, except for the C-terminal mini-domain, which was selected as the PAM-interacting (PI) domain from *Staphylococcus lugdunensis* Cas9. The resulting library had a theoretical complexity of 8192. The library was initially screened for Cas9 endonuclease activity using a bacterial live/dead assay, and candidate synthetic Cas9 endonucleases were further screened using a BFP disruption assay in HEK cells. This resulted in the identification of E2Cas9 as a candidate synthetic Cas9 endonuclease having high Cas9 endonuclease activity.

P2H12Cas9 is a synthetic RNA-guided endonuclease (RGEN) generated using homology-based gene family shuffling of sequence fragments of CRISPR-Cas9 endonucleases of four different *Staphylococcus* species (*Staphylococcus lugdunensis, Staphylococcus pasteuri, Staphylococcus microti,* and *Staphylococcus hyicus*). Briefly, the sequences of all four Cas9 endonucleases were compared to identify regions with high homology to serve as anchor points, breaking each of the Cas9 endonucleases up into 8 corresponding mini-domains. A library of gene family shuffled synthetic Cas9 endonucleases was prepared by randomly assigning each mini-domain to be derived from one of the four original Cas9 endonucleases, except for the C-terminal mini-domain, which was selected as the PAM-interacting (PI) domain from *Staphylococcus lugdunensis* Cas9. The resulting library had a theoretical complexity of 8192. The library was initially screened for Cas9 endonuclease activity using a bacterial live/dead assay, and candidate synthetic Cas9 endonucleases were further screened using a BFP disruption assay in HEK cells. This resulted in the identification of P2H12Cas9 as a candidate synthetic Cas9 endonuclease having high Cas9 endonuclease activity.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Additional embodiments are disclosed in further detail in the following examples, which are provided by way of illustration and are not in any way intended to limit the scope of this disclosure or the claims.

Example 1: General Experimental Procedures

The practice of the present disclosure will employ, unless otherwise indicated, techniques of molecular biology, microbiology, cell biology, biochemistry, nucleic acid chemistry, and immunology, which are known to those skilled in the art. Such techniques are explained in the literature, such as, Molecular Cloning: A Laboratory Manual, fourth edition (Sambrook et al., 2012) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2014); PCR: The Polymerase Chain Reaction, (Mullis et al., eds., 1994); Beaucage et al. eds., Current Protocols in Nucleic Acid Chemistry, John Wiley & Sons, Inc., New York, 2000, (including supplements through 2014), Gene Transfer and Expression in Mammalian Cells (Makrides, ed., Elsevier Sciences B.V., Amsterdam, 2003); and Current Protocols in Immunology (Horgan K and S. Shaw (1994), including supplements through 2014). As appropriate, procedures involving the use of commercially available kits and reagents are generally carried out in accordance with manufacturer defined protocols and/or parameters unless otherwise noted.

Example 2: Characterization of Lipid-Based Nanoparticles Containing mRNA Encoding Exemplary Site-Specific Endonuclease This Example describes experiments performed to characterize physical properties of exemplary LNP compositions in accordance with some embodiments of the disclosure. In these experiments, the particle size of eleven LNP compositions each containing an mRNA molecule encoding a site-directed endonuclease was evaluated and compared with a reference LNP composition containing SpCas9-encoding mRNA. As illustrated in FIG. 1A-1E, it was observed that smCas9 mRNA-LNPs of the disclosure had slightly increased size as assayed by dynamic light scattering (DLS) (FIG. 1A). Briefly, LNPs were diluted to 1 µg/mL RNA concentration in PBS and then serially diluted by 2-fold dilutions in a 384-well plate. The samples were then analyzed using a Wyatt DynaPro Plate Reader II for z-average measurement of particle diameter.

Figure 1B:
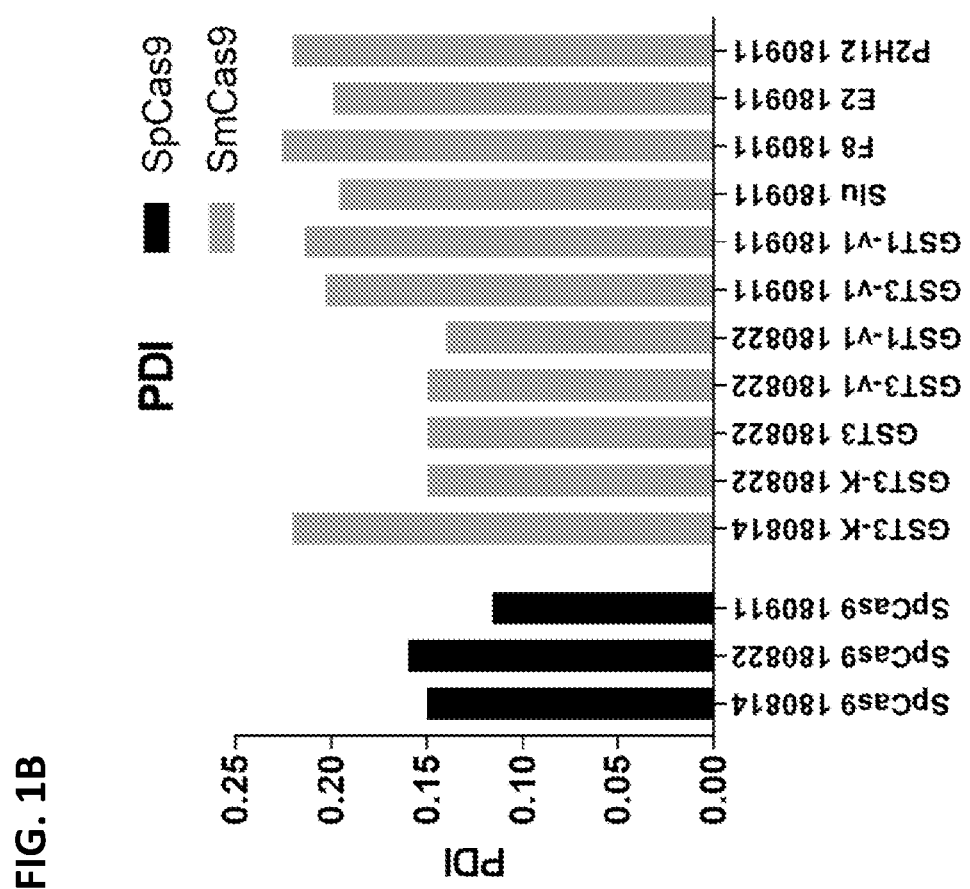
Figure 1C:
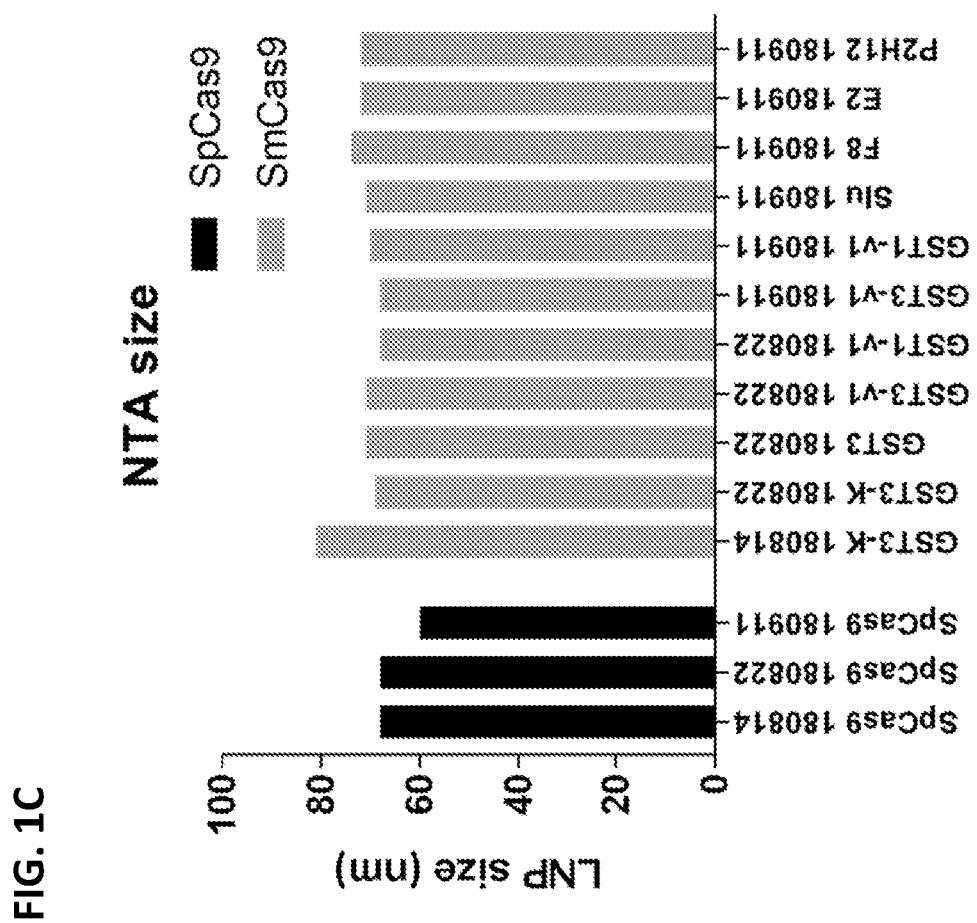
Figure 1D:
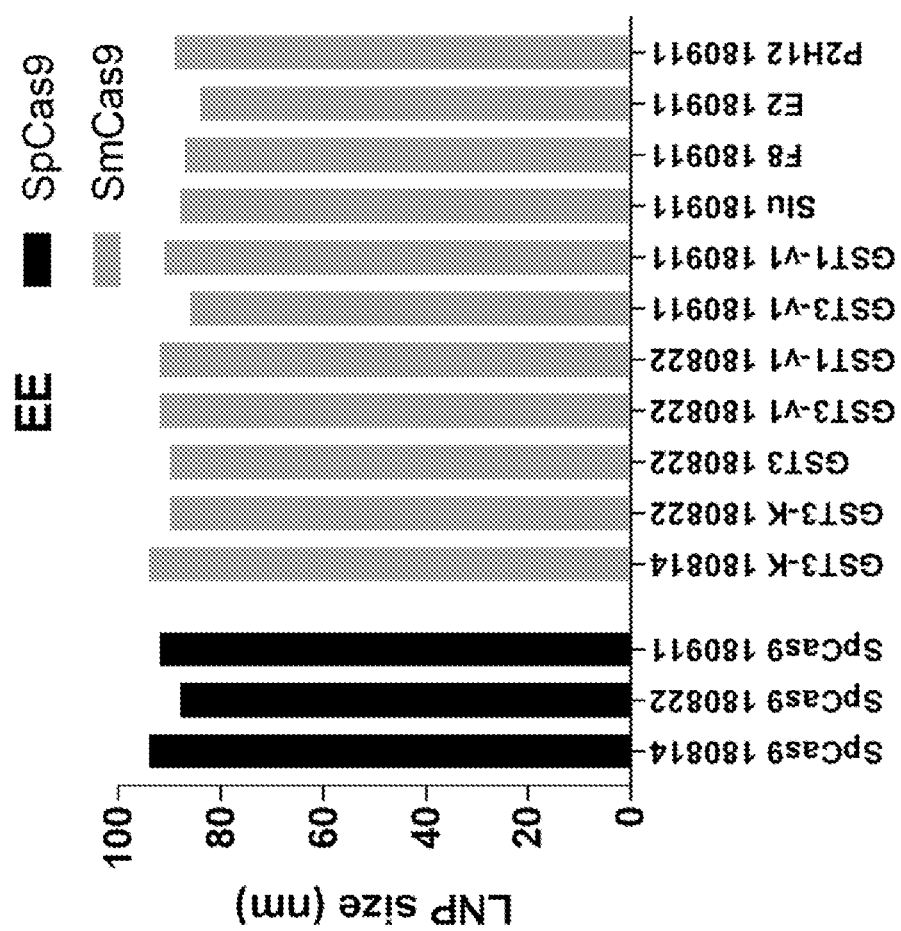
Figure 1E:
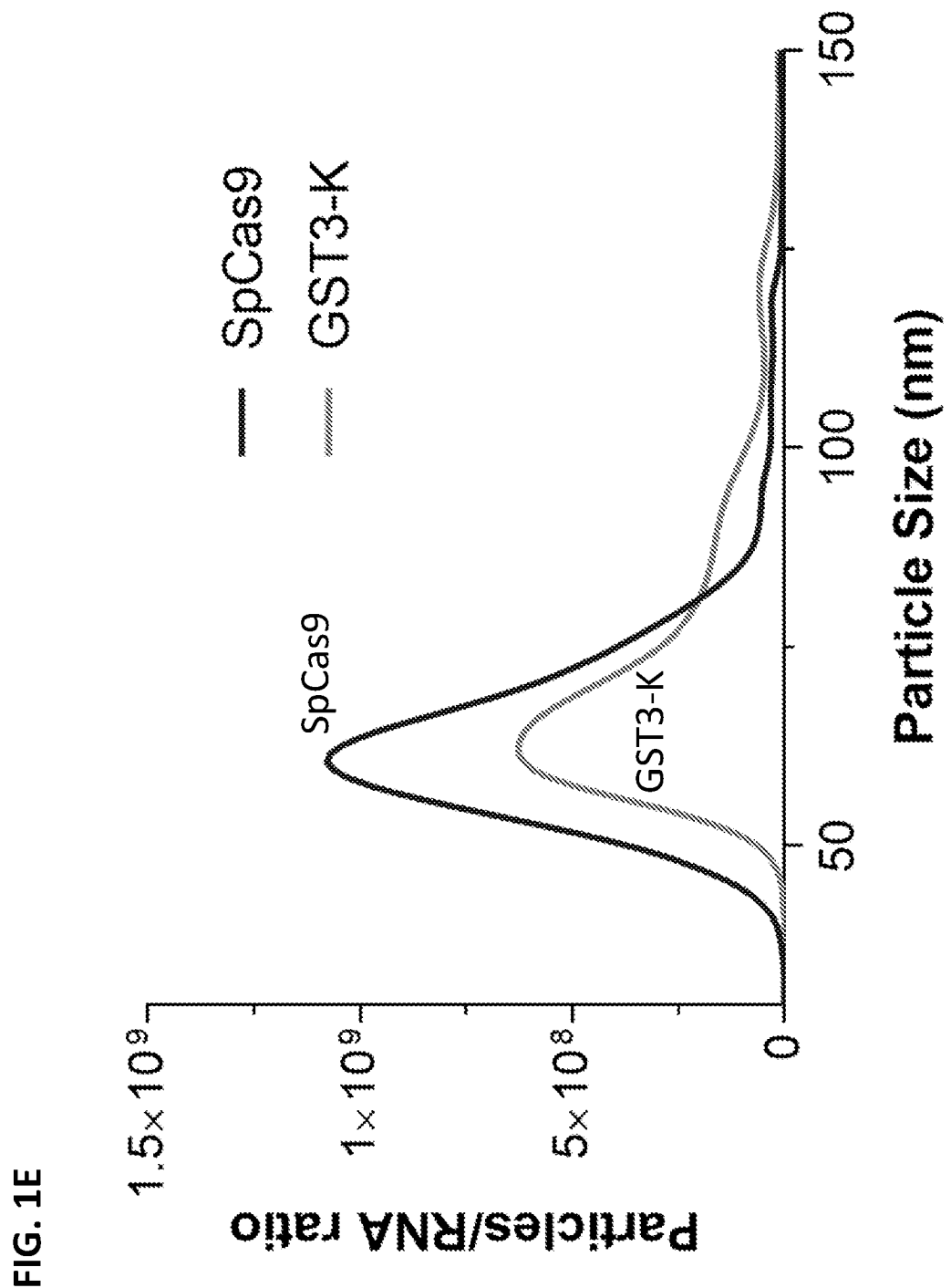

It was also observed that some smCas9 mRNA-LNPs had an increased heterogeneity of mixed LNP populations, as determined by polydispersity index (PDI), which suggests a more heterogeneous size population including some larger LNPs (FIG. 1B). LNPs were diluted to 1 µg/mL RNA concentration in PBS and then serially diluted by 2-fold dilutions in a 384-well plate. The samples were then analyzed using a Wyatt DynaPro Plate Reader II for polydispersity measurement.

Moreover, the results of nanoparticle tracking analyses (NTA) suggested a more heterogeneous size distribution for smCas9 GST3-K-LNPs, when compared to the reference SpCas9-LNPs. NTA was performed by diluting the LNPs to an appropriate working concentration in PBS and then measuring the average particle size (see FIG. 1C) of the samples using a Malvern Nanosight instrument. Further characterization of the distribution of the ratio of particles to RNA in relation with the particle size was calculated by normalizing the LNP size as measured by NTA to the concentration of encapsulated RNA as determined by Ribogreen testing, see FIG. 1E. Finally, as showed in FIG. 1D, no change in mRNA encapsulation efficiency into LNPs was observed in these experiments. Encapsulation efficiency was determined by Ribogreen analysis using Quant-iT Ribogreen RNA Assay Kit, Life Technologies Cat #R11490. Briefly, LNPs were diluted to a concentration of 1 µg/mL in the presence or absence of Triton® X-100 at 1% final dilution. Ribogreen fluorescent dye for measuring RNA content, which is non-permeable to LNPs, was then added to the samples and assessed per the manufacturer's recommendations against an appropriate standard curve. Encapsulation efficiency was calculated by subtracting the ratio of Ribogreen fluorescent signal in the samples without Triton® X-100 to that of the samples with Triton® X-100.

In Vitro Testing of smCas9 Variants in mRNA Format

Figure 2:
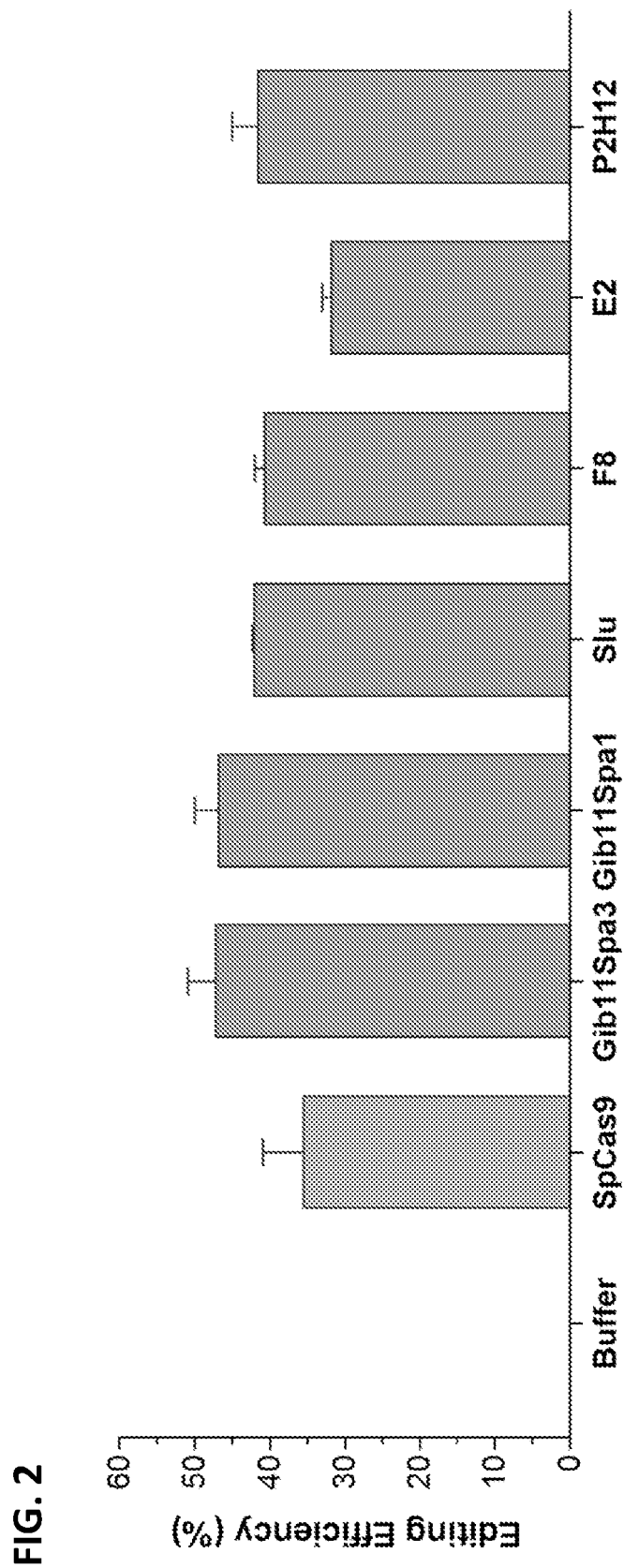
FIG. 2 graphically summarizes the results of experiments performed to evaluate the editing efficiency of various site-specific endonucleases delivered to murine cells by using a number of exemplary mRNA-LNP compositions in accordance with some embodiments of the disclosure (e.g., smLNP compositions). In these experiments, the endogenous albumin locus in murine Hepa 1-6 cells was targeted by several endonucleases, including the reference Cas9 protein from *Streptococcus pyogenes* (SpCas9), and small Cas9 variants (smCas9); Gib11Spa3, Gib11Spa1, Slu, F8, E2, and P2H12 after MessengerMAX™ transfection.

This Example describes experiments performed to assess the in vitro editing efficiency of exemplary LNP compositions in accordance with some embodiments of the disclosure. In these experiments, in vitro editing efficiency of six LNP compositions each containing an mRNA molecule encoding a site-directed endonuclease was evaluated and compared with a reference LNP composition containing SpCas9-encoding mRNA. Site-directed endonucleases used in these experiments were Gib11Spa3, Gib11Spa1, Slu, F8, E2, and P2H12 (see FIG. 2). In these experiments, the mRNA was transfected into murine Hepa 1-6 cells using the commercially available system lipofectamine MessengerMax following manufacturer's instructions (Thermo Fisher Scientific Cat #LMRNA003). The locus targeted was the albumin locus. The gRNA targeting the albumin gene that was used in all cell experiments shown was a 100-mer of the following sequence, 5'-ugcCAGUUCCCGAUCGUUACGUUUUAGUACU-CUGGAAACAGAAUCUACUGAAACAAGACAAUAU-GUCGUGUUUAUCCCAUCAAUUUAUUGGUGG-GAUuuu-3' (SEQ ID NO: 50), in which lowercase letters denote phosphorothioate linkages. Editing efficiencies were calculated by cell lysis and extraction of genomic DNA using Qiagen DNeasy Blood and Tissue Kit (Cat #69506) followed by PCR amplification of the targeted region of the albumin locus, sequencing, and TIDE analysis as described by Brinkman et al., Nucleic Acids Res. 2014 Dec. 16; 42 (22):e168. It was observed that the gene editing efficiency of the tested LNP compositions is comparable to that of the reference LNP composition. Remarkably, at least two LNP compositions comprising the site-directed endonucleases Gib11Spa3 and Gib11Spa1 appeared to have a significant superior efficiency over the reference polypeptide SpCas9.

In Vivo Testing of smCas9 Variants Delivered as mRNA-LNPs

Figure 3:
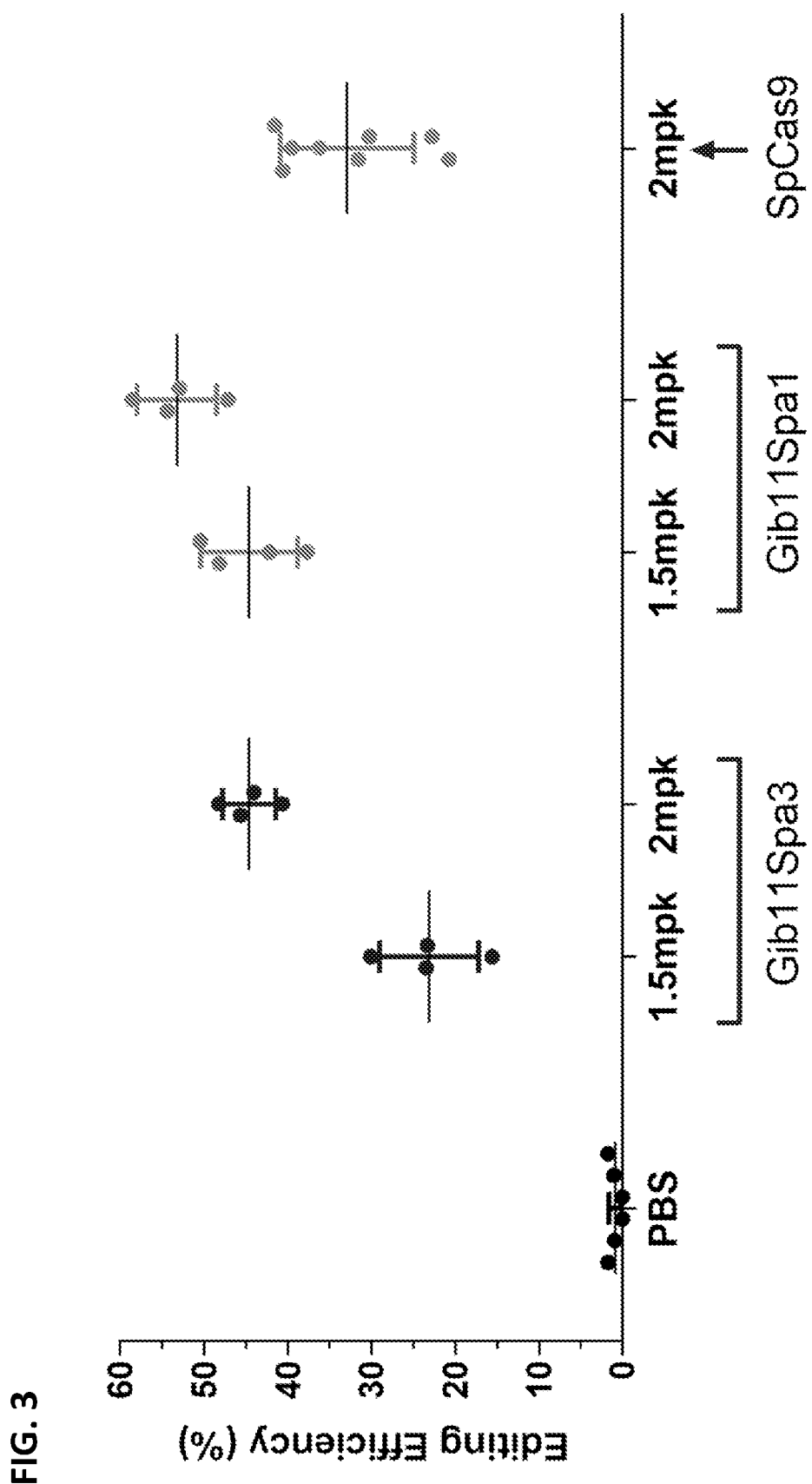
FIG. 3 graphically summarizes the results of experiments performed to demonstrate that smLNP compositions containing either Gib11Spa1 smCas9 or Gib11Spa3 smCas9 variants are more potent than LNP compositions containing SpCas9 in vivo when delivered into cells using mRNA-LNP compositions in accordance with some embodiments of the disclosure.

This Example describes experiments performed to assess the in vivo editing efficiency in C57BL/6 mice, exemplary LNP compositions in accordance with some embodiments of the disclosure. In these experiments, in vitro editing efficiency of two LNP compositions each containing an mRNA molecule encoding a site-directed endonuclease was evaluated and compared with a reference LNP composition containing SpCas9-encoding mRNA. The LNP compositions were administered to C57BL/6 mice by intravenous administration as a single dose, at different dosages. In FIG. 3, the dosages are expressed in mg of encapsulated RNA administered per kg of body weight, or "mpk." The locus targeted by this experiment is the albumin locus. It was observed that Gib11Spa3, when administered at a 1.5 mpk dose or a 2 mpk dose, had a significantly greater editing efficiency than SpCas9. Moreover, it was observed that both dosages of Gib11Spa1 (i.e., 1.5 and 2 mpk) had greater editing efficiency than the 2 mpk dose of SpCas9. Editing efficiencies for all mouse experiments were calculated by liver tissue homogenization and extraction of genomic DNA using Qiagen DNeasy Blood and Tissue Kit (Cat#69506) followed by PCR amplification of the targeted region of the albumin locus, sequencing, and TIDE analysis as described by Brinkman et al., Nucleic Acids Res. 2014 Dec. 16; 42 (22):e168.

Evaluation of mRNA Sequence and Chemistry Modifications

Figure 4:
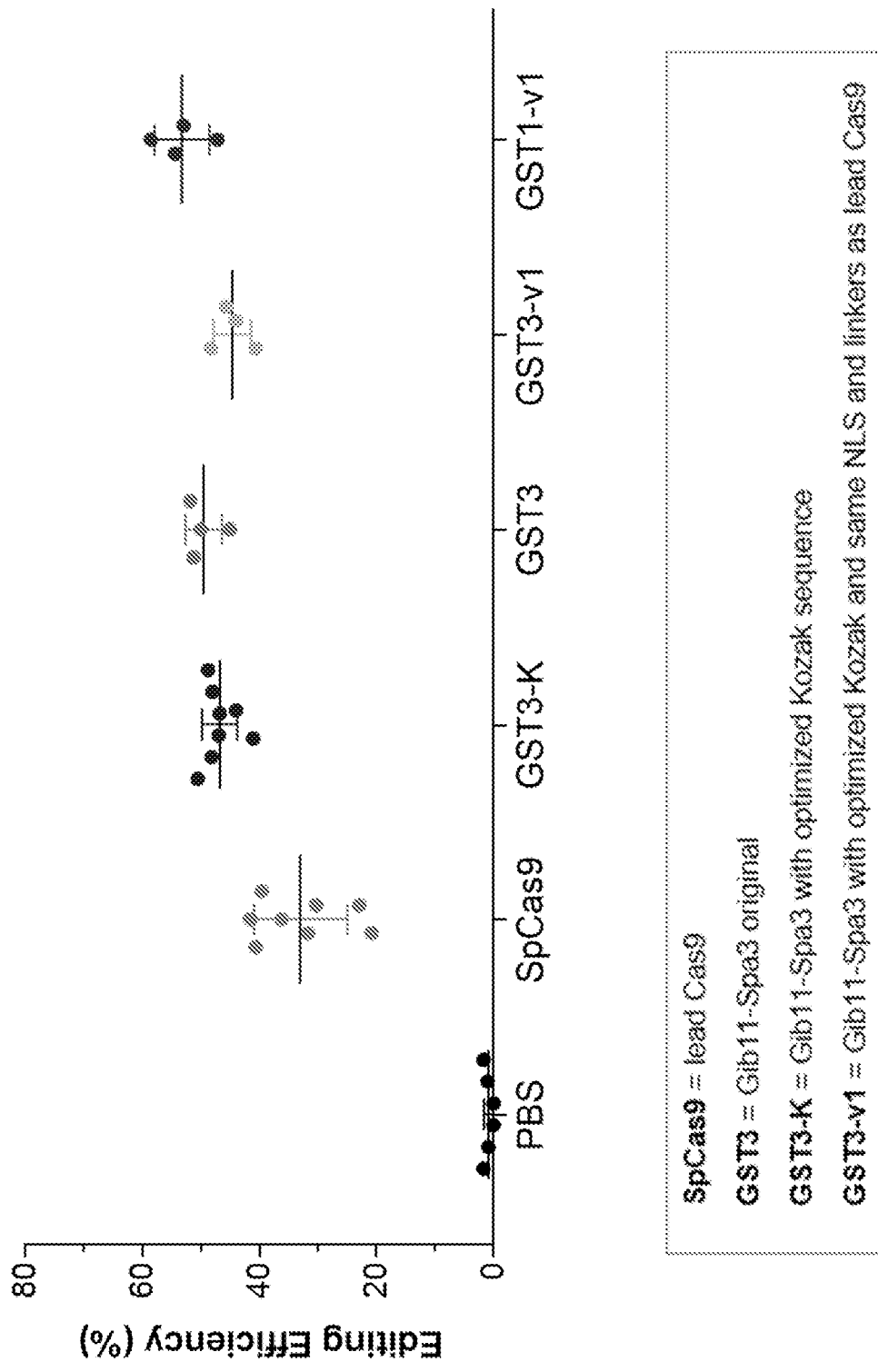
FIG. 4 is a graphical representation of the editing efficiency of smLNPs containing mRNAs encoding smCas9 GST3-K, smCas9 GST3, smCas9 GST3-v1, smCas9 GST1-v1, or LNPs containing the reference SpCas9, when administered intravenously in C57BL/6 mice. The target locus for these experiments was the albumin locus. Each dot represents whole liver TIDE analysis of one animal. These results demonstrated that all of the foregoing smCas9 variants performed better than SpCas9 when delivered in mRNA-LNP formulations according to the present disclosure.
Figure 6:
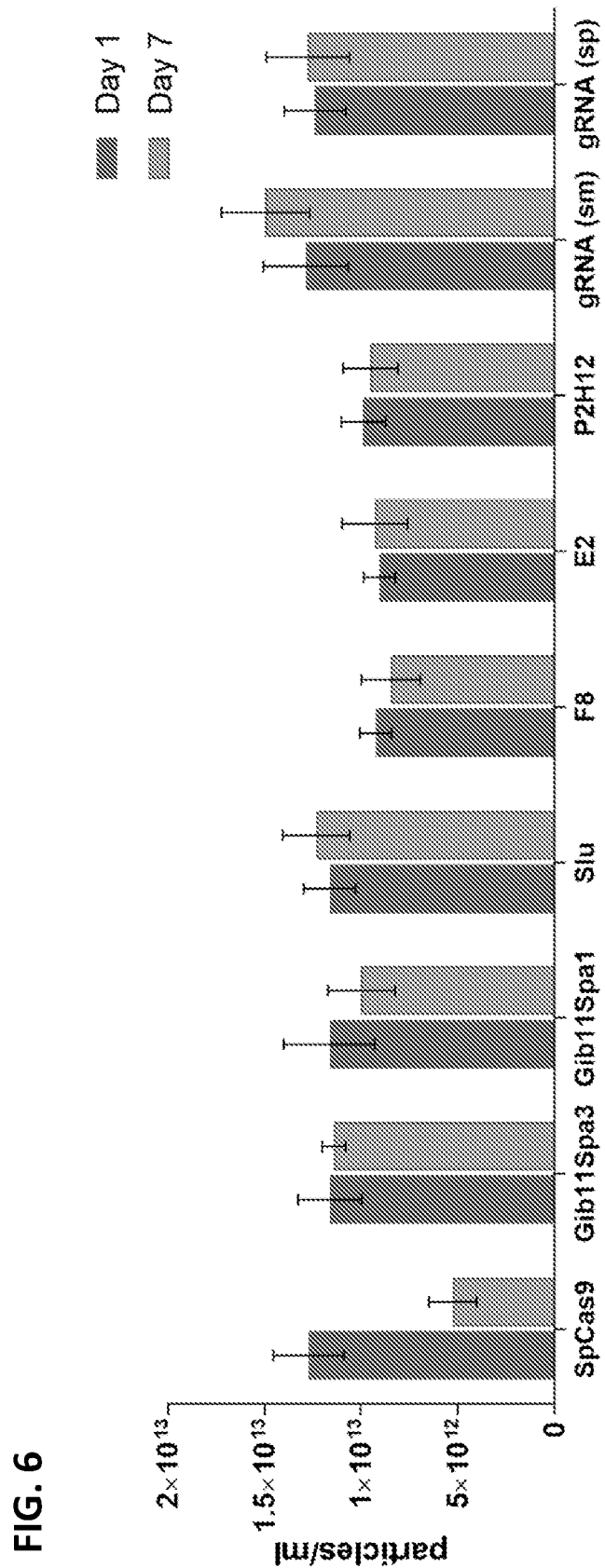
FIG. 6 graphically summarizes the results of experiments performed to evaluate changes in physicochemical properties (e.g., stability) of mRNA-LNPs during storage, as determined by nanoparticle tracking analysis (NTA). In these experiments, changes in mRNA-LNP concentrations were determined after 7-day storage at 2-8° C. The graph shows the number of nanoparticles per mL of solution, where the tested nanoparticles ranged from about 30 to about 500 nm in size and included different RNA components. These results demonstrated that while the concentration of particles diminished for SpCas9 after being stored for 7 days at 2-8° C., such concentration reduction was not observed for the smLNPs containing mRNA encoding each of the smCas9 variants.

This Example describes experiments performed to illustrate the editing efficiency of exemplary LNP samples each containing an mRNA molecule encoding the site-specific endonucleases smCas9 GST3 (GST3 mRNA, SEQ ID NO: 34; GST3 polypeptide, SEQ ID NO: 35), smCas9 GST3-K (GST3-K mRNA, SEQ ID NO: 36; GST3-K polypeptide, SEQ ID NO: 37), smCas9 GST3-v1 (GST3-v1 mRNA, SEQ ID NO: 38; GST3-v1 polypeptide, SEQ ID NO: 39), smCas9 GST1-v1 (GST1-v1 mRNA, SEQ ID NO: 40; GST1-v1 polypeptide, SEQ ID NO: 41), or the reference nuclease SpCas9, when administered intravenously in C57BL/6 mice at a dose of 2 mpk. The target locus for these experiments was the albumin locus of the C57BL/6 mice. The gRNA targeting the albumin gene that was used in all in vivo mouse experiments shown was a 100-mer of the following sequence, 5'-ugcCAGUUCCCGAUCGUUACGUUUU-AGUACUCUGGAAACAGAAUCUACUGAAACA AGACAAUAUGUCGUGUUUAUCCCAU-CAAUUUAUUGGUGGGAUuuu-3' (SEQ ID NO: 50), in which lowercase letters denote phosphorothioate linkages. The GST3 variant was the aforementioned Gib11Spa3 variant. The GST3-K was a Gib11Spa3 variant with a consensus Kozak consensus sequence. The GST3-v1 is the Gib11Spa3 variant with SpCas9 NLS (nuclear localization sequence)/linkers. The GST1-v1 is the Gib11Spa1 variant with SpCas9 NLS/linkers. See FIG. 6. It was observed that all smCas9 variants tested performed better than SpCas9 in mRNA-LNP format. The results also suggested that the variations in Gib11Spa3 construct design did not appear to have a significant impact on functional performance. See FIG. 4. All experimental parameters used in these experiments were similar to those described above for in vivo mouse testing.

Figure 5:
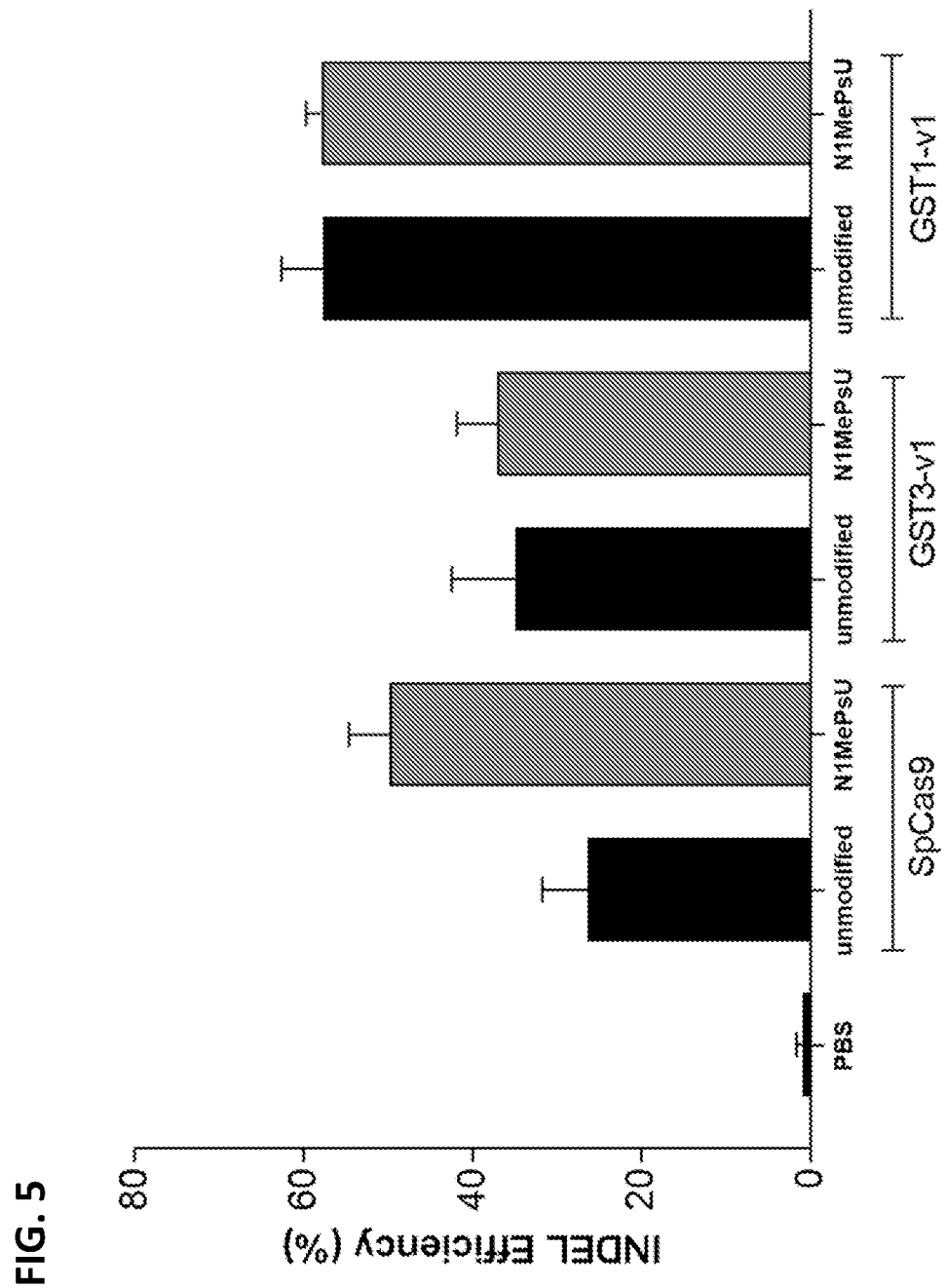
FIG. 5 is a bar graph showing the INDEL efficiency of smLNPs containing mRNAs encoding smCas9 GST3-v1, smCas9 GST1-v1, or LNPs containing the reference mRNA encoding SpCas9, when unmodified or modified with N1-methyl-pseudouridine base. In this experiment, the mRNA-LNPs were administered at a single dose of 2 mpk, intravenously, in C57BL/6 mice. These results demonstrated that (i) N1-methyl-pseudouridine modifications improved the performance for SpCas9 but not for GST3-v1 or GST1-v1, and (ii) that unmodified and base-modified mRNA performed well as smCas9 mRNA-LNP.

This example further describes experiments illustrating the impact of N1-methyl pseudouridine base modification on smCas9 and SpCas9 mRNA with respect to editing efficiency (as indicated by INDEL frequency) when delivered as mRNA-LNPs in vivo in C57BL/6 mice by single intravenous 2 mpk dose. See FIG. 5. All experimental parameters used in these experiments were similar to those described above for in vivo mouse testing. Here, mRNAs for SpCas9, smCas9 GST3-v1, and smCas9 GST1-v1 were modified with N1-methyl pseudouridine base, and the editing efficiencies of LNPs containing these mRNAs were measured and compared to the editing efficiencies of LNPs containing unmodified versions of the same mRNAs. N1-methyl pseudouridine base modification appeared to have an effect on editing efficiency only for SpCas9 mRNA-LNPs, where it lead to improved performance.

Improved LNP Stability

This Example describes experiments performed to measure the number of mRNA-LNPs per mL of solution before and after one week of storage at 2-8° C., where the mRNA encodes SpCas9 or an smCas9 variant. In this experiment, it was observed that while the number of mRNA-LNPs significantly decreases when the mRNA codes for SpCas9, no significant change was observed for the other compositions (i.e., with an mRNA coding for a smCas9 variant). Change in LNP concentration is indicative of particle aggregation and fusion. See FIG. 6. Before storage and 1 week after storage, LNP concentration was measured by NTA analysis of the samples using a Malvern Nanosight instrument. Between measurements at Day 1 and Day 7, LNPs were stored at 2-8° C.

Figure 7:
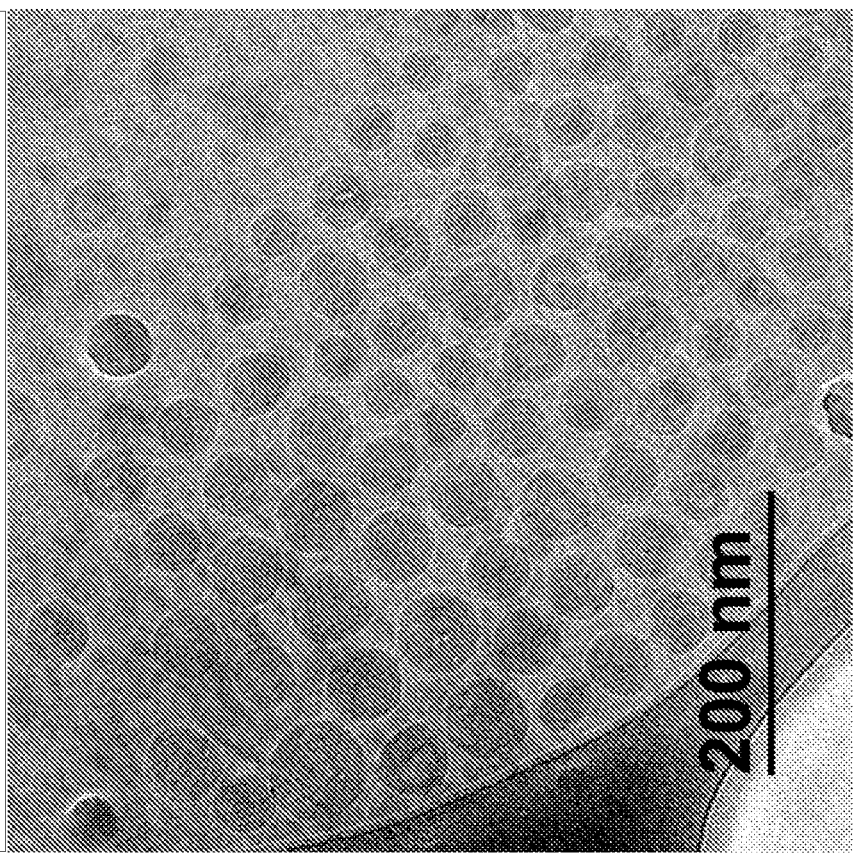
FIG. 7 pictorially summarizes the results of experiments performed to evaluate the morphological uniformity of smLNPs in accordance with some exemplary embodiments of the disclosure. In these experiments, images of LNPs containing either SpCas9 mRNA or smCas9 Gib11Spa3 mRNA were captured using cryo-transmission electron microscopy (cryoTEM).
Figure 7:
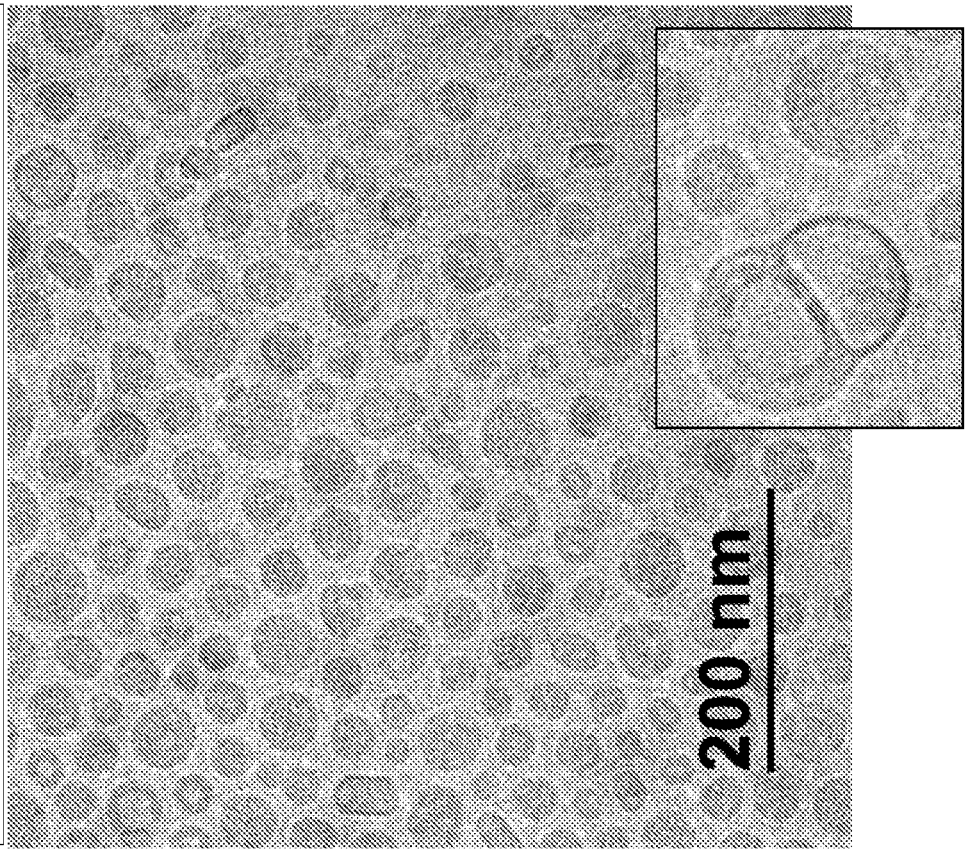

This Example further describes experiments performed to observe by transmission electron cryomicroscopy (cryoTEM) mRNA-LNPs when prepared with either the SpCas9 mRNA or the smCas9 Gib11Spa3 mRNA. See FIG. 7. It was observed that the LNPs carrying the smCas9 mRNA presented fewer morphologic irregularities than the mRNA-LNPs carrying the mRNA coding for SpCas9. CryoTEM analysis was performed by plunge freezing LNPs using semi-Cryoplunge 3 System and imaging on a JEOL 2100F 200 kV Field Emission Electron Microscope.

Figure 8:
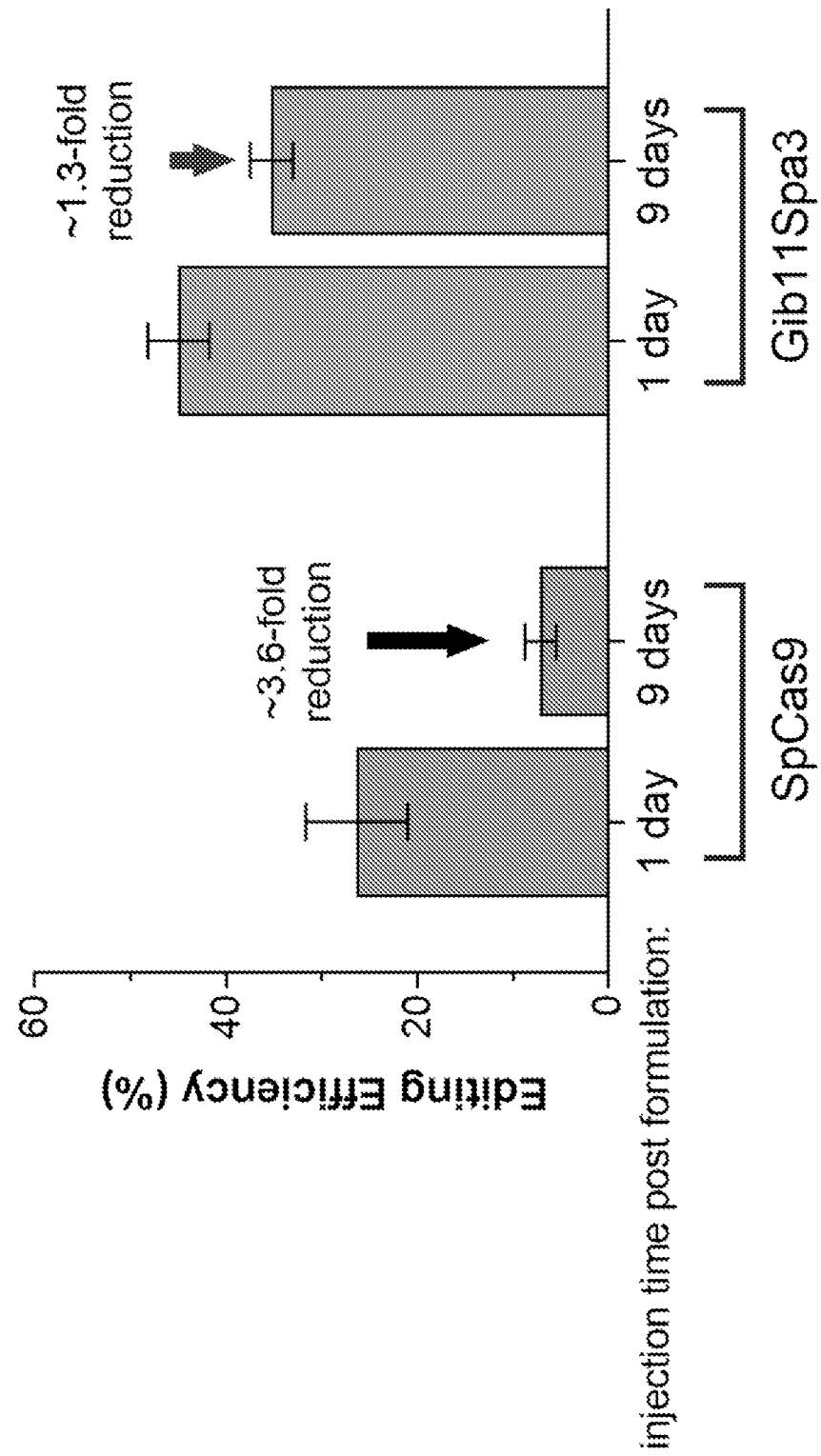
FIG. 8 graphically summarizes the results of experiments performed to demonstrate that SmCas9 delivered into cells using mRNA-LNP compositions in accordance with some embodiments of the disclosures show improved functional stability after 9 days of 2-8° C. storage compared to SpCas9.

This Example further describes experiments performed to measure the editing efficiency of formulations of mRNA-LNPs carrying mRNA encoding either the SpCas9 or the smCas9 variant Gib11Spa3, when injected in C57BL/6 mice intravenously at a dose of 2 mpk, either one day or nine days after the formulations were prepared and stored at 2-8° C., with the same LNP batch used in each group. See FIG. 8. It was observed that smCas9 as an mRNA payload produced a more stable LNP than SpCas9: a ~3.6-fold reduction of editing efficiency was observed for SpCas9 between the formulation injected one day and nine days after being prepared, whereas the reduction was of only ~1.3-fold for the smCas9. All experimental parameters used in these experiments were similar to those described above for in vivo mouse testing.

Example 3: Evaluation of LNPs in Methods of Treating Hemophilia A and Cardiovascular Disease Applicant contemplates using the following animal models to assess the effectiveness and safety of smCas9 mRNA LNPs: C57BL/6 mice, HemA knock-out mice, sprague dawley rat, and cynomolgus monkey. Without being bound to any particular theory, it is believed that smCas9 mRNA LNPs can be at least as effective as SpCas9 mRNA LNPs in all of these preclinical models.

In these experiments, smCas9 mRNA LNPs, particularly Gib11Spa1 and Gib11Spa3 variants, can effectively produce gene editing at the albumin locus in C57BL/6 mice. Additional experiments in this model include testing of smCas9 mRNA in various types of LNP formulations, assessment of Slu, E2, F8, and P2H12 variants, evaluation of the impact of base and sequence modification on smCas9 mRNA effectiveness, evaluation of dose response and multi-dose performance, and further evaluation of smCas9 mRNA LNP function during stability testing.

Applicant also contemplates using HemA knock-out mice to evaluate targeted integration of FVIII into the albumin locus; using Sprague Dawley rats to assess safety of smCas9 mRNA LNPs through assessment of liver toxicity and immune response; and using Cynomolgus monkey to assess gene editing efficacy, biodistribution, and safety. Guide-sequence testing in primary human hepatocytes is contemplated for assessing off-target effects of smCas9 mRNA LNPs.

LNP technology has a proven safety profile in the clinic, and it is believed that the LNP formulations with smCas9 mRNA can have an improved therapeutic index compared to current LNP formulations with spCas9 mRNA. Clinical safety and efficacy of smCas9 mRNA LNPs can be evaluated, e.g., by testing one or more of serum clinical chemistry, CBCs, neutralizing antibodies to Cas9 and LNPs, injection site inflammatory reactions, cytokine induction, and target biomarker activity.

Example 4: Evaluation of LNP Composition Containing mRNA Encoding smCas9 in Non-Human Primate Cells To further assess gene editing effectiveness, biodistribution, and safety of the smCas9-mRNA-LNP formulations described in Examples 2 and 3, a cynomolgus monkey (cynos) model is used.

In these experiments, an smCas9-mRNA-LNP described herein, for example in Examples 2 and 3, is formulated for administration. Formulations are administered to approximately 3 kg male cynos at doses ranging from 1-2 mg/kg via IV infusion. The cynos are subsequently monitored for safety concerns, euthanized within 8 days of receiving the infusion, and assessed for liver and spleen gene editing, biodistribution, and tolerability readouts. It is expected that LNP formulations delivering smCas9 mRNA that have been demonstrated to achieve high editing efficiency in mouse can perform similarly well across species, such as non-human primate species. Without intending to be bound by any particular theory, it is believed that the delivery and stability advantages observed with smCas9-mRNA-LNPs of the present disclosure are not unique to a specific testing model.

Example 5: In Vivo Safety of LNP Compositions Containing mRNA Encoding smCas9 in Rats To assess safety of exemplary smCas9-mRNA-LNP formulations in accordance with some embodiments of the disclosure, a rat toxicity study was carried out.

In these experiments, rats were injected with 2 mg/kg of smCas9 GST1 mRNA-LNPs or SpCas9 mRNA-LNPs (n=3 for each condition), with the only difference between the LNP formulations being their nucleic acid component. Rats injected with SpCas9 mRNA-LNPs demonstrated an acute toxicity response, with no survival observed in the cohort within 12 hours of dose administration. By contrast, rats injected with smCas9 GST1 mRNA-LNPs exhibited improved tolerability, as demonstrated by all rats in this cohort having survived until study termination on day seven post-injection. Given the rapid onset of toxicity observed with the SpCas9 mRNA-LNPs, it is unlikely that this was due to any effects of genome editing by the LNPs, which would be expected to take longer than 12 hours to manifest. These results suggest that for otherwise similarly formulated LNPs, those containing smCas9 mRNA are less toxic than those containing larger SpCas9 mRNA. These results are surprising since the lipid-to mRNA weight ratio in many smCas9-mRNA-LNPs was found to be greater than that in corresponding SpCas9-mRNA-LNPs, and total LNP lipid content is considered a driver of LNP toxicity.

Example 6: In Vivo Editing Efficiency of LNP Compositions Containing mRNA with Various Base Modifications To further assess the impact of different base modifications on smCas9 and SpCas9 mRNA-LNPs, in vivo INDEL analysis in mice was carried out.

C57BL/6 mice were injected with a single 1 mg/kg dose of one of the following mRNA-LNPs: Gib11Spa3 (N1-methylpseudouridine; with or without Geneious® uridine depletion/codon-optimization) and Gib11Spa1 (unmodified, N1-methylpseudouridine, pseudouridine, or 5-methoxyuridine; with or without Geneious® uridine depletion/codon-optimization). LNPs contained one of two different gRNAs targeting different loci in the mouse genome, gRNA T1 (all modifications) or gRNA T2 (only N1-methylpseudouridine modification). Results for INDEL frequency are shown in Table 1. Most of the Gib11Spa1 mRNA-LNPs showed improved editing efficiency when the mRNAs were uridine depleted and codon-optimized. Pseudouridine modification resulted in improved editing efficiency for Gib11Spa1 mRNA-LNPs as compared to the unmodified condition, though this effect was reduced when the mRNAs were uridine depleted and codon-optimized. By contrast, 5-methoxyuridine resulted in decreased editing efficiency for Gib11Spa1 mRNA-LNPs, both with and without uridine depletion and codon-optimization.

TABLE 1

| LNP Formulation | INDEL Frequency ± SD | |
|---|---|---|
| | Without uridine depletion/codon-optimization | With uridine depletion/codon-optimization |
| gRNA T1 | | |
| Gib11Spa1-unmodified | 32.3 ± 9.6 | 43.3 ± 1.7 |
| Gib11Spa1-N1-methylpseudouridine | 33.5 ± 5.6 | 44.8 ± 1.8 |
| Gib11Spa1-pseudouridine | 42.1 ± 4.0 | 44.8 ± 4.9 |
| Gib11Spa1-5-methoxyuridine | 15.5 ± 3.5 | 32.3 ± 3.5 |
| Gib11Spa3-N1-methylpseudouridine | 19.5 ± 6.9 | 19.1 ± 5.2 |
| gRNA T2 | | |
| Gib11Spa1-N1-methylpseudouridine | 30.3 ± 4.5 | 37.4 ± 5.9 |
| Gib11Spa3-N1-methylpseudouridine | 10.8 ± 5.4 | 11.3 ± 2.9 |

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

Sequence Listing

| SEQ ID NO | Sequence | Description |
|---|---|---|
| 1 | MNQKFILGLDIGITSVGYGLIDYETKNIIDAGVRLFPEANVENNEGRRSKRGSRRLKR RRIHRLERVKLLLTEYDLINKEQIPTSNNPYQIRVKGLSEILSKDELAIALLHLAKRR GIHNVDVAADKEETASDSLSTKDQINKNAKFLESRYVCELQKERLENEGHVRGVENRF LTKDIVREAKKIIDTQMQYYPEIDETFKEKYISLVETRREYFEGPGQGSPFGWNGDLK | Gib11SpaCas9-1 polypeptide |

| SEQ ID NO | Sequence | Description |
|---|---|---|
| | KWYEMLMGHCTYFPQELRSVKYAYSADLFNALNDLNNLIIQRDNSEKLEYHEKYHIIE<br>NVFKQKKKPTLKQIAKEIGVNPEDIKGYRITKSGTPEFTSFKLFHDLKKVVKDHAILD<br>DIDLLNQIAEILTIYQDKSIVAELGQLEYLMSEADKQSISELTGYTGTHSLSLKCMN<br>MIIDELWHSSMNQMEVFTYLNMRPKKYELKGYQRIPTDMIDDAILSPVVKRTFIQSIN<br>VINKVIEKYGIPEDIIIELARENNSDDRKKFINNLQKKNEATRKRINEIIGQTGNQNA<br>KRIVEKIRLHDQQEGKCLYSLESIPLEDLLNNPNHYEVDHIIPRSVSFDNSYHNKVLV<br>KQSENSKKSNLTPYQYFNSGKSKLSYNQFKQHILNLSKSQDRISKKKKEYLLEERDIN<br>KFEVQKEFINRNLVDTRYATRELTNYLKAYFSANNMNVKVKTINGSFTDYLRKVWKFK<br>KERNHGYKHHAEDALIIANADFLFKENKKLKAVNSVLEKPEIETKQLDIQVDSEDNYS<br>EMFIIPKQVQDIKDFRNFKYSHRVDKKPNRQLINDTLYSTRKKDNSTYIVQTIKDIYA<br>KDNTTLKKQFDKSPEKFLMYQHDPRTFEKLEVIMKQYANEKNPLAKYHEETGEYLTKY<br>SKKNNGPIVKSLKYIGNKLGSHLDVTHQFKSSTKKLVKLSIKNYRFDVYLTEKGYKFV<br>TIAYLNVFKKDNYYYIPKDKYQELKEKKKIKDTDQFIASFYKNDLIKLNGDLYKIIGV<br>NSDDRNIIELDYYDIKYKDYCEINNIKGEPRIKKTIGKKTESIEKFTTDVLGNLYLHS<br>TEKAPQLIFKRGL | |
| 2 | MNQKFILGLDIGITSVGYGLIDYETKNIIDAGVRLFPEANVENNEGRRSKRGSRRLKR<br>RRIHRLERVKLLLTEYDLINKEQIPTSNNPYQIRVKGLSEILSKDELAIALLHLAKRR<br>GIHNVDAADKEETASDSLSTKDQINKNAKFLESRYVCELQKERLENEGHVRGVENRF<br>LTKDIVREAKKIIDTQMQYYPEIDETFKEKYISLVETRREYFEGPGQGSPFGWNGDLK<br>KWYEMLMGHCTYFPQELRSVKYAYSADLFNALNDLNNLIIQRDNSEKLEYHEKYHIIE<br>NVFKQKKKPTLKQIAKEIGVNPEDIKGYRITKSGTPEFTSFKLFHDLKKVVKDHAILD<br>DIDLLNQIAEILTIYQDKSIVAELGQLEYLMSEADKQSISELTGYTGTHSLSLKCMN<br>MIIDELWHSSMNQMEVFTYLNMRPKKYELKGYQRIPTDMIDDAILSPVVKRTFIQSIN<br>VINKVIEKYGIPEDIIIELARENNSDDRKKFINNLQKKNEATRKRINEIIGQTGNQNA<br>KRIVEKIRLHDQQEGKCLYSLESIPLEDLLNNPNHYEVDHIIPRSVSFDNSYHNKVLV<br>KQSENSKKSNLTPYQYFNSGKSKLSYNQFKQHILNLSKSQDRISKKKKEYLLEERDIN<br>KFEVQKEFINRNLVDTRYATRELTSYLKAYFSANNMDVKVKTINGSFTNHLRKVWRFD<br>KYRNHGYKHHAEDALIIANADFLFKENKKLQNTNKILEKPTIENNTKKVTVEKEEDYN<br>NVFETPKLVEDIKQYRDYKFSHRVDKKPNRQLINDTLYSTRMKDEHDYIVQTITDIYG<br>KDNTNLKKQFNKNPEKFLMYQNDPKTFEKLSIIMKQYSDEKNPLAKYYEETGEYLTKY<br>SKKNNGPIVKKIKLLGNKVGNHLDVTNKYENSTKKLVKLSIKNYRFDVYLTEKGYKFV<br>TIAYLNVFKKDNYYYIPKDKYELKEKKKIKDTDQFIASFYKNDLIKLNGDLYKIIGVN<br>SDDRNIIELDYYDIKYKDYCEINNIKGEPRIKKTIGKKTESIEKFTTDVLGNLYLHST<br>EKAPQLIFKRGL | Gib11SpaCas9-3 polypeptide |
| 3 | MNQKFILGLDIGITSVGYGLIDYETKNIIDAGVRLFPEANVENNEGRRSKRGSRRLKR<br>RRIHRLDRVKHLLAEYDLLDLTNIPKSTNPYQTRVKGLNEKLSKDELVIALLHIAKRR<br>GIHNVDAADKEETASDSLSTKDQINKNAKFLESRYVCELQKERLENEGHVRGVENRF<br>LTKDIVREAKKIIDTQMQYYPEIDETFKEKYISLVETRREYFEGPGKGSPFGWEGNIK<br>KWFEQMMGHCTYFPEELRSVKYSYSAELFNALNDLNNLVITRDEDAKLNYGEKFQIIE<br>NVFKQKKTPNLKQIAIEIGVHETEIKGYRVNKSGTPEFTEFKLYHDLKSIVFDKSILE<br>NEAILDQIAEILTIYQDEQSIKEELNKLPEILNEQDKAEIAKLIGYNGTHRLSLKCIH<br>LINEELWQTSRNQMEIFNYLNIKPNKVDLSEQNKIPKDMVNDFILSPVVKRTFIQSIN<br>VINKVIEKYGIPEDIIIELARENNSDDRKKFINNLQKKNEATRKRINEIIGQTGNQNA<br>KRIVEKIRLHDQQEGKCLYSLKDIPLEDLLRNPNNYDIDHIIPRSVSFDDSMHNKVLV<br>RREQNAKKNNQTPYQYLTSGYADIKYSVFKQHVLNLAENKDRMTKKKREYLLEERDIN<br>KFEVQKEFINRNLVDTRYATRELTNYLKAYFSANNMNVKVKTINGSFTDYLRKVWKFK<br>KERNHGYKHHAEDALIIANADFLFKENKKLKAVNSVLEKPEIETKQLDIQVDSEDNYS<br>EMFIIPKQVQDIKDFRNFKYSHRVDKKPNRQLINDTLYSTRKKDNSTYIVQTIKDIYA<br>KDNTTLKKQFDKSPEKFLMYQHDPRTFEKLEVIMKQYANEKNPLAKYHEETGEYLTKY<br>SKKNNGPIVKSLKYIGNKLGSHLDVTHQFKSSTKKLVKLSIKPYRFDVYLTDKGYKFI<br>TISYLDVLKKDNYYYIPEQKYDKLKLGKAIDKNAKFIASFYKNDLIKLDGEIYKIIGV<br>NSDTRNMIELDLPDIRYKEYCELNNIKGEPRIKKTIGKKVNSIEKLTTDVLGNVFTNT<br>QYTKPQLLFKRGN | E2Cas9 polypeptide |
| 4 | MNQKFILGLDIGITSVGYGLIDYETKNIIDAGVRLFPEANVENNEGRRSKRGSRRLKR<br>RRIHRLERVKSLLSEYKIISGLAPTNNQPYNIRVKGLTEQLTKDELAVALLHIAKRRG<br>IHKIDVIDSNDDVGNELSTKEQLNKNSKLLKDKFVCQIQLERMNEGQVRGEKNRFKTA<br>DIIKEITQLLNVQKNFHQLDENFINKYIELVEMRREYFEGPGQGSPFGWNGDLKKWYE<br>MLMGHCTYFPQELRSVKYAYSADLFNALNDLNNLIIQRDNSEKLEYHEKYHIIENVFK<br>QKKKPTLKQIAKEIGVNPEDIKGYRITKSGTPEFTEFKLYHDLKSVLFDQSILENEDV<br>LDQIAEILTIYQDKDSIKSKLTELDILLNEEDKENIAQLTGYNGTHRLSLKCIRLVLE<br>EQWYSSRNQMEIFTHLNIKPKKINLTAANKIPKAMIDEFILSPVVKRTFIQSINVINK<br>VIEKYGIPEDIIIELARENNSDDRKKFINNLQKKNEATRKRINEIIGQTGNQNAKRIV<br>EKIRLHDQQEGKCLYSLESIALMDLLNNPQNYEVDHIIPRSVAFDNSIHNKVLVKQIE<br>NSKKGNRTPYQYLNSSDAKLSYNQFKQHILNLSKSKDRISKKKKDYLLEERDINKFEV<br>QKEFINRNLVDTRYATRELTSYLKAYFSANNMDVKVKTINGSFTNHLRKVWRFDKYRN<br>HGYKHHAEDALIIANADFLFKENKKLKAVNSVLEKPEIETKQLDIQVDSEDNYSEMFI<br>IPKQVQDIKDFRNFKYSHRVDKKPNRQLINDTLYSTRKKDNSTYIVQTIKDIYAKDNT<br>TLKKQFDKSPEKFLMYQHDPRTFEKLEVIMKQYANEKNPLAKYHEETGEYLTKYSKKN<br>NGPIVKSLKYIGNKLGSHLDVTHQFKSSTKKLVKLSIKPYRFDVYLTDKGYKFITISY | F8Cas9 polypeptide |

| Sequence Listing | | |
|---|---|---|
| SEQ ID NO | Sequence | Description |
| | LDVLKKDNYYYIPEQKYDKLKLGKAIDKNAKFIASFYKNDLIKLDGEIYKIIGVNSDT<br>RNMIELDLPDIRYKEYCELNNIKGEPRIKKTIGKKVNSIEKLTTDVLGNVFTNTQYTK<br>PQLLFKRGN | |
| 5 | MNQKFILGLDIGITSVGYGLIDYETKNIIDAGVRLFPEANVENNEGRRSKRGSRRLKR<br>RRIHRLERVKKLLEDYNLLDQSQIPQSTNPYAIRVKGLSEALSKDELVIALLHIAKRR<br>GIHNINVSSEDEDASNELSTKEQINRNNKLLKDKYVCEVQLQRLKEGQIRGEKNRFKT<br>TDILKEIDQLLKVQKDYHNLDIDFINQYKEIVETRREYFEGPGKGSPYGWEGDPKAWY<br>ETLMGHCTYFPDELRSVKYAYSADLFNALNDLNNLVIQRDGLSKLEYHEKYHIIENVF<br>KQKKKPTLKQIANEINVNPEDIKGYRITKSGKPEFTSFKLFHDLKKVVKDHAILDDID<br>LLNQIAEILTIYQDKDSIVAELGQLEYLMSEADKQSISELTGYTGTHSLSLKCMNMII<br>DELWHSSMNQMEVFTYLNMRPKKYELKGYQRIPTDMIDDAILSPVVKRTFIQSINVIN<br>KVIEKYGIPEDIIIELARENNSDDRKKFINNLQKKNEATRKRINEIIGQTGNQNAKRI<br>VEKIRLHDQQEGKCLYSLESIPLEDLLNNPNHYEVDHIIPRSVSFDNSYHNKVLVKQS<br>ENSKKSNLTPYQYFNSGKSKLSYNQFKQHILNLSKSQDRISKKKKEYLLEERDINKFE<br>VQKEFINRNLVDTRYATRELTNYLKAYFSANNMNVKVKTINGSFTDYLRKVWKFKKER<br>NHGYKHHAEDALIIANADFLFKENKKLKAVNSVLEKPEIETKQLDIQVDSEDNYSEMF<br>IIPKQVQDIKDFRNFKYSHRVDKKPNRQLINDTLYSTRKKDNSTYIVQTIKDIYAKDN<br>TTLKKQFDKSPEKFLMYQHDPRTFEKLEVIMKQYANEKNPLAKYHEETGEYLTKYSKK<br>NNGPIVKSLKYIGNKLGSHLDVTHQFKSSTKKLVKLSIKPYRFDVYLTDKGYKFITIS<br>YLDVLKKDNYYYIPEQKYDKLKLGKAIDKNAKFIASFYKNDLIKLDGEIYKIIGVNSD<br>TRNMIELDLPDIRYKEYCELNNIKGEPRIKKTIGKKVNSIEKLTTDVLGNVFTNTQYT<br>KPQLLFKRGN | P2H12Cas9<br>polypeptide |
| 6 | MNQKFILGLDIGITSVGYGLIDYETKNIIDAGVRLFPEANVENNEGRRSKRGSRRLKR<br>RRIHRLERVKKLLEDYNLLDQSQIPQSTNPYAIRVKGLSEALSKDELVIALLHIAKRR<br>GIHKIDVIDSNDDVGNELSTKEQLNKNSKLLKDKFVCQIQLERMNEGQVRGEKNRFKT<br>ADIIKEITQLLNVQKNFHQLDENFINKYIELVEMRREYFEGPGKGSPYGWEGDPKAWY<br>ETLMGHCTYFPDELRSVKYAYSADLFNALNDLNNLVIQRDGLSKLEYHEKYHIIENVF<br>KQKKKPTLKQIANEINVNPEDIKGYRITKSGKPQFTEFKLYHDLKSVLFDQSILENED<br>VLDQIAEILTIYQDKDSIKSKLTELDILLNEEDKENIAQLTGYTGTHRLSLKCIRLVL<br>EEQWYSSRNQMEIFTHLNIKPKKINLTAANKIPKAMIDEFILSPVVKRTFGQAINLIN<br>KIIEKYGVPEDIIIELARENNSDKQKFINEMQKKNENTRKRINEIIGKYGNQNAKRL<br>VEKIRLHDEQEGKCLYSLESIPLEDLLNNPNHYEVDHIIPRSVSFDNSYHNKVLVKQS<br>ENSKKSNLTPYQYFNSGKSKLSYNQFKQHILNLSKSQDRISKKKKEYLLEERDINKFE<br>VQKEFINRNLVDTRYATRELTNYLKAYFSANNMNVKVKTINGSFTDYLRKVWKFKKER<br>NHGYKHHAEDALIIANADFLFKENKKLKAVNSVLEKPEIETKQLDIQVDSEDNYSEMF<br>IIPKQVQDIKDFRNFKYSHRVDKKPNRQLINDTLYSTRKKDNSTYIVQTIKDIYAKDN<br>TTLKKQFDKSPEKFLMYQHDPRTFEKLEVIMKQYANEKNPLAKYHEETGEYLTKYSKK<br>NNGPIVKSLKYIGNKLGSHLDVTHQFKSSTKKLVKLSIKPYRFDVYLTDKGYKFITIS<br>YLDVLKKDNYYYIPEQKYDKLKLGKAIDKNAKFIASFYKNDLIKLDGEIYKIIGVNSD<br>TRNMIELDLPDIRYKEYCELNNIKGEPRIKKTIGKKVNSIEKLTTDVLGNVFTNTQYT<br>KPQLLFKRGN | SluCas9<br>polypeptide |
| 7 | ATGAACCAGAAATTTATCCTGGGTCTGGATATTGGTATTACCAGCGTTGGTTATGGCC<br>TGATTGATTACGAAACCAAAAACATTATTGATGCCGGTGTTCGTCTGTTTCCGGAAGC<br>AAATGTTGAAAATAATGAAGGTCGTCGTAGCAAACGTGGTAGCCGTCGTCTGAAACGT<br>CGTCGTATTCATCGTCTGGAACGTGTTAAACTGCTGCTGACCGAATATGATCTGATTA<br>ACAAAGAGCAGATTCCGACCAGCAATAACCCGTATCAGATTCGTGTTAAAGGTCTGAG<br>CGAAATCCTGAGCAAAGATGAACTGGCAATTGCACTGCTGCATCTGGCAAAACGCCGT<br>GGCATTCATAATGTTGATGTTGCAGCAGATAAAGAAGAAACCGCAAGCGATAGCCTGA<br>GCACCAAAGATCAGATTAACAAAAACGCCAAATTTCTGGAAAGCCGCTATGTTTGTGA<br>ACTGCAGAAAGAACGTCTGGAAAATGAAGGTCATGTTCGTGGTGTTGAAAATCGCTTT<br>CTGACGAAAGATATTGTGCGTGAGGCCAAAAAAATCATCGATACCCAGATGCAGTATT<br>ACCCGGAAATTGATGAAACCTTCAAAGAGAAATATATCAGCCTGGTTGAAACCCGTCG<br>CGAATATTTTGAAGGTCCTGGTCAGGGTAGCCCGTTTGGTTGGAATGGTGATCTGAAA<br>AAATGGTACGAAATGCTGATGGGTCACTGTACCTATTTTCCGCAAGAACTGCGTAGCG<br>TTAAATATGCCTATAGCGCAGACCTGTTTAATGCACTGAATGATCTGAACAACCTGAT<br>TATTCAGCGCGATAATAGCGAGAAACTGGAATACCATGAGAAGTATCACATCATCGAG<br>AACGTGTTCAAGCAGAAAAAAAGCCGACGCTGAAACAAATCGCAAAGAGATTGGCG<br>TTAACCCGGAAGATATTAAAGGTTATCGTATTACCAAAAGCGGCACACCGGAGTTTAC<br>ATCCTTTAAACTGTTCCACGATCTGAAAAAAGTGGTGAAAGATCATGCCATCCTGGAT<br>GATATTGATCTGCTGAATCAGATTGCAGAAATCCTGACCATCTATCAGGATAAAGATA<br>GCATTGTTGCAGAACTGGGTCAGCTGGAATATCTGATGAGCGAAGCCGATAAACAGAG<br>CATTAGCGAACTGACCGGTTATACCGGTACACATAGCCTGTCACTGAAATGCATGAAC<br>ATGATTATCGATGAACTGTGGCATAGCAGCATGAACCAGATGGAAGTTTTTACCTATC<br>TGAATATGCGTCCGAAAAAGTATGAGCTGAAAGGTTATCAGCGTATTCCGACCGATAT<br>GATTGATGATGCAATTCTGAGTCCGGTTGTGAAACGCACCTTTATTCAGAGCATCAAC<br>GTGATCAACAAAGTGATCGAGAAATATGGCATCCCCGAAGATATCATTATCGAACTGG<br>CACGTGAAAATAACTCCGATGATCGCAAAAAGTTCATCAACAACCTGCAGAAAAAGAA<br>TGAAGCAACCCGCAAACGCATTAACGAAATTATTGGTCAGACCGGTAATCAGAATGCC<br>AAACGTATTGTGGAAAAAATCCGTCTGCATGATCAGCAAGAGGGCAAATGTCTGTATA<br>GCCTGGAAAGCATTCCTCTGGAAGATCTGCTGAACAATCCGAATCATTATGAAGTGGA<br>TCACATTATTCCGCGTAGCGTGAGCTTTGATAATTCCTATCATAATAAAGTGCTGGTG | Original<br>Gib11SpaCas9-1<br>polynucleotide |

| SEQ ID NO | Sequence | Description |
|---|---|---|
| | AAACAGAGCGAAAACTCCAAAAAATCCAACCTGACACCGTATCAGTATTTCAATAGCG<br>GCAAATCCAAACTGAGCTACAACCAGTTTAAACAGCATATTCTGAACCTGAGCAAAAG<br>CCAGGATCGCATCAGCAAGAAGAAGAAGGAGTACCTGCTGGAAGAACGCGATATTAAC<br>AAATTTGAAGTGCAGAAAGAATTTATCAACCGCAACCTGGTTGATACCCGTTATGCAA<br>CCCGTGAACTGACCAATTATCTGAAAGCATATTTCAGCGCCAACAACATGAACGTGAA<br>AGTGAAAACGATTAACGGCAGCTTTACCGATTATCTGCGTAAAGTGTGGAAATTCAAA<br>AAAGAACGCAACCACGGCTATAAACATCATGCCGAAGATGCCCTGATTATTGCAAATG<br>CAGATTTCCTGTTTAAAGAAAACAAAAAACTGAAAGCCGTCAACAGCGTGCTGGAAAA<br>ACCGGAAATTGAGACAAAACAGCTGGACATTCAGGTTGATAGCGAAGATAATTACAGC<br>GAAATGTTTATCATCCCGAAACAGGTGCAGGATATCAAAGATTTTCGCAACTTCAAAT<br>ATAGCCACCGCGTTGACAAAAAACCTAATCGTCAGCTGATTAACGATACCCTGTATAG<br>CACCCGCAAAAAGATAACAGCACCTATATTGTGCAGACCATTAAAGACATCTACGCC<br>AAAGATAATACCACCCTGAAAAAACAGTTCGACAAAAGCCCAGAAAAATTTCTGATGT<br>ATCAGCATGATCCGCGTACCTTCGAAAAACTGGAAGTTATTATGAAACAGTATGCCAA<br>CGAGAAAAATCCGCTGGCCAAATATCACGAAGAAACCGGTAATATCTGACCAAATAT<br>TCCAAGAAGAACAACGGTCCGATCGTTAAATCCCTGAAATATATCGGTAATAAACTGG<br>GCAGCCATCTGGATGTTACCCATCAGTTTAAAAGCTCCACAAAGAAGCTGGTTAAGCT<br>GTCCATTAAAAACTATCGCTTCGATGTGTATCTGACCGAGAAAGGTTATAAGTTTGTG<br>ACCATTGCCTACCTGAATGTGTTCAAAAAAGACAACTATTACTATATTCCGAAAGACA<br>AATACCAAGAACTTAAAGAGAAGAAGAAAATCAAGGACACCGATCAGTTTATCGCCAG<br>CTTCTATAAAAACGATCTGATCAAGCTGAACGGCGACCTGTATAAAATCATTGGTGTG<br>AATAGTGATGACCGCAACATCATTGAGCTGGATTATTACGACATCAAATACAAGGATT<br>ACTGCGAGATCAACAACATTAAAGGTGAACCGCGTATCAAAAGACCATTGGCAAAAA<br>AACGGAAAGCATCGAAAAGTTTACCACCGATGTTCTGGGTAATCTGTATCTGCATAGT<br>ACCGAAAAAGCACCGCAGCTGATTTTCAAACGCGGTCTG | |
| 8 | ATGAACCAGAAATTTATCCTGGGTCTGGATATTGGTATTACCAGCGTTGGTTATGGCC<br>TGATTGATTACGAAACCAAAAACATTATTGATGCCGGTGTTCGTCTGTTTCCGGAAGC<br>AAATGTTGAAATAATGAAGGTCGTCGTAGCAAACGTGGTAGCCGTCGTCTGAAACGT<br>CGTCGTATTCATCGTCTGGAACGTGTTAAACTGCTGCTGACCGAATATGATCTGATTA<br>ACAAAGAGCAGATTCCGACCAGCAATAACCCGTATCAGATTCGTGTTAAAGGTCTGAG<br>CGAAATCCTGAGCAAAGATGAACTGGCAATTGCACTGCTGCATCTGGCAAAACGCCGT<br>GGCATTCATAATGTTGATGTTGCAGCAGATAAAGAAGAAACCGCAAGCGATAGCCTGA<br>GCACCAAAGATCAGATTAACAAAAACGCCAAATTTCTGGAAAGCCGCTATGTTTGTGA<br>ACTGCAGAAGAACGTCTGGAAATGAAGGTCATGTTCGTGGTGTTGAAATCGCTTT<br>CTGACGAAAGATATTGTGCGTGAGGCCAAAAAAATCATCGATACCCAGATGCAGTATT<br>ACCCGGAAATTGATGAAACCTTCAAAGAGAAATATATCAGCCTGGTTGAAACCCGTCG<br>CGAATATTTTGAAGGTCCTGGTCAGGGTAGCCCGTTTGGTTGGAATGGTGATCTGAAA<br>AAATGGTACGAAATGCTGATGGGTCACTGTACCTATTTTCCGCAAGAACTGCGTAGCG<br>TTAAATATGCCTATAGCGCAGACCTGTTTAATGCACTGAATGATCTGAACAACCTGAT<br>TATTCAGCGCGATAATAGCGAGAAACTGGAATACCATGAGAAGTATCACATCATCGAG<br>AACGTGTTCAAGCAGAAAAAAAAGCCGACGCTGAAACAAATCGCAAAAGAGATTGGCG<br>TTAACCCGGAAGATATTAAAGGTTATCGTATTACCAAAAGCGGCACACCGGAGTTTAC<br>ATCCTTTAAACTGTTCCACGATCTGAAAAAAGTGGTGAAAGATCATGCCATCCTGGAT<br>GATATTGATCTGCTGAATCAGATTGCAGAAATCCTGACCATCTATCAGGATAAAGATA<br>GCATTGTTGCAGAACTGGGTCAGCTGGAATATCTGATGAGCGAAGCCGATAAACAGAG<br>CATTAGCGAACTGACCGGTTATACCGGTACACATAGCCTGTCACTGAAATGCATGAAC<br>ATGATTATCGATGAACTGTGGCATAGCAGCATGAACCAGATGGAAGTTTTTACCTATC<br>TGAATATGCGTCCGAAAAAGTATGAGCTGAAAGGTTATCAGCGTATTCCGACCGATAT<br>GATTGATGATGCAATTCTGAGTCCGGTTGTGAAACGCACCTTTATTCAGACGATCACC<br>GTGATCAACAAAGTGATCGAGAAATATGGCATCCCCGAAGATATCATTATCGAACTGG<br>CACGTGAAAATAACTCCGATGATCGCAAAAAGTTCATCAACAACCTGCAGAAAAAGAA<br>TGAAGCAACCCGCAAACGCATTAACGAAATTATTGGTCAGACCGGTAATCAGAATGCC<br>AAACGTATTGTGGAAAAAATCCGTCTGCATGATCAGCAAGAGGGCAAATGTCTGTATA<br>GCCTGGAAAGCATTCCTCTGGAAGATCTGCTGAACAATCCGAATCATTATGAAGTGGA<br>TCACATTATTCCGCGTAGCGTGAGCTTTGATAATTCCTATCATAATAAAGTGCTGGTG<br>AAACAGAGCGAAAACTCCAAAAAATCCAACCTGACACCGTATCAGTATTTCAATAGCG<br>GCAAATCCAAACTGAGCTACAACCAGTTTAAACAGCATATTCTGAACCTGAGCAAAAG<br>CCAGGATCGCATCAGCAAGAAGAAGAAGGAGTACCTGCTGGAAGAACGCGATATTAAC<br>AAATTTGAAGTCCAGAAAGAGTTTATCAACCGCAATCTGGTTGATACCCGTTATGCAA<br>CCCGTGAACTGACCAGCTATCTGAAAGCATATTTCAGCGCCAATAACATGGACGTGAA<br>AGTGAAAACAATTAACGGCAGCTTTACCAACCATCTGCGTAAAGTTTGGCGCTTTGAT<br>AAATATCGCAACCACGGCTATAAACATCATGCCGAAGATGCACTGATTATTGCCAATG<br>CAGATTTCCTGTTCAAAGAAAACAAAAAACTGCAGAACACCAACAAGATCCTGGAAAA<br>ACCGACCATTGAAAACAACACCAAAAAGTGACCGTCGAGAAAGAAGAGGATTACAAC<br>AACGTTTTTGAAACCCGAAACTGGTCGAGGATATTAAACAGTATCGCGACTATAAAT<br>TCAGCCACCGCGTTGATAAAAAACCGAATCGTCAGCTGATTAACGATACCCTGTATAG<br>CACCCGTATGAAAGATGAGCATGATTATATTGTGCAGACCATCACGGATATCTATGCC<br>AAAGATAATACCAACCTGAAAAAACAGTTCAACAAAAACCCGGAAAAATTTCTGATGT<br>ATCAGAACGATCCGAAACCTTTGAGAAACTGAGCATCATCATGAAACAGTACAGCGA<br>CGAAAAAAACCCGCTGGCCAAATATTACGAAGAAACCGGTAATATCTGACCAAATAT<br>AGCAAGAAAACAACGGTCCGATCGTGAAAAAGATCAAACTGCTGGGTAATAAAGTGG<br>GCAATCATCTGGATGTGACCAACAAATATGAAAACTCCACGAAGAAGCTGGTTAAGCT<br>GTCCATTAAAAACTATCGCTTCGATGTGTATCTGACCGAGAAAGGTTATAAGTTTGTG | Original Gib11SpaCas9-3 polynucleotide |

Sequence Listing

| SEQ ID NO | Sequence | Description |
|---|---|---|
| | ACCATTGCCTACCTGAATGTGTTCAAAAAAGACAACTATTACTATATTCCGAAAGACA<br>AATACCAAGAACTTAAAGAGAAGAAGAAAATCAAGGACACCGATCAGTTTATCGCCAG<br>CTTCTATAAAAACGATCTGATCAAGCTGAACGGCGACCTGTATAAAATCATTGGTGTG<br>AATAGTGATGACCGCAACATCATTGAGCTGGATTATTACGACATCAAATACAAGGATT<br>ACTGCGAGATCAACAACATTAAAGGTGAACCGCGTATCAAAAAGACCATTGGCAAAAA<br>AACGGAAAGCATCGAAAGTTTACCACCGATGTTCTGGGTAATCTGTATCTGCATAGT<br>ACCGAAAAAGCACCGCAGCTGATTTTCAAACGCGGTCTG | |
| 9 | ATGAACCAGAAATTTATCCTGGGTCTGGATATTGGTATTACCAGCGTTGGTTATGGCC<br>TGATTGATTACGAAACCAAAAACATTATTGATGCCGGTGTTCGTCTGTTTCCGGAAGC<br>AAATGTTGAAAATAATGAAGGTCGTCGTAGCAAACGTGGTAGCCGTCGTCTGAAACGT<br>CGTCGTATTCATCGTCTGGATCGTGTTAAACATCTGCTGGCAGAATATGATCTGCTGG<br>ATCTGACCAATATTCCGAAAAGCACCAATCCGTATCAGACCCGTGTTAAAGGTCTGAA<br>TGAAAAGCTGAGCAAAGATGAACTGGTTATTGCACTGCTGCATATTGCAAAACGCCGT<br>GGCATTCATAACGTTGATGTTGCAGCAGATAAAGAAGAAACCGCAAGCGATAGCCTGA<br>GCACCAAAGATCAGATTAACAAAAACGCCAAATTTCTGGAAAGCCGCTATGTTGTGA<br>ACTGCAGAAGAACGTCTGGAAAATGAAGGTCATGTTCGTGGTGTTGAAAATCGCTTT<br>CTGACGAAAGATATTGTGCGTGAGGCCAAAAAAATCATCGATACCCAGATGCAGTATT<br>ACCCGGAAATTGATGAAACCTTCAAAGAGAATATATCAGCCTGGTTGAAACCCGTCG<br>CGAATATTTTGAAGGTCCGGGTAAAGGTAGCCCGTTTGGTTGGGAAGGTAATATCAAG<br>AAATGGTTTGAGCAGATGATGGGCCACTGTACCTATTTTCCAGAAGAACTGCGTAGCG<br>TCAAATATAGCTATTCAGCCGAACTGTTTAACGCCCTGAATGATCTGAATAATCTGGT<br>GATTACCCGTGATGAAGATGCCAACTGAATTATGGTGAGAAATTCCAGATCATCGAA<br>AACGTGTTCAAACAGAAGAAAACACCGAACCTGAAACAAATCGCCATTGAAATTGGTG<br>TGCATGAAACCGAAATCAAAGGTTATCGTGTGAACAAAAGCGGTACACCGGAATTTAC<br>CGAATTTAAACTGTATCATGACCTGAAAAGCATCGTGTTCGATAAAAGCATTCTGGAA<br>AATGAAGCCATCCTGGATCAGATTGCAGAAATTCTGACCCATCTATCAGGATGAGCAGA<br>GCATTAAAGAGGAACTGAATAAACTGCCGGAAATACTGAACGAACAGGATAAAGCAGA<br>AATCGCCAAACTGATTGGTTATAATGGCACCCATCGTCTGAGCCTGAAATGTATTCAC<br>CTGATTAATGAAGAACTGTGGCAGACCAGCCGTAATCAGATGGAAATTTTCAACTACC<br>TGAACATCAAACCGAACAAAGTGGATCTGAGTGAGCAGAACAAAATCCCGAAAGATAT<br>GGTGAACGACTTTATTCTGAGTCCGGTTGTGAAACGCACCTTTATTCAGAGCATCAAC<br>GTGATCAACAAAGTGATCGAGAAATATGGCATCCCCGAAGATATCATTATCGAACTGG<br>CACGTGAAAATAACTCCGATGATCGCAAAAAGTTCATCAACAACCTGCAGAAAAAGAA<br>TGAAGCAACCCGCAAACGCATTAACGAAATTATTGGTCAGACCGGTAATCAGAATGCC<br>AAACGTATTGTGGAAAAAATCCGTCTGCATGATCAGCAAGAGGGTAAATGTCTGTATA<br>GCCTGAAAGATATCCCGCTGGAAGATCTGCTGCGCAATCCGAACAATTATGATATCGA<br>CCATATTATTCCGCGAAGCGTGAGCTTTGATGATAGCATGCATAACAAAGTTCTGGTT<br>CGTCGCGAACAGAATGCCAAAAAGAATAATCAGACCCCGTATCAGTATCTGACCAGTG<br>GTTATGCAGATATCAAATACAGCGTGTTTAAGCAGCATGTTCTGAATCTGGCCGAAAA<br>TAAAGATCGCATGACCAAAAAAAGCGCGAGTATCTGCTGGAAGAACGCGACATTAAC<br>AAATTTGAAGTGCAGAAAGAATTTATCAACCGCAACCTGGTTGATACCCGTTATGCAA<br>CCCGTGAACTGACCAATTATCTGAAAGCATATTTCAGCGCCAACAACATGAACGTGAA<br>AGTGAAAACGATTAACGGCAGCTTTACCGATTATCTGCGTAAAGTGTGGAAATTCAAA<br>AAAGAACGCAACCACGGCTATAAACATCATGCCGAAGATGCCCTGATTATTGCAAATG<br>CAGATTTCCTGTTTAAAGAAAACAAAAACTGAAAGCCGTCAACAGCGTGCTGGAAAA<br>ACCGGAAATTGAGACAAAACAGCTGGACATTCAGGTTGATAGCGAAGATAATTACAGC<br>GAAATGTTTATCATCCCGAAACAGGTGCAGGATATCAAAGATTTTCGCAACTTCAAAT<br>ATAGCCACCGCGTTGACAAAAAACCTAATCGTCAGCTGATTAACGATACCCTGTATAG<br>CACCCGCAAAAAGATAACAGCACCTATATTGTGCAGACCATTAAAGACATCTACGCC<br>AAAGATAATACCACCCTGAAAAAACAGTTCGACAAAAGCCCAGAAAAATTTCTGATGT<br>ATCAGCATGATCCGCGTACCTTCGAAAAACTGGAAGTTATTATGAAACAGTATGCCAA<br>CGAGAAAAATCCGCTGGCCAAATATCACGAAGAAACCGGTGAATATCTGACCAAATAT<br>TCCAAGAAGAACAACGGTCCGATCGTTAAATCCCTGAAATATATCGGTAATAAACTGG<br>GCAGCCATCTGGATGTTACCCATCAGTTTAAAAGCTCCACAAAGAAGCTGGTTAAACT<br>GTCCATCAAACCGTATCGCTTTGATGTGTATCTGACCGACAAAGGCTATAAATTCATT<br>ACCATCAGCTATCTGGACGTGCTGAAAAAAGACAACTATTATTATATCCCGGAACAGA<br>AATATGATAAACTGAAACTGGGTAAAGCCATCGATAAAAACGCCAAATTTATCGCCAG<br>CTTCTACAAAAACGACCTGATTAAACTGGATGGCGAGATCTATAAAAATCATCGGTGTT<br>AATAGCGACACCCGCAATATGATTGAGCTGGATCTGCCGGATATTCGCTATAAAGAAT<br>ATTGCGAACTGAACAACATTAAAGGCGAACCGCGTATCAAAAAGACCATCGGCAAAAA<br>AGTGAATAGCATCGAGAAACTGACCACCGATGTTCTGGGTAATGTGTTTACCAATACC<br>CAGTATACCAAACCTCAGCTGCTGTTCAAACGCGGTAAT | Original E2Cas9 polynucleotide |
| 10 | ATGAACCAGAAATTTATCCTGGGTCTGGATATTGGTATTACCAGCGTTGGTTATGGCC<br>TGATTGATTACGAAACCAAAAACATTATTGATGCCGGTGTTCGTCTGTTTCCGGAAGC<br>AAATGTTGAAAATAATGAAGGTCGTCGTAGCAAACGTGGTAGCCGTCGTCTGAAACGT<br>CGTCGTATTCATCGTCTGGAACGTGTTAAAAGCCTGCTGAGCGAATATAAGATTATTA<br>GCGGTCTGGCACCGACCAATAATCAGCCGTATAACATTCGTGTTAAAGGTCTGACCGA<br>ACAGCTGACCAAAGATGAACTGGCAGTTGCACTGCTGCATATTGCCAAACGCCGTGGC<br>ATTCATAAAATCGATGTGATTGATAGCAATGACGATGTGGGTAATGAACTGAGCACCA<br>AGAACAGCTGAACAAAAATAGCAAACTGCTGAAAGACAAATTCGTGTGTCAGATTCA<br>GCTGGAACGTATGAATGAAGGCCAGGTTCGTGGTGAAAAGAATCGCTTTAAAACCGCA<br>GACATCATCAAAGAAATTATCCAGCTGCTGAACGTGCAGAAAAACTTCCATCAGCTGG | Original F8Cas9 polynucleotide |

Sequence Listing

| SEQ ID NO | Sequence | Description |
|---|---|---|
| | ATGAAAACTTCATCAACAAATACATCGAGCTGGTTGAAATGCGTCGCGAATATTTTGA<br>AGGTCCTGGTCAGGGTAGCCCGTTTGGTTGGAATGGTGATCTGAAAAAATGGTACGAA<br>ATGCTGATGGGTCACTGTACCTATTTTCCGCAAGAACTGCGTAGCGTTAAATATGCCT<br>ATAGCGCAGACCTGTTTAATGCACTGAATGATCTGAACAACCTGATTATTCAGCGCGA<br>TAATAGCGAGAAACTGGAATACCATGAGAAGTATCACATCATCGAGAACGTGTTCAAG<br>CAGAAAAAAAAGCCGACGCTGAAACAAATCGCAAAAGAGATTGGCGTTAACCCGGAAG<br>ATATTAAAGGTTATCGTATTACCAAAAGCGGTACACCGGAATTCACCGAATTTAAACT<br>GTATCACGATCTGAAAAGCGTGCTGTTTGATCAGAGCATTCTGGAAAATGAAGATGTG<br>CTGGACCAGATTGCAGAAATTCTGACCATTTATCAGGACAAAGACAGCATCAAAAGCA<br>AACTGACCGAACTGGATATTCTGCTGAATGAAGAAGATAAAGAGAACATTGCACAGCT<br>GACCGGTTATAACGGCACACATCGCCTGAGCCTGAAATGTATTCGTCTGGTACTGGAA<br>GAACAGTGGTATAGCAGCCGTAATCAGATGGAAATCTTTACCCATCTGAACATTAAAC<br>CGAAGAAAATCAATCTGACCGCAGCCAACAAAATTCCGAAAGCCATGATTGATGAGTT<br>TATTCTGAGTCCGGTTGTGAAACGCACCTTTATTCAGAGCATCAACGTGATCAACAAA<br>GTGATCGAGAATATGGCATCCCCGAAGATATCATTATCGAACTGGCACGTGAAAATA<br>ACTCCGATGATCGCAAAAGTTCATCAACAACCTGCAGAAAAAGAATGAAGCAACCCG<br>CAAACGCATTAACGAAATTATTGGTCAGACCGGTAATCAGAATGCCAAACGTATTGTG<br>GAAAAAATCCGTCTGCATGATCAGCAAGAGGGGAAATGTCTGTATAGCCTGGAAAGCA<br>TTGCCCTGATGGATCTGCTGAATAACCCGCAGAATTATGAAGTGGATCATATTATTCC<br>GCGTAGCGTGGCATTTGATAATTCCATTCATAACAAAGTGCTGGTGAAGCAGATCGAG<br>AATAGCAAAAAAGGTAATCGTACGCCGTATCAGTATCTGAATAGCAGTGATGCAAAAC<br>TGAGCTACAACCAGTTTAAACAGCATATTCTGAATCTGAGCAAAAGCAAAGATCGCAT<br>CAGCAAAAAAAAGAAGGACTACCTGCTGGAAGAACGCGATATCAACAAATTTGAAGTC<br>CAGAAAGAGTTTATCAACCGCAATCTGGTTGATACCCGTTATGCAACCCGTGAACTGA<br>CCAGCTATCTGAAAGCATATTTCAGCGCCAATAACATGGACGTGAAAGTGAAAACAAT<br>TAACGGCAGCTTTACCAACCATCTGCGTAAAGTTTGGCGCTTTGATAAATATCGCAAC<br>CACGGCTATAAACATCATGCAGAAGATGCCCTGATTATTGCAAATGCAGATTTCCTGT<br>TTAAAGAAAACAAAAAACTGAAAGCCGTCAACAGCGTGCTGGAAAAACCGGAAATTGA<br>GACAAAACAGCTGGACATTCAGGTTGATAGCGAAGATAATTACAGCGAAATGTTTATC<br>ATCCCGAAACAGGTGCAGGATATCAAAGATTTTCGCAACTTCAAATATAGCCACCGCG<br>TTGACAAAAAACCTAATCGTCAGCTGATTAACGATACCCTGTATAGCACCCGCAAAAA<br>AGATAACAGCACCTATATTGTGCAGACCATTAAAGACATCTACGCCAAAGATAATACC<br>ACCCTGAAAAAACAGTTCGACAAAAGCCCAGAAAAATTTCTGATGTATCAGCATGATC<br>CGCGTACCTTCGAAAAACTGGAAGTTATTATGAAACAGTATGCCAACGAGAAAAATCC<br>GCTGGCCAAATATCACGAAGAAACCGGTGAATATCGACCAAATATTCAAGAAGAAC<br>AACGGTCCGATCGTTAAATCCCTGAAATATATCGGTAATAAACTGGGCAGCCATCTGG<br>ATGTTACCCATCAGTTTAAAAGCTCCACAAAGAAGCTGGTTAAACTGTCCATCAAACC<br>GTATCGCTTTGATGTGTATCTGACCGACAAAGGCTATAAATTCATTACCATCAGCTAT<br>CTGGACGTGCTGAAAAAAGACAACTATTATTATATCCCGGAACAGAAATATGATAAAC<br>TGAAACTGGGTAAAGCCATCGATAAAAACGCCAAATTTATCGCCAGCTTCTACAAAAA<br>CGACCTGATTAAACTGGATGGCGAGATCTATAAAATCATCGGTGTTAATAGCGACACC<br>CGCAATATGATTGAGCTGGATCTGCCCGGATATTCGCTATAAAGAATATTGCGAACTGA<br>ACAACATTAAAGGCGAACCGCGTATCAAAAAGACCATCGGCAAAAAGTGAATAGCAT<br>CGAGAAACTGACCACCGATGTTCTGGGTAATGTGTTTACCAATACCCAGTATACCAAA<br>CCTCAGCTGCTGTTCAAACGCGGTAAT | |
| 11 | ATGAACCAGAAATTTATCCTGGGTCTGGATATTGGTATTACCAGCGTTGGTTATGGCC<br>TGATTGATTACGAAACCAAAAACATTATTGATGCCGGTGTTCGTCTGTTTCCGGAAGC<br>AAATGTTGAAAATAATGAAGGTCGTCGTAGCAAACGTGGTAGCCGTCGTCTGAAACGT<br>CGTCGTATTCATCGTCTGGAACGTGTTAAAAAACTGCTGGAAGATTATAACCTGCTGG<br>ATCAGAGCCAGATTCCGCAGAGCACCAATCCGTATGCAATTCGTGTTAAAGGTCTGAG<br>CGAAGCACTGAGCAAAGATGAACTGGTTATTGCACTGCTGCATATTGCAAAACGCCGT<br>GGCATTCATAATATCAATGTTAGCAGCGAAGATGAGGATGCAAGCAATGAACTGAGCA<br>CCAAAGAACAAATTAACCGCAATAATAAGCTGCTGAAGGACAAATATGTTTGCGAAGT<br>TCAGCTGCAGCGTCTGAAAGAAGGTCAGATTCGCGGAGAAAAAAATCGCTTTAAAACC<br>ACCGATATCCTGAAAGAAATTGATCAGCTGCTTAAAGTGCAGAAGGATTATCATAACC<br>TGGACATCGATTTCATCAACCAGTACAAAGAAATCGTTGAAACCCGTCGCGAATATTT<br>TGAAGGTCCGGGTAAAGGTAGCCCGTATGGTTGGGAAGGTGATCCGAAAGCATGGTAT<br>GAAACCCTGATGGGTCATTGTACCTATTTTCCGGATGAACTGCGTAGCGTTAAATATG<br>CCTATAGCGCAGACCTGTTTAATGCACTGAATGATCTGAATAACCTGGTGATTCAGCG<br>TGATGGTCTGAGCAAACTGGAATATCATGAGAAATATCACATCATCGAAACGTGTTC<br>AAACAGAAGAAGAAACCGACCCTGAAACAAATCGCCAACGAATTAATGTGAACCCGG<br>AAGATATTAAAGGCTACCGTATTACCAAAAGCGGCAAACCGGAATTTACATCCTTTAA<br>ACTGTTCCACGATCTGAAAAAGTGGTGAAAGATCATGCCATCCTGGATGATATTGAT<br>CTGCTGAATCAGATTGCAGAAATCCTGACCATCTATCAGGATAAAGATAGCATTGTTG<br>CAGAACTGGGTCAGCTGGAATATCTGATGAGCGAAGCCGATAAACAGAGCATTAGCGA<br>ACTGACCGGTTATACCGGTACACATAGCCTGTCACTGAAATGCATGAACATGATTATC<br>GATGAACTGTGGCATAGCAGCATGAACCAGATGGAAGTTTTTACCTATCTGAATATGC<br>GTCCGAAAAGTATGAGCTGAAAGGTTATCAGCGTATTCCGACCGATATGATTGATGA<br>TGCAATTCTGAGTCCGGTTGTGAAACGCACCTTTATTCAGAGCATCAACGTGATCAAC<br>AAAGTGATCGAGAATATGGCATCCCCGAAGATATCATTATCGAACTGGCACGTGAAA<br>ATAACTCCGATGATCGCAAAAGTTCATCAACAACCTGCAGAAAAAGAATGAAGCAAC<br>CCGCAAACGCATTAACGAAATTATTGGTCAGACCGGTAATCAGAATGCCAAACGTATT<br>GTGGAAAAAATCCGTCTGCATGATCAGCAAGAGGGTAAATGTCTGTATAGCCTGGAAA | Original P2H12Cas9 polynucleotide |

| SEQ ID NO | Sequence | Description |
|---|---|---|
| | GCATTCCTCTGGAAGATCTGCTGAACAATCCGAATCATTATGAAGTGGATCACATTAT<br>TCCGCGTAGCGTGAGCTTTGATAATTCCTATCATAATAAAGTGCTGGTGAAACAGAGC<br>GAAAACTCCAAAAAATCCAACCTGACACCGTATCAGTATTTCAATAGCGGCAAATCCA<br>AACTGAGCTACAACCAGTTTAAACAGCATATTCTGAACCTGAGCAAAAGCCAGGATCG<br>CATCAGCAAGAAGAAGAAGGAGTACCTGCTGGAAGAACGCGATATTAACAAATTTGAA<br>GTGCAGAAAGAATTTATCAACCGCAACCTGGTTGATACCCGTTATGCAACCCGTGAAC<br>TGACCAATTATCTGAAAGCATATTTCAGCGCCAACAACATGAACGTGAAAGTGAAAAC<br>GATTAACGGCAGCTTTACCGATTATCTGCGTAAAGTGTGGAAATTCAAAAAAGAACGC<br>AACCACGGCTATAAACATCATGCCGAAGATGCCCTGATTATTGCAAATGCAGATTTCC<br>TGTTTAAAGAAAACAAAAAACTGAAAGCCGTCAACAGCGTGCTGGAAAAACCGGAAAT<br>TGAGACAAAACAGCTGGACATTCAGGTTGATAGCGAAGATAATTACAGCGAAATGTTT<br>ATCATCCCGAAACAGGTGCAGGATATCAAAGATTTTCGCAACTTCAAATATAGCCACC<br>GCGTTGACAAAAAACCTAATCGTCAGCTGATTAACGATACCCTGTATAGCACCCGCAA<br>AAAAGATAACAGCACCTATATTGTGCAGACCATTAAAGACATCTACGCCAAAGATAAT<br>ACCACCCTGAAAAAACAGTTCGACAAAAGCCCAGAAAAATTTCTGATGTATCAGCATG<br>ATCCGCGTACCTTCGAAAAACTGGAAGTTATTATGAAACAGTATGCCAACGAGAAAAA<br>TCCGCTGGCCAAATATCACGAAGAAACCGGTGAATATCTGACCAAATATTCCAAGAAG<br>AACAACGGTCCGATCGTTAAATCCCTGAAATATATCGGTAATAAACTGGGCAGCCATC<br>TGGATGTTACCCATCAGTTTAAAAGCTCCACAAAGAAGCTGGTTAAACTGTCCATCAA<br>ACCGTATCGCTTTGATGTGTATCTGACCGACAAAGGCTATAAATTCATTACCATCAGC<br>TATCTGGACGTGCTGAAAAAAGACAACTATTATTATATCCCGGAACAGAAATATGATA<br>AACTGAAACTGGGTAAAGCCATCGATAAAAACGCCAAATTTATCGCCAGCTTCTACAA<br>AAACGACCTGATTAAACTGGATGGCGAGATCTATAAAATCATCGGTGTTAATAGCGAC<br>ACCCGCAATATGATTGAGCTGGATCTGCCGGATATTCGCTATAAAGAATATTGCGAAC<br>TGAACAACATTAAAGGCGAACCGCGTATCAAAAAGACCATCGGCAAAAAAGTGAATAG<br>CATCGAGAAACTGACCACCGATGTTCTGGGTAATGTGTTTACCAATACCCAGTATACC<br>AAACCTCAGCTGCTGTTCAAACGCGGTAAT | |
| 12 | ATGAACCAGAAATTTATCCTGGGTCTGGATATTGGTATTACCAGCGTTGGTTATGGCC<br>TGATTGATTACGAAACCAAAAACATTATTGATGCCGGTGTTCGTCGTTTCCGGAAGC<br>AAATGTTGAAAATAATGAAGGTCGTCGTAGCAAACGTGGTAGCCGTCGTCTGAAACGT<br>CGTCGTATTCATCGTCTGGAACGTGTTAAAAAACTGCTGGAAGATTATAACCTGCTGG<br>ATCAGAGCCAGATTCCGCAGAGCACCAATCCGTATGCAATTCGTGTTAAAGGTCTGAG<br>CGAAGCACTGAGCAAAGATGAACTGGTTATTGCACTGCTGCATATTGCAAAACGCCGT<br>GGCATTCATAAAATCGATGTGATTGATAGCAATGACGATGTGGGTAATGAACTGAGCA<br>CCAAAGAACAGCTGAACAAAAATAGCAAACTGCTGAAAGACAAATTCGTGTGTCAGAT<br>TCAGCTGGAACGTATGAATGAAGGCCAGGTTCGTGGTGAAAAGAATCGCTTTAAAACC<br>GCAGACATCATCAAAGAAATTATCCAGCTGCTGAACGTGCAGAAAAACTTCCATCAGC<br>TGGATGAAAACTTCATCAACAAATACATCGAGCTGGTTGAAATGCGTCGCGAATATTT<br>TGAAGGTCCGGGTAAAGGTAGCCCCGTATGGTTGGGAAGGTGATCCGAAAGCATGGTAT<br>GAAACCCTGATGGGTCATTGTACCTATTTTCCGGATGAACTGCGTAGCGTTAAATATG<br>CCTATAGCGCAGACCTGTTTAATGCACTGAATGATCTGAATAACCTGGTGATTCAGCG<br>TGATGGTCTGAGCAAACTGGAATATCATGAGAAATATCACATCATCGAAACGTGTTC<br>AAACAGAAGAAGAAACCGACCCTGAAACAAATCGCCAACGAATTAATGTGAACCCGG<br>AAGATATTAAAGGCTACCGTATTACCAAAAGCGGTAAACCGCAGTTCACCGAATTTAA<br>ACTGTATCACGATCTGAAAAGCGTGCTGTTTGATCAGAGCATTCTGGAAAATGAAGAT<br>GTGCTGGACCAGATTGCAGAAATTCTGACCATTTATCAGGACAAAGACAGCATCAAAA<br>GCAAACTGACCGAACTGGATATTCTGCTGAATGAAGAAGATAAAGAGAACATTGCACA<br>GCTGACCGGTTATACCGGCACCCATCGTCTGAGCCTGAAATGTATTCGTCTGGTACTG<br>GAAGAACAGTGGTATAGCAGCCGTAATCAGATGGAAATCTTTACCCATCTGAACATTA<br>AACCGAAGAAAATCAATCTGACCGCAGCCAACAAAATTCCGAAAGCCATGATTGATGA<br>GTTTATTCTGAGTCCGGTTGTGAAACGTACCTTTGGTCAGGCAATTAACCTGATCAAC<br>AAAATCATTGAAAATATGGCGTGCCTGAGGATATCATTATTGAACTGGCACGTGAAA<br>ACAACAGCAAAGATAAACAGAAATTCATCAACGAGATGCAGAAGAAGAACGAAAATAC<br>CCGCAAACGGATTAACGAGATCATTGGCAAATATGGTAATCAGAATGCCAAACGCCTG<br>GTGGAAAAAATTCGTCTGCATGATGAACAAGAGGGCAAATGTCTGTATAGCCTGGAAA<br>GCATTCCTCTGGAAGATCTGCTGAACAATCCGAATCATTATGAAGTGGATCACATTAT<br>TCCGCGTAGCGTGAGCTTTGATAATTCCTATCATAATAAAGTGCTGGTGAAACAGAGC<br>GAAAACTCCAAAAAATCCAACCTGACACCGTATCAGTATTTCAATAGCGGCAAATCCA<br>AACTGAGCTACAACCAGTTTAAACAGCATATTCTGAACCTGAGCAAAAGCCAGGATCG<br>CATCAGCAAGAAGAAGAAGGAGTACCTGCTGGAAGAACGCGACATCAACAAATTTGAA<br>GTGCAGAAAGAATTTATCAACCGCAACCTGGTTGATACCCGTTATGCAACCCGTGAAC<br>TGACCAATTATCTGAAAGCATATTTCAGCGCCAACAACATGAACGTGAAAGTGAAAAC<br>GATTAACGGCAGCTTTACCGATTATCTGCGTAAAGTGTGGAAATTCAAAAAAGAACGC<br>AACCACGGCTATAAACATCATGCCGAAGATGCCCTGATTATTGCAAATGCAGATTTCC<br>TGTTTAAAGAAAACAAAAAACTGAAAGCCGTCAACAGCGTGCTGGAAAAACCGGAAAT<br>TGAGACAAAACAGCTGGACATTCAGGTTGATAGCGAAGATAATTACAGCGAAATGTTT<br>ATCATCCCGAAACAGGTGCAGGATATCAAAGATTTTCGCAACTTCAAATATAGCCACC<br>GCGTTGACAAAAAACCTAATCGTCAGCTGATTAACGATACCCTGTATAGCACCCGCAA<br>AAAAGATAACAGCACCTATATTGTGCAGACCATTAAAGACATCTACGCCAAAGATAAT<br>ACCACCCTGAAAAAACAGTTCGACAAAAGCCCAGAAAAATTTCTGATGTATCAGCATG<br>ATCCGCGTACCTTCGAAAAACTGGAAGTTATTATGAAACAGTATGCCAACGAGAAAAA<br>TCCGCTGGCCAAATATCACGAAGAAACCGGTGAATATCTGACCAAATATTCCAAGAAG<br>AACAACGGTCCGATCGTTAAATCCCTGAAATATATCGGTAATAAACTGGGCAGCCATC | Original SluCas9 polynucleotide |

Sequence Listing

| SEQ ID NO | Sequence | Description |
|---|---|---|
| | TGGATGTTACCCATCAGTTTAAAAGCTCCACAAAGAAGCTGGTTAAACTGTCCATCAA<br>ACCGTATCGCTTTGATGTGTATCTGACCGACAAAGGCTATAAATTCATTACCATCAGC<br>TATCTGGACGTGCTGAAAAAAGACAACTATTATTATATCCCGGAACAGAAATATGATA<br>AACTGAAACTGGGTAAAGCCATCGATAAAAACGCCAAATTTATCGCCAGCTTCTACAA<br>AAACGACCTGATTAAACTGGATGGCGAGATCTATAAAATCATCGGTGTTAATAGCGAC<br>ACCCGCAATATGATTGAGCTGGATCTGCCGGATATTCGCTATAAAGAATATTGCGAAC<br>TGAACAACATTAAAGGCGAACCGCGTATCAAAAAGACCATCGGCAAAAAAGTGAATAG<br>CATCGAGAAACTGACCACCGATGTTCTGGGTAATGTGTTTACCAATACCCAGTATACC<br>AAACCTCAGCTGCTGTTCAAACGCGGTAAT | |
| 13 | ATGAACCAGAAGTTCATTCTCGGTCTGGACATTGGCATTACTAGCGTGGGATACGGCT<br>TGATTGACTACGAGACTAAGAACATCATCGATGCCGGCGTCCGCCTGTTCCCGGAAGC<br>CAACGTGGAGAACAATGAGGGCCGGAGGTCGAAGAGAGGCTCCCGCCGCCTGAAGCGG<br>CGGCGAATCCACCGGCTGGAGAGAGTGAAGCTGCTGCTCACCGAATACGACCTGATCA<br>ACAAAGAACAGATCCCGACCTCCAACAACCCGTACCAGATCAGAGTGAAGGGTCTGTC<br>AGAAATCCTGTCCAAGGACGAACTGGCAATCGCCCTGCTGCACCTGGCCAAGCGGCGC<br>GGAATCCACAACGTGGATGTGGCTGCCGACAAGGAAGAAACCGCTTCCGACTCCCTGA<br>GCACTAAGGACCAGATCAACAAGAACGCCAAGTTCTTGGAGTCCCGCTACGTGTGCGA<br>GCTGCAGAAGGAACGGCTGGAAAACGAAGGTCACGTGCGCGGAGTGGAAAACCGGTTC<br>CTGACAAAGGACATTGTGCGCGAAGCGAAGAAGATCATTGATCCCAAATGCAGTACT<br>ACCCTGAAATCGACGAGACTTTCAAGGAAAAGTACATTTCCTGGTGGAAACCCGGCG<br>GGAATACTTCGAAGGCCCCGGACAGGGATCGCCGTTCGGATGGAACGGGGACCTCAAG<br>AAGTGGTACGAGATGCTGATGGGCACTGTACCTACTTTCCGCAAGAACTGCGCTCCG<br>TGAAGTACGCGTACTCCGCGGATCTCTTCAACGCGTTGAATGACCTGAACAACCTGAT<br>CATTCAGAGAGACAATTCCGAAAAGCTCGAGTACCACGAGAAGTATCACATCATCGAG<br>AATGTGTTCAAGCAGAAGAAGAAACCGACCCTCAAGCAAATCGCCAAGGAGATTGGCC<br>TCAACCCAGAGGACATCAAGGGATATCGGATTACCAAGAGCGGCACTCCCGAGTTTAC<br>CTCTTTCAAGCTGTTTCATGATCTGAAGAAAGTCGTGAAGGACCATGCCATTCTCGAC<br>GACATTGATCTCCTGAATCAGATCGCAGAGGATCCTGACTATCTACCAAGACAAGGACT<br>CGATTGTGGCAGAGCTGGGTCAGCTCGAATACCTGATGTCCGAGGCCGACAAGCAGTC<br>CATCTCCGAACTGACAGGGTACACGGGGACTCATAGCCTGTCGCTGAAGTGCATGAAC<br>ATGATCATTGATGAACTGTGGCACAGCTCCATGAACCAAATGGAAGTGTTTACCTACC<br>TCAACATGCGCCCTAAGAAGTACGAACTGAAAGGCTACCAGCGCATCCCCACCGACAT<br>GATCGACGACGCGATCTTGTCCCCTGTGGTCAAGAGGACCTTCATTCAATCCATCAAC<br>GTGATCAACAAGGTCATCGAAAAGTACGGAATACCAGAAGATATCATCATTGAGCTCG<br>CTCGGGAGAACAACTCGGATGACCGGAAGAAGTTCATCAACAATCTTCAGAAGAAGAA<br>CGAAGCGACTCGGAAACGGATCAACGAGATCATCGGACAGGACGGAAACCAGAACGCC<br>AAACGGATTGTCGAAAAGATTAGACTGCACGACCAGCAGGAAGGGAAGTGCCTGTACT<br>CACTCGAGTCAATACCGCTCGAGGACCTGTTGAACAACCCTAACCACTATGAAGTGGA<br>CCACATCATCCCTCGGTCCGTGAGCTTCGACAACTCGTACCACAACAAAGTGCTCGTG<br>AAGCAGTCCGAAAACTCCAAGAAATCCAACCTGACCCCGTACCAATACTTCAATTCGG<br>GAAAGTCGAAGCTGTCGTACAACCAGTTCAAACAACACATACTCAACCTTAGCAAAAG<br>CCAGGATCGCATTTCCAAGAAGAAGAAGGAATACCTCCTCGAGGAAAGGGACATCAAC<br>AAGTTCGAAGTGCAGAAAGAGTTCATCAATCGCAACTTGGTGGATACCAGATATGCCA<br>CCCGGGAACTCACCAACTATCTCAAGGCCTACTTTTCCGCCAACAACATGAACGTGAA<br>GGTCAAGACCATCAACGGGTCCTTCACTGACTACCTGAGAAAGGTCTGGAAGTTCAAG<br>AAGGAACGCAACCACGGATACAAGCACCACGCTGAGGACGCTCTGATCATCGCCAATG<br>CCGACTTCCTGTTCAAGGAAAACAAGAAGCTGAAAGCTGTCAACTCAGTGCTGGAAAA<br>GCCTGAAATCGAGACTAAGCAGCTGGATATCCAAGTGGACTCTGAGGACAACTACAGC<br>GAGATGTTCATCATCCCTAAACAAGTGCAGGATATCAAGGACTTTCGCAACTTCAAGT<br>ACTCACACCGGGTGGACAAGAAACCGAATAGACAGCTGATCAACGACACGTTGTATTC<br>CACCCGGAAGAAGGATAACTCAACCTACATTGTGCAGACTATCAAGGATATCTACGCC<br>AAAGATAACACTACTCTGAAGAAACAATTCGACAAGTCCCCAGAGAAGTTCCTGATGT<br>ACCAGCACGACCCCCGAACCTTTGAGAAGCTTGAAGTGATCATGAAGCAGTACGCCAA<br>CGAGAAGAACCCGCTGGCCAAGTACCATGAAGAAACCGGAGAATACCTGACCAAGTAC<br>AGCAAGAAGAACAACGGTCCCATTGTCAAGAGCCTGAAGTACATCGGCAACAAGCTGG<br>GATCCCACCTCGACGTGACACATCAGTTCAAGTCGTCGACTAAGAAGCTTGTGAAGCT<br>GTCAATCAAGAACTATAGATTCGACGTGTACTTGACCGAAAAGGGATACAAGTTCGTG<br>ACCATAGCCTATCTGAACGTGTTCAAGAAAGATAACTACTACTACATCCCAAGGACA<br>AGTACCAGGAGCTCAAAGAAAAGAAGAAGATCAAAGACACCGACCAGTTCATTGCCTC<br>CTTCTACAAGAACGACCTGATCAAACTGAACGGCGACCTCTACAAGATCATTGGAGTG<br>AACAGCGATGACAGGAACATCATTGAGCTGGACTACTACGACATCAAGTACAAGGACT<br>ACTGCGAGATCAACAACATCAAGGGCGAACCCCGGATCAAGAAAACTATTGGAAAGAA<br>AACCGAGTCCATTGAGAAGTTCACCACTGACGTGCTGGGAAACCTTTACCTCCACTCC<br>ACCGAGAAGGCACCACAACTGATCTTCAAGCGCGGCCTG | Codon-optimized Gib11SpaCas9-1 polynucleotide |
| 14 | ATGAACCAGAAGTTCATTCTCGGTCTGGACATTGGCATTACTAGCGTGGGATACGGCT<br>TGATTGACTACGAGACTAAGAACATCATCGATGCCGGCGTCCGCCTGTTCCCGGAAGC<br>CAACGTGGAGAACAATGAGGGCCGGAGGTCGAAGAGAGGCTCCCGCCGCCTGAAGCGG<br>CGGCGAATCCACCGGCTGGAGAGAGTGAAGCTGCTGCTCACCGAATACGACCTGATCA<br>ACAAAGAACAGATCCCGACCTCCAACAACCCGTACCAGATCAGAGTGAAGGGTCTGTC<br>AGAAATCCTGTCCAAGGACGAACTGGCAATCGCCCTGCTGCACCTGGCCAAGCGGCGC<br>GGAATCCACAACGTGGATGTGGCTGCCGACAAGGAAGAAACCGCTTCCGACTCCCTGA<br>GCACTAAGGACCAGATCAACAAGAACGCCAAGTTCTTGGAGTCCCGCTACGTGTGCGA | Codon-optimized Gib11SpaCas9-3 polynucleotide |

Sequence Listing

| SEQ ID NO | Sequence | Description |
|---|---|---|
| | GCTGCAGAAGGAACGGCTGGAAAACGAAGGTCACGTGCGCGGAGTGGAAAACCGGTTC<br>CTGACAAAGGACATTGTGCGCGAAGCGAAGAAGATCATTGATACCCAAATGCAGTACT<br>ACCCTGAAATCGACGAGACTTTTCAAGGAAAAGTACATTTCCCTGGTGGAAACCCGGCG<br>GGAATACTTCGAAGGCCCCGGACAGGGATCGCCGTTCGGATGGAACGGGGACCTCAAG<br>AAGTGGTACGAGATGCTGATGGGGCACTGTACCTACTTTCCGCAAGAACTGCGCTCCG<br>TGAAGTACGCGTACTCCGCGGATCTCTTCAACGCGTTGAATGACCTGAACAACCTGAT<br>CATTCAGAGAGACAATTCCGAAAAGCTCGAGTACCACGAGAAGTATCACATCATCGAG<br>AATGTGTTCAAGCAGAAGAAGAAACCGACCCTCAAGCAAATCGCCAAGGAGATTGGCG<br>TCAACCCAGAGGACATCAAGGGATATCGGATTACCAAGAGCGGCACTCCCGAGTTTAC<br>CTCTTTCAAGCTGTTTCATGATCTGAAGAAAGTCGTGAAGGACCATGCCATTCTCGAC<br>GACATTGATCTCCTGAATCAGATCGCAGAGATCCTGACTATCTACCAAGACAAGGACT<br>CGATTGTGGCAGAGCTGGGTCAGCTCGAATACCTGATGTCCGAGGCCGACAAGCAGTC<br>CATCTCCGAACTGACAGGGTACACGGGGACTCATAGCCTGTCGCTGAAGTGCATGAAC<br>ATGATCATTGATGAACTGTGGCACAGCTCCATGAACCAAATGGAAGTGTTTACCTACC<br>TCAACATGCGCCCTAAGAAGTACGAACTGAAAGGCTACCAGCGCATCCCCACCGACAT<br>GATCGACGACGCGATCTTGTCCCCTGTGGTCAAGAGGACCTTCATTCAATCCATCAAC<br>GTGATCAACAAGGTCATCGAAAAGTACGGTATTCCAGAAGATATCATCATTGAGCTCG<br>CTCGGGAGAACAACTCGGATGACCGGAAGAAGTTCATCAACAATCTTCAGAAGAAGAA<br>CGAAGCGACTCGGAAACGGATCAACGAGATCATCGGACAGACCGGAAACCAGAACGCC<br>AAACGGATTGTCGAAAAGATTAGACTGCACGACCAGCAGGAAGGGAAGTGCCTGTACT<br>CACTCGAGTCAATACCGCTCGAGGACCTGTTGAACAACCCTAACCACTATGAAGTGGA<br>CCACATCATCCCTCGGTCCGTGAGCTTCGACAACTCGTACCACAACAAAGTGCTCGTG<br>AAGCAGTCCGAAAACTCCAAGAAATCCAACCTGACCCCGTACCAATACTTCAATTCGG<br>GAAAGTCGAAGCTGTCGTACAACCAGTTCAAACAACACATACTCAACCTTAGCAAAAG<br>CCAGGATCGCATTTCCAAGAAGAAGAAGGAATACCTCCTCGAGGAAAGGGACATCAAC<br>AAGTTCGAAGTGCAGAAAGAGTTCATCAATCGCAACTTGGTGGATACCAGATATGCCA<br>CCCGGGAACTCACCAGCTATCTCAAGGCCTACTTTTCCGCCAACAACATGGACGTGAA<br>GGTCAAGACCATCAACGGGTCCTTCACTAACCATCTGAGAAAGGTCTGGCGGTTTGAC<br>AAGTACCGCAACCACGGATACAAGCACCACGCTGAAGACGCTCTGATCATCGCCAATG<br>CCGACTTCCTGTTCAAGGAAAACAAGAAGCTGCAGAACACGAACAAGATTCTGGAAAA<br>GCCTACCATTGAGAACAACACTAAGAAGGTCACCGTGGAGAAGGAAGAGGACTACAAC<br>AACGTGTTCGAAACTCCTAAACTGGTGGAGGATATCAAGCAATACCGCGACTACAAGT<br>TCTCACACCGGGTGGACAAGAAACCGAATAGACAGCTGATCAACGACGTTGTATTC<br>CACCCGGATGAAGGATGAGCATGACTACATTGTGCAGACTATCACCGATATCTACGGA<br>AAAGATAACACTAACCTGAAGAAACAATTCAACAAGAACCCAGAGAAGTTCCTGATGT<br>ACCAGAACGACCCCAAGACCTTTGAGAAGCTTTCCATCATCATGAAGCAGTACTCCGA<br>CGAGAAGAACCCGCTGGCCAAGTACTACGAAGAAACCGGAGAATACCTGACCAAGTAC<br>AGCAAGAAGAACAACGGTCCCATTGTCAAGAAGATCAAGCTGCTCGGCAACAAGGTCG<br>GAAACCACCTCGACGTGACAAACAAGTACGAGAACTCGACTAAGAAGCTTGTGAAGCT<br>GTCAATCAAGAACTATAGATTCGACGTGTACTTGACCGAAAAGGGATACAAGTTCGTG<br>ACCATAGCCTATCTGAACGTGTTCAAGAAAGATAACTACTACTACATCCCCAAGGACA<br>AGTACCAGGAGCTCAAAGAAAAGAAGAAGATCAAAGACACCGACCAGTTCATTGCCTC<br>CTTCTACAAGAACGACCTGATCAAACTGAACGGCGACCTCTACAAGATCATTGGAGTG<br>AACAGCGATGACAGGAACATCATTGAGCTGGACTACTACGACATCAAGTACAAGGACT<br>ACTGCGAGATCAACAACATCAAGGGCGAACCCCGGATCAAGAAAACTATTGGAAAGAA<br>AACCGAGTCCATTGAGAAGTTCACCACTGACGTGCTGGGAAACCTTTACCTCCACTCC<br>ACCGAGAAGGCACCACAACTGATCTTCAAGCGCGGCCTG | |
| 15 | ATGAACCAAAAGTTCATTCTGGGGCTCGATATCGGCATCACCTCCGTGGGATATGGTC<br>TGATCGACTACGAGACTAAGAACATCATCGACGCTGGAGTGCGACTGTTCCCGGAAGC<br>GAACGTGGAGAACAACGAAGGCCGCAGATCCAAGCGCGGGTCCAGAAGGCTCAAGAGG<br>CGGAGGATCCATAGACTGACAGAGTGAAGCACCTCCTTGCCGAATACGATCTGTTGG<br>ACCTTACCAACATTCCCAAGAGCACCAACCCGTACCAAACCAGAGTGAAGGGCCTGAA<br>CGAAAAGCTGTCGAAAGATGAACTGGTCATTGCCCTGCTGCATATTGCCAAACGGCGC<br>GGAATCCATAACGTGGACGTGGCCGCTGACAAGGAAGAGACTGCGTCCGACTCGCTGT<br>CAACCAAGGACCAGATCAACAAGAACGCCAAATTCCTGGAAAGCCGCTACGTCTGCGA<br>GCTTCAAAAAGAACGGCTGGAGAACGAGGGACACGTCAGGGGAGTGGAGAACCGGTTC<br>CTGACCAAGGACATCGTCGGGAAGCCAAGAAGATCATCGACACCCAAATGCAGTATT<br>ATCCGGAAATTGATGAAACTTTTAAGGAGAAGTACATTTCCCTGGTGGAAACTCGGAG<br>GGAGTACTTCGAGGGACCTGGAAAGGGATCCCCTTTCGGCTGGAAGGGAACATTAAG<br>AAGTGGTTTGAACAGATGATGGGCCATTGCACTTACTTTCCGGAAGAACTCCGGTCCG<br>TGAAGTACTCATACTCTGCCGAGCTGTTCAATGCACTCAACGACCTTAACAACTTGGT<br>GATCACCCGCGATGAAGATGCCAAGTTGAACTACGGAGAAAAGTTCCAGATCATCGAG<br>AACGTGTTCAAGCAGAAAAAGACCCCAAATCTGAAGCAGATTGCCATCGAAATTGGCG<br>TGCACGAGACTGAGATCAAGGGATACCGGGTCAACAAGTCCGGCACGCCAGAGTTCAC<br>CGAGTTCAAGCTGTACCACGATCTGAAGTCGATCGTGTTTGACAAGTCCATCCTGGAA<br>AACGAAGCCATTCTGGACCAGATTGCTGAGATCCTGACCATCTACCAGGACGAGCAAT<br>CGATTAAGGAAGAACTGAACAAGCTCCCCGAGATTCTGAACGAACAGGATAAGGCCGA<br>GATCGCGAAGCTCATTGGTTACAATGGTACCCACCGCTTGTCCCTTAAGTGCATCCAT<br>CTGATCAATGAGGAACTGTGGCAGACCAGCCGGAACCAGATGGAGATCTTCAATTACT<br>TGAACATCAAGCCGAACAAGGTGGACCTGTCCGAACAGAACAAGATACCCAAGGACAT<br>GGTCAACGACTTTATCCTCTCACCGGTGGTCAAGCGCACCTTCATTCAATCTATCAAC<br>GTGATCAACAAGGTCATCGAGAAGTACGGCATTCCTGAGGATATCATCATCGAGCTGG<br>CTCGGGAGAACAACTCAGACGATAGGAAGAAGTTCATTAACAACCTCCAGAAAAAGAA | Codon-optimized E2Cas9 polynucleotide |

| SEQ ID NO | Sequence | Description |
|---|---|---|
| | CGAGGCCACTCGCAAGCGGATTAATGAGATCATCGGTCAGACCGGGAACCAGAACGCC<br>AAGCGGATCGTGGAAAAGATTCGGCTCCACGACCAACAGGAGGGAAAGTGTCTGTACT<br>CGCTGAAGGACATTCCCCTGGAGGACCTCCTGAGGAACCCAAACAACTACGACATCGA<br>TCACATAATCCCCCGCAGCGTGTCATTCGACGATTCCATGCATAACAAGGTCCTCGTG<br>CGGAGAGAGCAGAATGCCAAGAAGAACAACCAGACTCCGTACCAGTACCTGACGTCCG<br>GCTACGCAGACATCAAGTACTCAGTGTTCAAACAGCACGTGCTCAACCTGGCCGAGAA<br>CAAGGACAGGATGACCAAGAAGAAGCGCGAATACCTTCTCGAGGAACGGGATATCAAT<br>AAGTTCGAGGTGCAGAAGGAGTTTATCAATAGAAACCTGGTGGACACTCGCTATGCCA<br>CCCGCGAACTGACCAACTACCTGAAGGCGTACTTCTCCGCCAACAACATGAACGTGAA<br>GGTCAAAACTATTAACGGCAGCTTCACCGACTATCTGCGCAAGGTCTGGAAGTTCAAG<br>AAGGAACGCAACCACGGTTACAAGCACCACGCGGAAGATGCGCTGATTATCGCCAACG<br>CTGACTTCCTGTTCAAGGAAAACAAGAAGCTCAAGGCCGTGAACTCAGTGCTCGAGAA<br>GCCTGAAATCGAGACTAAGCAGCTGGACATCCAGGTCGATTCGGAAGATAACTACTCC<br>GAAATGTTCATCATCCCTAAGCAAGTGCAGGACATCAAGGACTTCAGGAATTTCAAGT<br>ACAGCCATCGCGTGGACAAGAAGCCAAACAGACAGCTGATCAACGATACACTGTATTC<br>CACCCGGAAGAAGGACAACTCCACCTACATCGTCCAAACCATTAAGGACATCTACGCA<br>AAGGACAACACCACGCTTAAGAAGCAGTTCGACAAGAGCCCCGAAAAGTTCCTCATGT<br>ACCAGCACGACCCCAGAACCTTCGAGAAGCTTGAAGTGATCATGAAGCAGTACGCCAA<br>CGAAAAGAACCCACTGGCTAAGTACCACGAGGAAACCGGCGAATACCTGACCAAGTAC<br>TCCAAAAGAACAACGGACCGATCGTCAAGTCCCTGAAGTACATTGGGAACAAGCTCG<br>GCTCGCACCTCGATGTGACCCACCAGTTCAAGTCCTCGACCAAAAAGCTCGTGAAGCT<br>GTCCATCAAGCCGTACCGGTTCGACGTGTACCTGACTGACAAGGGATATAAGTTCATC<br>ACCATTTCCTACCTCGACGTGTTGAAGAAGGATAACTACTACTACATTCCGGAACAGA<br>AGTACGACAAGCTCAAGCTCGGAAAGGCCATCGACAAAAATGCGAAGTTCATCGCGAG<br>CTTCTACAAGAATGACTTGATCAAGCTGGATGGCGAAATCTACAAGATCATCGGGTC<br>AACTCCGATACCCGCAACATGATTGAGCTGGATCTGCCCGACATTCGGTACAAGGAAT<br>ACTGCGAGCTGAACAACATCAAGGGAGAACCGCGGATCAAGAAAACCATCGGAAAGAA<br>AGTGAACAGCATCGAGAAACTGACTACTGACGTCCTGGGAAACGTGTTCACCAACACA<br>CAATACACCAAACCCCAGCTGCTGTTTAAGCGCGGGAAC | |
| 16 | ATGAACCAAAAGTTCATTCTGGGGCTCGATATCGGCATCACCTCCGTGGGATATGGTC<br>TGATCGACTACGAGACTAAGAACATCATCGACGCTGGAGTGCGACTGTTCCCGGAAGC<br>GAACGTGGAGAACAACGAAGGCCGCAGATCCAAGCGCTGGTTCCAGAAGGCTCAAGAGG<br>CGGAGGATCCATAGACTCGAGAGAGTGAAGTCGCTCCTTTCGGAATACAAGATTATCA<br>GCGGTCTTGCCCCCACCAACAACCAACCGTACAACATCAGAGTGAAGGGCCTGACCGA<br>ACAGCTGACCAAAGATGAACTGGCCGTCGCCCTGCTGCATATTGCCAAACGGCGCGGA<br>ATCCATAAGATCGACGTGATTGACAGCAACGATGACGTGGGAAACGAGCTGTCAACCA<br>AGGAACAGCTTAACAAGAACAGCAAATTGCTGAAGGACAAGTTTGTCTGCCAAATTCA<br>ACTGGAACGGATGAACGAGGGACAAGTCAGGGGAGAGAAAAACCGGTTCAAGACCGCC<br>GACATCATCAAGGAGATCATCCAACTGCTGAACGTGCAGAAGAACTTCCACCAACTGG<br>ATGAAAACTTCATTAACAAGTACATTGAACTGGTGGAAATGCGGAGGGAGTACTTCGA<br>GGGACCTGGACAGGGATCCCCTTTCGGCTGGAATGGGGACCTTAAGAAGTGGTACGAA<br>ATGTTGATGGGCCATTGCACTTACTTTCCGCAAGAACTCCGGTCCGTGAAGTACGCAT<br>ACTCTGCCGACCTGTTCAATGCACTCAACGACCTTAACAACTTGATCATCCAGCGCGA<br>TAACTCGGAAAAGTTGGAATACCACGAAAAGTATCACATCATCGAGAACGTGTTCAAG<br>CAGAAAAAGAAGCCAACTCTGAAGCAGATTGCCAAGGAAATTGGCGTGAATCCGGAGG<br>ATATCAAGGGATACCGGATCACTAAGTCCGGCACGCCAGAGTTCACCGAGTTCAAGCT<br>GTACCACGATCTGAAGTCGGTGCTCTTTGACCAGTCCATCCTGGAAACGAAGATGTG<br>CTGGACCAGATTGCTGAGATCCTGACCATCTACCAGGACAAGGACTCGATTAAGTCCA<br>AGCTCACCGAGCTGGACATTCTGCTGAACGAAGAAGATAAGGAGAACATCGCGCAGCT<br>CACCGGTTACAATGGTACCCACCGCTTGTCCCTTAAGTGCATCCGCCTGGTGCTGGAG<br>GAACAGTGGTACTCGAGCCGGAACCAGATGGAGATCTTCACTCACTTGAACATCAAGC<br>CGAAAAAGATTAACCTGACTGCCGCCAACAAGATACCCAAGGCCATGATCGACGAGTT<br>TATCCTCTCACCGGTTGGTCAAGCGCACCTTCATTCAATCTATCAACGTGATCAACAAG<br>GTCATCGAGAAGTACGGCATTCCTGAGGATATCATCATCGAGCTGGCTCGGGAGAACA<br>ACTCAGACGATAGGAAGAAGTTCATTAACAACCTCCAGAAAAAGAACGAGGCCACTCG<br>CAAGCGGATTAATGAGATCATCGGTCAGACCGGGAACCAGAACGCCAAGCGGATCGTG<br>GAAAAGATTCGGCTCCACGACCAACAGGAGGGAAAGTGTCTGTACTCGCTGGAGTCGA<br>TTGCACTGATGGACCTCCTGAACAACCCACAGAACTACGAAGTCGATCACATAATCCC<br>CCGCAGCGTGGCATTCGACAACTCCATCCATAACAAGGTCCTCGTGAAGCAGATCGAG<br>AATAGCAAGAAGGGGAACCGGACTCCGTACCAGTACCTGAACTCCTCCGACGCCAAGC<br>TGTCATACAATCAGTTCAAACAGCACATTCTCAACCTGTCCAAGTCAAAGGACAGGAT<br>CTCCAAGAAGAAGAAGGACTACCTTCTCGAGGAACGGGATATCAATAAGTTCGAGGTG<br>CAGAAGGAGTTTATCAATAGAAACCTGGTGGACACTCGCTATGCCACCCGCGAACTGA<br>CCAGCTACCTGAAGGCGTACTTCTCCGCCAACAACATGGACGTGAAGGTCAAAACTAT<br>TAACGGCAGCTTCACCAACCATCTGCGCAAGGTCTGGAGGTTCGACAAGTACCGCAAC<br>CACGGTTACAAGCACCACGCGGAAGATGCGCTGATTATCGCCAACGCTGACTTCCTGT<br>TCAAGGAAAACAAGAAGCTCAAGGCCGTGAACTCAGTGCTCGAGAAGCCTGAAATCGA<br>GACTAAGCAGCTGGACATCCAGGTCGATTCGGAAGATAACTACTCCGAAATGTTCATC<br>ATCCCTAAGCAAGTGCAGGACATCAAGGACTTCAGGAATTTCAAGTACAGCCATCGCG<br>TGGACAAGAAGCCAAACAGACAGCTGATCAACGATACACTGTATTCCACCCGGAAGAA<br>GGACAACTCCACCTACATCGTCCAAACCATTAAGGACATCTACGCAAAGGACAACACC<br>ACGCTTAAGAAGCAGTTCGACAAGAGCCCCGAAAAGTTCCTCATGTACCAGCACGACC<br>CCAGAACCTTCGAGAAGCTTGAAGTGATCATGAAGCAGTACGCCAACGAAAAGAACCC | Codon-<br>optimized<br>F8Cas9<br>polynucleotide |

Sequence Listing

| SEQ ID NO | Sequence | Description |
|---|---|---|
| | ACTGGCTAAGTACCACGAGGAAACCGGCGAATACCTGACCAAGTACTCCAAAAAGAAC<br>AACGGACCGATCGTCAAGTCCCTGAAGTACATTGGGAACAAGCTCGGCTCGCACCTCG<br>ATGTGACCCACCAGTTCAAGTCCTCGACCAAAAAGCTCGTGAAGCTGTCCATCAAGCC<br>GTACCGGTTCGACGTGTACCTGACTGACAAGGGATATAAGTTCATCACCATTTCCTAC<br>CTCGACGTGTTGAAGAAGGATAACTACTACTACATTCCGGAACAGAAGTACGACAAGC<br>TCAAGCTCGGAAAGGCCATCGACAAAAATGCGAAGTTCATCGCGAGCTTCTACAAGAA<br>TGACTTGATCAAGCTGGATGGCGAAATCTACAAGATCATCGGGGTCAACTCCGATACC<br>CGCAACATGATTGAGCTGGATCTGCCCGACATTCGGTACAAGGAATACTGCGAGCTGA<br>ACAACATCAAGGGAGAACCGCGGATCAAGAAAACCATCGGAAAGAAAGTGAACAGCAT<br>CGAGAAACTGACTACTGACGTCCTGGGAAACGTGTTCACCAACACACAATACACCAAA<br>CCCCAGCTGCTGTTTAAGCGCGGGAAC | |
| 17 | ATGAACCAAAAGTTCATTCTGGGGCTCGATATCGGCATCACCTCCGTGGGATATGGTC<br>TGATCGACTACGAGACTAAGAACATCATCGACGCTGGAGTGCGACTGTTCCCGGAAGC<br>GAACGTGGAGAACAACGAAGGCCGCAGATCCAAGCGCGGGTCCAGAAGGCTCAAGAGG<br>CGGAGGATCCATAGACTCGAGAGAGTGAAGAAGCTCCTTGAAGATTACAATCTGTTGG<br>ACCAGTCACAGATTCCCCAAAGCACCAACCCGTACGCCATCAGAGTGAAGGGCCTGTC<br>AGAAGCACTGTCGAAAGATGAACTGGTCATTGCCCTGCTGCATATTGCCAAACGGCGC<br>GGAATCCATAACATCAACGTGTCGAGCGAAGATGAGGACGCGTCCAACGAACTGTCAA<br>CCAAGGAACAGATCAACCGGAACAACAAACTGCTGAAGGACAAATACGTCTGCGAGGT<br>GCAGCTTCAACGGCTGAAAGAGGGACAGATCAGGGGAGAGAAAAACCGGTTCAAGACC<br>ACCGACATCCTTAAGGAGATCGACCAACTCCTGAAAGTGCAGAAGGACTATCACAACC<br>TCGACATTGATTTTATCAACCAGTACAAGGAGATTGTGGAAACTCGGAGGGAGTACTT<br>CGAGGGACCTGGAAAGGGATCCCCTTATGGCTGGGAAGGGGACCCCAAGGCTTGGTAC<br>GAAACCCTGATGGCCATTGCACTTACTTTCCGGATGAACTCCGGTCCGTGAAGTACG<br>CTTACTCTGCCGACCTGTTCAATGCACTCAACGACCTTAACAACTTGGTGATCCAACG<br>CGATGGTCTTTCCAAGTTGGAGTACCACGAAAGTACCACATCATCGAGAACGTGTTC<br>AAGCAGAAAAAGAAGCCAACTCTGAAGCAGATTGCCAACGAAATTAACGTGAACCCCG<br>AGGATATCAAGGGATACCGGATTACCAAGTCCGGCAAACCAGAGTTCACCTCATTCAA<br>GCTGTTTCACGATCTGAAGAAGGTCGTGAAGGACCACGCCATCCTGGATGACATTGAT<br>CTTCTGAACCAGATTGCTGAGATCCTGACCATCTACCAGGACAAGGACTCGATTGTGG<br>CCGAACTGGGACAGCTCGAGTACCTGATGTCCGAAGCCGATAAGCAGTCCATCAGCGA<br>ACTCACCGGTTACACCGGTACCCACTCCTTGTCCCTTAAGTGCATGAACATGATCATT<br>GACGAACTGTGGCACTCCAGCATGAACCAGATGGAGGTGTTCACCTACTTGAACATGC<br>GCCCGAAGAAGTACGAGCTGAAGGGCTACCAGCGCATACCCACGGACATGATCGACGA<br>CGCCATCCTCTCACCGGTGGTCAAGCGCACCTTCATTAATCTATCAACGTGATCAAC<br>AAGGTCATCGAGAAGTACGGCATTCCTGAGGATATCATCATCGAGCTGGCTCGGGAGA<br>ACAACTCAGACGATAGGAAGAAGTTCATTAACAACCTCCAGAAAAAGAACGAGGCCAC<br>TCGCAAGCGGATTAATGAGATCATCGGTCAGACCGGGAACCAGAACGCCAAGCGGATC<br>GTGGAAAAGATTCGGCTCCACGACCAACAGGAGGGAAAGTGTCTGTACTCGCTGGAGT<br>CCATTCCCCTGGAGGACCTCCTGAACAACCCAAACCACTACGAGGTCGATCACATAAT<br>CCCCCGCAGCGTGTCATTCGACAACTCCTACCATAACAAGGTCCTCGTGAAGCAGTCG<br>GAGAATAGCAAGAAGTCGAACCTGACTCCGTACCAGTACTTCAACTCCGGCAAATCCA<br>AGCTGTCCTACAATCAGTTCAAACAGCACATTCTCAACCTGTCAAGAGCCAGGACAG<br>GATTTCGAAGAAGAAGAAGGAATACCTTCTCGAGGAACGGGATATCAATAAGTTCGAG<br>GTGCAGAAGGAGTTTATCAATAGAAACCTGGTGGACACTCGCTATGCCACCCGCGAAC<br>TGACCAACTACCTGAAGGCGTACTTCTCCGCCAACAACATGAACGTGAAGGTCAAAAC<br>TATTAACGGCAGCTTCACCGACTATCTGCGCAAGGTCTGGAAGTTCAAGAAGGAACGC<br>AACCACGGTTACAAGCACCACGCGGAAGATGCGCTGATTATCGCCAACGCTGACTTCC<br>TGTTCAAGGAAAACAAGAAGCTCAAGGCCGTGAACTCAGTGCTCAGAAGCCTGAAAT<br>CGAGACTAAGCAGCTGGACATCCAGGTCGATTCGGAAGATAACTACTCCGAAATGTTC<br>ATCATCCCTAAGCAAGTGCAGGACATCAAGGACTTCAGGAATTTCAAGTACAGCCATC<br>GCGTGGACAAGAAGCCAAACAGACAGCTGATCAACGATACACTGTATTCCACCCGGAA<br>GAAGGACAACTCCACCTACATCGTCCAAACCATTAAGGACATCTACGCAAAGGACAAC<br>ACCACGCTTAAGAAGCAGTTCGACAAGAGCCCCGAAAAGTTCCTCATGTACCAGCACG<br>ACCCCAGAACCTTCGAGAAGCTTGAAGTGATCATGAAGCAGTACGCCAACGAAAAGAA<br>CCCACTGGCTAAGTACCACGAGGAAACCGGCGAATACCTGACCAAGTACTCCAAAAAG<br>AACAACGGACCGATCGTCAAGTCCCTGAAGTACATTGGGAACAAGCTCGGCTCGCACC<br>TCGATGTGACCCACCAGTTCAAGTCCTCGACCAAAAAGCTCGTGAAGCTGTCCATCAA<br>GCCGTACCGGTTCGACGTGTACCTGACTGACAAGGGATATAAGTTCATCACCATTTCC<br>TACCTCGACGTGTTGAAGAAGGATAACTACTACTACATTCCGGAACAGAAGTACGACA<br>AGCTCAAGCTCGGAAAGGCCATCGACAAAAATGCGAAGTTCATCGCGAGCTTCTACAA<br>GAATGACTTGATCAAGCTGGATGGCGAAATCTACAAGATCATCGGGGTCAACTCCGAT<br>ACCCGCAACATGATTGAGCTGGATCTGCCCGACATTCGGTACAAGGAATACTGCGAGC<br>TGAACAACATCAAGGGAGAACCGCGGATCAAGAAAACCATCGGAAAGAAAGTGAACAG<br>CATCGAGAAACTGACTACTGACGTCCTGGGAAACGTGTTCACCAACACACAATACACC<br>AAACCCCAGCTGCTGTTTAAGCGCGGGAAC | Codon-optimized P2H12Cas9 polynucleotide |
| 18 | ATGAACCAAAAGTTCATTCTGGGGCTCGATATCGGCATCACCTCCGTGGGATATGGTC<br>TGATCGACTACGAGACTAAGAACATCATCGACGCTGGAGTGCGACTGTTCCCGGAAGC<br>GAACGTGGAGAACAACGAAGGCCGCAGATCCAAGCGCGGGTCCAGAAGGCTCAAGAGG<br>CGGAGGATCCATAGACTCGAAAGAGTGAAGAAGCTCCTTGAAGATTACAATCTGTTGG<br>ACCAGAGCCAGATTCCCCAAAGCACCAACCCGTACGCCATCAGAGTGAAGGGCCTGTC<br>CGAAGCCCTGTCGAAAGATGAACTGGTCATTGCCCTGCTGCATATTGCCAAACGGCGC | Codon-optimized SluCas9-1 polynucleotide |

| SEQ ID NO | Sequence | Description |
|---|---|---|
| | GGAATCCATAAGATCGACGTGATAGACTCCAACGATGACGTGGGCAACGAACTGTCAA<br>CCAAGGAGCAGCTGAACAAGAACTCGAAACTGCTGAAGGACAAGTTCGTCTGCCAAAT<br>TCAACTGGAACGGATGAACGAGGGACAAGTCAGGGGAGAGAAAAACCGGTTCAAGACC<br>GCGGACATCATCAAGGAGATCATCCAACTCCTGAATGTGCAGAAGAACTTTCACCAGC<br>TGGATGAAAACTTCATTAACAAGTACATTGAACTGGTGGAAATGCGGAGGGAGTACTT<br>CGAGGGGACCTGGAAAGGGATCCCCTTACGGCTGGGAAGGGGACCCCAAGGCTTGGTAC<br>GAAACGCTCATGGGCCATTGCACTTACTTTCCGGACGAACTCCGGTCCGTGAAGTACG<br>CATACTCTGCCGATCTGTTCAATGCACTCAACGACCTTAACAACTTGGTGATCCAGCG<br>CGATGGCCTGTCCAAGTTGGAATACCACGAAAAGTATCACATCATCGAGAACGTGTTC<br>AAGCAGAAAAAGAAGCCAACTCTGAAGCAGATTGCCAACGAAATTAACGTGAACCCCG<br>AGGATATCAAGGGATACCGGATCACTAAGTCCGGCAAACCACAGTTCACCGAGTTCAA<br>GCTGTACCACGATCTGAAGTCGGTGCTCTTTGACCAGTCCATCCTGGAAAACGAAGAT<br>GTGCTGGACCAGATTGCTGAGATCCTGACCATCTACCAGGACAAGGACTCGATTAAGA<br>GCAAGCTCACGGAGCTGGACATTCTGCTGAACGAAGAGGATAAGGAGAACATCGCGCA<br>GCTCACTGGTTACACCGGTACCCACCGCTTGTCCCTTAAGTGCATCCGGCTGGTCCTC<br>GAGGAACAATGGTACTCCAGCCGGAACCAGATGGAGATCTTCACGCACTTGAACATCA<br>AGCCGAAGAAGATTAACCTGACCGCTGCGAACAAGATACCCAAGGCCATGATCGACGA<br>GTTTATCCTCTCACCGGTGGTCAAGCGCACCTTCGGACAAGCCATCAACCTCATCAAC<br>AAGATTATCGAGAAGTACGGCGTGCCTGAGGATATCATCATCGAGCTGGCTCGGGAGA<br>ACAACTCAAAGGATAAGCAGAAGTTCATTAACGAGATGCAGAAAAAGAACGAGAACAC<br>TCGCAAGCGGATTAATGAGATCATCGGTAAATACGGGAACCAGAAGCGCCAAGCGGCTT<br>GTGGAAAAGATTCGGCTCCACGACGAGCAGGAGGGAAAGTGTCTGTACTCGCTGGAGA<br>GCATTCCCTGGAGGACCTCCTGAACAACCCAAACCACTACGAAGTGGATCACATAAT<br>CCCCCGCAGCGTGTCATTCGACAATTCCTACCATAACAAGGTCCTCGTGAAGCAGTCC<br>GAGAATAGCAAGAAGTCCAACCTGACTCCGTACCAGTACTTCAACTCCGGCAAATCCA<br>AGCTGTCCTACAACCAGTTCAAACAGCACATCCTCAACCTGTCAAAGAGCCAGGACAG<br>GATCTCGAAGAAGAAGAAGGAATACCTTCTCGAGGAACGGGATATCAATAAGTTCGAG<br>GTGCAGAAGGAGTTTATCAATAGAAACCTGGTGGACACTCGCTATGCCACCCGCGAAC<br>TGACCAACTACCTGAAGGCGTACTTCTCCGCCAACAACATGAACGTGAAGGTCAAAAC<br>TATTAACGGCAGCTTCACCGACTATCTGCGCAAGGTCTGGAAGTTCAAGAAGGAACGC<br>AACCACGGTTACAAGCACCACGCGGAAGATGCGCTGATTATCGCCAACGCTGACTTCC<br>TGTTCAAGGAAAACAAGAAGCTCAAGGCCGTGAACTCAGTGCTCGAGAAGCCTGAAAT<br>CGAGACTAAGCAGCTGGACATCCAGGTCGATTCGGAAGATAACTACTCCGAAATGTTC<br>ATCATCCCTAAGCAAGTGCAGGACATCAAGGACTTCAGGAATTTCAAGTACAGCCATC<br>GCGTGGACAAGAAGCCAAACAGACAGCTGATCAACGATACACTGTATTCCACCCGGAA<br>GAAGGACAACTCCACCTACATCGTCCAAACCATTAAGGACATCTACGCAAAGGACAAC<br>ACCACGCTTAAGAAGCAGTTCGACAAGAGCCCCGAAAAGTTCCTCATGTACCAGCACG<br>ACCCCAGAACCTTCGAGAAGCTTGAAGTGATCATGAAGCAGTACGCCAACGAAAAGAA<br>CCCACTGGCTAAGTACCACGAGGAAACCGGCGAATACCTGACCAAGTACTCCAAAAAG<br>AACAACGGACCGATCGTCAAGTCCCTGAAGTACATTGGGAACAAGCTCGGCTCGCACC<br>TCGATGTGACCCACCAGTTCAAGTCCTCGACCAAAAAGCTCGTGAAGCTGTCCATCAA<br>GCCGTACCGGTTCGACGTGTACCTGACTGACAAGGGATATAAGTTCATCACCATTTCC<br>TACCTCGACGTGTTGAAGAAGGATAACTACTACTACATTCCGGAACAGAAGTACGACA<br>AGCTCAAGCTCGGAAAGGCCATCGACAAAAATGCGAAGTTCATCGCGAGCTTCTACAA<br>GAATGACTTGATCAAGCTGGATGGCGAAATCTACAAGATCATCGGGGTCAACTCCGAT<br>ACCCGCAACATGATTGAGCTGGATCTGCCCGACATTCGGTACAAGGAATACTGCGAGC<br>TGAACAACATCAAGGGAGAACCGCGGATCAAGAAAACCATCGGAAAGAAAGTGAACAG<br>CATCGAGAAACTGACTACTGACGTCCTGGGAAACGTGTTCACCAACACACAATACACC<br>AAACCCCAGCTGCTGTTTAAGCGCGGGAAC | |
| 19 | ATGAACCAGAAGTTCATCCTGGGCCTCGACATCGGCATCACCTCTGTTGGCTACGGCC<br>TGATCGACTACGAGACAAAGAACATCATCGATGCCGGCGTGCGGCTGTTCCCTGAGGC<br>CAACGTGGAAAACAACGAGGGCCGCAGAAGCAAGAGAGGCAGCAGAAGGCTGAAGCGG<br>CGGAGAATCCACCGGCTGGAAAGAGTGAAGAAGCTGCTCGGAGACTACAACCTGCTGG<br>ACCAGTCTCAGATCCCTCAGAGCACAAACCCCTACGCCATCAGAGTGAAGGGCCTGTC<br>TGAGGCCCTGAGCAAGGACGAGCTGGTTATCGCCCTGCTGCACATTGCCAAGCGGAGA<br>GGCATCCACAAGATCGACGTGATCGACAGCAACGACGACGTGGGCAATGAGCTGAGCA<br>CCAAAGAGCAGCTGAACAAGAACAGCAAGCTGCTGAAGGACAAGTTCGTGTGCCAGAT<br>TCAGCTGGAACGGATGAATGAGGGCCAAGTGCGGGGCGAGAAGAACAGATTCAAGACC<br>GCCGACATCATCAAAGAGATCATCCAGCTGCTCAACGTGCAGAAGAACTTCCACCAGC<br>TGGACGAGAACTTCATCAACAAGTACATCGAGCTGGTCGAGATGCGGCGCGAGTACTT<br>TGAAGGCCCTGGAAAGGGCAGCCCTTATGGCTGGGAAGGCGATCCCAAGGCTTGGTAC<br>GAGACACTGATGGGCCACTGCACCTACTTTCCCGACGAGCTGAGAAGCGTGAAGTACG<br>CCTACAGCGCCGACCTGTTCAACGCCCTGAACGACCTGAACAACCTCGTGATCCAGAG<br>AGATGGCCTGTCCAAGCTGGAATACCACGAGAAGTACCACATCATTGAGAACGTGTTC<br>AAGCAGAAGAAGAAGCCCACACTGAAGCAGATCGCCAACGAGATCAACGTGAACCCCG<br>AGGACATCAAGGGCTACAGAATCACCAAGAGCGGCAAGCCCCAGTTCACCGAGTTCAA<br>GCTGTACCACGATCTGAAGTCCGTGCTGTTCGACCAGAGCATCCTGGAAAACGAGGAC<br>GTGCTGGATCAGATCGCCGAGATCCTGACCATCTACCAGGACAAGGACAGCATCAAGA<br>GCAAGCTGACCGAGCTGGACATCCTGCTGAACGAAGAGGACAAAGAGAATATCGCCCA<br>GCTGACCGGCTACACCGGCACACATAGACTGAGCCTGAAGTGCATCCGGCTGGTGCTG<br>GAAGAACAGTGGTACTCCAGCCGGAACCAGATGGAAATCTTCACCCACCTGAACATCA<br>AGCCCAAGAAGATCAACCTGACCGCCGCCAACAAGATCCCCAAGGCCATGATCGACGA<br>GTTCATTCTGAGCCCCGTGGTCAAGAGAACCTTCGGCCAGGCCATCAATCTGATCAAC | Codon-optimized S1uCas9-2 polynucleotide |

| SEQ ID NO | Sequence | Description |
|---|---|---|
|  | AAGATTATCGAGAAGTATGGCGTGCCCGAGGATATCATCATCGAACTGGCCAGAGAGA<br>ACAACAGCAAGGACAAGCAAAAGTTCATCAACGAGATGCAGAAAAAGAACGAGAACAC<br>CCGGAAGCGGATCAACGAAATCATCGGGAAGTACGGCAACCAGAACGCCAAGAGACTG<br>GTGGAAAAGATCCGGCTGCACGACGAGCAAGAGGGCAAGTGTCTGTACAGCCTGGAAT<br>CTATCCCTCTCGAGGATCTGCTGAACAATCCCAACCACTACGAGGTGGACCACATTAT<br>CCCCAGAAGCGTGTCCTTCGACAACAGCTACCACAACAAGGTGCTGGTCAAGCAGAGC<br>GAGAACTCCAAGAAGTCCAATCTGACCCCTTACCAGTACTTCAACAGCGGCAAGTCTA<br>AGCTGAGCTACAACCAGTTTAAGCAGCACATCCTGAACCTCAGCAAGAGCCAGGACCG<br>GATCAGCAAGAAGAAgAAAGAGTACCTGCTCGAAGAGAGGGACATTAACAAGTTCGAG<br>GTGCAGAAAGAGTTTATCAACCGGAACCTGGTGGACACCAGATACGCCACCAGAGAGC<br>TGACCAACTACCTGAAGGCCTACTTCAGCGCCAACAACATGAACGTGAAAGTCAAGAC<br>CATCAACGGCAGCTTCACCGACTACCTGCGGAAAGTGTGGAAGTTTAAGAAAGAGCGG<br>AACCACGGCTACAAGCACCACGCCGAAGATGCCCTGATTATCGCCAATGCCGACTTCC<br>TGTTCAAAGAGAACAAGAAACTGAAGGCCGTGAACAGCGTGCTGGAAAAGCCCGAGAT<br>CGAGACAAAACAGCTCGACATCCAGGTGGACAGCGAGGACAACTACAGCGAGATGTTC<br>ATCATCCCCAAACAGGTGCAGGATATCAAGGACTTCCGGAACTTCAAGTACAGCCACC<br>GCGTGGACAAGAAGCCTAACCGGCAGCTGATCAATGACACCCTGTACAGCACCCGCAA<br>GAAGGACAACAGCACCTACATCGTGCAGACGATCAAGGACATCTACGCCAAGGACAAT<br>ACGACCCTGAAGAAGCAGTTCGACAAGAGCCCCGAGAAGTTCCTGATGTACCAGCACG<br>ACCCCAGGACCTTCGAGAAGCTGGAAGTGATCATGAAGCAGTACGCTAATGAGAAGAA<br>CCCGCTGGCCAAGTACCACGAGGAAACCGGCGAGTACCTGAAGCAAGTACTCTAAGAAG<br>AACAACGGCCCCATCGTGAAGTCCCTGAAGTATATCGGCAACAAGCTGGGCAGCCACC<br>TGGACGTGACACACCAGTTCAAGAGCAGCACCAAGAAGCTGGTCAAACTGTCCATCAA<br>GCCaTACCGCTTCGACGTGTACCTGACAGACAAGGGGTACAAGTTTATCACCATCAGC<br>TACCTCGACGTGCTGAAGAAGGATAACTACTACTACATCCCCGAGCAGAAGTACGACA<br>AGCTGAAGCTGGAAAAGCCATCGACAAGAATGCCAAGTTCATTGCCAGCTTCTACAA<br>GAACGACCTCATCAAGCTGGACGGCGAGATCTACAAGATCATCGGCGTGAACTCCGAC<br>ACACGGAACATGATTGAGCTGGACCTGCCTGACATCCGGTACAAAGAGTACTGCGAAC<br>TGAACAATATCAAGGGCGAGCCCCGGATCAAAAAGACGATCGGCAAGAAAGTGAACAG<br>CATTGAGAAGCTGACCACCGATGTGCTGGGCAATGTGCTTCACCAACACACAGTACACC<br>AAGCCTCAGCTGCTGTTCAAGCGGGGCAAT | |
| 20 | AGGAAATAAGAGAGAAAGAAGAGTAAGAAGAAATATAAGAGCCACC | 5' UTR |
| 21 | GCGGCCGCTTAATTAAGCTGCCTTCTGCGGGGCTTGCCTTCTGGCCATGCCCTTCTTC<br>TCTCCCTTGCACCTGTACCTCTTGGTCTTTGAATAAAGCCTGAGTAGGAAGTCTAG | 3' UTR |
| 22 | AAACGGCCTGCCGCGACCAAGAAAGCCGGCCAGGCCAAGAAGAAGAAG | nucleoplasmin NLS, nucleotide |
| 23 | KRPAATKKAGQAKKKK | nucleoplasmin NLS, amino acid |
| 24 | CCTAAGAAGAAGCGCAAGGTC | SV40 NLS, nucleotide |
| 25 | PKKKRKV | SV40 NLS, amino acid |
| 26 | GGTGGTGGCGGATCGGGGGGGGCGGTAGCGGGGGGGGGGGCTCTGGCTCG | gly/ser linker 1, nucleotide |
| 27 | GGGGSGGGGSGGGGSGS | gly/ser linker 1, amino acid |
| 28 | GGGGGCTCCGGAGGATCCGGTGGCAGCGGCCCC | gly/ser linker 2, nucleotide |
| 29 | GGSGGSGGSGP | gly/ser linker 2, amino acid |
| 30 | GGGGGCGGAGGAGGCTCA | gly/ser linker 3, nucleotide |
| 31 | GGGGGS | gly/ser linker 3, amino acid |
| 32 | CATCACCATCACCACCAT | 6xHis tag, nucleotide |
| 33 | HHHHHH | 6xHis tag, amino acid |

| SEQ ID NO | Sequence | Description |
|---|---|---|
| 34 | AGGAAATAAGAGAGAAAAGAAGAGTAAGAAGAAATATAAGAGCCACCATGAAACGGCC<br>TGCCGCGACCAAGAAAGCCGGCCAGGCCAAGAAGAAGAAGGGTGGTGGCGGATCGGGG<br>GGGGGCGGTAGCGGGGGGGGGGGCTCTGGCTCGATGAACCAGAAGTTCATTCTCGGTC<br>TGGACATTGGCATTACTAGCGTGGGATACGGCTTGATTGACTACGAGACTAAGAACAT<br>CATCGATGCCGGCGTCCGCCTGTTCCCGGAAGCCAACGTGGAGAACAATGAGGGCCGG<br>AGGTCGAAGAGAGGCTCCCGCCGCCTGAAGCGGCGGCGAATCCACCGGCTGGAGAGAG<br>TGAAGCTGCTGCTCACCGAATACGACCTGATCAACAAAGAACAGATCCCGACCTCCAA<br>CAACCCGTACCAGATCAGAGTGAAGGGTCTGTCAGAAATCCTGTCCAAGGACGAACTG<br>GCAATCGCCCTGCTGCACCTGGCCAAGCGGCGCGGAATCCACAACGTGGATGTGGCTG<br>CCGACAAGGAAGAAACCGCTTCCGACTCCCTGAGCACTAAGGACCAGATCAACAAGAA<br>CGCCAAGTTCTTGGAGTCCCGCTACGTGTGCGAGCTGCAGAAGGAACGGCTGGAAAAC<br>GAAGGTCACGTGCGCGGAGTGGAAAACCGGTTCCTGACAAAGGACATTGTGCGCGAAG<br>CGAAGAAGATCATTGATACCCAAATGCAGTACTACCCTGAAATCGACGAGACTTTCAA<br>GGAAAAGTACATTTCCCTGGTGGAAACCCGGCGGGAATACTTCGAAGGCCCCGGACAG<br>GGATCGCCGTTCGGATGGAACGGGGACCTCAAGAAGTGGTACGAGATGCTGATGGGGC<br>ACTGTACCTACTTTCCGCAAGAACTGCGCTCCGTGAAGTACGCGTACTCCGCGGATCT<br>CTTCAACGCGTTGAATGACCTGAACAACCTGATCATTCAGAGAGACAATTCCAGAAAG<br>CTCGAGTACCACGAGAAGTATCACATCATCGAGAATGTGTTCAAGCAGAAGAAGAAAC<br>CGACCCTCAAGCAAATCGCCAAGGAGATTGGCGTCAACCCAGAGGACATCAAGGGATA<br>TCGGATTACCAAGAGCGGCACTCCCGAGTTTACCTCTTTCAAGCTGTTTCATGATCTG<br>AAGAAAGTCGTGAAGGACCATGCCATTCTCGACGACATTGATCTCCTGAATCAGATCG<br>CAGAGATCCTGACTATCTACCAAGACAAGGACTCGATTGTGGCAGAGCTGGGTCAGCT<br>CGAATACCTGATGTCCGAGGCCGACAAGCAGTCCATCTCCGAACTGACAGGGTACACG<br>GGGACTCATAGCCTGTCGCTGAAGTGCATGAACATGATCATTGATGAACTGTGGCACA<br>GCTCCATGAACCAAATGGAAGTGTTTACCTACCTCAACATGCGCCCTAAGAAGTACGA<br>ACTGAAAGGCTACCAGCGCATCCCCACCGACATGATCGACGACGCGATCTTGTCCCCT<br>GTGGTCAAGAGGACCTTCATTCAATCCATCAACGTGATCAACAAGGTCATCGAAAAGT<br>ACGGTATTCCAGAAGATATCATCATTGAGCTCGCTCGGGAGAACAACTCGGATGACCG<br>GAAGAAGTTCATCAACAATCTTCAGAAGAAGAACGAAGCGACTCGGAAACGGATCAAC<br>GAGATCATCGGACAGACCGGAAACCAGAACGCCAAACGGATTGTCGAAAAGATTAGAC<br>TGCACGACCAGCAGGAAGGGAAGTGCCTGTACTCACTCGAGTCAATACCGCTCGAGGA<br>CCTGTTGAACAACCCTAACCACTATGAAGTGGACCACATCATCCCTCGGTCCGTGAGC<br>TTCGACAACTCGTACCACAACAAAGTGCTCGTGAAGCAGTCCGAAAACTCCAAGAAAT<br>CCAACCTGACCCCGTACCAATACTTCAATTCGGGAAAGTCGAAGCTGTCGTACAACCA<br>GTTCAAACAACACATACTCAACCTTAGCAAAAGCCAGGATCGCATTTCAAGAAGAAG<br>AAGGAATACCTCCTCGAGGAAAGGGACATCAACAAGTTCGAAGTGCAGAAAGAGTTCA<br>TCAATCGCAACTTGGTGGATACCAGATATGCCACCCGGGAACTCACCAGCTATCTCAA<br>GGCCTACTTTTCCGCCAACAACATGGACGTGAAGGTCAAGACCATCAACGGGTCCTTC<br>ACTAACCATCTGAGAAAGGTCTGGCGGTTTGACAAGTACCGCAACCACGGATACAAGC<br>ACCACGCTGAAGACGCTCTGATCATCGCCAATGCCGACTTCCTGTTCAAGGAAAACAA<br>GAAGCTGCAGAACACGAACAAGATTCTGGAAAAGCCTACCATTGAGAACAACACTAAG<br>AAGGTCACCGTGGAGAAGGAAGAGGACTACAACAACGTGTTCGAAACTCCTAAACTGG<br>TGGAGGATATCAAGCAATACCGCGACTACAAGTTCTCACACCGGGTGGACAAGAAACC<br>GAATAGACAGCTGATCAACGACACGTTGTATTCCACCCGGATGAAGGATGAGCATGAC<br>TACATTGTGCAGACTATCACCGATATCTACGGAAAAGATAACACTAACCTGAAGAAAC<br>AATTCAACAAGAACCCAGAGAAGTTCCTGATGTACCAGAACGACCCCAAGACCTTTGA<br>GAAGCTTTCCATCATCATGAAGCAGTACTCCGACGAGAAGAACCCGCTGGCCAAGTAC<br>TACGAAGAAACCGGAGAATACCTGACCAAGTACAGCAAGAAGAACAACGGTCCCATTG<br>TCAAGAAGATCAAGCTGCTCGGCAACAAGGTCGGAAACCACCTCGACGTGACAAACAA<br>GTACGAGAACTCGACTAAGAAGCTTGTGAAGCTGTCAATCAAGAACTATAGATTCGAC<br>GTGTACTTGACCGAAAAGGGGATACAAGTTCGTGACCATAGCCTATCTGAACGTGTTCA<br>AGAAAGATAACTACTACTACATCCCCAAGGACAAGTACCAGGAGCTCAAAGAAAAGAA<br>GAAGATCAAAGACACCGACCAGTTCATTGCCTCCTTCTACAAGAACGACCTGATCAAA<br>CTGAACGGCGACCTCTACAAGATCATTGGAGTGAACAGCGATGACAGGAACATCATTG<br>AGCTGGACTACTACGACATCAAGTACAAGGACTACTGCGAGATCAACAACATCAAGGG<br>CGAACCCCGGATCAAGAAACTATTGGAAAGAAAACCGAGTCCATTGAGAAGTTCACC<br>ACTGACGTGCTGGGAAACCTTTACCTCCACTCCACCGAGAAGGCACCACAACTGATCT<br>TCAAGCGCGGCCTGGGGGGCTCCGGAGGATCCGGTGGCAGCGGCCCCCCGAAGAAGAA<br>GCGCAAAGTCGGGGGCGGAGGAGGCTCACATCACCATCACCACCATTAATAAGCGGCC<br>GCTTAATTAAGCTGCCTTCTGCGGGCTTGCCTTCTGGCCATGCCCTTCTTCTCTCCC<br>TTGCACCTGTACCTCTTGGTCTTTGAATAAAGCCTGAGTAGGAAGTCTAG | GST3, nucleotide |
| 35 | MKRPAATKKAGQAKKKKGGGGSGGGGSGGGGSGSMNQKFILGLDIGITSVGYGLIDYE<br>TKNIIDAGVRLFPEANVENNEGRRSKRGSRRLKRRRIHRLERVKLLLLFTEYDLINKEQI<br>PTSNNPYQIRVKGLSEILSKDELAIALLHLAKRRGIHNVDVAADKEETASDSLSTKDQ<br>INKNAKFLESRYVCELQKERLENEGHVRGVENRFLTKDIVREAKKIIDTQMQYYPEID<br>ETFKEKYISLVETRREYFEGPGQGSPFGWNGDLKKWYEMLMGHCTYFPQELRSVKYAY<br>SADLFNALNDLNNLIIQRDNSEKLEYHEKYHIIENVFKQKKKPTLKQIAKEIGVNPED<br>IKGYRITKSGTPEFTSFKLFHDLKKVVKDHAILDDIDLLNQIAEILTIYQDKDSIVAE<br>LGQLEYLMSEADKQSISELTGYTGTHSLSLKCMNMIIDELWHSSMNQMEVFTYLNMRP<br>KKYELKGYQRIPTDMIDDAILSPVVKRTFIQSINVINKVIEKYGIPEDIIELARENN<br>SDDRKKFINNLQKKNEATRKRINEIIGQTGNQNAKRIVEKIRLHDQQEGKCLYSLESI<br>PLEDLLNNPNHYEVDHIIPRSVSFDNSYHNKVLVKQSENSKKSNLTPYQYFNSGKSKL<br>SYNQFKQHILNLSKSQDRISKKKKEYLLEERDINKFEVQKEFINRNLVDTRYATRELT | GST3, amino acid |

Sequence Listing

| SEQ ID NO | Sequence | Description |
|---|---|---|
| | SYLKAYFSANNMDVKVKTINGSFTNHLRKVWRFDKYRNHGYKHHAEDALIIANADFLF<br>KENKKLQNTNKILEKPTIENNTKKVTVEKEEDYNNVFETPKLVEDIKQYRDYKFSHRV<br>DKKPNRQLINDTLYSTRMKDEHDYIVQTITDIYGKDNTNLKKQFNKNPEKFLMYQNDP<br>KTFEKLSIIMKQYSDEKNPLAKYYEETGEYLTKYSKKNNGPIVKKIKLLGNKVGNHLD<br>VTNKYENSTKKLVKLSIKNYRFDVYLTEKGYKFVTIAYLNVFKKDNYYYIPKDKYQEL<br>KEKKKIKDTDQFIASFYKNDLIKLNGDLYKIIGVNSDDRNIIELDYYDIKYKDYCEIN<br>NIKGEPRIKKTIGKKTESIEKFTTDVLGNLYLHSTEKAPQLIFKRGLGGSGGSGGSGP<br>PKKKRKVGGGGGSHHHHHH | |
| 36 | AGGAAATAAGAGAGAAAAGAAGAGTAAGAAGAAATATAAGAGCCACCATGGCGAAACG<br>GCCTGCCGCGACCAAGAAAGCCGGCCAGGCCAAGAAGAAGAAGGGTGGTGGCGGATCG<br>GGGGGGGGCGGTAGCGGGGGGGGGGGCTCTGGCTCGATGAACCAGAAGTTCATTCTG<br>GTCTGGACATTGGCATTACTAGCGTGGGATACGGCTTGATTGACTACGAGACTAAGAA<br>CATCATCGATGCCGGCGTCCGCCTGTTCCCGGAAGCCAACGTGGAGAACAATGAGGGC<br>CGGAGGTCGAAGAGAGGCTCCCGCCGCCTGAAGCGGCGGCGAATCCACCGGCTGGAGA<br>GAGTGAAGCTGCTGCTCACCGAATACGACCTGATCAACAAAGAACAGATCCCGACCTC<br>CAACAACCCGTACCAGATCAGAGTGAAGGGTCTGTCAGAAATCCTGTCCAAGGACGAA<br>CTGGCAATCGCCCTGCTGCACCTGGCCAAGCGGCGCGGAATCCACAACGTGGATGTGG<br>CTGCCGACAAGGAAGAAACCGCTTCCGACTCCCTGAGCACTAAGGACCAGATCAACAA<br>GAACGCCAAGTTCTTGGAGTCCCGCTACGTGTGCGAGCTGCAGAAGGAACGGCTGGAA<br>AACGAAGGTCACGTGCGCGGAGTGGAAAACCGGTTCCTGACAAAGGACATTGTGCGCG<br>AAGCGAAGAAGATCATTGATACCCAAATGCAGTACTACCCTGAAATCGACGAGACTTT<br>CAAGGAAAAGTACATTTCCCTGGTGGAAACCCGGCGGGAATACTTCGAAGGCCCCGGA<br>CAGGGATCGCCGTTCGGATGGAACGGGGACCTCAAGAAGTGGTACGAGATGCTGATGG<br>GGCACTGTACCTACTTTCCGCAAGAACTGCGCTCCGTGAAGTACGCGTACTCCGCGGA<br>TCTCTTCAACGCGTTGAATGACCTGAACAACCTGATCATTCAGAGAGACAATTCCGAA<br>AAGCTCGAGTACCACGAGAAGTATCACATCATCGAGAATGTGTTCAAGCAGAAGAAGA<br>AACCGACCCTCAAGCAAATCGCCAAGGAGATTGGCGTCAACCCAGAGGACATCAAGGG<br>ATATCGGATTACCAAGAGCGGCACTCCCGAGTTTACCTCTTTCAAGCTGTTTCATGAT<br>CTGAAGAAAGTCGTGAAGGACCATGCCATTCTCGACGACATTGATCTCCTGAATCAGA<br>TCGCAGAGATCCTGACTATCTACCAAGACAAGGACTCGATTGTGGCAGAGCTGGGTCA<br>GCTCGAATACCTGATGTCCGAGGCCGACAAGCAGTCCATCTCCGAACTGACAGGGTAC<br>ACGGGGACTCATAGCCTGTCGCTGAAGTGCATGAACATGATCATTGATGAACTGTGGC<br>ACAGCTCCATGAACCAAATGGAAGTGTTTACCTACCTCAACATGCGCCCTAAGAAGTA<br>CGAACTGAAAGGCTACCAGCGCATCCCCACCGACATGATCGACGACGCGATCTTGTCC<br>CCTGTGGTCAAGAGGACCTTCATTCAATCCATCAACGTGATCAACAAGGTCATCGAAA<br>AGTACGGTATTCCAGAAGATATCATCATTGAGCTCGCTCGGGAGAACAACTCGGATGA<br>CCGGAAGAAGTTCATCAACAATCTTCAGAAGAAGAACGAAGCGACTCGGAAACGGATC<br>AACGAGATCATCGGACAGACCGGAAACCAGAACGCCAAACGGATTGTCGAAAAGATTA<br>GACTGCACGACCAGCAGGAAGGGAAGTGCCTGTACTCACTCGAGTCAATACCGCTCGA<br>GGACCTGTTGAACAACCCTAACCACTATGAAGTGGACCACATCATCCCTCGGTCCGTG<br>AGCTTCGACAACTCGTACCACAACAAAGTGCTCGTGAAGCAGTCCGAAAACTCCAAGA<br>AATCCAACCTGACCCCGTACCAATACTTCAATTCGGGAAAGTCGAAGCTGTCGTACAA<br>CCAGTTCAAACAACACATACTCAACCTTAGCAAAAGCCAGGATCGCATTTCCAAGAAG<br>AAGAAGGAATACCTCCTCGAGGAAAGGGACATCAACAAGTTCGAAGTGCAGAAAGAGT<br>TCATCAATCGCCAACTTGGTGGATACCAGATATGCCACCCGGGAACTCACCAGCTATCT<br>CAAGGCCTACTTTTCCGCCAACAACATGGACGTGAAGGTCAAGACCATCAACGGGTCC<br>TTCACTAACCATCTGAGAAAGGTCTGGCGGTTTGACAAGTACCGCAACCACGGATACA<br>AGCACCACGCTGAAGACGCTCTGATCATCGCCAATGCCGACTTCCTGTTCAAGGAAAA<br>CAAGAAGCTGCAGAACACGAACAAGATTCTGGAAAAGCCTACCATTGAGAACAACACT<br>AAGAAGGTCACCGTGGAGAAGGAAGAGGACTACAACAACGTGTTCGAAACTCCTAAAC<br>TGGTGGAGGATATCAAGCAATACCGCGACTACAAGTTCTCACACCGGGTGGACAAGAA<br>ACCGAATAGACAGCTGATCAACGACACGTTGTATTCCACCCGGATGAAGGATGAGCAT<br>GACTACATTGTGCAGACTATCACCGATATCTACGGAAAAGATAACCTAACCTGAAGA<br>AACAATTCAACAAGAACCCAGAGAAGTTCCTGATGTACCAGAACGACCCCAAGACCTT<br>TGAGAAGCTTTCCATCATCATGAAGCAGTACTCCGACGAGAAGAACCCGCTGGCCAAG<br>TACTACGAAGAAACCGGAGAATACCTGACCAAGTACAGCAAGAAGAACAACGGTCCCA<br>TTGTCAAGAAGATCAAGCTGCTCGGCAACAAGGTCGGAAACCACCTCGACGTGACAAA<br>CAAGTACGAGAACTCGACTAAGAAGCTTGTGAAGCTGTCAATCAAGAACTATAGATTC<br>GACGTGTACTTGACCGAAAAGGGATACAAGTTCGTGACCATAGCCTATCTGAACGTGT<br>TCAAGAAAGATAACTACTACTACATCCCCAAGGACAAGTACCAGGAGCTCAAAGAAAA<br>GAAGAAGATCAAAGACACCGACCAGTTCATTGCCTCCTTCTACAAGAACGACCTGATC<br>AAACTGAACGGCGACCTCTACAAGATCATTGGAGTGAACAGCGATGACAGGAACATCA<br>TTGAGCTGGACTACTACGACATCAAGTACAAGGACTACTGCGAGATCAACAACATCAA<br>GGGCGAACCCCGGATCAAGAAAACTATTGGAAAGAAAACCGAGTCCATTGAGAAGTTC<br>ACCACTGACGTGCTGGGAAACCTTTACCTCCACTCCACCGAGAAGGCACCACAACTGA<br>TCTTCAAGCGCGGCCTGGGGGCTCCGGAGGATCCGGTGGCAGCGGCCCCCCGAAGAA<br>GAAGCGCAAAGTCGGGGGCGGAGGAGGCTCACATCACCATCACCACCATTGATAAGCG<br>GCCGCTTAATTAAGCTGCCTTCTGCGGGGCTTGCCTTCTGGCCATGCCCTTCTTCTCT<br>CCCTTGCACCTGTACCTCTTGGTCTTTGAATAAAGCCTGAGTAGGAAGTCTAG | GST3-K,<br>nucleotide |
| 37 | MAKRPAATKKAGQAKKKKGGGGSGGGGSGGGGSGSMNQKFILGLDIGITSVGYGLIDY<br>ETKNIIDAGVRLFPEANVENNEGRRSKRGSRRLKRRRIHRLERVKLLLTEYDLINKEQ<br>IPTSNNPYQIRVKGLSEILSKDELAIALLHLAKRRGIHNVDVAADKEETASDSLSTKD | GST3-K, amino acid |

| SEQ ID NO | Sequence | Description |
|---|---|---|
|  | QINKNAKFLESRYVCELQKERLENEGHVRGVENRFLTKDIVREAKKIIDTQMQYYPEI |  |
|  | DETFKEKYISLVETRREYFEGPGQGSPFGWNGDLKKWYEMLMGHCTYFPQELRSVKYA |  |
|  | YSADLFNALNDLNNLIIQRDNSEKLEYHEKYHIIENVFKQKKKPTLKQIAKEIGVNPE |  |
|  | DIKGYRITKSGTPEFTSFKLFHDLKKVVKDHAILDDIDLLNQIAEILTIYQDKDSIVA |  |
|  | ELGQLEYLMSEADKQSISELTGYTGTHSLSLKCMNMIIDELWHSSMNQMEVFTYLNMR |  |
|  | PKKYELKGYQRIPTDMIDDAILSPVVKRTFIQSINVINKVIEKYGIPEDIIIELAREN |  |
|  | NSDDRKKFINNLQKKNEATRKRINEIIGQTGNQNAKRIVEKIRLHDQQEGKCLYSLES |  |
|  | IPLEDLLNNPNHYEVDHIIPRSVSFDNSYHNKVLVKQSENSKKSNLTPYQYFNSGKSK |  |
|  | LSYNQFKQHILNLSKSQDRISKKKKEYLLEERDINKFEVQKEFINRNLVDTRYATREL |  |
|  | TSYLKAYFSANNMDVKVKTINGSFTNHLRKVWRFDKYRNHGYKHHAEDALIIANADFL |  |
|  | FKENKKLQNTNKILEKPTIENNTKKVTVEKEEDYNNVFETPKLVEDIKQYRDYKFSHR |  |
|  | VDKKPNRQLINDTLYSTRMKDEHDYIVQTITDIYGKDNTNLKKQFNKNPEKFLMYQND |  |
|  | PKTFEKLSIIMKQYSDEKNPLAKYYEETGEYLTKYSKKNNGPIVKKIKLLGNKVGNHL |  |
|  | DVTNKYENSTKKLVKLSIKNYRFDVYLTEKGYKFVTIAYLNVFKKDNYYYIPKDKYQE |  |
|  | LKEKKKIKDTDQFIASFYKNDLIKLNGDLYKIIGVNSDDRNIIELDYYDIKYKDYCEI |  |
|  | NNIKGEPRIKKTIGKKTESIEKFTTDVLGNLYLHSTEKAPQLIFKRGLGGSGGSGGSG |  |
|  | PPKKKRKVGGGGGSHHHHHH |  |
| 38 | AGGAAATAAGAGAGAAAAGAAGAGTAAGAAGAAATATAAGAGCCACCATGGCCCCTAA | GST3-v1, nucleotide |
|  | GAAGAAGCGCAAGGTCATGAACCAGAAGTTCATTCTCGGTCTGGACATTGGCATTACT |  |
|  | AGCGTGGGATACGGCTTGATTGACTACGAGACTAAGAACATCATCGATGCCGGCGTCC |  |
|  | GCCTGTTCCCGGAAGCCAACGTGGAGAACAATGAGGGCCGGAGGTCGAAGAGAGGCTC |  |
|  | CCGCCGCCTGAAGCGGCGGCGAATCCACCGGCTGGAGAGAGTGAAGCTGCTGCTCACC |  |
|  | GAATACGACCTGATCAACAAAGAACAGATCCCGACCTCCAACAACCCGTACCAGATCA |  |
|  | GAGTGAAGGGTCTGTCAGAAATCCTGTCCAAGGACGAACTGGCAATCGCCCTGCTGCA |  |
|  | CCTGGCCAAGCGGCGCGGAATCCACAACGTGGATGTGGCTGCCGACAAGGAAGAAACC |  |
|  | GCTTCCGACTCCCTGAGCACTAAGGACCAGATCAACAAGAACGCCAAGTTCTTGGAGT |  |
|  | CCCGCTACGTGTGCGAGCTGCAGAAGGAACGGCTGGAAAACGAAGGTCACGTGCGCGG |  |
|  | AGTGGAAAACCGGTTCCTGACAAAGGACATTGTGCGCGAAGCGAAGAAGATCATTGAT |  |
|  | ACCCAAATGCAGTACTACCCTGAAATCGACGAGACTTTCAAGGAAAAGTACATTTCCC |  |
|  | TGGTGGAAACCCGGCGGGAATACTTCGAAGGCCCCGGACAGGGATCGCCGTTCGGATG |  |
|  | GAACGGGGACCTCAAGAAGTGGTACGAGATGCTGATGGGGCACTGTACCTACTTTCCG |  |
|  | CAAGAACTGCGCTCCGTGAAGTACGCGTACTCCGCGGATCTCTTCAACGCGTTGAATG |  |
|  | ACCTGAACAACCTGATCATTCAGAGAGACAATTCCGAAAAGTCGAGTACCACGAGAA |  |
|  | GTATCACATCATCGAGAATGTGTTCAAGCAGAAGAAGAAACCGACCCTCAAGCAAATC |  |
|  | GCCAAGGAGATTGGCGTCAACCCAGAGGACATCAAGGGATATCGGATTACCAAGAGCG |  |
|  | GCACTCCCGAGTTTACCTCTTTCAAGCTGTTTCATGATCTGAAGAAAGTCGTGAAGGA |  |
|  | CCATGCCATTCTCGACGACATTGATCTCCTGAATCAGATCGCAGAGATCCTGACTATC |  |
|  | TACCAAGACAAGGACTCGATTGTGGCAGAGCTGGGTCAGCTCGAATACCTGATGTCCG |  |
|  | AGGCCGACAAGCAGTCCATCTCCGAACTGACAGGGTACACGGGGACTCATAGCCTGTC |  |
|  | GCTGAAGTGCATGAACATGATCATTGATGAACTGTGGCACAGCTCCATGAACCAAATG |  |
|  | GAAGTGTTTACCTACCTCAACATGCGCCCTAAGAAGTACGAACTGAAAGGCTACCAGC |  |
|  | GCATCCCCACCGACATGATCGACGACGCGATCTTGTCCCCTGTGGTCAAGAGGACCTT |  |
|  | CATTCAATCCATCAACGTGATCAACAAGGTCATCGAAAAGTACGGAATACCAGAAGAT |  |
|  | ATCATCATTGAGCTCGCTCGGGAGAACAACTCGGATGACCGGAAGAAGTTCATCAACA |  |
|  | ATCTTCAGAAGAAGAACGAAGCGACTCGGAAACGGATCAACGAGATCATCGGACAGAC |  |
|  | CGGAAACCAGAACGCCAAACGGATTGTCGAAAAGATTAGACTGCACGACCAGCAGGAA |  |
|  | GGGAAGTGCCTGTACTCACTCGAGTCAATACCGCTCGAGGACCTGTTGAACAACCCTA |  |
|  | ACCACTATGAAGTGGACCACATCATCCCTCGGTCCGTGAGCTTCGACAACTCGTACCA |  |
|  | CAACAAAGTGCTCGTGAAGCAGTCCGAAAACTCCAAGAAATCCAACCTGACCCCGTAC |  |
|  | CAATACTTCAATTCGGGAAAGTCGAAGCTGTCGTACAACCAGTTCAAACAACACATAC |  |
|  | TCAACCTTAGCAAAAGCCAGGATCGCATTTCCAAGAAGAAGAAGGAATACCTCCTCGA |  |
|  | GGAAAGGGACATCAACAAGTTCGAAGTGCAGAAAGAGTTCATCAATCGCAACTTGGTG |  |
|  | GATACCAGATATGCCACCCGGGAACTCACCAGCTATCTCAAGGCCTACTTTTCCGCCA |  |
|  | ACAACATGGACGTGAAGGTCAAGACCATCAACGGGTCCTTCACTAACCATCTGAGAAA |  |
|  | GGTCTGGCGGTTTGACAAGTACCGCAACCACGGATACAAGCACCACGCTGAGGACGCT |  |
|  | CTGATCATCGCCAATGCCGACTTCCTGTTCAAGGAAAACAAGAAGCTGCAGAACACGA |  |
|  | ACAAGATTCTGGAAAAGCCTACCATTGAGAACAACACTAAGAAGGTCACCGTGGAGAA |  |
|  | GGAAGAGGACTACAACAACGTGTTCGAAACTCCTAAACTGGTGGAGGATATCAAGCAA |  |
|  | TACCGCGACTACAAGTTCTCACACCGGGTGGACAAGAAACCGAATAGACAGCTGATCA |  |
|  | ACGACACGTTGTATTCCACCCGGATGAAGGATGAGCATGACTACATTGTGCAGACTAT |  |
|  | CACCGATATCTACGGAAAAGATAACACTAACCTGAAGAAACAATTCAACAAGAACCCA |  |
|  | GAGAAGTTCCTGATGTACCAGAACGACCCCAAGACCTTTGAGAAGCTTTCCATCATCA |  |
|  | TGAAGCAGTACTCCGACGAGAAGAACCCGCTGGCCAAGTACTACGAAGAAACCGGAGA |  |
|  | ATACCTGACCAAGTACAGCAAGAAGAACAACGGTCCCATTGTCAAGAAGATCAAGCTG |  |
|  | CTCGGCAACAAGGTCGGAAACCACCTCGACGTGACAAACAAGTACGAGAACTCGACTA |  |
|  | AGAAGCTTGTGAAGCTGTCAATCAAGAACTATAGATTCGACGTGTACTTGACCGAAAA |  |
|  | GGGATACAAGTTCGTGACCATAGCCTATCTGAACGTGTTCAAGAAAGATAACTACTAC |  |
|  | TACATCCCCAAGGACAAGTACCAGGAGCTCAAAGAAAAGAAGAAGATCAAAGACACCG |  |
|  | ACCAGTTCATTGCCTCCTTCTACAAGAACGACCTGATCAAACTGAACGGCGACCTCTA |  |
|  | CAAGATCATTGGAGTGAACAGCGATGACAGGAACATCATTGAGCTGGACTACTACGAC |  |
|  | ATCAAGTACAAGGACTACTGCGAGATCAACAACATCAAGGGCGAACCCCGGATCAAGA |  |
|  | AAACTATTGGAAAGAAAACCGAGTCCATTGAGAAGTTCACCACTGACGTGCTGGGAAA |  |
|  | CCTTTACCTCCACTCCACCGAGAAGGCACCACAACTGATCTTCAAGCGCGGCCTGAAA |  |

| SEQ ID NO | Sequence | Description |
|---|---|---|
| | CGGCCCGCCGCAACCAAGAAGGCCGGCCAGGCGAAGAAGAAGAAATGAGCGGCCGCTT<br>AATTAAGCTGCCTTCTGCGGGGCTTGCCTTCTGGCCATGCCCTTCTTCTCTCCCTTGC<br>ACCTGTACCTCTTGGTCTTTGAATAAAGCCTGAGTAGGAAGTCTAG | |
| 39 | MAPKKKRKVMNQKFILGLDIGITSVGYGLIDYETKNIIDAGVRLFPEANVENNEGRRS<br>KRGSRRLKRRIHRLERVKLLLTEYDLINKEQIPTSNNPYQIRVKGLSEILSKDELAI<br>ALLHLAKRRGIHNVDVAADKEETASDSLSTKDQINKNAKFLESRYVCELQKERLENEG<br>HVRGVENRFLTKDIVREAKKIIDTQMQYYPEIDETFKEKYISLVETRREYFEGPGQGS<br>PFGWNGDLKKWYEMLMGHCTYFPQELRSVKYAYSADLFNALNDLNNLIIQRDNSEKLE<br>YHEKYHIIENVFKQKKKPTLKQIAKEIGVNPEDIKGYRITKSGTPEFTSFKLFHDLKK<br>VVKDHAILDDIDLLNQIAEILTIYQDKDSIVAELGQLEYLMSEADKQSISELTGYTGT<br>HSLSLKCMNMIIDELWHSSMNQMEVFTYLNMRPKKYELKGYQRIPTDMIDDAILSPVV<br>KRTFIQSINVINKVIEKYGIPEDIIIELARENNSDDRKKFINNLQKKNEATRKRINEI<br>IGQTGNQNAKRIVEKIRLHDQQEGKCLYSLESIPLEDLLNNPNHYEVDHIIPRSVSFD<br>NSYHNKVLVKQSENSKKSNLTPYQYFNSGKSKLSYNQFKQHILNLSKSQDRISKKKKE<br>YLLEERDINKFEVQKEFINRNLVDTRYATRELTSYLKAYFSANNMDVKVKTINGSFTN<br>HLRKVWRFDKYRNHGYKHHAEDALIIANADFLFKENKKLQNTNKILEKPTIENNTKKV<br>TVEKEEDYNNVFETPKLVEDIKQYRDYKFSHRVDKKPNRQLINDTLYSTRMKDEHDYI<br>VQTITDIYGKDNTNLKKQFNKNPEKFLMYQNDPKTFEKLSIIMKQYSDEKNPLAKYYE<br>ETGEYLTKYSKKNNGPIVKKIKLLGNKVGNHLDVTNKYENSTKKLVKLSIKNYRFDVY<br>LTEKGYKFVTIAYLNVFKKDNYYYIPKDKYQELKEKKKIKDTDQFIASFYKNDLIKLN<br>GDLYKIIGVNSDDRNIIELDYYDIKYKDYCEINNIKGEPRIKKTIGKKTESIEKFTTD<br>VLGNLYLHSTEKAPQLIFKRGLKRPAATKKAGQAKKKK | GST3-v1, amino acid |
| 40 | AGGAAATAAGAGAGAAAAGAAGAGTAAGAAGAAATATAAGAGCCACCATGGCCCCTAA<br>GAAGAAGCGCAAGGTCATGAACCAGAAGTTCATTCTCGGTCTGGACATTGGCATTACT<br>AGCGTGGGATACGGCTTGATTGACTACGAGACTAAGAACATCATCGATGCCGGCGTCC<br>GCCTGTTCCCGGAAGCCAACGTGGAGAACAATGAGGGCCGGAGGTCGAAGAGAGGCTC<br>CCGCCGCCTGAAGCGGCGGCGAATCCACCGGCTGGAGAGATGAAGCTGCTGCTCACC<br>GAATACGACCTGATCAACAAAGAACAGATCCCGACCTCCAACAACCCGTACCAGATCA<br>GAGTGAAGGGTCTGTCAGAAATCCTGTCCAAGGACGAACTGGCAATCGCCCTGCTGCA<br>CCTGGCCAAGCGGCGCGGAATCCACAACGTGGATGTGGCTGCCGACAAGGAAGAAACC<br>GCTTCCGACTCCCTGAGCACTAAGGACCAGATCAACAAGAACGCCAAGTTCTTGGAGT<br>CCCGCTACGTGTGCGAGCTGCAGAAGGAACGGCTGGAAAACGAAGGTCACGTGCGCGG<br>AGTGGAAAACCGGTTCCTGACAAAGGACATTGTGCGCGAAGCGAAGAAGATCATTGAT<br>ACCCAAATGCAGTACTACCCTGAAATCGACGAGACTTTCAAGGAAAAGTACATTTCCC<br>TGGTGGAAACCCGGCGGGAATACTTCGAAGGCCCCGGACAGGGATCGCCGTTCGGATG<br>GAACGGGGACCTCAAGAAGTGGTACGAGATGCTGATGGGGCACTGTACCTACTTTCCG<br>CAAGAACTGCGCTCCGTGAAGTACGCGTACTCCGCGGATCTCTTCAACGCGTTGAATG<br>ACCTGAACAACCTGATCATTCAGAGAGACAATTCCGAAAAGCTCGAGTACCACGAGAA<br>GTATCACATCATCGAGAATGTGTTCAAGCAGAAGAAGAAACCGACCCTCAAGCAAATC<br>GCCAAGGAGATTGGCGTCAACCCAGAGGACATCAAGGGGATATCGGATTACCAAGAGCG<br>GCACTCCCGAGTTTACCTCTTTCAAGCTGTTTCATGATCTGAAGAAAGTCGTGAAGGA<br>CCATGCCATTCTCGACGACATTGATCTCCTGAATCAGATCGCAGAGATCCTGACTATC<br>TACCAAGACAAGGACTCGATTGTGGCAGAGCTGGGTCAGCTCGAATACCTGATGTCCG<br>AGGCCGACAAGCAGTCCATCTCCGAACTGACAGGGTACACGGGGACTCATAGCCTGTC<br>GCTGAAGTGCATGAACATGATCATTGATGAACTGTGGCACAGCTCCATGAACCAAATG<br>GAAGTGTTTACCTACCTCAACATGCGCCCTAAGAAGTACGAACTGAAAGGCTACCAGC<br>GCATCCCCACCGACATGATCGACGACGCGATCTTGTCCCCTGTGGTCAAGAGGACCTT<br>CATTCAATCCATCAACGTGATCAACAAGGTCATCGAAAAGTACGGAATACCAGAAGAT<br>ATCATCATTGAGCTCGCTCGGGAGAACAACTCGGATGACCGGAAGAAGTTCATCAACA<br>ATCTTCAGAAGAAGAACGAAGCGACTCGGAAACGGATCAACGAGATCATCGGACAGAC<br>CGGAAACCAGAACGCCAAACGGATTGTCGAAAAGATTAGACTGCACGACCAGCAGGAA<br>GGGAAGTGCCTGTACTCACTCGAGTCAATACCGCTCGAGGACCTGTTGAACAACCCTA<br>ACCACTATGAAGTGGACCACATCATCCCTCGGTCCGTGAGCTTCGACAACTCGTACCA<br>CAACAAAGTGCTCGTGAAGCAGTCCGAAAACTCCAAGAAATCCAACCTGACCCCGTAC<br>CAATACTTCAATTCGGGAAAGTCGAAGCTGTCGTACAACCAGTTCAAACAACACATAC<br>TCAACCTTAGCAAAAGCCAGGATCGCATTTCCAAGAAGAAGAAGGAATACCTCCTCGA<br>GGAAAGGGACATCAACAAGTTCGAAGTGCAGAAAGAGTTCATCAATCGCAACTTGGTG<br>GATACCAGATATGCCACCCGGGAACTCACCAACTATCTCAAGGCCTACTTTTCCGCCA<br>ACAACATGAACGTGAAGGTCAAGACCATCAACGGGTCCTTCACTGACTACCTGAGAAA<br>GGTCTGGAAGTTCAAGAAGGAACGCAACCACGGATACAAGCACCACGCTGAGGACGCT<br>CTGATCATCGCCAATGCCGACTTCCTGTTCAAGGAAAACAAGAAGCTGAAAGCTGTCA<br>ACTCAGTGCTGGAAAAGCCTGAAATCGAGACTAAGCAGCTGGATATCCAAGTGGACTC<br>TGAGGACAACTACAGCGAGATGTTCATCATCCCTAAACAAGTGCAGGATATCAAGGAC<br>TTTCGCAACTTCAAGTACTCACACCGGGTGGACAAGAAACCGAATAGACAGCTGATCA<br>ACGACACGTTGTATTCCACCCGGAAGAAGGATAACTCAACCTACATTGTGCAGACTAT<br>CAAGGATATCTACGCCAAAGATAACACTACTCTGAAGAAACAATTCGACAAGTCCCCA<br>GAGAAGTTCCTGATGTACCAGCACGACCCCCGAACCTTTGAGAAGCTTGAAGTGATCA<br>TGAAGCAGTACGCCAACGAGAAGAACCCGCTGGCCAAGTACCATGAAGAAACCGGAGA<br>ATACCTGACCAAGTACAGCAAGAAGAACAACGGTCCCATTGTCAAGAGCCTGAAGTAC<br>ATCGGCAACAAGCTGGATCCCACCTCGACGTGACACATCAGTTCAAGTCGTCGACTA<br>AGAAGCTTGTGAAGCTGTCAATCAAGAACTATAGATTCGACGTGTACTTGACCGAAAA<br>GGGATACAAGTTCGTGACCATAGCCTATCTGAACGTGTTCAAGAAAGATAACTACTAC | GST1-v1, nucleotide |

| SEQ ID NO | Sequence | Description |
|---|---|---|
| | TACATCCCCAAGGACAAGTACCAGGAGCTCAAAGAAAAGAAGAAGATCAAAGACACCG<br>ACCAGTTCATTGCCTCCTTCTACAAGAACGACCTGATCAAACTGAACGGCGACCTCTA<br>CAAGATCATTGGAGTGAACAGCGATGACAGGAACATCATTGAGCTGGACTACTACGAC<br>ATCAAGTACAAGGACTACTGCGAGATCAACAACATCAAGGGCGAACCCCGGATCAAGA<br>AAACTATTGGAAAGAAAACCGAGTCCATTGAGAAGTTCACCACTGACGTGCTGGGAAA<br>CCTTTACCTCCACTCCACCGAGAAGGCACCACAACTGATCTTCAAGCGCGGCCTGAAA<br>CGGCCCGCCGCAACCAAGAAGGCCGGCCAGGCGAAGAAGAAGAAATGAGCGGCCGCTT<br>AATTAAGCTGCCTTCTGCGGGGCTTGCCTTCTGGCCATGCCCTTCTTCTCTCCCTTGC<br>ACCTGTACCTCTTGGTCTTTGAATAAAGCCTGAGTAGGAAGTCTAG | |
| 41 | MAPKKKRKVMNQKFILGLDIGITSVGYGLIDYETKNIIDAGVRLFPEANVENNEGRRS<br>KRGSRRLKRRRIHRLERVKLLLTEYDLINKEQIPTSNNPYQIRVKGLSEILSKDELAI<br>ALLHLAKRRGIHNVDVAADKEETASDSLSTKDQINKNAKFLESRYVCELQKERLENEG<br>HVRGVENRFLTKDIVREAKKIIDTQMQYYPEIDETFKEKYISLVETRREYFEGPGQGS<br>PFGWNGDLKKWYEMLMGHCTYFPQELRSVKYAYSADLFNALNDLNNLIIQRDNSEKLE<br>YHEKYHIIENVFKQKKKPTLKQIAKEIGVNPEDIKGYRITKSGTPEFTSFKLFHDLKK<br>VVKDHAILDDIDLLNQIAEILTIYQDKDSIVAELGQLEYLMSEADKQSISELTGYTGT<br>HSLSLKCMNMIIDELWHSSMNQMEVFTYLNMRPKKYELKGYQRIPTDMIDDAILSPVV<br>KRTFIQSINVINKVIEKYGIPEDIIIELARENNSDDRKKFINNLQKKNEATRKRINEI<br>IGQTGNQNAKRIVEKIRLHDQQEGKCLYSLESIPLEDLLNNPNHYEVDHIIPRSVSFD<br>NSYHNKVLVKQSENSKKSNLTPYQYFNSGKSKLSYNQFKQHILNLSKSQDRISKKKKE<br>YLLEERDINKFEVQKEFINRNLVDTRYATRELTNYLKAYFSANNMNVKVKTINGSFTD<br>YLRKVWKFKKERNHGYKHHAEDALIIANADFLFKENKKLKAVNSVLEKPEIETKQLDI<br>QVDSEDNYSEMFIIPKQVQDIKDFRNFKYSHRVDKKPNRQLINDTLYSTRKKDNSTYI<br>VQTIKDIYAKDNTTLKKQFDKSPEKFLMYQHDPRTFEKLEVIMKQYANEKNPLAKYHE<br>ETGEYLTKYSKKNNGPIVKSLKYIGNKLGSHLDVTHQFKSSTKKLVKLSIKNYRFDVY<br>LTEKGYKFVTIAYLNVFKKDNYYYIPKDKYQELKEKKKIKDTDQFIASFYKNDLIKLN<br>GDLYKIIGVNSDDRNIIELDYYDIKYKDYCEINNIKGEPRIKKTIGKKTESIEKFTTD<br>VLGNLYLHSTEKAPQLIFKRGLKRPAATKKAGQAKKKK | GST1-v1, amino acid |
| 42 | AGGAAATAAGAGAGAAAAGAAGAGTAAGAAGAAATATAAGAGCCACCATGGCCCCCAA<br>GAAGAAACGCAAAGTCATGAACCAAAAGTTCATTCTGGGGCTCGATATCGGCATCACC<br>TCCGTGGGATATGGTCTGATCGACTACGAGACTAAGAACATCATCGACGCTGGAGTGC<br>GACTGTTCCCGGAAGCGAACGTGGAGAACAACGAAGGCCGCAGATCCAAGCGCGGGTC<br>CAGAAGGCTCAAGAGGCGGAGGATCCATAGACTCGAAAGAGTGAAGAAGCTCCTTGAA<br>GATTACAATCTGTTGGACCAGAGCCAGATTCCCCAAAGCACCAACCCGTACGCCATCA<br>GAGTGAAGGGCCTGTCCGAAGCCCTGTCGAAAGATGAACTGGTCATTGCCCTGCTGCA<br>TATTGCCAAACGGCGCGGAATCCATAAGATCGACGTGATAGACTCCAACGATGACGTG<br>GGCAACGAACTGTCAACCAAGGAGCAGCTGAACAAGAACTCGAAACTGCTGAAGGACA<br>AGTTCGTCTGCCAAATTCAACTGGAACGGATGAACGAGGGACAAGTCAGGGGAGAGAA<br>AAACCGGTTCAAGACCGCGGACATCATCAAGGAGATCATCCAACTCCTGAATGTGCAG<br>AAGAACTTTCACCAGCTGGATGAAAACTTCATTAACAAGTACATTGAACTGGTGGAAA<br>TGCGGAGGGAGTACTTCGAGGGACCTGGAAAGGGATCCCCTTACGGCTGGGAAGGGGA<br>CCCCAAGGCTTGGTACGAAACGCTCATGGGCCATTGCACTTACTTTCCGGACGAACTC<br>CGGTCCGTGAAGTACGCATACTCTGCCGATCTGTTCAATGCACTCAACGACCTTAACA<br>ACTTGGTGATCCAGCGCGATGGCCTGTCCAAGTTGGAATACCACGAAAAGTATCACAT<br>CATCGAGAACGTGTTCAAGCAGAAAAAGAAGCCAACTCTGAAGCAGATTGCCAACGAA<br>ATTAACGTGAACCCCGAGGATATCAAGGGATACCGGATCACTAAGTCCGGCAAACCAC<br>AGTTCACCGAGTTCAAGCTGTACCACGATCTGAAGTCGGTGCTCTTTGACCAGTCCAT<br>CCTGGAAAACGAAGATGTGCTGGACCAGATTGCTGAGATCCTGACCATCTACCAGGAC<br>AAGGACTCGATTAAGAGCAAGCTCACGGAGCTGGACATTCTGCTGAACGAAGAGGATA<br>AGGAGAACATCGCGCAGCTCACTGGTTACACCGGTACCCACCGCTTGTCCCTTAAGTG<br>CATCCGGCTGGTCCTCGAGGAACAATGGTACTCCAGCCGGAACCAGATGGAGATCTTC<br>ACGCACTTGAACATCAAGCCGAAGAAGATTAACCTGACCGCTGCGAACAAGATACCCA<br>AGGCCATGATCGACGAGTTTATCCTCTCACCGGTGGTCAAGCGCACCTTCGGACAAGC<br>CATCAACCTCATCAACAAGATTATCGAGAAGTACGGCGTGCCTGAGGATATCATCATC<br>GAGCTGGCTCGGGAGAACAACTCAAAGGATAAGCAGAAGTTCATTAACGAGATGCAGA<br>AAAAGAACGAGAACACTCGCAAGCGGATTAATGAGATCATCGGTAAATACGGGAACCA<br>GAACGCCAAGCGGCTTGTGGAAAAGATTCGGCTCCACGACGAGCAGGAGGGAAAGTGT<br>CTGTACTCGCTGGAGAGCATTCCCCTGGAGGACCTCCTGAACAACCCAAACCACTACG<br>AAGTGGATCACATAATCCCCCGCAGCGTGTCATTCGACAATTCCTACCATAACAAGGT<br>CCTCGTGAAGCAGTCCGAGAATAGCAAGAAGTCCAACCTGACTCCGTACCAGTACTTC<br>AACTCCGGCAAATCCAAGCTGTCCTACAACCAGTTCAAACAGCACATCCTCAACCTGT<br>CAAAGAGCCAGGACAGGATCTCGAAGAAGAAGAAGGAATACCTTCTCGAGGAACGGGA<br>TATCAATAAGTTCGAGGTGCAGAAGGAGTTTATCAATAGAAACCTGGTGGACACTCGC<br>TATGCCACCCGCGAACTGACCAACTACCTGAAGGCGTACTTCTCCGCCAACAACATGA<br>ACGTGAAGGTCAAAACTATTAACGGCAGCTTCACCGACTATCTGCGCAAGGTCTGGAA<br>GTTCAAGAAGGAACGCAACCACGGTTACAAGCACCACGCGGAAGATGCGCTGATTATC<br>GCCAACGCTGACTTCCTGTTCAAGGAAAACAAGAAGCTCAAGGCCGTGAACTCAGTGC<br>TCGAGAAGCCTGAAATCGAGACTAAGCAGCTGGACATCCAGGTCGATTCGGAAGATAA<br>CTACTCCGAAATGTTCATCATCCCTAAGCAAGTGCAGGACATCAAGGACTTCAGGAAT<br>TTCAAGTACAGCCATCGCGTGGACAAGAAGCCAAACAGACAGCTGATCAACGATACAC<br>TGTATTCCACCCGGAAGAAGGACAACTCCACCTACATCGTCCAAACCATTAAGGACAT<br>CTACGCAAAGGACAACACCACGCTTAAGAAGCAGTTCGACAAGAGCCCCGAAAAGTTC | Slu, nucleotide |

Sequence Listing

| SEQ ID NO | Sequence | Description |
|---|---|---|
| | CTCATGTACCAGCACGACCCCAGAACCTTCGAGAAGCTTGAAGTGATCATGAAGCAGT<br>ACGCCAACGAAAAGAACCCACTGGCTAAGTACCACGAGGAAACCGGCGAATACCTGAC<br>CAAGTACTCCAAAAAGAACAACGGACCGATCGTCAAGTCCCTGAAGTACATTGGGAAC<br>AAGCTCGGCTCGCACCTCGATGTGACCCACCAGTTCAAGTCCTCGACCAAAAAGCTCG<br>TGAAGCTGTCCATCAAGCCGTACCGGTTCGACGTGTACCTGACTGACAAGGGATATAA<br>GTTCATCACCATTTCCTACCTCGACGTGTTGAAGAAGGATAACTACTACTACATTCCG<br>GAACAGAAGTACGACAAGCTCAAGCTCGGAAAGGCCATCGACAAAAATGCGAAGTTCA<br>TCGCGAGCTTCTACAAGAATGACTTGATCAAGCTGGATCTGCCCGACATTCGGTAC<br>AAGGAATACTGCGAGCTGAACAACATCAAGGGAGAACCGCGGATCAAGAAAACCATCG<br>GAAAGAAAGTGAACAGCATCGAGAAACTGACTACTGACGTCCTGGGAAACGTGTTCAC<br>CAACACACAATACACCAAACCCCAGCTGCTGTTTAAGCGCGGGAACAAGCGCCCTGCC<br>GCAACTAAGAAGGCCGGACAGGCCAAAAAGAAGAAATGAGCGGCCGCTTAATTAAGCT<br>GCCTTCTGCGGGGCTTGCCTTCTGGCCATGCCCTTCTTCTCTCCCTTGCACCTGTACC<br>TCTTGGTCTTTGAATAAAGCCTGAGTAGGAAG | |
| 43 | MAPKKKRKVMNQKFILGLDIGITSVGYGLIDYETKNIIDAGVRLFPEANVENNEGRRS<br>KRGSRRLKRRIHRLERVKKLLEDYNLLDQSQIPQSTNPYAIRVKGLSEALSKDELVI<br>ALLHIAKRRGIHKIDVIDSNDDVGNELSTKEQLNKNSKLLKDKFVCQIQLERMNEGQV<br>RGEKNRFKTADIIKEITQLLNVQKNFHQLDENFINKYIELVEMRREYFEGPGKGSPYG<br>WEGDPKAWYETLMGHCTYFPDELRSVKYAYSADLFNALNDLNNLVIQRDGLSKLEYHE<br>KYHIIENVFKQKKKPTLKQIANEINVNPEDIKGYRITKSGKPQFTEFKLYHDLKSVLF<br>DQSILENEDVLDQIAEILTIYQDKDSIKSKLTELDILLNEEDKENIAQLTGYTGTHRL<br>SLKCIRLVLEEQWYSSRNQMEIFTHLNIKPKKINLTAANKIPKAMIDEFILSPVVKRT<br>FGQAINLINKIIEKYGVPEDIIIELARENNSKDKQKFINEMQKKNENTRKKRINEIIGK<br>YGNQNAKRLVEKIRLHDEQEGKCLYSLESIPLEDLLNNPNHYEVDHIIPRSVSFDNSY<br>HNKVLVKQSENSKKSNLTPYQYFNSGKSKLSYNQFKQHILNLSKSQDRISKKKKEYLL<br>EERDINKFEVQKEFINRNLVDTRYATRELTNYLKAYFSANNMNVKVKTINGSFTDYLR<br>KVWKFKKERNHGYKHHAEDALIIANADFLFKENKKLKAVNSVLEKPEIETKQLDIQVD<br>SEDNYSEMFIIPKQVQDIKDFRNFKYSHRVDKKPNRQLINDTLYSTRKKDNSTYIVQT<br>IKDIYAKDNTTLKKQFDKSPEKFLMYQHDPRTFEKLEVIMKQYANEKNPLAKYHEETG<br>EYLTKYSKKNNGPIVKSLKYIGNKLGSHLDVTHQFKSSTKKLVKLSIKPYRFDVYLTD<br>KGYKFITISYLDVLKKDNYYYIPEQKYDKLKLGKAIDKNAKFIASFYKNDLIKLDGEI<br>YKIIGVNSDTRNMIELDLPDIRYKEYCELNNIKGEPRIKKTIGKKVNSIEKLTTDVLG<br>NVFTNTQYTKPQLLFKRGNKRPAATKKAGQAKKKK | S1u, amino acid |
| 44 | AGGAAATAAGAGAGAAAAGAAGAGTAAGAAGAAATATAAGAGCCACCATGGCCCCCAA<br>GAAGAAACGCAAAGTCATGAACCAAAAGTTCATTCTGGGGCTCGATATCGGCATCACC<br>TCCGTGGGATATGGTCTGATCGACTACGAGACTAAGAACATCATCGACGCTGGAGTGC<br>GACTGTTCCCGGAAGCGAACGTGGAGAACAACGAAGGCCGCAGATCCAAGCGCGGGTC<br>CAGAAGGCTCAAGAGGCGGAGGATCCATAGACTCGAGAGTGAAGTCGCTCCTTTCG<br>GAATACAAGATTATCAGCGGTCTTGCCCCCACCAACAACCAACCGTACAACATCGAG<br>TGAAGGGCCTGACCGAACAGCTGACCAAAGATGAACTGGCCGTCGCCCTGCTGCATAT<br>TGCCAAACGGCGCGGAATCCATAAGATCGACGTGATTGACAGCAACGATGACGTGGGA<br>AACGAGCTGTCAACCAAGGAACAGCTTAACAAGAACAGCAAATTGCTGAAGGACAAGT<br>TTGTCTGCCAAATTCAACTGGAACGGATGAACGAGGGACAAGTCAGGGGAGAGAAAA<br>CCGGTTCAAGACCGCCGACATCATCAAGGAGATCATCCAACTGCTGAACGTGCAGAAG<br>AACTTCCACCAACTGGATGAAAACTTCATTAACAAGTACATTGAACTGGTGGAAATGC<br>GGAGGGAGTACTTCGAGGGACCTGGACAGGGATCCCCTTTCGGCTGGAATGGGGACCT<br>TAAGAAGTGGTACGAAATGTTGATGGGCCATTGCACTTACTTTCCGCAAGAACTCCGG<br>TCCGTGAAGTACGCATACTCTGCCGACCTGTTCAATGCACTCAACGACCTTAACAACT<br>TGATCATCCAGCGCGATAACTCGGAAAAGTTGGAATACCACGAAAAGTATCACATCAT<br>CGAGAACGTGTTCAAGCAGAAAAAGAAGCCAACTCTGAAGCAGATTGCCAAGGAAATT<br>GGCGTGAATCCGGAGGATATCAAGGGATACCGGATCACTAAGTCCGGCACGCAGAGT<br>TCACCGAGTTCAAGCTGTACCACGATCTGAAGTCGGTGCTCTTTGACCAGTCCATCCT<br>GGAAAACGAAGATGTGCTGGACCAGATTGCTGAGATCCTGACCATCTACCAGGACAAG<br>GACTCGATTAAGTCCAAGCTCACCGAGCTGGACATTCTGCTGAACGAAGAAGATAAGG<br>AGAACATCGCGCAGCTCACCGGTTACAATGGTACCCACCGCTTGTCCCTTAAGTGCAT<br>CCGCCTGGTGCTGGAGGAACAGTGGTACTCGAGCCGGAACCAGATGGAGATCTTCACT<br>CACTTGAACATCAAGCCGAAAAGATTAACCTGACTGCCGCCAACAAGATACCCAAGG<br>CCATGATCGACGAGTTTATCCTCTCACCGGTGGTCAAGCGCACCTTCATTCAATCTAT<br>CAACGTGATCAACAAGGTCATCGAGAAGTACGGCATTCCTGAGGATATCATCATCGAG<br>CTGGCTCGGGAGAACAACTCAGACGATAGGAAGAAGTTCATTAACAACCTCCAGAAAA<br>AGAACGAGGCCACTCGCAAGCGGATTAATGAGATCATCGGTCAGACCGGGAACCAGAA<br>CGCCAAGCGGATCGTGGAAAAGATTCGGCTCCACGACCAACAGGAGGGAAAGTGTCTG<br>TACTCGCTGGAGTCGATTGCACTGATGGACCTCCTGAACAACCCACAGAACTACGAAG<br>TCGATCACATAATCCCCCGCAGCGTGGCATTCGACAACTCCATCCATAACAAGGTCCT<br>CGTGAAGCAGATCGAGAATAGCAAGAAGGGGAACCGGACTCCGTACCAGTACCTGAAC<br>TCCTCCGACGCCAAGCTGTCATACAATCAGTTCAAACAGCACATTCTCAACCTGTCCA<br>AGTCAAAGGACAGGATCTCCAAGAAGAAGAAGGACTACCTTCTCGAGGAACGGGATAT<br>CAATAAGTTCGAGGTGCAGAAGGAGTTTATCAATAGAAACCTGGTGGACACTCGCTAT<br>GCCACCCGCGAACTGACCAGCTACCTGAAGGCGTACTTCTCCGCCAACAACATGGACG<br>TGAAGGTCAAAACTATTAACGGCAGCTTCACCGACCATCTGCGCAAGGTCTGGAGGTT<br>CGACAAGTACCGCAACCACGGTTACAAGCACCACGCGGAAGATGCGCTGATTATCGCC | F8 nucleotide |

| SEQ ID NO | Sequence | Description |
|---|---|---|
| | AACGCTGACTTCCTGTTCAAGGAAAACAAGAAGCTCAAGGCCGTGAACTCAGTGCTCG<br>AGAAGCCTGAAATCGAGACTAAGCAGCTGGACATCCAGGTCGATTCGGAAGATAACTA<br>CTCCGAAATGTTCATCATCCCTAAGCAAGTGCAGGACATCAAGGACTTCAGGAATTTC<br>AAGTACAGCCATCGCGTGGACAAGAAGCCAAACAGACAGCTGATCAACGATACACTGT<br>ATTCCACCCGGAAGAAGGACAACTCCACCTACATCGTCCAAACCATTAAGGACATCTA<br>CGCAAAGGACAACACCACGCTTAAGAAGCAGTTCGACAAGAGCCCCGAAAAGTTCCTC<br>ATGTACCAGCACGACCCCAGAACCTTCGAGAAGCTTGAAGTGATCATGAAGCAGTACG<br>CCAACGAAAAGAACCCACTGGCTAAGTACCACGAGGAAACCGGCGAATACCTGACCAA<br>GTACTCCAAAAAGAACAACGGACCGATCGTCAAGTCCCTGAAGTACATTGGGAACAAG<br>CTCGGCTCGCACCTCGATGTGACCCACCAGTTCAAGTCCTCGACCAAAAAGCTCGTGA<br>AGCTGTCCATCAAGCCGTACCGGTTCGACGTGTACCTGACTGACAAGGGATATAAGTT<br>CATCACCATTTCCTACCTCGACGTGTTGAAGAAGGATAACTACTACTACATTCCGGAA<br>CAGAAGTACGACAAGCTCAAGCTCGAAAGGCCATCGACAAAAATGCGAAGTTCATCG<br>CGAGCTTCTACAAGAATGACTTGATCAAGCTGGATGGCGAAATCTACAAGATCATCGG<br>GGTCAACTCCGATACCCGCAACATGATTGAGCTGGATCTGCCCGACATTCGGTACAAG<br>GAATACTGCGAGCTGAACAACATCAAGGGAGAACCGCGGATCAAGAAAACCATCGGAA<br>AGAAAGTGAACAGCATCGAGAAACTGACTACTGACGTCCTGGAAACGTGTTCACCAA<br>CACACAATACACCAAACCCCAGCTGCTGTTTAAGCGCGGGAACAAGCGCCCTGCCGCA<br>ACTAAGAAGGCCGGACAGGCCAAAAAGAAGAAATGAGCGGCCGCTTAATTAAGCTGCC<br>TTCTGCGGGGCTTGCCTTCTGGCCATGCCCTTCTTCTCTCCCTTGCACCTGTACCTCT<br>TGGTCTTTGAATAAAGCCTGAGTAGGAAG | |
| 45 | MAPKKKRKVMNQKFILGLDIGITSVGYGLIDYETKNIIDAGVRLFPEANVENNEGRRS<br>KRGSRRLKRRIHRLERVKSLLSEYKIISGLAPTNNQPYNIRVKGLTEQLTKDELAVA<br>LLHIAKRRGIHKIDVIDSNDDVGNELSTKEQLNKNSKLLKDKFVCQIQLERMNEGQVR<br>GEKNRFKTADIIKEITQLLNVQKNFHQLDENFINKYIELVEMRREYFEGPGQGSPFGW<br>NGDLKKWYEMLMGHCTYFPQELRSVKYAYSADLFNALNDLNNLIIQRDNSEKLEYHEK<br>YHIIENVFKQKKKPTLKQIAKEIGVNPEDIKGYRITKSGTPEFTEFKLYHDLKSVLFD<br>QSILENEDVLDQIAEILTIYQDKDSIKSKLTELDILLNEEDKENIAQLTGYNGTHRLS<br>LKCIRLVLEEQWYSSRNQMEIFTHLNIKPKKINLTAANKIPKAMIDEFILSPVVKRTF<br>IQSINVINKVIEKYGIPEDIIIELARENNSDDRKKFINNLQKKNEATRKRINEIIGQT<br>GNQNAKRIVEKIRLHDQQEGKCLYSLESIALMDLLNNPQNYEVDHIIPRSVAFDNSIH<br>NKVLVKQIENSKKGNRTPYQYLNSSDAKLSYNQFKQHILNLSKSKDRISKKKKDYLLE<br>ERDINKFEVQKEFINRNLVDTRYATRELTSYLKAYFSANNMDVKVKTINGSFTNHLRK<br>VWRFDKYRNHGYKHHAEDALIIANADFLFKENKKLKAVNSVLEKPEIETKQLDIQVDS<br>EDNYSEMFIIPKQVQDIKDFRNFKYSHRVDKKPNRQLINDTLYSTRKKDNSTYIVQTI<br>KDIYAKDNTTLKKQFDKSPEKFLMYQHDPRTFEKLEVIMKQYANEKNPLAKYHEETGE<br>YLTKYSKKNNGPIVKSLKYIGNKLGSHLDVTHQFKSSTKKLVKLSIKPYRFDVYLTDK<br>GYKFITISYLDVLKKDNYYYIPEQKYDKLKLGKAIDKNAKFIASFYKNDLIKLDGEIY<br>KIIGVNSDTRNMIELDLPDIRYKEYCELNNIKGEPRIKKTIGKKVNSIEKLTTDVLGN<br>VFTNTQYTKPQLLFKRGNKRPAATKKAGQAKKKK | F8, amino acid |
| 46 | AGGAAATAAGAGAGAAAAGAAGAGTAAGAAGAAATATAAGAGCCACCATGGCCCCCAA<br>GAAGAAACGCAAAGTCATGAACCAAAAGTTCATTCTGGGGCTCGATATCGGCATCACC<br>TCCGTGGGATATGGTCTGATCGACTACGAGACTAAGAACATCATCGACGCTGGAGTGC<br>GACTGTTCCCGGAAGCGAACGTGGAGAACAACGAAGGCCGCAGATCCAAGCGCGGGTC<br>CAGAAGGCTCAAGAGGCGGAGGATCCATAGACTCGACAGAGTGAAGCACCTCCTTGCC<br>GAATACGATCTGTTGGACCTTACCAACATTCCCAAGAGCACCAACCCGTACCAAACCA<br>GAGTGAAGGGCCTGAACGAAAAGCTGTCGAAAGATGAACTGGTCATTGCCCTGCTGCA<br>TATTGCCAAACGGCGCGGAATCCATAACGTGGACGTGGCCGCTGACAAGGAAGAGACT<br>GCGTCCGACTCGCTGTCAACCAAGGACCAGATCAACAAGAACGCCAAATTCCTGGAAA<br>GCCGCTACGTCTGCGAGCTTCAAAAAGAACGGCTGGAGAACGAGGGACACGTCAGGGG<br>AGTGGAGAACCGGTTCCTGACCAAGGACATCGTGCGGGAAGCCAAGAAGATCATCGAC<br>ACCCAAATGCAGTATTATCCGGAAATTGATGAAACTTTTAAGGAGAAGTACATTTCCC<br>TGGTGGAAACTCGGAGGGAGTACTTCGAGGGACCTGGAAAGGGATCCCCTTTCGGCTG<br>GGAAGGGAACATTAAGAAGTGGTTTGAACAGATGATGGGCATTGCACTTACTTTCCG<br>GAAGAACTCCGGTCCGTGAAGTACTCATACTCTGCCGAGCTGTTCAATGCACTCAACG<br>ACCTTAACAACTTGGTGATCACCCGCGATGAAGATGCCAAGTTGAACTACGGAGAAAA<br>GTTCCAGATCATCGAGAACGTGTTCAAGCAGAAAAAGACCCCAAATCTGAAGCAGATT<br>GCCATCGAAATTGGCGTGCACGAGACTGAGATCAAGGGATACCGGGTCAACAAGTCCG<br>GCACGCCAGAGTTCACCGAGTTCAAGCTGTACCACGATCTGAAGTCGATCGTGTTTGA<br>CAAGTCCATCCTGGAAAACGAAGCCATTCTGGACCAGATTGCTGAGATCCTGACCATC<br>TACCAGGACGAGCAATCGATTAAGGAAGAACTGAACAAGCTCCCCGAGATTCTGAACG<br>AACAGGATAAGGCCGAGATCGCGAAGCTCATTGGTTACAATGGTACCCACCGCTTGTC<br>CCTTAAGTGCATCCATCTGATCAATGAGGAACTGTGGCAGACCAGCCGGAACCAGATG<br>GAGATCTTCAATTACTTGAACATCAAGCCGAACAAGGTGGACCTGTCCGAACAGAACA<br>AGATACCCAAGGACATGGTCAACGACTTTATCCTCTCACCGGTGGTCAAGCGCACCTT<br>CATTCAATCTATCAACGTGATCAACAAGGTCATCGAGAAGTACGGCATTCCTGAGGAT<br>ATCATCATCGAGCTGGCTCGGGAGAACAACTCAGACGATAGGAAGAAGTTCATTAACA<br>ACCTCCAGAAAAAGAACGAGGCCACTCGCAAGCGGATTAATGAGATCATCGGTCAGAC<br>CGGGAACCAGAACGCCAAGCGGATCGTGAAAAGATTCGGCTCCACGACCAACAGGAG<br>GGAAAGTGTCTGTACTCGCTGAAGGACATTCCCCTGGAGGACCTCCTGAGGAACCCAA<br>ACAACTACGACATCGATCACATAATCCCCCGCAGCGTGTCATTCGACGATTCCATGCA<br>TAACAAGGTCCTCGTGCGGAGAGAGCAGAATGCCAAGAAGAACAACCAGACTCCGTAC | E2, nucleotide |

| SEQ ID NO | Sequence | Description |
|---|---|---|
| | CAGTACCTGACGTCCGGCTACGCAGACATCAAGTACTCAGTGTTCAAACAGCACGTGC | |
| | TCAACCTGGCCGAGAACAAGGACAGGATGACCAAGAAGAAGCGCGAATACCTTCTCGA | |
| | GGAACGGGATATCAATAAGTTCGAGGTGCAGAAGGAGTTTATCAATAGAAACCTGGTG | |
| | GACACTCGCTATGCCACCCGCGAACTGACCAACTACCTGAAGGCGTACTTCTCCGCCA | |
| | ACAACATGAACGTGAAGGTCAAAACTATTAACGGCAGCTTCACCGACTATCTGCGCAA | |
| | GGTCTGGAAGTTCAAGAAGGAACGCAACCACGGTTACAAGCACCACGCGGAAGATGCG | |
| | CTGATTATCGCCAACGCTGACTTCCTGTTCAAGGAAAACAAGAAGCTCAAGGCCGTGA | |
| | ACTCAGTGCTCGAGAAGCCTGAAATCGAGACTAAGCAGCTGGACATCCAGGTCGATTC | |
| | GGAAGATAACTACTCCGAAATGTTCATCATCCCTAAGCAAGTGCAGGACATCAAGGAC | |
| | TTCAGGAATTTCAAGTACAGCCATCGCGTGGACAAGAAGCCAAACAGACAGCTGATCA | |
| | ACGATACACTGTATTCCACCCGGAAGAAGGACAACTCCACCTACATCGTCCAAACCAT | |
| | TAAGGACATCTACGCAAAGGACAACACCACGCTTAAGAAGCAGTTCGACAAGAGCCCC | |
| | GAAAAGTTCCTCATGTACCAGCACGACCCCAGAACCTTCGAGAAGCTTGAAGTGATCA | |
| | TGAAGCAGTACGCCAACGAAAAGAACCCACTGGCTAAGTACCACGAGGAAACCGGCGA | |
| | ATACCTGACCAAGTACTCCAAAAAGAACAACGGACCGATCGTCAAGTCCCTGAAGTAC | |
| | ATTGGGAACAAGCTCGGCTCGCACCTCGATGTGACCCACCAGTTCAAGTCCTCGACCA | |
| | AAAAGCTCGTGAAGCTGTCCATCAAGCCGTACCGGTTCGACGTGTACCTGACTGACAA | |
| | GGGATATAAGTTCATCACCATTTCCTACCTCGACGTGTTGAAGAAGGATAACTACTAC | |
| | TACATTCCGGAACAGAAGTACGACAAGCTCAAGCTCGGAAAGGCCATCGACAAAAATG | |
| | CGAAGTTCATCGCGAGCTTCTACAAGAATGACTTGATCAAGCTGGATGGCGAAATCTA | |
| | CAAGATCATCGGGGTCAACTCCGATACCCGCAACATGATTGAGCTGGATCTGCCCGAC | |
| | ATTCGGTACAAGGAATACTGCGAGCTGAACAACATCAAGGGAGAACCGCGGATCAAGA | |
| | AAACCATCGGAAAGAAAGTGAACAGCATCGAGAACTGACTACTGACGTCCTGGGAAA | |
| | CGTGTTCACCAACACACAATACACCAAACCCCAGCTGCTGTTTAAGCGCGGGAACAAG | |
| | CGCCCTGCCGCAACTAAGAAGGCCGGACAGGCCAAAAAGAAGAAATGAGCGGCCGCTT | |
| | AATTAAGCTGCCTTCTGCGGGGCTTGCCTTCTGGCCATGCCCTTCTTCTCTCCCTTGC | |
| | ACCTGTACCTCTTGGTCTTTGAATAAAGCCTGAGTAGGAAG | |
| 47 | MAPKKKRKVMNQKFILGLDIGITSVGYGLIDYETKNIIDAGVRLFPEANVENNEGRRS<br>KRGSRRLKRRRIHRLDRVKHLLAEYDLLDLTNIPKSTNPYQTRVKGLNEKLSKDELVI<br>ALLHIAKRRGIHNVDVAADKEETASDSLSTKDQINKNAKFLESRYVCELQKERLENEG<br>HVRGVENRFLTKDIVREAKKIIDTQMQYYPEIDETFKEKYISLVETRREYFEGPGKGS<br>PFGWEGNIKKWFEQMMGHCTYFPEELRSVKYSYSAELFNALNDLNNLVITRDEDAKLN<br>YGEKFQIIENVFKQKKTPNLKQIAIEIGVHETEIKGYRVNKSGTPEFTEFKLYHDLKS<br>IVFDKSILENEAILDQIAEILTIYQDEQSIKEELNKLPEILNEQDKAEIAKLIGYNGT<br>HRLSLKCIHLINEELWQTSRNQMEIFNYLNIKPNKVDLSEQNKIPKDMVNDFILSPVV<br>KRTFIQSINVINKVIEKYGIPEDIIIELARENNSDDRKKFINNLQKKNEATRKRINEI<br>IGQTGNQNAKRIVEKIRLHDQQEGKCLYSLKDIPLEDLLRNPNNYDIDHIIPRSVSFD<br>DSMHNKVLVRREQNAKKNNQTPYQYLTSGYADIKYSVFKQHVLNLAENKDRMTKKKRE<br>YLLEERDINKFEVQKEFINRNLVDTRYATRELTNYLKAYFSANNMNVKVKTINGSFTD<br>YLRKVWKFKKERNHGYKHHAEDALIIANADFLFKENKKLKAVNSVLEKPEIETKQLDI<br>QVDSEDNYSEMFIIPKQVQDIKDFRNFKYSHRVDKKPNRQLINDTLYSTRKKDNSTYI<br>VQTIKIDYAKDNTTLKKQFDKSPEKFLMYQHDPRTFEKLEVIMKQYANEKNPLAKYHE<br>ETGEYLTKYSKKNNGPIVKSLKYIGNKLGSHLDVTHQFKSSTKKLVKLSIKPYRFDVY<br>LTDKGYKFITISYLDVLKKDNYYYIPEQKYDKLKLGKAIDKNAKFIASFYKNDLIKLD<br>GEIYKIIGVNSDTRNMIELDLPDIRYKEYCELNNIKGEPRIKKTIGKKVNSIEKLTTD<br>VLGNVFTNTQYTKPQLLFKRGNKRPAATKKAGQAKKKK | E2, amino acid |
| 48 | AGGAAATAAGAGAGAAAAGAAGAGTAAGAAGAAATATAAGAGCCACCATGGCCCCCAA<br>GAAGAAACGCAAAGTCATGAACCAAAAGTTCATTCTGGGGCTCGATATCGGCATCACC<br>TCCGTGGGATATGGTCTGATCGACTACGAGACTAAGAACATCATCGACGCTGGAGTGC<br>GACTGTTCCCGGAAGCGAACGTGGAGAACAACGAAGGCCGCAGATCCAAGCGCGGGTC<br>CAGAAGGCTCAAGAGGCGGAGGATCCATAGACTCGAGAGAGTGAAGAAGCTCCTTGAA<br>GATTACAATCTGTTGGACAGTCACAGATTCCCAAAGCACCAACCCGTACGCCATCA<br>GAGTCAAGGGCCTGTCAGAAGCACTGTCGAAAGATGAACTGGTCATTGCCCTGCTGCA<br>TATTGCCAAACGGCGCGGAATCCATAACATCAACGTGTCGAGCGAAGATGAGGACGCG<br>TCCAACGAACTGTCAACCAAGGAACAGATCAACCGGAACAACAAACTGCTGAAGGACA<br>AATACGTCTGCGAGGTGCAGCTTCAACGGCTGAAAGAGGGACAGATCAGGGGAGAGAA<br>AAACCGGTTCAAGACCACCGACATCCTTAAGGAGATCGACCAACTCCTGAAAGTGCAG<br>AAGGACTATCACAACCTCGACATTGATTTTATCAACCAGTACAAGGAGATTGTGGAAA<br>CTCGGAGGGAGTACTTCGAGGGACCTGGAAAGGGATCCCCTTATGGCTGGGAAGGGGA<br>CCCCAAGGCTTGGTACGAAACCCTGATGGGCCATTGCACTTACTTTCCGGATGAACTC<br>CGGTCCGTGAAGTACGCTTACTCTGCCGACCTGTTCAATGCACTCAACGACCTTAACA<br>ACTTGGTGATCCAACGCGATGGTCTTTCCAAGTTGGAGTACCACGAAAAGTACCACAT<br>CATCGAGAACGTGTTCAAGCAGAAAAAGAAGCCAACTCTGAAGCAGATTGCCAACGAA<br>ATTAACGTGAACCCCGAGGATATCAAGGGATACCGGATTACCAAGTCCGCAAACCAG<br>AGTTCACCTCATTCAAGCTGTTTCACGATCTGAAGAAGGTCGTGAAGGACCACGCCAT<br>CCTGGATGACATTGATCTTCTGAACCAGATTGCTGAGATCCTGACCATCTACCAGGAC<br>AAGGACTCGATTGTGGCCGAACTGGGACAGCTCGAGTACCTGATGTCCGAAGCCGATA<br>AGCAGTCCATCAGCGAACTCACCGGTTACACCGGTACCCACTCCTTGTCCCTTAAGTG<br>CATGAACATGATCATTGACGAACTGTGGCACTCCAGCATGAACCAGATGGAGGTGTTC<br>ACCTACTTGAACATGCGCCCGAAGAAGTACGAGCTGAAGGGCTACCAGCGCATACCCA<br>CGGACATGATCGACGACGCCATCCTCTCACCGGTGGTCAAGCGCACCTTCATTCAATC<br>TATCAACGTGATCAACAAGGTCATCGAGAAGTACGGCATTCCTGAGGATATCATCATC | P2H12, nucleotide |

Sequence Listing

| SEQ ID NO | Sequence | Description |
|---|---|---|
| | GAGCTGGCTCGGGAGAACAACTCAGACGATAGGAAGAAGTTCATTAACAACCTCCAGA<br>AAAAGAACGAGGCCACTCGCAAGCGGATTAATGAGATCATCGGTCAGACCGGGAACCA<br>GAACGCCAAGCGGATCGTGGAAAAGATTCGGCTCCACGACCAACAGGAGGGAAAGTGT<br>CTGTACTCGCTGGAGTCCATTCCCCTGGAGGACCTCCTGAACAACCCAAACCACTACG<br>AGGTCGATCACATAATCCCCCGCAGCGTGTCATTCGACAACTCCTACCATAACAAGGT<br>CCTCGTGAAGCAGTCGGAGAATAGCAAGAAGTCGAACCTGACTCCGTACCAGTACTTC<br>AACTCCGGCAAATCCAAGCTGTCCTACAATCAGTTCAAACAGCACATTCTCAACCTGT<br>CCAAGAGCCAGGACAGGATTTCGAAGAAGAAGAAGGAATACCTTCTCGAGGAACGGGA<br>TATCAATAAGTTCGAGGTGCAGAAGGAGTTTATCAATAGAAACCTGGTGGACACTCGC<br>TATGCCACCCGCGAACTGACCAACTACCTGAAGGCGTACTTCTCCGCCAACAACATGA<br>ACGTGAAGGTCAAAACTATTAACGGCAGCTTCACCGACTATCTGCGCAAGGTCTGGAA<br>GTTCAAGAAGGAACGCAACCACGGTTACAAGCACCACGCGGAAGATGCGCTGATTATC<br>GCCAACGCTGACTTCCTGTTCAAGGAAAACAAGAAGCTCAAGGCCGTGAACTCAGTGC<br>TCGAGAAGCCTGAAATCGAGACTAAGCAGCTGGACATCCAGGTCGATTCGGAAGATAA<br>CTACTCCGAAATGTTCATCATCCCTAAGCAAGTGCAGGACATCAAGGACTTCAGGAAT<br>TTCAAGTACAGCCATCGCGTGGACAAGAAGCCAAACAGACAGCTGATCAACGATACAC<br>TGTATTCCACCCGGAAGAAGGACAACTCCACCTACATCGTCCAAACCATTAAGGACAT<br>CTACGCAAAGGACAACACCACGCTTAAGAAGCAGTTCGACAAGAGCCCCGAAAAGTTC<br>CTCATGTACCAGCACGACCCCAGAACCTTCGAGAAGCTTGAAGTGATCATGAAGCAGT<br>ACGCCAACGAAAAGAACCCACTGGCTAAGTACCACGAGGAAACCGGCGAATACCTGAC<br>CAAGTACTCCAAAAAGAACAACGGACCGATCGTCAAGTCCCTGAAGTACATTGGGAAC<br>AAGCTCGGCTCGCACCTCGATGTGACCCACCAGTTCAAGTCCTCGACCAAAAAGCTCG<br>TGAAGCTGTCCATCAAGCCGTACCGGTTCGACGTGTACCTGACTGACAAGGGATATAA<br>GTTCATCACCATTTCCTACCTCGACGTGTTGAAGAAGGATAACTACTACTACATTCCG<br>GAACAGAAGTACGACAAGCTCAAGCTCGGAAAGGCCATCGACAAAAATGCGAAGTTCA<br>TCGCGAGCTTCTACAAGAATGACTTGATCAAGCTGGATGGCGAAATCTACAAGATCAT<br>CGGGGTCAACTCCGATACCCGCAACATGATTGAGCTGGATCTGCCCGACATTCGGTAC<br>AAGGAATACTGCGAGCTGAACAACATCAAGGGAGAACCGCGGATCAAGAAACCATCG<br>GAAAGAAAGTGAACAGCATCGAGAAACTGACTACTGACGTCCTGGGAAACGTGTTCAC<br>CAACACACAATACACCAAACCCCAGCTGCTGTTTAAGCGCGGGAACAAGCGCCCTGCC<br>GCAACTAAGAAGGCCGGACAGGCCAAAAAGAAGAAATGAGCGGCCGCTTAATTAAGCT<br>GCCTTCTGCGGGGCTTGCCTTCTGGCCATGCCCTTCTTCTCTCCCTTGCACCTGTACC<br>TCTTGGTCTTTGAATAAAGCCTGAGTAGGAAG | |
| 49 | MAPKKKRKVMNQKFILGLDIGITSVGYGLIDYETKNIIDAGVRLFPEANVENNEGRRS<br>KRGSRRLKRRRIHRLERVKKLLEDYNLLDQSQIPQSTNPYAIRVKGLSEALSKDELVI<br>ALLHIAKRRGIHNINVSSEDEDASNELSTKEQINRNNKLLKDKYVCEVQLQRLKEGQI<br>RGEKNRFKTTDILKEIDQLLKVQKDYHNLDIDFINQYKEIVETRREYFEGPGKGSPYG<br>WEGDPKAWYETLMGHCTYFPDELRSVKYAYSADLFNALNDLNNLVIQRDGLSKLEYHE<br>KYHIIENVFKQKKKPTLKQIANEINVNPEDIKGYRITKSGKPEFTSFKLFHDLKKVVK<br>DHAILDDIDLLNQIAEILTIYQDKDSIVAELGQLEYLMSEADKQSISELTGYTGTHSL<br>SLKCMNMIIDELWHSSMNQMEVFTYLNMRPKKYELKGYQRIPTDMIDDAILSPVVKRT<br>FIQSINVINKVIEKYGIPEDIIIELARENNSDDRKKFINNLQKKNEATRKRINEIIGQ<br>TGNQNAKRIVEKIRLHDQQEGKCLYSLESIPLEDLLNNPNHYEVDHIIPRSVSFDNSY<br>HNKVLVKQSENSKKSNLTPYQYFNSGKSKLSYNQFKQHILNLSKSQDRISKKKKEYLL<br>EERDINKFEVQKEFINRNLVDTRYATRELTNYLKAYFSANNMNVKVKTINGSFTDYLR<br>KVWKFKKERNHGYKHHAEDALIIANADFLFKENKKLKAVNSVLEKPEIETKQLDIQVD<br>SEDNYSEMFIIPKQVQDIKDFRNFKYSHRVDKKPNRQLINDTLYSTRKKDNSTYIVQT<br>IKDIYAKDNTTLKKQFDKSPEKFLMYQHDPRTFEKLEVIMKQYANEKNPLAKYHEETG<br>EYLTKYSKKNNGPIVKSLKYIGNKLGSHLDVTHQFKSSTKKLVKLSIKPYRFDVYLTD<br>KGYKFITISYLDVLKKDNYYYIPEQKYDKLKLGKAIDKNAKFIASFYKNDLIKLDGEI<br>YKIIGVNSDTRNMIELDLPDIRYKEYCELNNIKGEPRIKKTIGKKVNSIEKLTTDVLG<br>NVFTNTQYTKPQLLFKRGNKRPAATKKAGQAKKKK | P2H12, amino acid |
| 50 | ugcCAGUUCCCGAUCGUUACGUUUUAGUACUCUGGAAACAGAAUCUACUGAAACAAGA<br>CAAUAUGUCGUGUUUAUCCCAUCAAUUUAUUGGUGGGAUuuu<br>"lowercase letters denote phosphorothioate linkages" | gRNA targeting albumin gene |

---

What is claimed is:

1. A lipid-based nanoparticle (LNP) composition comprising: a nucleic acid molecule comprising a nucleotide sequence encoding a synthetic RNA-guided endonuclease; and one or more lipid moieties selected from the group consisting of amino lipids, ionizable lipids, neutral lipids, PEG lipids, helper lipids, and cholesterol or cholesterol derivatives, wherein the nucleic acid molecule is 3.8 kb or less in length, and wherein the synthetic RNA-guided endonuclease comprises amino acid sequence of SEQ ID NO: 1, SEQ ID NO: 2, SEQ ID NO: 3, SEQ ID NO: 4, SEQ ID NO 5, or a sequence having at least 95% sequence identity to SEQ ID NO: 1, SEQ ID NO: 2, SEQ ID NO: 3, SEQ ID NO: 4, or SEQ ID NO 5.

2. The LNP composition of claim 1, wherein the nucleic acid molecule is 3.7 kb or less in length.

3. The LNP composition of claim 1, wherein the nucleic acid molecule is 3.5 kb or less in length.

4. The LNP composition of claim 1, wherein the nucleic acid molecule is a messenger RNA (mRNA).

5. The LNP composition of claim 1, wherein the nucleotide sequence encoding the synthetic RNA-guided endonuclease is operably linked to at least one additional nucleotide sequence.

6. The LNP composition of claim 5, wherein the at least one additional nucleotide sequence comprises an untranslated terminal region (UTR), a consensus Kozak signal, a nucleotide sequence encoding a nuclear localization signal (NLS) chosen from a nucleoplasm NLS or a SV40 NLS, a nucleotide sequence encoding a linker peptide, a nucleotide sequence encoding a tag peptide, or a combination thereof.

7. The LNP composition of claim 1, wherein the nucleic acid molecule comprises a nucleotide sequence selected from the group consisting of SEQ ID NO: 7, SEQ ID NO: 8, SEQ ID NO: 9, SEQ ID NO: 10, and SEQ ID NO: 11.

8. The LNP composition of claim 1, wherein the nucleotide sequence is codon-optimized for expression in a host cell.

9. The LNP composition of claim 8, wherein the host cell is a mammalian cell.

10. The LNP composition of claim 9, wherein the mammalian cell is a human cell, a murine cell, or a non-human primate (NHP) cell.

11. The LNP composition of claim 1, further comprising a guide RNA (gRNA) or a nucleic acid molecule encoding the gRNA.

12. The LNP composition of claim 1, wherein the LNP composition comprises C12-200, cholesterol, DOPE, PEG-DMPE, or a combination thereof.

13. The LNP composition of claim 1, wherein
   (a) the LNP composition has a lower rate of change in stability as compared to a reference LNP composition comprising a reference nucleic acid molecule comprising a nucleotide sequence encoding an RNA-guided endonuclease, wherein the reference nucleic acid molecule is SpCas9; or
   (b) the LNP composition has a lower rate of decrease in functional performance as compared to that of a reference LNP composition comprising a reference nucleic acid molecule comprising a nucleotide sequence encoding an RNA-guided endonuclease, wherein the reference nucleic acid molecule is SpCas9; or (c) the LNP composition has an average particle diameter larger than that of a reference LNP composition comprising a reference nucleic acid molecule comprising a nucleotide sequence encoding an RNA-guided endonuclease, wherein the reference nucleic acid molecule is SpCas9; or (d) a combination of (a), (b), and (c).

14. The LNP composition of claim 13, wherein (e) the LNP composition has a rate of change in stability that is at least 5% less than the corresponding rate of the reference LNP composition; or (f) the LNP composition has a rate of decrease in functional performance that is at least 5% less than the corresponding rate of the reference LNP composition; or (g) the LNP composition has an average particle diameter that is at least 10% larger than the average particle diameter of the reference LNP composition; or (h) a combination of (a), (b), and (c).

15. A method for delivering a nucleic acid molecule into a cell in vitro, comprising contacting the cell in vitro with an LNP composition according to claim 1.

16. A method for editing a genome of a cell in vitro, comprising providing to the cell in vitro, an LNP composition according to claim 1.

17. The LNP composition of claim 1, wherein the synthetic RNA guided endonuclease comprises fragments from RNA-guided endonucleases obtained from at least two bacterial species.

18. The LNP composition of claim 17, wherein the bacterial species are selected from the group consisting of *Staphylococcus lugdunensis*, *Staphylococcus pasteuri*, *Staphylococcus microti* and *Staphylococcus hyicus*.

* * * * *

SEQUENCE LISTING

<160> NUMBER OF SEQ ID NOS: 50

<210> SEQ ID NO 1
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Gib11SpaCas9-1 polypeptide

<400> SEQUENCE: 1

```
Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Gln Gly Ser Pro
    210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
            260                 265                 270

Gln Arg Asp Asn Ser Glu Lys Leu Glu Tyr His Glu Lys Tyr His Ile
        275                 280                 285

Ile Glu Asn Val Phe Lys Gln Lys Lys Lys Pro Thr Leu Lys Gln Ile
    290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu
            340                 345                 350

Leu Asn Gln Ile Ala Glu Ile Leu Thr Ile Tyr Gln Asp Lys Asp Ser
        355                 360                 365

Ile Val Ala Glu Leu Gly Gln Leu Glu Tyr Leu Met Ser Glu Ala Asp
    370                 375                 380

Lys Gln Ser Ile Ser Glu Leu Thr Gly Tyr Thr Gly Thr His Ser Leu
385                 390                 395                 400
```

-continued

Ser Leu Lys Cys Met Asn Met Ile Ile Asp Glu Leu Trp His Ser Ser
            405                 410                 415

Met Asn Gln Met Glu Val Phe Thr Tyr Leu Asn Met Arg Pro Lys Lys
        420                 425                 430

Tyr Glu Leu Lys Gly Tyr Gln Arg Ile Pro Thr Asp Met Ile Asp Asp
        435                 440                 445

Ala Ile Leu Ser Pro Val Val Lys Arg Thr Phe Ile Gln Ser Ile Asn
450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
            515                 520                 525

Ile Arg Leu His Asp Gln Gln Glu Gly Lys Cys Leu Tyr Ser Leu Glu
        530                 535                 540

Ser Ile Pro Leu Glu Asp Leu Leu Asn Asn Pro Asn His Tyr Glu Val
545                 550                 555                 560

Asp His Ile Ile Pro Arg Ser Val Ser Phe Asp Asn Ser Tyr His Asn
                565                 570                 575

Lys Val Leu Val Lys Gln Ser Glu Asn Ser Lys Lys Ser Asn Leu Thr
                580                 585                 590

Pro Tyr Gln Tyr Phe Asn Ser Gly Lys Ser Lys Leu Ser Tyr Asn Gln
        595                 600                 605

Phe Lys Gln His Ile Leu Asn Leu Ser Lys Ser Gln Asp Arg Ile Ser
        610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Ser Ala Asn
                660                 665                 670

Asn Met Asn Val Lys Val Lys Thr Ile Asn Gly Ser Phe Thr Asp Tyr
        675                 680                 685

Leu Arg Lys Val Trp Lys Phe Lys Lys Glu Arg Asn His Gly Tyr Lys
        690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Tyr Ser His Arg Val Asp Lys Lys Pro Asn Arg
        770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
                805                 810                 815

```
Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
            835                 840                 845

Tyr Ala Asn Glu Lys Asn Pro Leu Ala Lys Tyr His Glu Glu Thr Gly
850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
            885                 890                 895

His Gln Phe Lys Ser Ser Thr Lys Leu Val Lys Leu Ser Ile Lys
            900                 905                 910

Asn Tyr Arg Phe Asp Val Tyr Leu Thr Glu Lys Gly Tyr Lys Phe Val
            915                 920                 925

Thr Ile Ala Tyr Leu Asn Val Phe Lys Lys Asp Asn Tyr Tyr Ile
    930                 935                 940

Pro Lys Asp Lys Tyr Gln Glu Leu Lys Glu Lys Lys Ile Lys Asp
945                 950                 955                 960

Thr Asp Gln Phe Ile Ala Ser Phe Tyr Lys Asn Asp Leu Ile Lys Leu
                965                 970                 975

Asn Gly Asp Leu Tyr Lys Ile Ile Gly Val Asn Ser Asp Asp Arg Asn
            980                 985                 990

Ile Ile Glu Leu Asp Tyr Tyr Asp Ile Lys Tyr Lys Asp Tyr Cys Glu
            995                 1000                1005

Ile Asn Asn Ile Lys Gly Glu Pro Arg Ile Lys Lys Thr Ile Gly
    1010                1015                1020

Lys Lys Thr Glu Ser Ile Glu Lys Phe Thr Thr Asp Val Leu Gly
    1025                1030                1035

Asn Leu Tyr Leu His Ser Thr Glu Lys Ala Pro Gln Leu Ile Phe
    1040                1045                1050

Lys Arg Gly Leu
    1055

<210> SEQ ID NO 2
<211> LENGTH: 1056
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Gib11SpaCas9-3 polypeptide

<400> SEQUENCE: 2

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95
```

```
Ser Glu Ile Leu Ser Lys Asp Glu Leu Ala Ile Ala Leu Leu His Leu
            100                 105                 110

Ala Lys Arg Arg Gly Ile His Asn Val Asp Val Ala Ala Asp Lys Glu
            115                 120                 125

Glu Thr Ala Ser Asp Ser Leu Ser Thr Lys Asp Gln Ile Asn Lys Asn
130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
            195                 200                 205

Val Glu Thr Arg Arg Glu Tyr Phe Glu Gly Pro Gly Gln Gly Ser Pro
            210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
            260                 265                 270

Gln Arg Asp Asn Ser Glu Lys Leu Glu Tyr His Glu Lys Tyr His Ile
            275                 280                 285

Ile Glu Asn Val Phe Lys Gln Lys Lys Pro Thr Leu Lys Gln Ile
            290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu
            340                 345                 350

Leu Asn Gln Ile Ala Glu Ile Leu Thr Ile Tyr Gln Asp Lys Asp Ser
            355                 360                 365

Ile Val Ala Glu Leu Gly Gln Leu Glu Tyr Leu Met Ser Glu Ala Asp
370                 375                 380

Lys Gln Ser Ile Ser Glu Leu Thr Gly Tyr Thr Gly Thr His Ser Leu
385                 390                 395                 400

Ser Leu Lys Cys Met Asn Met Ile Ile Asp Glu Leu Trp His Ser Ser
                405                 410                 415

Met Asn Gln Met Glu Val Phe Thr Tyr Leu Asn Met Arg Pro Lys Lys
            420                 425                 430

Tyr Glu Leu Lys Gly Tyr Gln Arg Ile Pro Thr Asp Met Ile Asp Asp
            435                 440                 445

Ala Ile Leu Ser Pro Val Val Lys Arg Thr Phe Ile Gln Ser Ile Asn
            450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510
```

```
Ile Ile Gly Gln Thr Gly Asn Gln Asn Ala Lys Arg Ile Val Glu Lys
            515                 520                 525

Ile Arg Leu His Asp Gln Gln Glu Gly Lys Cys Leu Tyr Ser Leu Glu
        530                 535                 540

Ser Ile Pro Leu Glu Asp Leu Leu Asn Asn Pro Asn His Tyr Glu Val
545                 550                 555                 560

Asp His Ile Ile Pro Arg Ser Val Ser Phe Asp Asn Ser Tyr His Asn
                    565                 570                 575

Lys Val Leu Val Lys Gln Ser Glu Asn Ser Lys Lys Ser Asn Leu Thr
                580                 585                 590

Pro Tyr Gln Tyr Phe Asn Ser Gly Lys Ser Lys Leu Ser Tyr Asn Gln
            595                 600                 605

Phe Lys Gln His Ile Leu Asn Leu Ser Lys Ser Gln Asp Arg Ile Ser
        610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                    645                 650                 655

Ala Thr Arg Glu Leu Thr Ser Tyr Leu Lys Ala Tyr Phe Ser Ala Asn
                660                 665                 670

Asn Met Asp Val Lys Val Lys Thr Ile Asn Gly Ser Phe Thr Asn His
            675                 680                 685

Leu Arg Lys Val Trp Arg Phe Asp Lys Tyr Arg Asn His Gly Tyr Lys
        690                 695                 700

His His Ala Glu Asp Ala Leu Ile Ile Ala Asn Ala Asp Phe Leu Phe
705                 710                 715                 720

Lys Glu Asn Lys Lys Leu Gln Asn Thr Asn Lys Ile Leu Glu Lys Pro
                    725                 730                 735

Thr Ile Glu Asn Asn Thr Lys Lys Val Thr Val Glu Lys Glu Glu Asp
                740                 745                 750

Tyr Asn Asn Val Phe Glu Thr Pro Lys Leu Val Glu Asp Ile Lys Gln
            755                 760                 765

Tyr Arg Asp Tyr Lys Phe Ser His Arg Val Asp Lys Lys Pro Asn Arg
        770                 775                 780

Gln Leu Ile Asn Asp Thr Leu Tyr Ser Thr Arg Met Lys Asp Glu His
785                 790                 795                 800

Asp Tyr Ile Val Gln Thr Ile Thr Asp Ile Tyr Gly Lys Asp Asn Thr
                    805                 810                 815

Asn Leu Lys Lys Gln Phe Asn Lys Asn Pro Glu Lys Phe Leu Met Tyr
                820                 825                 830

Gln Asn Asp Pro Lys Thr Phe Glu Lys Leu Ser Ile Ile Met Lys Gln
            835                 840                 845

Tyr Ser Asp Glu Lys Asn Pro Leu Ala Lys Tyr Glu Glu Thr Gly
        850                 855                 860

Glu Tyr Leu Thr Lys Tyr Ser Lys Lys Asn Asn Gly Pro Ile Val Lys
865                 870                 875                 880

Lys Ile Lys Leu Leu Gly Asn Lys Val Gly Asn His Leu Asp Val Thr
                    885                 890                 895

Asn Lys Tyr Glu Asn Ser Thr Lys Lys Leu Val Lys Leu Ser Ile Lys
                900                 905                 910

Asn Tyr Arg Phe Asp Val Tyr Leu Thr Glu Lys Gly Tyr Lys Phe Val
            915                 920                 925
```

Thr Ile Ala Tyr Leu Asn Val Phe Lys Lys Asp Asn Tyr Tyr Tyr Ile
            930                 935                 940

Pro Lys Asp Lys Tyr Glu Leu Lys Glu Lys Lys Ile Lys Asp Thr
945                 950                 955                 960

Asp Gln Phe Ile Ala Ser Phe Tyr Lys Asn Asp Leu Ile Lys Leu Asn
                965                 970                 975

Gly Asp Leu Tyr Lys Ile Ile Gly Val Asn Ser Asp Asp Arg Asn Ile
            980                 985                 990

Ile Glu Leu Asp Tyr Tyr Asp Ile Lys Tyr Lys Asp Tyr Cys Glu Ile
            995                 1000                1005

Asn Asn Ile Lys Gly Glu Pro Arg Ile Lys Lys Thr Ile Gly Lys
        1010                1015                1020

Lys Thr Glu Ser Ile Glu Lys Phe Thr Thr Asp Val Leu Gly Asn
        1025                1030                1035

Leu Tyr Leu His Ser Thr Glu Lys Ala Pro Gln Leu Ile Phe Lys
        1040                1045                1050

Arg Gly Leu
        1055

<210> SEQ ID NO 3
<211> LENGTH: 1057
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: E2Cas9 polypeptide

<400> SEQUENCE: 3

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

Asp Arg Val Lys His Leu Leu Ala Glu Tyr Asp Leu Leu Asp Leu Thr
65                  70                  75                  80

Asn Ile Pro Lys Ser Thr Asn Pro Tyr Gln Thr Arg Val Lys Gly Leu
                85                  90                  95

Asn Glu Lys Leu Ser Lys Asp Glu Leu Val Ile Ala Leu Leu His Ile
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

-continued

Val Glu Thr Arg Arg Glu Tyr Phe Glu Gly Pro Gly Lys Gly Ser Pro
    210                 215                 220

Phe Gly Trp Glu Gly Asn Ile Lys Lys Trp Phe Glu Gln Met Met Gly
225                 230                 235                 240

His Cys Thr Tyr Phe Pro Glu Glu Leu Arg Ser Val Lys Tyr Ser Tyr
                245                 250                 255

Ser Ala Glu Leu Phe Asn Ala Leu Asn Asp Leu Asn Asn Leu Val Ile
            260                 265                 270

Thr Arg Asp Glu Asp Ala Lys Leu Asn Tyr Gly Glu Lys Phe Gln Ile
        275                 280                 285

Ile Glu Asn Val Phe Lys Gln Lys Lys Thr Pro Asn Leu Lys Gln Ile
    290                 295                 300

Ala Ile Glu Ile Gly Val His Glu Thr Glu Ile Lys Gly Tyr Arg Val
305                 310                 315                 320

Asn Lys Ser Gly Thr Pro Glu Phe Thr Glu Phe Lys Leu Tyr His Asp
                325                 330                 335

Leu Lys Ser Ile Val Phe Asp Lys Ser Ile Leu Glu Asn Glu Ala Ile
            340                 345                 350

Leu Asp Gln Ile Ala Glu Ile Leu Thr Ile Tyr Gln Asp Glu Gln Ser
        355                 360                 365

Ile Lys Glu Glu Leu Asn Lys Leu Pro Glu Ile Leu Asn Glu Gln Asp
    370                 375                 380

Lys Ala Glu Ile Ala Lys Leu Ile Gly Tyr Asn Gly Thr His Arg Leu
385                 390                 395                 400

Ser Leu Lys Cys Ile His Leu Ile Asn Glu Glu Leu Trp Gln Thr Ser
                405                 410                 415

Arg Asn Gln Met Glu Ile Phe Asn Tyr Leu Asn Ile Lys Pro Asn Lys
            420                 425                 430

Val Asp Leu Ser Glu Gln Asn Lys Ile Pro Lys Asp Met Val Asn Asp
        435                 440                 445

Phe Ile Leu Ser Pro Val Val Lys Arg Thr Phe Ile Gln Ser Ile Asn
    450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
        515                 520                 525

Ile Arg Leu His Asp Gln Gln Glu Gly Lys Cys Leu Tyr Ser Leu Lys
    530                 535                 540

Asp Ile Pro Leu Glu Asp Leu Leu Arg Asn Pro Asn Asn Tyr Asp Ile
545                 550                 555                 560

Asp His Ile Ile Pro Arg Ser Val Ser Phe Asp Ser Met His Asn
                565                 570                 575

Lys Val Leu Val Arg Arg Glu Gln Asn Ala Lys Lys Asn Asn Gln Thr
            580                 585                 590

Pro Tyr Gln Tyr Leu Thr Ser Gly Tyr Ala Asp Ile Lys Tyr Ser Val
        595                 600                 605

Phe Lys Gln His Val Leu Asn Leu Ala Glu Asn Lys Asp Arg Met Thr
    610                 615                 620

```
Lys Lys Lys Arg Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
            645                 650                 655

Ala Thr Arg Glu Leu Thr Asn Tyr Leu Lys Ala Tyr Phe Ser Ala Asn
            660                 665                 670

Asn Met Asn Val Lys Val Lys Thr Ile Asn Gly Ser Phe Thr Asp Tyr
            675                 680                 685

Leu Arg Lys Val Trp Lys Phe Lys Lys Glu Arg Asn His Gly Tyr Lys
    690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
    755                 760                 765

Phe Arg Asn Phe Lys Tyr Ser His Arg Val Asp Lys Lys Pro Asn Arg
    770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
            805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
            835                 840                 845

Tyr Ala Asn Glu Lys Asn Pro Leu Ala Lys Tyr His Glu Glu Thr Gly
    850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
            885                 890                 895

His Gln Phe Lys Ser Ser Thr Lys Lys Leu Val Lys Leu Ser Ile Lys
            900                 905                 910

Pro Tyr Arg Phe Asp Val Tyr Leu Thr Asp Lys Gly Tyr Lys Phe Ile
    915                 920                 925

Thr Ile Ser Tyr Leu Asp Val Leu Lys Lys Asp Asn Tyr Tyr Tyr Ile
    930                 935                 940

Pro Glu Gln Lys Tyr Asp Lys Leu Lys Leu Gly Lys Ala Ile Asp Lys
945                 950                 955                 960

Asn Ala Lys Phe Ile Ala Ser Phe Tyr Lys Asn Asp Leu Ile Lys Leu
            965                 970                 975

Asp Gly Glu Ile Tyr Lys Ile Ile Gly Val Asn Ser Asp Thr Arg Asn
            980                 985                 990

Met Ile Glu Leu Asp Leu Pro Asp Ile Arg Tyr Lys Glu Tyr Cys Glu
            995                 1000                1005

Leu Asn Asn Ile Lys Gly Glu Pro Arg Ile Lys Lys Thr Ile Gly
    1010                1015                1020

Lys Lys Val Asn Ser Ile Glu Lys Leu Thr Asp Val Leu Gly
    1025                1030                1035
```

-continued

```
Asn Val Phe Thr Asn Thr Gln Tyr Thr Lys Pro Gln Leu Leu Phe
        1040                1045                1050

Lys Arg Gly Asn
    1055

<210> SEQ ID NO 4
<211> LENGTH: 1053
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: F8Cas9 polypeptide

<400> SEQUENCE: 4

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Ile His Arg Leu
    50                  55                  60

Glu Arg Val Lys Ser Leu Leu Ser Glu Tyr Lys Ile Ile Ser Gly Leu
65                  70                  75                  80

Ala Pro Thr Asn Asn Gln Pro Tyr Asn Ile Arg Val Lys Gly Leu Thr
                85                  90                  95

Glu Gln Leu Thr Lys Asp Glu Leu Ala Val Ala Leu Leu His Ile Ala
            100                 105                 110

Lys Arg Arg Gly Ile His Lys Ile Asp Val Ile Asp Ser Asn Asp Asp
        115                 120                 125

Val Gly Asn Glu Leu Ser Thr Lys Glu Gln Leu Asn Lys Asn Ser Lys
    130                 135                 140

Leu Leu Lys Asp Lys Phe Val Cys Gln Ile Gln Leu Glu Arg Met Asn
145                 150                 155                 160

Glu Gly Gln Val Arg Gly Glu Lys Asn Arg Phe Lys Thr Ala Asp Ile
                165                 170                 175

Ile Lys Glu Ile Ile Gln Leu Leu Asn Val Gln Lys Asn Phe His Gln
            180                 185                 190

Leu Asp Glu Asn Phe Ile Asn Lys Tyr Ile Glu Leu Val Glu Met Arg
        195                 200                 205

Arg Glu Tyr Phe Glu Gly Pro Gly Gln Gly Ser Pro Phe Gly Trp Asn
    210                 215                 220

Gly Asp Leu Lys Lys Trp Tyr Glu Met Leu Met Gly His Cys Thr Tyr
225                 230                 235                 240

Phe Pro Gln Glu Leu Arg Ser Val Lys Tyr Ala Tyr Ser Ala Asp Leu
                245                 250                 255

Phe Asn Ala Leu Asn Asp Leu Asn Asn Leu Ile Ile Gln Arg Asp Asn
            260                 265                 270

Ser Glu Lys Leu Glu Tyr His Glu Lys Tyr His Ile Ile Glu Asn Val
        275                 280                 285

Phe Lys Gln Lys Lys Lys Pro Thr Leu Lys Gln Ile Ala Lys Glu Ile
    290                 295                 300

Gly Val Asn Pro Glu Asp Ile Lys Gly Tyr Arg Ile Thr Lys Ser Gly
305                 310                 315                 320
```

```
Thr Pro Glu Phe Thr Glu Phe Lys Leu Tyr His Asp Leu Lys Ser Val
                325             330             335

Leu Phe Asp Gln Ser Ile Leu Glu Asn Glu Asp Val Leu Asp Gln Ile
            340             345             350

Ala Glu Ile Leu Thr Ile Tyr Gln Asp Lys Asp Ser Ile Lys Ser Lys
            355             360             365

Leu Thr Glu Leu Asp Ile Leu Leu Asn Glu Glu Asp Lys Glu Asn Ile
        370             375             380

Ala Gln Leu Thr Gly Tyr Asn Gly Thr His Arg Leu Ser Leu Lys Cys
385             390             395             400

Ile Arg Leu Val Leu Glu Glu Gln Trp Tyr Ser Ser Arg Asn Gln Met
                405             410             415

Glu Ile Phe Thr His Leu Asn Ile Lys Pro Lys Ile Asn Leu Thr
            420             425             430

Ala Ala Asn Lys Ile Pro Lys Ala Met Ile Asp Glu Phe Ile Leu Ser
            435             440             445

Pro Val Val Lys Arg Thr Phe Ile Gln Ser Ile Asn Val Ile Asn Lys
    450             455             460

Val Ile Glu Lys Tyr Gly Ile Pro Glu Asp Ile Ile Glu Leu Ala
465             470             475             480

Arg Glu Asn Asn Ser Asp Asp Arg Lys Lys Phe Ile Asn Asn Leu Gln
                485             490             495

Lys Lys Asn Glu Ala Thr Arg Lys Arg Ile Asn Glu Ile Ile Gly Gln
                500             505             510

Thr Gly Asn Gln Asn Ala Lys Arg Ile Val Glu Lys Ile Arg Leu His
            515             520             525

Asp Gln Gln Glu Gly Lys Cys Leu Tyr Ser Leu Glu Ser Ile Ala Leu
        530             535             540

Met Asp Leu Leu Asn Asn Pro Gln Asn Tyr Glu Val Asp His Ile Ile
545             550             555             560

Pro Arg Ser Val Ala Phe Asp Asn Ser Ile His Asn Lys Val Leu Val
                565             570             575

Lys Gln Ile Glu Asn Ser Lys Lys Gly Asn Arg Thr Pro Tyr Gln Tyr
            580             585             590

Leu Asn Ser Ser Asp Ala Lys Leu Ser Tyr Asn Gln Phe Lys Gln His
        595             600             605

Ile Leu Asn Leu Ser Lys Ser Lys Asp Arg Ile Ser Lys Lys Lys Lys
    610             615             620

Asp Tyr Leu Leu Glu Glu Arg Asp Ile Asn Lys Phe Glu Val Gln Lys
625             630             635             640

Glu Phe Ile Asn Arg Asn Leu Val Asp Thr Arg Tyr Ala Thr Arg Glu
                645             650             655

Leu Thr Ser Tyr Leu Lys Ala Tyr Phe Ser Ala Asn Asn Met Asp Val
            660             665             670

Lys Val Lys Thr Ile Asn Gly Ser Phe Thr Asn His Leu Arg Lys Val
        675             680             685

Trp Arg Phe Asp Lys Tyr Arg Asn His Gly Tyr Lys His His Ala Glu
    690             695             700

Asp Ala Leu Ile Ile Ala Asn Ala Asp Phe Leu Phe Lys Glu Asn Lys
705             710             715             720

Lys Leu Lys Ala Val Asn Ser Val Leu Glu Lys Pro Glu Ile Glu Thr
                725             730             735
```

```
Lys Gln Leu Asp Ile Gln Val Asp Ser Glu Asp Asn Tyr Ser Glu Met
            740                 745                 750

Phe Ile Ile Pro Lys Gln Val Gln Asp Ile Lys Asp Phe Arg Asn Phe
            755                 760                 765

Lys Tyr Ser His Arg Val Asp Lys Lys Pro Asn Arg Gln Leu Ile Asn
        770                 775                 780

Asp Thr Leu Tyr Ser Thr Arg Lys Lys Asp Asn Ser Thr Tyr Ile Val
785                 790                 795                 800

Gln Thr Ile Lys Asp Ile Tyr Ala Lys Asp Asn Thr Thr Leu Lys Lys
            805                 810                 815

Gln Phe Asp Lys Ser Pro Glu Lys Phe Leu Met Tyr Gln His Asp Pro
            820                 825                 830

Arg Thr Phe Glu Lys Leu Glu Val Ile Met Lys Gln Tyr Ala Asn Glu
            835                 840                 845

Lys Asn Pro Leu Ala Lys Tyr His Glu Glu Thr Gly Glu Tyr Leu Thr
        850                 855                 860

Lys Tyr Ser Lys Lys Asn Asn Gly Pro Ile Val Lys Ser Leu Lys Tyr
865                 870                 875                 880

Ile Gly Asn Lys Leu Gly Ser His Leu Asp Val Thr His Gln Phe Lys
            885                 890                 895

Ser Ser Thr Lys Lys Leu Val Lys Leu Ser Ile Lys Pro Tyr Arg Phe
            900                 905                 910

Asp Val Tyr Leu Thr Asp Lys Gly Tyr Lys Phe Ile Thr Ile Ser Tyr
            915                 920                 925

Leu Asp Val Leu Lys Lys Asp Asn Tyr Tyr Ile Pro Glu Gln Lys
930                 935                 940

Tyr Asp Lys Leu Lys Leu Gly Lys Ala Ile Asp Lys Asn Ala Lys Phe
945                 950                 955                 960

Ile Ala Ser Phe Tyr Lys Asn Asp Leu Ile Lys Leu Asp Gly Glu Ile
            965                 970                 975

Tyr Lys Ile Ile Gly Val Asn Ser Asp Thr Arg Asn Met Ile Glu Leu
            980                 985                 990

Asp Leu Pro Asp Ile Arg Tyr Lys Glu Tyr Cys Glu Leu Asn Asn Ile
            995                1000                1005

Lys Gly Glu Pro Arg Ile Lys Lys Thr Ile Gly Lys Lys Val Asn
        1010                1015                1020

Ser Ile Glu Lys Leu Thr Thr Asp Val Leu Gly Asn Val Phe Thr
        1025                1030                1035

Asn Thr Gln Tyr Thr Lys Pro Gln Leu Leu Phe Lys Arg Gly Asn
        1040                1045                1050

<210> SEQ ID NO 5
<211> LENGTH: 1054
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: P2H12Cas9 polypeptide

<400> SEQUENCE: 5

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30
```

Val Arg Leu Phe Pro Glu Ala Asn Val Glu Asn Asn Glu Gly Arg Arg
            35                  40                  45

Ser Lys Arg Gly Ser Arg Leu Lys Arg Arg Ile His Arg Leu
 50                  55                  60

Glu Arg Val Lys Lys Leu Leu Glu Asp Tyr Asn Leu Leu Asp Gln Ser
 65                  70                  75                  80

Gln Ile Pro Gln Ser Thr Asn Pro Tyr Ala Ile Arg Val Lys Gly Leu
                 85                  90                  95

Ser Glu Ala Leu Ser Lys Asp Glu Leu Val Ile Ala Leu Leu His Ile
                100                 105                 110

Ala Lys Arg Arg Gly Ile His Asn Ile Asn Val Ser Ser Glu Asp Glu
            115                 120                 125

Asp Ala Ser Asn Glu Leu Ser Thr Lys Glu Gln Ile Asn Arg Asn Asn
130                 135                 140

Lys Leu Leu Lys Asp Lys Tyr Val Cys Glu Val Gln Leu Gln Arg Leu
145                 150                 155                 160

Lys Glu Gly Gln Ile Arg Gly Glu Lys Asn Arg Phe Lys Thr Thr Asp
                165                 170                 175

Ile Leu Lys Glu Ile Asp Gln Leu Leu Lys Val Gln Lys Asp Tyr His
            180                 185                 190

Asn Leu Asp Ile Asp Phe Ile Asn Gln Tyr Lys Glu Ile Val Glu Thr
            195                 200                 205

Arg Arg Glu Tyr Phe Glu Gly Pro Gly Lys Gly Ser Pro Tyr Gly Trp
210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
                260                 265                 270

Gly Leu Ser Lys Leu Glu Tyr His Glu Lys Tyr His Ile Ile Glu Asn
            275                 280                 285

Val Phe Lys Gln Lys Lys Pro Thr Leu Lys Gln Ile Ala Asn Glu
            290                 295                 300

Ile Asn Val Asn Pro Glu Asp Ile Lys Gly Tyr Arg Ile Thr Lys Ser
305                 310                 315                 320

Gly Lys Pro Glu Phe Thr Ser Phe Lys Leu Phe His Asp Leu Lys Lys
                325                 330                 335

Val Val Lys Asp His Ala Ile Leu Asp Asp Ile Asp Leu Leu Asn Gln
            340                 345                 350

Ile Ala Glu Ile Leu Thr Ile Tyr Gln Asp Lys Asp Ser Ile Val Ala
            355                 360                 365

Glu Leu Gly Gln Leu Glu Tyr Leu Met Ser Glu Ala Asp Lys Gln Ser
            370                 375                 380

Ile Ser Glu Leu Thr Gly Tyr Thr Gly Thr His Ser Leu Ser Leu Lys
385                 390                 395                 400

Cys Met Asn Met Ile Ile Asp Glu Leu Trp His Ser Ser Met Asn Gln
                405                 410                 415

Met Glu Val Phe Thr Tyr Leu Asn Met Arg Pro Lys Lys Tyr Glu Leu
            420                 425                 430

Lys Gly Tyr Gln Arg Ile Pro Thr Asp Met Ile Asp Asp Ala Ile Leu
            435                 440                 445

```
Ser Pro Val Val Lys Arg Thr Phe Ile Gln Ser Ile Asn Val Ile Asn
    450                 455                 460
Lys Val Ile Glu Lys Tyr Gly Ile Pro Glu Asp Ile Ile Glu Leu
465                 470                 475                 480
Ala Arg Glu Asn Ser Asp Asp Arg Lys Lys Phe Ile Asn Asn Leu
                485                 490                 495
Gln Lys Lys Asn Glu Ala Thr Arg Lys Arg Ile Asn Glu Ile Ile Gly
            500                 505                 510
Gln Thr Gly Asn Gln Asn Ala Lys Arg Ile Val Glu Lys Ile Arg Leu
        515                 520                 525
His Asp Gln Gln Glu Gly Lys Cys Leu Tyr Ser Leu Glu Ser Ile Pro
    530                 535                 540
Leu Glu Asp Leu Leu Asn Asn Pro Asn His Tyr Glu Val Asp His Ile
545                 550                 555                 560
Ile Pro Arg Ser Val Ser Phe Asp Asn Ser Tyr His Asn Lys Val Leu
                565                 570                 575
Val Lys Gln Ser Glu Asn Ser Lys Lys Ser Asn Leu Thr Pro Tyr Gln
            580                 585                 590
Tyr Phe Asn Ser Gly Lys Ser Lys Leu Ser Tyr Asn Gln Phe Lys Gln
        595                 600                 605
His Ile Leu Asn Leu Ser Lys Ser Gln Asp Arg Ile Ser Lys Lys Lys
    610                 615                 620
Lys Glu Tyr Leu Leu Glu Glu Arg Asp Ile Asn Lys Phe Glu Val Gln
625                 630                 635                 640
Lys Glu Phe Ile Asn Arg Asn Leu Val Asp Thr Arg Tyr Ala Thr Arg
                645                 650                 655
Glu Leu Thr Asn Tyr Leu Lys Ala Tyr Phe Ser Ala Asn Asn Met Asn
            660                 665                 670
Val Lys Val Lys Thr Ile Asn Gly Ser Phe Thr Asp Tyr Leu Arg Lys
        675                 680                 685
Val Trp Lys Phe Lys Lys Glu Arg Asn His Gly Tyr Lys His His Ala
    690                 695                 700
Glu Asp Ala Leu Ile Ile Ala Asn Ala Asp Phe Leu Phe Lys Glu Asn
705                 710                 715                 720
Lys Lys Leu Lys Ala Val Asn Ser Val Leu Glu Lys Pro Glu Ile Glu
                725                 730                 735
Thr Lys Gln Leu Asp Ile Gln Val Asp Ser Glu Asp Asn Tyr Ser Glu
            740                 745                 750
Met Phe Ile Ile Pro Lys Gln Val Gln Asp Ile Lys Asp Phe Arg Asn
        755                 760                 765
Phe Lys Tyr Ser His Arg Val Asp Lys Lys Pro Asn Arg Gln Leu Ile
    770                 775                 780
Asn Asp Thr Leu Tyr Ser Thr Arg Lys Asp Asn Ser Thr Tyr Ile
785                 790                 795                 800
Val Gln Thr Ile Lys Asp Ile Tyr Ala Lys Asp Asn Thr Thr Leu Lys
                805                 810                 815
Lys Gln Phe Asp Lys Ser Pro Glu Lys Phe Leu Met Tyr Gln His Asp
            820                 825                 830
Pro Arg Thr Phe Glu Lys Leu Glu Val Ile Met Lys Gln Tyr Ala Asn
        835                 840                 845
Glu Lys Asn Pro Leu Ala Lys Tyr His Glu Glu Thr Gly Glu Tyr Leu
850                 855                 860
```

```
Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
                885                 890                 895

Lys Ser Ser Thr Lys Lys Leu Val Lys Leu Ser Ile Lys Pro Tyr Arg
                900                 905                 910

Phe Asp Val Tyr Leu Thr Asp Lys Gly Tyr Lys Phe Ile Thr Ile Ser
                915                 920                 925

Tyr Leu Asp Val Leu Lys Lys Asp Asn Tyr Tyr Ile Pro Glu Gln
        930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                965                 970                 975

Ile Tyr Lys Ile Ile Gly Val Asn Ser Asp Thr Arg Asn Met Ile Glu
                980                 985                 990

Leu Asp Leu Pro Asp Ile Arg Tyr Lys Glu Tyr Cys Glu Leu Asn Asn
                995                 1000                1005

Ile Lys Gly Glu Pro Arg Ile Lys Lys Thr Ile Gly Lys Lys Val
        1010                1015                1020

Asn Ser Ile Glu Lys Leu Thr Thr Asp Val Leu Gly Asn Val Phe
        1025                1030                1035

Thr Asn Thr Gln Tyr Thr Lys Pro Gln Leu Leu Phe Lys Arg Gly
        1040                1045                1050

Asn
```

<210> SEQ ID NO 6
<211> LENGTH: 1054
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: SluCas9 polypeptide

<400> SEQUENCE: 6

```
Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
                20                  25                  30

Val Arg Leu Phe Pro Glu Ala Asn Val Glu Asn Asn Glu Gly Arg Arg
                35                  40                  45

Ser Lys Arg Gly Ser Arg Arg Leu Lys Arg Arg Arg Ile His Arg Leu
50                  55                  60

Glu Arg Val Lys Lys Leu Leu Glu Asp Tyr Asn Leu Leu Asp Gln Ser
65                  70                  75                  80

Gln Ile Pro Gln Ser Thr Asn Pro Tyr Ala Ile Arg Val Lys Gly Leu
                85                  90                  95

Ser Glu Ala Leu Ser Lys Asp Glu Leu Val Ile Ala Leu Leu His Ile
                100                 105                 110

Ala Lys Arg Arg Gly Ile His Lys Ile Asp Val Ile Asp Ser Asn Asp
                115                 120                 125

Asp Val Gly Asn Glu Leu Ser Thr Lys Glu Gln Leu Asn Lys Asn Ser
                130                 135                 140
```

```
Lys Leu Leu Lys Asp Lys Phe Val Cys Gln Ile Gln Leu Glu Arg Met
145                 150                 155                 160

Asn Glu Gly Gln Val Arg Gly Glu Lys Asn Arg Phe Lys Thr Ala Asp
                165                 170                 175

Ile Ile Lys Glu Ile Ile Gln Leu Leu Asn Val Gln Lys Asn Phe His
            180                 185                 190

Gln Leu Asp Glu Asn Phe Ile Asn Lys Tyr Ile Glu Leu Val Glu Met
        195                 200                 205

Arg Arg Glu Tyr Phe Glu Gly Pro Lys Gly Ser Pro Tyr Gly Trp
210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
        275                 280                 285

Val Phe Lys Gln Lys Lys Pro Thr Leu Lys Gln Ile Ala Asn Glu
290                 295                 300

Ile Asn Val Asn Pro Glu Asp Ile Lys Gly Tyr Arg Ile Thr Lys Ser
305                 310                 315                 320

Gly Lys Pro Gln Phe Thr Glu Phe Lys Leu Tyr His Asp Leu Lys Ser
                325                 330                 335

Val Leu Phe Asp Gln Ser Ile Leu Glu Asn Glu Asp Val Leu Asp Gln
            340                 345                 350

Ile Ala Glu Ile Leu Thr Ile Tyr Gln Asp Lys Asp Ser Ile Lys Ser
        355                 360                 365

Lys Leu Thr Glu Leu Asp Ile Leu Leu Asn Glu Glu Asp Lys Glu Asn
370                 375                 380

Ile Ala Gln Leu Thr Gly Tyr Thr Gly Thr His Arg Leu Ser Leu Lys
385                 390                 395                 400

Cys Ile Arg Leu Val Leu Glu Glu Gln Trp Tyr Ser Ser Arg Asn Gln
                405                 410                 415

Met Glu Ile Phe Thr His Leu Asn Ile Lys Pro Lys Lys Ile Asn Leu
            420                 425                 430

Thr Ala Ala Asn Lys Ile Pro Lys Ala Met Ile Asp Glu Phe Ile Leu
        435                 440                 445

Ser Pro Val Val Lys Arg Thr Phe Gly Gln Ala Ile Asn Leu Ile Asn
450                 455                 460

Lys Ile Ile Glu Lys Tyr Gly Val Pro Glu Asp Ile Ile Glu Leu
465                 470                 475                 480

Ala Arg Glu Asn Asn Ser Lys Asp Lys Gln Lys Phe Ile Asn Glu Met
                485                 490                 495

Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
        515                 520                 525

His Asp Glu Gln Glu Gly Lys Cys Leu Tyr Ser Leu Glu Ser Ile Pro
530                 535                 540

Leu Glu Asp Leu Leu Asn Asn Pro Asn His Tyr Glu Val Asp His Ile
545                 550                 555                 560
```

```
Ile Pro Arg Ser Val Ser Phe Asp Asn Ser Tyr His Asn Lys Val Leu
                565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
        595                 600                 605

His Ile Leu Asn Leu Ser Lys Ser Gln Asp Arg Ile Ser Lys Lys Lys
    610                 615                 620

Lys Glu Tyr Leu Leu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
        675                 680                 685

Val Trp Lys Phe Lys Lys Glu Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
        755                 760                 765

Phe Lys Tyr Ser His Arg Val Asp Lys Lys Pro Asn Arg Gln Leu Ile
    770                 775                 780

Asn Asp Thr Leu Tyr Ser Thr Arg Lys Lys Asp Asn Ser Thr Tyr Ile
785                 790                 795                 800

Val Gln Thr Ile Lys Asp Ile Tyr Ala Lys Asp Asn Thr Thr Leu Lys
                805                 810                 815

Lys Gln Phe Asp Lys Ser Pro Glu Lys Phe Leu Met Tyr Gln His Asp
            820                 825                 830

Pro Arg Thr Phe Glu Lys Leu Glu Val Ile Met Lys Gln Tyr Ala Asn
        835                 840                 845

Glu Lys Asn Pro Leu Ala Lys Tyr His Glu Glu Thr Gly Glu Tyr Leu
    850                 855                 860

Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
                885                 890                 895

Lys Ser Ser Thr Lys Lys Leu Val Lys Leu Ser Ile Lys Pro Tyr Arg
            900                 905                 910

Phe Asp Val Tyr Leu Thr Asp Lys Gly Tyr Lys Phe Ile Thr Ile Ser
        915                 920                 925

Tyr Leu Asp Val Leu Lys Lys Asp Asn Tyr Tyr Ile Pro Glu Gln
    930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                965                 970                 975
```

Ile Tyr Lys Ile Ile Gly Val Asn Ser Asp Thr Arg Asn Met Ile Glu
            980                 985                 990

Leu Asp Leu Pro Asp Ile Arg Tyr Lys Glu Tyr Cys Glu Leu Asn Asn
            995                1000                1005

Ile Lys Gly Glu Pro Arg Ile Lys Lys Thr Ile Gly Lys Lys Val
       1010                1015                1020

Asn Ser Ile Glu Lys Leu Thr Thr Asp Val Leu Gly Asn Val Phe
       1025                1030                1035

Thr Asn Thr Gln Tyr Thr Lys Pro Gln Leu Leu Phe Lys Arg Gly
       1040                1045                1050

Asn

<210> SEQ ID NO 7
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Original Gib11SpaCas9-1 polynucleotide

<400> SEQUENCE: 7

```
atgaaccaga aatttatcct gggtctggat attggtatta ccagcgttgg ttatggcctg      60
attgattacg aaaccaaaaa cattattgat gccggtgttc gtctgttccc ggaagcaaat     120
gttgaaaata tgaaggtcg tcgtagcaaa cgtggtagcc gtcgtctgaa acgtcgtcgt      180
attcatcgtc tggaacgtgt taaactgctg ctgaccgaat atgatctgat taacaaagag     240
cagattccga ccagcaataa cccgtatcag attcgtgtta aggtctgag cgaaatcctg      300
agcaaagatg aactggcaat tgcactgctg catctggcaa acgccgtgg cattcataat      360
gttgatgttg cagcagataa agaagaaacc gcaagcgata gcctgagcac caaagatcag     420
attaacaaaa cgccaaatt tctggaaagc cgctatgttt gtgaactgca gaaagaacgt     480
ctggaaaatg aaggtcatgt tcgtggtgtt gaaaatcgct ttctgacgaa agatattgtg     540
cgtgaggcca aaaaaatcat cgatacccag atgcagtatt acccggaaat tgatgaaacc    600
ttcaaagaga atatatcag cctggttgaa acccgtcgcg aatattttga aggtcctggt      660
cagggtagcc cgtttggttg aatggtgat ctgaaaaaat ggtacgaaat gctgatgggt      720
cactgtacct attttccgca agaactgcgt agcgttaaat atgcctatag cgcagacctg     780
tttaatgcac tgaatgatct gaacaacctg attattcagc gcgataatag cgagaaactg     840
gaataccatg agaagtatca catcatcgag aacgtgttca gcagaaaaa aaagccgacg      900
ctgaaacaaa tcgcaaaaga gattggcgtt aacccggaag atattaaagg ttatcgtatt      960
accaaaagcg gcacaccgga gtttacatcc tttaaactgt ccacgatct gaaaaagtg      1020
gtgaaagatc atgccatcct ggatgatatt gatctgctga tcagattgc agaaatcctg     1080
accatctatc aggataaaga tagcattgtt gcagaactgg gtcagctgga atatctgatg    1140
agcgaagccg ataaacagag cattagcgaa ctgaccggtt ataccggtac acatagcctg    1200
tcactgaaat gcatgaacat gattatcgat gaactgtggc atagcagcat gaaccagatg    1260
gaagttttta cctatctgaa tatgcgtccg aaaaagtatg agctgaaagg ttatcagcgt    1320
attccgaccg atatgattga tgatgcaatt ctgagtccgg ttgtgaaacg caccttatt    1380
cagagcatca acgtgatcaa caaagtgatc gagaaatatg catccccga agatatcatt    1440
```

```
atcgaactgg cacgtgaaaa taactccgat gatcgcaaaa agttcatcaa caacctgcag    1500
aaaaagaatg aagcaacccg caaacgcatt aacgaaatta ttggtcagac cggtaatcag    1560
aatgccaaac gtattgtgga aaaaatccgt ctgcatgatc agcaagaggg caaatgtctg    1620
tatagcctgg aaagcattcc tctggaagat ctgctgaaca atccgaatca ttatgaagtg    1680
gatcacatta ttccgcgtag cgtgagcttt gataattcct atcataataa agtgctggtg    1740
aaacagagcg aaaactccaa aaaatccaac ctgacaccgt atcagtattt caatagcggc    1800
aaatccaaac tgagctacaa ccagtttaaa cagcatattc tgaacctgag caaaagccag    1860
gatcgcatca gcaagaagaa gaaggagtac ctgctggaag aacgcgatat taacaaattt    1920
gaagtgcaga aagaatttat caaccgcaac ctggttgata cccgttatgc aacccgtgaa    1980
ctgaccaatt atctgaaagc atatttcagc gccaacaaca tgaacgtgaa agtgaaaacg    2040
attaacggca gctttaccga ttatctgcgt aaagtgtgga attcaaaaa agaacgcaac    2100 cacggctata acatcatgc cgaagatgcc ctgattattg caaatgcaga tttcctgttt    2160
aaagaaaaca aaaaactgaa agccgtcaac agcgtgctgg aaaaaccgga aattgagaca    2220
aaacagctgg acattcaggt tgatagcgaa gataattaca gcgaaatgtt tatcatcccg    2280
aaacaggtgc aggatatcaa agattttcgc aacttcaaat atagccaccg cgttgacaaa    2340
aaacctaatc gtcagctgat taacgatacc ctgtatagca cccgcaaaaa agataacagc    2400
acctatattg tgcagaccat taaagacatc tacgccaaag ataataccac cctgaaaaaa    2460
cagttcgaca aaagcccaga aaatttctg atgtatcagc atgatccgcg taccttcgaa    2520
aaactggaag ttattatgaa acagtatgcc aacgagaaaa atccgctggc caaatatcac    2580
gaagaaaccg gtgaatatct gaccaaatat tccaagaaga caacggtcc gatcgttaaa    2640 tccctgaaat atatcggtaa taaactgggc agccatctgg atgttaccca tcagtttaaa    2700
agctccacaa agaagctggt taagctgtcc attaaaaact atcgcttcga tgtgtatctg    2760
accgagaaag gttataagtt tgtgaccatt gcctacctga atgtgttcaa aaaagacaac    2820
tattactata ttccgaaaga caaataccaa gaacttaaag agaagaagaa aatcaaggac    2880
accgatcagt ttatcgccag cttctataaa acgatctga tcaagctgaa cggcgacctg    2940
tataaaatca ttggtgtgaa tagtgatgac cgcaacatca ttgagctgga ttattacgac    3000
atcaaataca aggattactg cgagatcaac aacattaaag gtgaaccgcg tatcaaaaag    3060
accattggca aaaaaacgga aagcatcgaa aagtttacca ccgatgttct gggtaatctg    3120
tatctgcata gtaccgaaaa agcaccgcag ctgattttca aacgcggtct g             3171
```

<210> SEQ ID NO 8
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Original Gib11SpaCas9-3 polynucleotide

<400> SEQUENCE: 8

```
atgaaccaga aatttatcct gggtctggat attggtatta ccagcgttgg ttatggcctg      60
attgattacg aaaccaaaaa cattattgat gccggtgttc gtctgttcc ggaagcaaat     120 gttgaaaata tgaaggtcg tcgtagcaaa cgtggtagcc gtcgtctgaa acgtcgtcgt     180
attcatcgtc tggaacgtgt taaactgctg ctgaccgaat atgatctgat taacaaagag     240
```

```
cagattccga ccagcaataa cccgtatcag attcgtgtta aaggtctgag cgaaatcctg      300
agcaaagatg aactggcaat tgcactgctg catctggcaa aacgccgtgg cattcataat      360
gttgatgttg cagcagataa agaagaaacc gcaagcgata gcctgagcac caaagatcag      420
attaacaaaa acgccaaatt tctggaaagc cgctatgttt gtgaactgca gaaagaacgt      480
ctggaaaatg aaggtcatgt tcgtggtgtt gaaaatcgct ttctgacgaa agatattgtg      540
cgtgaggcca aaaaatcat cgatacccag atgcagtatt acccggaaat tgatgaaacc       600
ttcaaagaga atatatcag cctggttgaa acccgtcgcg aatattttga aggtcctggt       660
cagggtagcc cgtttggttg aatggtgat ctgaaaaaat ggtacgaaat gctgatgggt       720
cactgtacct attttccgca agaactgcgt agcgttaaat atgcctatag cgcagacctg      780
tttaatgcac tgaatgatct gaacaacctg attattcagc gcgataatag cgagaaactg      840
gaataccatg agaagtatca catcatcgag aacgtgttca agcagaaaaa aaagccgacg      900
ctgaaacaaa tcgcaaaaga gattggcgtt aacccggaag atattaaagg ttatcgtatt       960
accaaaagcg gcacaccgga gtttacatcc tttaaactgt tccacgatct gaaaaaagtg     1020
gtgaaagatc atgccatcct ggatgatatt gatctgctga atcagattgc agaaatcctg     1080
accatctatc aggataaaga tagcattgtt gcagaactgg gtcagctgga atatctgatg     1140
agcgaagccg ataaacagag cattagcgaa ctgaccggtt ataccggtac acatagcctg     1200
tcactgaaat gcatgaacat gattatcgat gaactgtggc atagcagcat gaaccagatg     1260
gaagttttta cctatctgaa tatgcgtccg aaaaagtatg agctgaaagg ttatcagcgt     1320
attccgaccg atatgattga tgatgcaatt ctgagtccgg ttgtgaaacg cacctttatt     1380
cagagcatca acgtgatcaa caaagtgatc gagaaatatg gcatccccga agatatcatt     1440
atcgaactgg cacgtgaaaa taactccgat gatcgcaaaa agttcatcaa caacctgcag     1500
aaaaagaatg aagcaacccg caaacgcatt aacgaaatta ttggtcagac cggtaatcag     1560
aatgccaaac gtattgtgga aaaaatccgt ctgcatgatc agcaagaggg caaatgtctg     1620
tatagcctgg aaagcattcc tctggaagat ctgctgaaca atccgaatca ttatgaagtg     1680
gatcacatta ttccgcgtag cgtgagcttt gataattcct atcataataa agtgctggtg     1740
aaacagagcg aaaactccaa aaaatccaac ctgacaccgt atcagtattt caatagcggc     1800
aaatccaaac tgagctacaa ccagtttaaa cagcatattc tgaacctgag caaaagccag     1860
gatcgcatca gcaagaagaa gaaggagtac ctgctggaag aacgcgatat caacaaattt     1920
gaagtccaga aagagtttat caaccgcaat ctggttgata cccgttatgc aacccgtgaa     1980
ctgaccagct atctgaaagc atatttcagc gccaataaca tggacgtgaa agtgaaaaca     2040
attaacggca gctttaccaa ccatctgcgt aaagtttggc gctttgataa atatcgcaac     2100
cacggctata acatcatgc cgaagatgca ctgattattg ccaatgcaga tttcctgttc      2160
aaagaaaaca aaaactgca gaacaccaac aagatcctgg aaaaccgac cattgaaaac       2220 aacaccaaaa agtgaccgt cgagaaagaa gaggattaca caacgttttt tgaaaccccg      2280
aaactggtcg aggatattaa acagtatcgc gactataaat tcagccaccg cgttgataaa     2340
aaaccgaatc gtcagctgat taacgatacc ctgtatagca cccgtatgaa agatgagcat     2400
gattatattg tgcagaccat cacggatatc tatggcaaag ataataccaa cctgaaaaaa     2460
cagttcaaca aaaaccccgga aaatttctg atgtatcaga acgatccgaa aacctttgag      2520 aaactgcagca tcatcatgaa acagtacagc gacgaaaaaa accccgctggc caaatattac     2580 gaagaaaccg gtgaatatct gaccaaatat agcaagaaaa acaacggtcc gatcgtgaaa     2640
```

-continued

```
aagatcaaac tgctgggtaa taaagtgggc aatcatctgg atgtgaccaa caaatatgaa    2700
aactccacga agaagctggt taagctgtcc attaaaaact atcgcttcga tgtgtatctg    2760
accgagaaag gttataagtt tgtgaccatt gcctacctga atgtgttcaa aaaagacaac    2820
tattactata ttccgaaaga caaataccaa gaacttaaag agaagaagaa aatcaaggac    2880
accgatcagt ttatcgccag cttctataaa aacgatctga tcaagctgaa cggcgacctg    2940
tataaaatca ttggtgtgaa tagtgatgac cgcaacatca ttgagctgga ttattacgac    3000
atcaaataca aggattactg cgagatcaac aacattaaag gtgaaccgcg tatcaaaaag    3060
accattggca aaaaaacgga aagcatcgaa aagtttacca ccgatgttct gggtaatctg    3120
tatctgcata gtaccgaaaa agcaccgcag ctgatttttca aacgcggtct g            3171
```

<210> SEQ ID NO 9
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Original E2Cas9 polynucleotide

<400> SEQUENCE: 9

```
atgaaccaga aatttatcct gggtctggat attggtatta ccagcgttgg ttatggcctg      60
attgattacg aaaccaaaaa cattattgat gccggtgttc gtctgtttcc ggaagcaaat     120
gttgaaaata tgaaggtcg tcgtagcaaa cgtggtagcc gtcgtctgaa acgtcgtcgt      180
attcatcgtc tggatcgtgt taaacatctg ctggcagaat atgatctgct ggatctgacc     240
aatattccga aaagcaccaa tccgtatcag accgtgttta aggtctgaa tgaaaagctg      300 agcaaagatg aactggttat tgcactgctg catattgcaa acgccgtgg cattcataac      360 gttgatgttg cagcagataa agaagaaacc gcaagcgata gcctgagcac caaagatcag     420
attaacaaaa acgccaaatt tctggaaagc cgctatgttt gtgaactgca gaaagaacgt     480
ctggaaaatg aaggtcatgt tcgtggtgtt gaaaatcgct ttctgacgaa agatattgtg     540
cgtgaggcca aaaaaatcat cgatacccag atgcagtatt acccggaaat tgatgaaacc     600
ttcaaagaga aatatatcag cctggttgaa acccgtcgcg aatatttttga aggtccgggt    660 aaaggtagcc gtttggttg ggaaggtaat atcaagaaat ggtttgagca tgatgatggc     720
cactgtacct atttttccaga gaactgcgt agcgtcaaat atagctattc agccgaactg     780
tttaacgccc tgaatgatct gaataatctg gtgattaccc gtgatgaaga tgccaaactg     840
aattatggtg agaaattcca gatcatcgaa aacgtgttca acagaagaa acaccgaac      900 ctgaaacaaa tcgccattga aattggtgtg catgaaaccg aaatcaaagg ttatcgtgtg     960
aacaaaagcg gtacccgga atttaccgaa ttttaaactgt atcatgacct gaaaagcatc    1020
gtgttcgata aaagcattct ggaaaatgaa gccatcctgg atcagattgc agaaattctg    1080
accatctatc aggatgagca gagcattaaa gaggaactga taaactgcc ggaaatactg    1140 aacgaacagg ataaagcaga atcgccaaa ctgattggtt ataatggcac catcgtctg     1200 agcctgaaat gtattcacct gattaatgaa gaactgtggc agaccagccg taatcagatg    1260 gaaatttttca actacctgaa catcaaaccg aacaaagtgg atctgagtga gcagaacaaa   1320
atcccgaaag atatggtgaa cgactttatt ctgagtccgg ttgtgaaacg cacctttatt    1380
cagagcatca acgtgatcaa caaagtgatc gagaaatatg gcatccccga agatatcatt    1440
```

```
atcgaactgg cacgtgaaaa taactccgat gatcgcaaaa agttcatcaa caacctgcag    1500
aaaaagaatg aagcaacccg caaacgcatt aacgaaatta ttggtcagac cggtaatcag    1560
aatgccaaac gtattgtgga aaaaatccgt ctgcatgatc agcaagaggg taaatgtctg    1620
tatagcctga agatatccc gctggaagat ctgctgcgca atccgaacaa ttatgatatc    1680
gaccatatta ttccgcgaag cgtgagcttt gatgatagca tgcataacaa agttctggtt    1740
cgtcgcgaac agaatgccaa aaagaataat cagaccccgt atcagtatct gaccagtggt    1800
tatgcagata tcaaatacag cgtgtttaag cagcatgttc tgaatctggc cgaaaataaa    1860
gatcgcatga ccaaaaaaaa gcgcgagtat ctgctggaag aacgcgacat taacaaattt    1920
gaagtgcaga agaatttat caaccgcaac ctggttgata cccgttatgc aacccgtgaa    1980
ctgaccaatt atctgaaagc atatttcagc gccaacaaca tgaacgtgaa agtgaaaacg    2040
attaacggca gctttaccga ttatctgcgt aaagtgtgga aattcaaaaa agaacgcaac    2100
cacggctata acatcatgc cgaagatgcc ctgattattg caaatgcaga tttcctgttt    2160
aaagaaaaca aaaaactgaa agccgtcaac agcgtgctgg aaaaaccgga aattgagaca    2220
aaacagctgg acattcaggt tgatagcgaa gataattaca gcgaaatgtt tatcatcccg    2280
aaacaggtgc aggatatcaa agatttttcgc aacttcaaat atagccaccg cgttgacaaa    2340
aaacctaatc gtcagctgat taacgatacc ctgtatagca cccgcaaaaa agataacagc    2400
acctatattg tgcagaccat taaagacatc tacgccaaag ataataccac cctgaaaaaa    2460
cagttcgaca aaagcccaga aaatttctg atgtatcagc atgatccgcg taccttcgaa    2520
aaactggaag ttattatgaa acagtatgcc aacgagaaaa atccgctggc caaatatcac    2580
gaagaaaccg gtgaatatct gaccaaatat tccaagaaga caacggtcc gatcgttaaa    2640 tccctgaaat atatcggtaa taaactgggc agccatctgg atgttaccca tcagtttaaa    2700
agctccacaa agaagctggt taaactgtcc atcaaaccgt atcgctttga tgtgtatctg    2760
accgacaaag gctataaatt cattaccatc agctatctgg acgtgctgaa aaaagacaac    2820
tattattata tcccggaaca gaaatatgat aaactgaaac tgggtaaagc catcgataaa    2880
aacgccaaat ttatcgccag cttctacaaa aacgacctga ttaaactgga tggcgagatc    2940
tataaaatca tcggtgttaa tagcgacacc cgcaatatga ttgagctgga tctgccggat    3000
attcgctata agaatattg cgaactgaac aacattaaag cgaaccgcg tatcaaaaag    3060 accatcggca aaaagtgaa tagcatcgag aaactgacca ccgatgttct gggtaatgtg    3120
tttaccaata cccagtatac caaacctcag ctgctgttca aacgcggtaa t               3171
```

<210> SEQ ID NO 10
<211> LENGTH: 3159
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Original F8Cas9 polynucleotide

<400> SEQUENCE: 10

```
atgaaccaga aatttatcct gggtctggat attggtatta ccagcgttgg ttatggcctg      60
attgattacg aaaccaaaaa cattattgat gccggtgttc gtctgtttcc ggaagcaaat     120
gttgaaaata tgaaggtcg tcgtagcaaa cgtggtagcc gtcgtctgaa acgtcgtcgt     180
attcatcgtc tggaacgtgt taaagccctg ctgagcgaat ataagattat tagcggtctg     240
```

```
gcaccgacca ataatcagcc gtataacatt cgtgttaaag gtctgaccga acagctgacc    300
aaagatgaac tggcagttgc actgctgcat attgccaaac gccgtggcat tcataaaatc    360
gatgtgattg atagcaatga cgatgtgggt aatgaactga gcaccaaaga acagctgaac    420
aaaaatagca aactgctgaa agacaaattc gtgtgtcaga ttcagctgga acgtatgaat    480
gaaggccagg ttcgtggtga aaagaatcgc tttaaaaccg cagacatcat caaagaaatt    540
atccagctgc tgaacgtgca gaaaaacttc catcagctgg atgaaaactt catcaacaaa    600
tacatcgagc tggttgaaat gcgtcgcgaa tattttgaag gtcctggtca gggtagcccg    660
tttggttgga atggtgatct gaaaaaatgg tacgaaatgc tgatgggtca ctgtacctat    720
tttccgcaag aactgcgtag cgttaaatat gcctatagcg cagacctgtt taatgcactg    780
aatgatctga acaacctgat tattcagcgc gataatagcg agaaactgga ataccatgag    840
aagtatcaca tcatcgagaa cgtgttcaag cagaaaaaaa agccgacgct gaaacaaatc    900
gcaaaagaga ttggcgttaa cccggaagat attaaaggtt atcgtattac caaaagcggt    960
acaccggaat tcaccgaatt taaactgtat cacgatctga aaagcgtgct gtttgatcag   1020
agcattctgg aaaatgaaga tgtgctggac cagattgcag aaattctgac catttatcag   1080
gacaaagaca gcatcaaaag caaactgacc gaactggata ttctgctgaa tgaagaagat   1140
aaagagaaca ttgcacagct gaccggttat aacggcacac atcgcctgag cctgaaatgt   1200
attcgtctgg tactggaaga acagtggtat agcagccgta atcagatgga aatctttacc   1260
catctgaaca ttaaaccgaa gaaaatcaat ctgaccgcag ccaacaaaat tccgaaagcc   1320
atgattgatg agtttattct gagtccggtt gtgaaacgca cctttattca gagcatcaac   1380
gtgatcaaca aagtgatcga gaaatatggc atccccgaag atatcattat cgaactggca   1440
cgtgaaaata actccgatga tcgcaaaaag ttcatcaaca acctgcagaa aaagaatgaa   1500
gcaacccgca aacgcattaa cgaaattatt ggtcagaccg gtaatcagaa tgccaaacgt   1560
attgtggaaa aaatccgtct gcatgatcag caagagggga aatgtctgta tagcctggaa   1620
agcattgccc tgatggatct gctgaataac ccgcagaatt atgaagtgga tcatattatt   1680
ccgcgtagcg tggcatttga taattccatt cataacaaag tgctggtgaa gcagatcgag   1740
aatagcaaaa aaggtaatcg tacgccgtat cagtatctga atagcagtga tgcaaaactg   1800
agctacaacc agtttaaaca gcatattctg aatctgagca aaagcaaaga tcgcatcagc   1860
aaaaaaaaga aggactacct gctggaagaa cgcgatatca acaaatttga agtccagaaa   1920
gagtttatca accgcaatct ggttgatacc cgttatgcaa cccgtgaact gaccagctat   1980
ctgaaagcat atttcagcgc caataacatg gacgtgaaag tgaaaacaat taacggcagc   2040
tttaccaacc atctgcgtaa agtttggcgc tttgataaat atcgcaacca cggctataaa   2100
catcatgcag aagatgccct gattattgca aatgcagatt tcctgtttaa agaaaacaaa   2160
aaactgaaag ccgtcaacag cgtgctggaa aaaccggaaa ttgagacaaa acagctggac   2220
attcaggttg atagcgaaga taattacagc gaaatgttta tcatcccgaa acaggtgcag   2280
gatatcaaag attttcgcaa cttcaaatat agccaccgcg ttgacaaaaa acctaatcgt   2340
cagctgatta cgataccct gtatagcacc cgcaaaaaag ataacagcac ctatattgtg   2400
cagaccatta aagacatcta cgccaaagat aataccaccc tgaaaaaaca gttcgacaaa   2460
agcccagaaa aatttctgat gtatcagcat gatccgcgta ccttcgaaaa actggaagtt   2520
attatgaaac agtatgccaa cgagaaaaat ccgctggcca atatcacga agaaaccggt   2580
```

| | |
|---|---|
| gaatatctga ccaaatattc aagaagaac aacggtccga tcgttaaatc cctgaaatat | 2640 |
| atcggtaata aactgggcag ccatctggat gttacccatc agtttaaaag ctccacaaag | 2700 |
| aagctggtta aactgtccat caaaccgtat cgctttgatg tgtatctgac cgacaaaggc | 2760 |
| tataaattca ttaccatcag ctatctggac gtgctgaaaa aagacaacta ttattatatc | 2820 |
| ccggaacaga aatatgataa actgaaactg gtaaagcca tcgataaaaa cgccaaattt | 2880 |
| atcgccagct tctacaaaaa cgacctgatt aaactggatg gcgagatcta aaaatcatc | 2940 |
| ggtgttaata gcgacacccg caatatgatt gagctggatc tgccggatat tcgctataaa | 3000 |
| gaatattgcg aactgaacaa cattaaaggc gaaccgcgta tcaaaaagac catcggcaaa | 3060 |
| aaagtgaata gcatcgagaa actgaccacc gatgttctgg gtaatgtgtt taccaatacc | 3120 |
| cagtatacca aacctcagct gctgttcaaa cgcggtaat | 3159 |

<210> SEQ ID NO 11
<211> LENGTH: 3162
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Original P2H12Cas9 polynucleotide

<400> SEQUENCE: 11

| | |
|---|---|
| atgaaccaga aatttatcct gggtctggat attggtatta ccagcgttgg ttatggcctg | 60 |
| attgattacg aaaccaaaaa cattattgat gccggtgttc gtctgtttcc ggaagcaaat | 120 |
| gttgaaaata tgaaggtcg tcgtagcaaa cgtggtagcc gtcgtctgaa acgtcgtcgt | 180 |
| attcatcgtc tggaacgtgt taaaaaactg ctggaagatt ataacctgct ggatcagagc | 240 |
| cagattccgc agagcaccaa tccgtatgca attcgtgtta aggtctgag cgaagcactg | 300 |
| agcaaagatg aactggttat tgcactgctg catattgcaa aacgccgtgg cattcataat | 360 |
| atcaatgtta gcagcgaaga tgaggatgca agcaatgaac tgagcaccaa gaacaaatt | 420 |
| aaccgcaata taagctgct gaaggacaaa tatgtttgcg aagttcagct gcagcgtctg | 480 |
| aaagaaggtc agattcgcgg agaaaaaaat cgctttaaaa ccaccgatat cctgaaagaa | 540 |
| attgatcagc tgcttaaagt gcagaaggat tatcataacc tggacatcga tttcatcaac | 600 |
| cagtacaaag aaatcgttga aacccgtcgc gaatattttg aaggtccggg taaaggtagc | 660 |
| ccgtatggtt gggaaggtga tccgaaagca tggtatgaaa ccctgatggg tcattgtacc | 720 |
| tatttccgg atgaactgcg tagcgttaaa tatgcctata gcgcagacct gtttaatgca | 780 |
| ctgaatgatc tgaataaacct ggtgattcag cgtgatggtc tgagcaaact ggaatatcat | 840 |
| gagaaatatc acatcatcga aaacgtgttc aaacagaaga gaaaccgac cctgaaacaa | 900 |
| atcgccaacg aaattaatgt gaacccggaa gatattaaag ctaccgtat taccaaaagc | 960 |
| ggcaaaccgg aatttacatc ctttaaactg ttccacgatc tgaaaaagt ggtgaaagat | 1020 |
| catgccatcc tggatgatat tgatctgctg aatcagattg cagaaatcct gaccatctat | 1080 |
| caggataaag atagcattgt tgcagaactg ggtcagctgg aatatctgat gagcgaagcc | 1140 |
| gataaacaga gcattagcga actgaccggt tataccggta cacatagcct gtcactgaaa | 1200 |
| tgcatgaaca tgattatcga tgaactgtgg catagcagca tgaaccagat ggaagttttt | 1260 |
| acctatctga atatgcgtcc gaaaaagtat gagctgaaag ttatcagcg tattccgacc | 1320 |
| gatatgattg atgatgcaat tctgagtccg gttgtgaaac gcacctttat tcagagcatc | 1380 |

-continued

| | |
|---|---|
| aacgtgatca acaaagtgat cgagaaatat ggcatccccg aagatatcat tatcgaactg | 1440 |
| gcacgtgaaa ataactccga tgatcgcaaa aagttcatca acaacctgca gaaaaagaat | 1500 |
| gaagcaaccc gcaaacgcat taacgaaatt attggtcaga ccggtaatca gaatgccaaa | 1560 |
| cgtattgtgg aaaaaatccg tctgcatgat cagcaagagg gtaaatgtct gtatagcctg | 1620 |
| gaaagcattc ctctggaaga tctgctgaac aatccgaatc attatgaagt ggatcacatt | 1680 |
| attccgcgta gcgtgagctt tgataattcc tatcataata aagtgctggt gaaacagagc | 1740 |
| gaaaactcca aaaatccaa cctgacaccg tatcagtatt tcaatagcgg caaatccaaa | 1800 |
| ctgagctaca accagtttaa acagcatatt ctgaacctga gcaaaagcca ggatcgcatc | 1860 |
| agcaagaaga agaaggagta cctgctggaa gaacgcgata ttaacaaatt tgaagtgcag | 1920 |
| aaagaattta tcaaccgcaa cctggttgat acccgttatg caacccgtga actgaccaat | 1980 |
| tatctgaaag catatttcag cgccaacaac atgaacgtga agtgaaaac gattaacggc | 2040 |
| agctttaccg attatctgcg taaagtgtgg aaattcaaaa aagaacgcaa ccacggctat | 2100 |
| aaacatcatg ccgaagatgc cctgattatt gcaaatgcag atttcctgtt taagaaaaac | 2160 |
| aaaaaactga agccgtcaa cagcgtgctg gaaaaaccgg aaattgagac aaaacagctg | 2220 |
| gacattcagg ttgatagcga agataattac agcgaaatgt ttatcatccc gaaacaggtg | 2280 |
| caggatatca aagattttcg caacttcaaa tatagccacc gcgttgacaa aaaacctaat | 2340 |
| cgtcagctga ttaacgatac cctgtatagc acccgcaaaa aagataacag cacctatatt | 2400 |
| gtgcagacca ttaaagacat ctacgccaaa gataatacca ccctgaaaaa acagttcgac | 2460 |
| aaaagcccag aaaatttct gatgtatcag catgatccgc gtaccttcga aaaactggaa | 2520 |
| gttattatga acagtatgc caacgagaaa atccgctggg ccaaatatca cgaagaaacc | 2580 |
| ggtgaatatc tgaccaaata ttccaagaag acaacggtc cgatcgttaa atccctgaaa | 2640 |
| tatatcggta ataaactggg cagccatctg gatgttaccc atcagtttaa aagctccaca | 2700 |
| aagaagctgg ttaaactgtc catcaaaccg tatcgctttg atgtgtatct gaccgacaaa | 2760 |
| ggctataaat tcattaccat cagctatctg gacgtgctga aaaagacaa ctattattat | 2820 |
| atcccggaac agaaatatga taactgaaa ctgggtaaag ccatcgataa aaacgccaaa | 2880 |
| tttatcgcca gcttctacaa aaacgacctg attaaactgg atggcgagat ctataaaatc | 2940 |
| atcggtgtta atagcgacac ccgcaatatg attgagctgg atctgccgga tattcgctat | 3000 |
| aaagaatatt gcgaactgaa caacattaaa ggcgaaccgc gtatcaaaaa gaccatcggc | 3060 |
| aaaaaagtga atagcatcga gaaactgacc accgatgttc tgggtaatgt gtttaccaat | 3120 |
| acccagtata ccaaacctca gctgctgttc aaacgcggta at | 3162 |

<210> SEQ ID NO 12
<211> LENGTH: 3162
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Original SluCas9 polynucleotide

<400> SEQUENCE: 12

| | |
|---|---|
| atgaaccaga aatttatcct gggtctggat attggtatta ccagcgttgg ttatggcctg | 60 |
| attgattacg aaaccaaaaa cattattgat gccggtgttc gtctgtttcc ggaagcaaat | 120 |
| gttgaaaata tgaaggtcg tcgtagcaaa cgtggtagcc gtcgtctgaa acgtcgtcgt | 180 |

```
attcatcgtc tggaacgtgt taaaaaactg ctggaagatt ataacctgct ggatcagagc    240
cagattccgc agagcaccaa tccgtatgca attcgtgtta aaggtctgag cgaagcactg    300
agcaaagatg aactggttat tgcactgctg catattgcaa aacgccgtgg cattcataaa    360
atcgatgtga ttgatagcaa tgacgatgtg ggtaatgaac tgagcaccaa agaacagctg    420
aacaaaaata gcaaactgct gaaagacaaa ttcgtgtgtc agattcagct ggaacgtatg    480
aatgaaggcc aggttcgtgg tgaaaagaat cgctttaaaa ccgcagacat catcaaagaa    540
attatccagc tgctgaacgt gcagaaaaac ttccatcagc tggatgaaaa cttcatcaac    600
aaatacatcg agctggttga aatgcgtcgc gaatattttg aaggtccggg taaaggtagc    660
ccgtatggtt gggaaggtga tccgaaagca tggtatgaaa ccctgatggg tcattgtacc    720
tattttccgg atgaactgcg tagcgttaaa tatgcctata cgcagacct gtttaatgca    780 ctgaatgatc tgaataacct ggtgattcag cgtgatggtc tgagcaaact ggaatatcat    840
gagaaatatc acatcatcga aaacgtgttc aaacagaaga gaaaccgac cctgaaacaa    900 atcgccaacg aaattaatgt gaacccggaa gatattaaag ctaccgtat taccaaaagc    960 ggtaaaccgc agttcaccga atttaaactg tatcacgatc tgaaaagcgt gctgtttgat    1020
cagagcattc tggaaaatga agatgtgctg gaccagattg cagaaattct gaccatttat    1080
caggacaaag acagcatcaa aagcaaactg accgaactgg atattctgct gaatgaagaa    1140
gataaagaga cattgcaca gctgaccggt tataccggca cccatcgtct gagcctgaaa    1200
tgtattcgtc tggtactgga gaacagtgg tatagcagcc gtaatcagat ggaaatcttt    1260
acccatctga acattaaacc gaagaaaatc aatctgaccg cagccaacaa aattccgaaa    1320
gccatgattg atgagtttat tctgagtccg gttgtgaaac gtacctttgg tcaggcaatt    1380
aacctgatca caaaatcat tgaaaaatat ggcgtgcctg aggatatcat tattgaactg    1440
gcacgtgaaa acaacagcaa agataaacag aaattcatca cgagatgca gaagaagaac    1500 gaaaatacc gcaaacggat taacgagatc attggcaaat atggtaatca gaatgccaaa    1560
cgcctggtgg aaaaaattcg tctgcatgat gaacaagagg gcaaatgtct gtatagcctg    1620
gaaagcattc tctctggaaga tctgctgaac aatccgaatc attatgaagt ggatcacatt    1680
attccgcgta gcgtgagctt tgataattcc tatcataata agtgctggt gaaacagagc    1740 gaaaactcca aaaatccaa cctgacaccg tatcagtatt tcaatagcgg caaatccaaa    1800
ctgagctaca ccagtttaa acagcatatt ctgaacctga gcaaaagcca ggatcgcatc    1860
agcaagaaga gaaggagta cctgctggaa gaacgcgaca tcaacaaatt tgaagtgcag    1920
aaagaattta tcaaccgcaa cctggttgat acccgttatg caacccgtga actgaccaat    1980
tatctgaaag catatttcag cgccaacaac atgaacgtga agtgaaaac gattaacggc    2040 agctttaccg attatctgcg taaagtgtgg aaattcaaaa aagaacgcaa ccacggctat    2100
aaacatcatg ccgaagatgc cctgattatt gcaaatgcag atttcctgtt taaagaaaac    2160
aaaaaactga agccgtcaa cagcgtgctg gaaaaaccgg aaattgagac aaaacagctg    2220
gacattcagg ttgatagcga agataattac agcgaaatgt ttatcatccc gaaacaggtg    2280
caggatatca agattttcg caacttcaaa tatagccacc gcgttgacaa aaaacctaat    2340
cgtcagctga ttaacgatac cctgtatagc acccgcaaaa aagataacag cacctatatt    2400
gtgcagacca ttaaagacat ctacgccaaa gataatacca ccctgaaaaa acagttcgac    2460
aaaagcccag aaaatttct gatgtatcag catgatccgc gtaccttcga aaaactggaa    2520
gttattatga acagtatgc caacgagaaa aatccgctgg ccaaatatca cgaagaaacc    2580
```

```
ggtgaatatc tgaccaaata ttccaagaag aacaacggtc cgatcgttaa atccctgaaa    2640
tatatcggta ataaactggg cagccatctg gatgttaccc atcagtttaa aagctccaca    2700
aagaagctgg ttaaactgtc catcaaaccg tatcgctttg atgtgtatct gaccgacaaa    2760
ggctataaat tcattaccat cagctatctg gacgtgctga aaaaagacaa ctattattat    2820
atcccggaac agaaatatga taaactgaaa ctgggtaaag ccatcgataa aaacgccaaa    2880
tttatcgcca gcttctacaa aaacgacctg attaaactgg atggcgagat ctataaaatc    2940
atcggtgtta atagcgacac ccgcaatatg attgagctgg atctgccgga tattcgctat    3000
aaagaatatt gcgaactgaa caacattaaa ggcgaaccgc gtatcaaaaa gaccatcggc    3060
aaaaaagtga atagcatcga gaaactgacc accgatgttc tgggtaatgt gtttaccaat    3120
acccagtata ccaaacctca gctgctgttc aaacgcggta at                      3162
```

<210> SEQ ID NO 13
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized Gib11SpaCas9-1 polynucleotide

<400> SEQUENCE: 13

```
atgaaccaga agttcattct cggtctggac attggcatta ctagcgtggg atacggcttg      60
attgactacg agactaagaa catcatcgat gccggcgtcc gcctgttccc ggaagccaac     120
gtggagaaca atgagggccg gaggtcgaag agaggctccc gccgcctgaa gcggcggcga     180
atccaccggc tggagagagt gaagctgctg ctcaccgaat acgacctgat caacaaagaa     240
cagatcccga cctccaacaa cccgtaccag atcagagtga agggtctgtc agaaatcctg     300
tccaaggaca aactggcaat cgccctgctg cacctggcca gcggcgcgg aatccacaac     360 gtggatgtgg ctgccgacaa ggaagaaacc gcttccgact ccctgagcac taaggaccag     420
atcaacaaga acgccaagtt cttggagtcc cgctacgtgt gcgagctgca aaggaacgg     480 ctggaaaacg aaggtcacgt gcgcggagtg gaaaaccggt tcctgacaaa ggacattgtg     540
cgcgaagcga agaagatcat tgatacccaa atgcagtact accctgaaat cgacgagact     600
ttcaaggaaa agtacatttc cctggtggaa accggcgggg aatacttcga aggccccgga     660
cagggatcgc cgttcggatg gaacggggac ctcaagaagt ggtacgagat gctgatgggg     720
cactgtacct actttccgca agaactgcgc tccgtgaagt acgcgtactc cgcggatctc     780
ttcaacgcgt tgaatgacct gaacaacctg atcattcaga gagacaattc cgaaaagctc     840
gagtaccacg agaagtatca catcatcgag aatgtgttca gcagaagaa gaaaccgacc     900 ctcaagcaaa tcgccaagga gattggcgtc aacccagagg acatcaaggg atatcggatt     960
accaagagcg gcactcccga gtttacctct ttcaagctgt tcatgatct gaagaaagtc    1020 gtgaaggacc atgccattct cgacgacatt gatctcctga atcagatcgc agagatcctg    1080
actatctacc aagacaagga ctcgattgtg gcagagctgg gtcagctcga atacctgatg    1140
tccgaggccg acaagcagtc catctccgaa ctgacagggt acacggggac tcatagcctg    1200
tcgctgaagt gcatgaacat gatcattgat gaactgtggc acagctccat gaaccaaatg    1260
gaagtgttta cctacctcaa catgcgccct aagaagtacg aactgaaagg ctaccagcgc    1320
atccccaccg acatgatcga cgacgcgatc ttgtcccctg tggtcaagag gaccttcatt    1380
```

```
caatccatca acgtgatcaa caaggtcatc gaaaagtacg gaataccaga agatatcatc    1440
attgagctcg ctcgggagaa caactcggat gaccggaaga agttcatcaa caatcttcag    1500
aagaagaacg aagcgactcg gaaacggatc aacgagatca tcggacagac cggaaaccag    1560
aacgccaaac ggattgtcga aaagattaga ctgcacgacc agcaggaagg gaagtgcctg    1620
tactcactcg agtcaatacc gctcgaggac ctgttgaaca accctaacca ctatgaagtg    1680
gaccacatca tccctcggtc cgtgagcttc gacaactcgt accacaacaa agtgctcgtg    1740
aagcagtccg aaaactccaa gaaatccaac ctgaccccgt accaatactt caattcggga    1800
aagtcgaagc tgtcgtacaa ccagttcaaa caacacatac tcaaccttag caaaagccag    1860
gatcgcattt ccaagaagaa gaaggaatac ctcctcgagg aaagggacat caacaagttc    1920
gaagtgcaga aagagttcat caatcgcaac ttggtggata ccagatatgc cacccgggaa    1980
ctcaccaact atctcaaggc ctactttttcc gccaacaaca tgaacgtgaa ggtcaagacc    2040
atcaacgggt ccttcactga ctacctgaga aaggtctgga agttcaagaa ggaacgcaac    2100
cacggataca agcaccacgc tgaggacgct ctgatcatcg ccaatgccga cttcctgttc    2160
aaggaaaaca agaagctgaa agctgtcaac tcagtgctgg aaaagcctga atcgagact    2220 aagcagctgg atatccaagt ggactctgag gacaactaca gcgagatgtt catcatccct    2280
aaacaagtgc aggatatcaa ggactttcgc aacttcaagt actcacaccg ggtggacaag    2340
aaaccgaata gacagctgat caacgacacg ttgtattcca cccggaagaa ggataactca    2400
acctacattg tgcagactat caaggatatc tacgccaaag ataacactac tctgaagaaa    2460
caattcgaca gtccccaga gaagttcctg atgtaccagc acgaccccg aacctttgag    2520 aagcttgaag tgatcatgaa gcagtacgcc aacgagaaga cccgctggc caagtaccat    2580 gaagaaaccg gagaatacct gaccaagtac agcaagaaga caacggtcc cattgtcaag    2640 agcctgaagt acatcggcaa caagctggga tcccacctcg acgtgacaca tcagttcaag    2700
tcgtcgacta agaagcttgt gaagctgtca atcaagaact atagattcga cgtgtacttg    2760
accgaaaagg gatacaagtt cgtgaccata gcctatctga acgtgttcaa gaaagataac    2820
tactactaca tcccccaagga caagtaccag gagctcaaag aaaagaagaa gatcaaagac    2880
accgaccagt tcattgcctc cttctacaag aacgacctga tcaaactgaa cggcgacctc    2940
tacaagatca ttggagtgaa cagcgatgac aggaacatca ttgagctgga ctactacgac    3000
atcaagtaca aggactactg cgagatcaac aacatcaagg gcgaaccccg gatcaagaaa    3060
actattggaa agaaaaccga gtccattgag aagttcacca ctgacgtgct gggaaaacctt    3120 tacctccact ccaccgagaa ggcaccacaa ctgatcttca gcgcggcct g               3171
```

<210> SEQ ID NO 14
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized Gib11SpaCas9-3 polynucleotide

<400> SEQUENCE: 14

```
atgaaccaga agttcattct cggtctggac attggcatta ctagcgtggg atacggcttg      60
attgactacg agactaagaa catcatcgat gccggcgtcc gctgttccc ggaagccaac     120 gtggagaaca atgagggccg gaggtcgaag agaggctccc gccgcctgaa gcggcggcga     180
```

```
atccaccggc tggagagagt gaagctgctg ctcaccgaat acgacctgat caacaaagaa    240
cagatcccga cctccaacaa cccgtaccag atcagagtga agggtctgtc agaaatcctg    300
tccaaggacg aactggcaat cgccctgctg cacctggcca agcggcgcgg aatccacaac    360
gtggatgtgg ctgccgacaa ggaagaaacc gcttccgact ccctgagcac taaggaccag    420
atcaacaaga acgccaagtt cttggagtcc cgctacgtgt gcgagctgca gaaggaacgg    480
ctggaaaacg aaggtcacgt gcgcggagtg gaaaaccggt tcctgacaaa ggacattgtg    540
cgcgaagcga agaagatcat tgatacccaa atgcagtact accctgaaat cgacgagact    600
ttcaaggaaa gtacatttc cctggtggaa acccggcggg aatacttcga aggcccggga    660
cagggatcgc cgttcggatg aacggggac ctcaagaagt ggtacgagat gctgatgggg    720
cactgtacct actttccgca agaactgcgc tccgtgaagt acgcgtactc cgcggatctc    780
ttcaacgcgt tgaatgacct gaacaacctg atcattcaga gagacaattc cgaaaagctc    840
gagtaccacg agaagtatca catcatcgag aatgtgttca agcagaagaa gaaaccgacc    900
ctcaagcaaa tcgccaagga gattggcgtc aacccagagg acatcaaggg atatcggatt    960
accaagagcg gcactcccga gtttacctct ttcaagctgt tcatgatctg aagaaagtc    1020 gtgaaggacc atgccattct cgacgacatt gatctcctga atcagatcgc agagatcctg    1080
actatctacc aagacaagga ctcgattgtg gcagagctgg gtcagctcga atacctgatg    1140
tccgaggccg acaagcagtc catctccgaa ctgacagggt acacggggac tcatagcctg    1200
tcgctgaagt gcatgaacat gatcattgat gaactgtggc acagctccat gaaccaaatg    1260
gaagtgttta cctacctcaa catgcgccct aagaagtacg aactgaaagg ctaccagcgc    1320
atccccaccg acatgatcga cgacgcgatc ttgtcccctg tggtcaagag gaccttcatt    1380
caatccatca acgtgatcaa caaggtcatc gaaaagtacg gtattccaga agatatcatc    1440
attgagctcg ctcgggagaa caactcggat gaccggaaga agttcatcaa caatcttcag    1500
aagaagaacg aagcgactcg gaaacggatc aacgagatca tcggacagac cggaaaccag    1560
aacgccaaac ggattgtcga aaagattaga ctgcacgacc agcaggaagg gaagtgcctg    1620
tactcactcg agtcaatacc gctcgaggac ctgttgaaca accctaacca ctatgaagtg    1680
gaccacatca tccctcggtc cgtgagcttc gacaactcgt accacaacaa agtgctcgtg    1740
aagcagtccg aaaactccaa gaaatccaac ctgacccccgt accaatactt caattcggga    1800
aagtcgaagc tgtcgtacaa ccagttcaaa caacacatac tcaaccttag caaaagccag    1860
gatcgcattt ccaagaagaa gaaggaatac ctcctcgagg aaagggacat caacaagttc    1920
gaagtgcaga aagagttcat caatcgcaac ttggtggata ccagatatgc cacccgggaa    1980
ctcaccagct atctcaaggc ctactttccc gccaacaaca tggacgtgaa ggtcaagacc    2040
atcaacgggt ccttcactaa ccatctgaga aaggtctggc ggtttgacaa gtaccgcaac    2100
cacggataca agcaccacgc tgaagacgct ctgatcatcg ccaatgccga cttcctgttc    2160
aaggaaaaca agaagctgca gaacacgaac aagattctgg aaaagcctac cattgagaac    2220
aacactaaga aggtcaccgt gggagaaggaa gaggactaca acaacgtgtt cgaaactcct    2280
aaactggtgg aggatatcaa gcaataccgc gactacaagt tctcacaccg ggtggacaag    2340
aaaccgaata gacagctgat caacgacacg ttgtattcca cccggatgaa ggatgagcat    2400
gactacattg tgcagactat caccgatatc tacggaaaag ataacactaa cctgaagaaa    2460
caattcaaca gaacccaga gaagttcctg atgtaccaga acgaccccaa gacctttgag    2520
```

| | |
|---|---|
| aagctttcca tcatcatgaa gcagtactcc gacgagaaga acccgctggc caagtactac | 2580 |
| gaagaaaccg gagaatacct gaccaagtac agcaagaaga caacggtcc cattgtcaag | 2640 |
| aagatcaagc tgctcggcaa caaggtcgga aaccacctcg acgtgacaaa caagtacgag | 2700 |
| aactcgacta agaagcttgt gaagctgtca atcaagaact atagattcga cgtgtacttg | 2760 |
| accgaaaagg gatacaagtt cgtgaccata gcctatctga acgtgttcaa gaaagataac | 2820 |
| tactactaca tcccccaagga caagtaccag gagctcaaag aaaagaagaa gatcaaagac | 2880 |
| accgaccagt tcattgcctc cttctacaag aacgacctga tcaaactgaa cggcgacctc | 2940 |
| tacaagatca ttggagtgaa cagcgatgac aggaacatca ttgagctgga ctactacgac | 3000 |
| atcaagtaca aggactactg cgagatcaac aacatcaagg gcgaaccccg gatcaagaaa | 3060 |
| actattggaa agaaaaccga gtccattgag aagttcacca ctgacgtgct gggaaacctt | 3120 |
| tacctccact ccaccgagaa ggcaccacaa ctgatcttca agcgcggcct g | 3171 |

<210> SEQ ID NO 15
<211> LENGTH: 3171
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized E2Cas9 polynucleotide

<400> SEQUENCE: 15

| | |
|---|---|
| atgaaccaaa agttcattct ggggctcgat atcggcatca cctccgtggg atatggtctg | 60 |
| atcgactacg agactaagaa catcatcgac gctggagtgc gactgttccc ggaagcgaac | 120 |
| gtggagaaca acgaaggccg cagatccaag cgcgggtcca gaaggctcaa gaggcggagg | 180 |
| atccatagac tcgacagagt gaagcacctc cttgccgaat acgatctgtt ggaccttacc | 240 |
| aacattccca gagcaccaa cccgtaccaa accagagtga agggcctgaa cgaaaagctg | 300 |
| tcgaaagatg aactggtcat tgccctgctg catattgcca acggcgcgg aatccataac | 360 |
| gtggacgtgg ccgctgacaa ggaagagact gcgtccgact cgctgtcaac caaggaccag | 420 |
| atcaacaaga acgccaaatt cctggaaagc cgctacgtct gcgagcttca aaagaacgg | 480 |
| ctggagaacg agggacacgt caggggagtg gagaaccggt tcctgaccaa ggacatcgtg | 540 |
| cgggaagcca gaagatcat cgacacccaa atgcagtatt atccggaaat tgatgaaact | 600 |
| tttaaggaga agtacatttc cctggtggaa actcggaggg agtacttcga gggacctgga | 660 |
| aagggatccc ctttcggctg gaagggaac attaagaagt ggtttgaaca gatgatgggc | 720 |
| cattgcactt actttccgga agaactccgg tccgtgaagt actcatactc tgccgagctg | 780 |
| ttcaatgcac tcaacgacct taacaacttg gtgatcaccc gcgatgaaga tgccaagttg | 840 |
| aactacggag aaaagttcca gatcatcgag aacgtgttca gcagaaaaa gaccccaaat | 900 |
| ctgaagcaga ttgccatcga aattggcgtg cacgagactg agatcaaggg ataccgggtc | 960 |
| aacaagtccg gcacgccaga gttcaccgag ttcaagctgt accacgatct gaagtcgatc | 1020 |
| gtgtttgaca gtccatcct ggaaaacgaa gccattctgg accagattgc tgagatcctg | 1080 |
| accatctacc aggacgagca atcgattaag gaagaactga caagctccc cgagattctg | 1140 |
| aacgaacagg ataaggccga gatcgcgaag ctcattggtt acaatggtac ccaccgcttg | 1200 |
| tcccttaagt gcatccatct gatcaatgag gaactgtggc agaccagccg gaaccagatg | 1260 |
| gagatcttca attacttgaa catcaagccg aacaaggtgg acctgtccga acagaacaag | 1320 |

```
atacccaagg acatggtcaa cgactttatc ctctcaccgg tggtcaagcg caccttcatt   1380
caatctatca acgtgatcaa caaggtcatc gagaagtacg gcattcctga ggatatcatc   1440
atcgagctgg ctcgggagaa caactcagac gataggaaga agttcattaa caacctccag   1500
aaaaagaacg aggccactcg caagcggatt aatgagatca tcggtcagac cgggaaccag   1560
aacgccaagc ggatcgtgga aaagattcgg ctccacgacc aacaggaggg aaagtgtctg   1620
tactcgctga aggacattcc cctggaggac ctcctgagga acccaaacaa ctacgacatc   1680
gatcacataa tcccccgcag cgtgtcattc gacgattcca tgcataacaa ggtcctcgtg   1740
cggagagagc agaatgccaa gaagaacaac cagactccgt accagtacct gacgtccggc   1800
tacgcagaca tcaagtactc agtgttcaaa cagcacgtgc tcaacctggc cgagaacaag   1860
gacaggatga ccaagaagaa gcgcgaatac cttctcgagg aacgggatat caataagttc   1920
gaggtgcaga aggagtttat caatagaaac ctggtggaca ctcgctatgc caccccgcgaa   1980
ctgaccaact acctgaaggc gtacttctcc gccaacaaca tgaacgtgaa ggtcaaaact   2040
attaacggca gcttcaccga ctatctgcgc aaggtctgga gttcaagaa ggaacgcaac   2100
cacggttaca agcaccacgc ggaagatgcg ctgattatcg ccaacgctga cttcctgttc   2160
aaggaaaaca agaagctcaa ggccgtgaac tcagtgctcg agaagcctga aatcgagact   2220
aagcagctgg acatccaggt cgattcggaa gataactact ccgaaatgtt catcatccct   2280
aagcaagtgc aggacatcaa ggacttcagg aatttcaagt acagccatcg cgtggacaag   2340
aagccaaaca gacagctgat caacgataca ctgtattcca cccggaagaa ggacaactcc   2400
acctacatcg tccaaaccat taaggacatc tacgcaaagg acaacaccac gcttaagaag   2460
cagttcgaca agagccccga aaagttcctc atgtaccagc acgacccag aaccttcgag   2520
aagcttgaag tgatcatgaa gcagtacgcc aacgaaaaga cccactggc taagtaccac   2580
gaggaaaccg gcgaatacct gaccaagtac tccaaaaaga caacggacc gatcgtcaag   2640
tccctgaagt acattgggaa caagctcggc tcgcacctcg atgtgaccca ccagttcaag   2700
tcctcgacca aaaagctcgt gaagctgtcc atcaagccgt accggttcga cgtgtacctg   2760
actgacaagg gatataagtt catcaccatt tcctacctcg acgtgttgaa gaaggataac   2820
tactactaca ttccggaaca gaagtacgac aagctcaagc tcggaaaggc catcgacaaa   2880
aatgcgaagt catcgcgag cttctacaag aatgacttga tcaagctgga tggcgaaatc   2940
tacaagatca tcggggtcaa ctccgatacc cgcaacatga ttgagctgga tctgcccgac   3000
attcggtaca aggaatactg cgagctgaac aacatcaagg agaaccgcg gatcaagaaa   3060
accatcggaa agaaagtgaa cagcatcgag aaactgacta ctgacgtcct gggaaacgtg   3120
ttcaccaaca cacaatacac caaaccccag ctgctgttta gcgcgggaa c              3171
```

<210> SEQ ID NO 16  
<211> LENGTH: 3159  
<212> TYPE: DNA  
<213> ORGANISM: Artificial sequence  
<220> FEATURE:  
<223> OTHER INFORMATION: Synthetic polynucleotide  
<220> FEATURE:  
<221> NAME/KEY: misc_feature  
<223> OTHER INFORMATION: Codon-optimized F8Cas9 polynucleotide

<400> SEQUENCE: 16

```
atgaaccaaa agttcattct ggggctcgat atcggcatca cctccgtggg atatggtctg    60
atcgactacg agactaagaa catcatcgac gctggagtgc gactgttccc ggaagcgaac   120
```

```
gtggagaaca acgaaggccg cagatccaag cgcgggtcca gaaggctcaa gaggcggagg      180
atccatagac tcgagagagt gaagtcgctc ctttcggaat acaagattat cagcggtctt      240
gcccccacca acaaccaacc gtacaacatc agagtgaagg gcctgaccga acagctgacc      300
aaagatgaac tggccgtcgc cctgctgcat attgccaaac ggcgcggaat ccataagatc      360
gacgtgattg acagcaacga tgacgtggga aacgagctgt caaccaagga acagcttaac      420
aagaacagca aattgctgaa ggacaagttt gtctgccaaa ttcaactgga acggatgaac      480
gagggacaag tcaggggaga gaaaaaccgg ttcaagaccg ccgacatcat caaggagatc      540
atccaactgc tgaacgtgca gaagaacttc caccaactgg atgaaaactt cattaacaag      600
tacattgaac tggtggaaat gcggagggag tacttcgagg gacctggaca gggatcccct      660
ttcggctgga tgggggacct taagaagtgg tacgaaatgt tgatgggcca ttgcacttac      720
tttccgcaag aactccggtc cgtgaagtac gcatactctg ccgacctgtt caatgcactc      780 aacgaccttta caacttgat catccagcgc gataactcgg aaaagttgga ataccacgaa      840
aagtatcaca tcatcgagaa cgtgttcaag cagaaaaaga agccaactct gaagcagatt      900
gccaaggaaa ttggcgtgaa tccggaggat atcaagggat accggatcac taagtccggc      960
acgccagagt tcaccgagtt caagctgtac cacgatctga gtcggtgct ctttgaccag     1020 tccatcctgg aaaacgaaga tgtgctggac cagattgctg agatcctgac catctaccag     1080
gacaaggact cgattaagtc caagctcacc gagctggaca ttctgctgaa cgaagaagat     1140
aaggagaaca tcgcgcagct caccggttac aatggtaccc accgcttgtc ccttaagtgc     1200
atccgcctgg tgctggagga acagtggtac tcgagccgga accagatgga gatcttcact     1260
cacttgaaca tcaagccgaa aaagattaac ctgactgccg ccaacaagat acccaaggcc     1320
atgatcgacg agtttatcct ctcaccggtg gtcaagcgca ccttcattca atctatcaac     1380
gtgatcaaca aggtcatcga gaagtacggc attcctgagg atatcatcat cgagctggct     1440
cgggagaaca actcagacga taggaagaag ttcattaaca acctccagaa aaagaacgag     1500
gccactcgca agcggattaa tgagatcatc ggtcagaccg ggaaccagaa cgccaagcgg     1560
atcgtggaaa agattcggct ccacgaccaa caggagggaa agtgtctgta ctcgctggag     1620
tcgattgcac tgatggacct cctgaacaac ccacagaact acgaagtcga tcacataatc     1680 cccgcagcg tggcattcga caactccatc cataacaagg tcctcgtgaa gcagatcgag     1740
aatagcaaga aggggaaccg gactccgtac cagtacctga actcctccga cgccaagctg     1800
tcatacaatc agttcaaaca gcacattctc aacctgtcca gtcaaaggga caggatctcc     1860
aagaagaaga aggactacct tctcgaggaa cgggatatca ataagttcga ggtgcagaag     1920
gagtttatca atagaaacct ggtggacact cgctatgcca cccgcgaact gaccagctac     1980
ctgaaggcgt acttctccgc caacaacatg gacgtgaagg tcaaaactat taacggcagc     2040
ttcaccaacc atctgcgcaa ggtctggagg ttcgacaagt accgcaacca cggttacaag     2100
caccacgcgg aagatgcgct gattatcgcc aacgctgact tcctgttcaa ggaaaacaag     2160
aagctcaagg ccgtgaactc agtgctcgag aagcctgaaa tcgagactaa gcagctggac     2220
atccaggtcg attcggaaga taactactcc gaaatgttca tcatccctaa gcaagtgcag     2280
gacatcaagg acttcaggaa tttcaagtac agccatcgcg tggacaagaa gccaaacaga     2340
cagctgatca acgatacact gtattccacc cggaagaagg acaactccac ctacatcgtc     2400
caaaccatta aggacatcta cgcaaaggac aacaccacgc ttaagaagca gttcgacaag     2460
agccccgaaa agttcctcat gtaccagcac gaccccagaa ccttcgagaa gcttgaagtg     2520
```

| | |
|---|---|
| atcatgaagc agtacgccaa cgaaaagaac ccactggcta agtaccacga ggaaaccggc | 2580 |
| gaatacctga ccaagtactc caaaaagaac aacggaccga tcgtcaagtc cctgaagtac | 2640 |
| attgggaaca agctcggctc gcacctcgat gtgacccacc agttcaagtc ctcgaccaaa | 2700 |
| aagctcgtga agctgtccat caagccgtac cggttcgacg tgtacctgac tgacaaggga | 2760 |
| tataagttca tcaccatttc ctacctcgac gtgttgaaga aggataacta ctactacatt | 2820 |
| ccggaacaga gtacgacaa gctcaagctc ggaaaggcca tcgacaaaaa tgcgaagttc | 2880 |
| atcgcgagct tctacaagaa tgacttgatc aagctggatg cgaaatcta caagatcatc | 2940 |
| ggggtcaact ccgatacccg caacatgatt gagctggatc tgcccgacat tcggtacaag | 3000 |
| gaatactgcg agctgaacaa catcaaggga gaaccgcgga tcaagaaaac catcggaaag | 3060 |
| aaagtgaaca gcatcgagaa actgactact gacgtcctgg gaaacgtgtt caccaacaca | 3120 |
| caatacacca acccccagct gctgtttaag cgcgggaac | 3159 |

<210> SEQ ID NO 17
<211> LENGTH: 3162
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized P2H12Cas9 polynucleotide

<400> SEQUENCE: 17

| | |
|---|---|
| atgaaccaaa agttcattct ggggctcgat atcggcatca cctccgtggg atatggtctg | 60 |
| atcgactacg agactaagaa catcatcgac gctggagtgc gactgttccc ggaagcgaac | 120 |
| gtggagaaca acgaaggccg cagatccaag cgcgggtcca aaggctcaa gaggcggagg | 180 |
| atccatagac tcgagagagt gaagaagctc cttgaagatt acaatctgtt ggaccagtca | 240 |
| cagattcccc aaagcaccaa cccgtacgcc atcagagtga agggcctgtc agaagcactg | 300 |
| tcgaaagatg aactggtcat tgccctgctg catattgcca acggcgcgg aatccataac | 360 |
| atcaacgtgt cgagcgaaga tgaggacgcg tccaacgaac tgtcaaccaa ggaacagatc | 420 |
| aaccggaaca caaaactgct gaaggacaaa tacgtctgcg aggtgcagct tcaacggctg | 480 |
| aaagagggac agatcagggg agagaaaaac cggttcaaga ccaccgacat ccttaaggag | 540 |
| atcgaccaac tcctgaaagt gcagaaggac tatcacaacc tcgacattga tttatcaac | 600 |
| cagtacaagg agattgtgga aactcggagg gagtacttcg agggacctgg aaagggatcc | 660 |
| ccttatggct gggaagggga ccccaaggct tggtacgaaa ccctgatggg ccattgcact | 720 |
| tactttccgg atgaactccg gtccgtgaag tacgcttact ctgccgacct gttcaatgca | 780 |
| ctcaacgacc ttaacaactt ggtgatccaa cgcgatggtc tttccaagtt ggagtaccac | 840 |
| gaaaagtacc acatcatcga gaacgtgttc aagcagaaaa agaagccaac tctgaagcag | 900 |
| attgccaacg aaattaacgt gaaccccgag gatatcaagg gataccggat taccaagtcc | 960 |
| ggcaaaccag agttcaccct attcaagctg tttcacgatc tgaagaaggt cgtgaaggac | 1020 |
| cacgccatcc tggatgacat tgatcttctg aaccagattg ctgagatcct gaccatctac | 1080 |
| caggacaagg actcgattgt ggccgaactg ggacagctcg agtacctgat gtccgaagcc | 1140 |
| gataagcagt ccatcagcga actcaccggt tacaccggta cccactcctt gtcccttaag | 1200 |
| tgcatgaaca tgatcattga cgaactgtgg cactccagca tgaaccagat ggaggtgttc | 1260 |
| acctacttga acatgcgccc gaagaagtac gagctgaagg gctaccagcg catacccacg | 1320 |

```
gacatgatcg acgacgccat cctctcaccg gtggtcaagc gcaccttcat tcaatctatc    1380
aacgtgatca acaaggtcat cgagaagtac ggcattcctg aggatatcat catcgagctg    1440
gctcgggaga caactcaga cgataggaag aagttcatta acaacctcca gaaaagaac     1500 gaggccactc gcaagcggat taatgagatc atcggtcaga ccgggaacca gaacgccaag    1560
cggatcgtgg aaaagattcg gctccacgac caacaggagg gaaagtgtct gtactcgctg    1620
gagtccattc ccctggagga cctcctgaac aacccaaacc actacgaggt cgatcacata    1680
atcccccgca gcgtgtcatt cgacaactcc taccataaca aggtcctcgt gaagcagtcg    1740
gagaatagca agaagtcgaa cctgactccg taccagtact tcaactccgg caaatccaag    1800
ctgtcctaca atcagttcaa acagcacatt ctcaacctgt ccaagagcca ggacaggatt    1860
tcgaagaaga agaaggaata ccttctcgag aacgggata tcaataagtt cgaggtgcag     1920
aaggagttta tcaatagaaa cctggtggac actcgctatg ccacccgcga actgaccaac    1980
tacctgaagg cgtacttctc cgccaacaac atgaacgtga aggtcaaaac tattaacggc    2040
agcttcaccg actatctgcg caaggtctgg aagttcaaga aggaacgcaa ccacggttac    2100
aagcaccacg cggaagatgc gctgattatc gccaacgctg acttcctgtt caaggaaaac    2160
aagaagctca aggccgtgaa ctcagtgctc gagaagcctg aaatcgagac taagcagctg    2220
gacatccagg tcgattcgga agataactac tccgaaatgt tcatcatccc taagcaagtg    2280
caggacatca aggacttcag gaatttcaag tacagccatc gcgtggacaa gaagccaaac    2340
agacagctga tcaacgatac actgtattcc acccggaaga aggacaactc cacctacatc    2400
gtccaaacca ttaaggacat ctacgcaaag gacaacacca cgcttaagaa gcagttcgac    2460
aagagccccg aaaagttcct catgtaccag cacgaccccca gaaccttcga gaagcttgaa    2520
gtgatcatga agcagtacgc caacgaaaag aacccactgg ctaagtacca cgaggaaacc    2580
ggcgaatacc tgaccaagta ctccaaaaag aacaacggac cgatcgtcaa gtccctgaag    2640
tacattggga acaagctcgg ctcgcacctc gatgtgaccc accagttcaa gtcctcgacc    2700
aaaaagctcg tgaagctgtc catcaagccg taccggttcg acgtgtacct gactgacaag    2760
ggatataagt tcatcaccat ttcctacctc gacgtgttga agaaggataa ctactactac    2820
attccggaac agaagtacga caagctcaag ctcggaaagg ccatcgacaa aaatgcgaag    2880
ttcatcgcga gcttctacaa gaatgacttg atcaagctgg atggcgaaat ctacaagatc    2940
atcggggtca actccgatac ccgcaacatg attgagctgg atctgcccga cattcggtac    3000
aaggaatact gcgagctgaa caacatcaag ggagaaccgc ggatcaagaa accatcgga    3060 aagaaagtga acagcatcga gaaactgact actgacgtcc tgggaaacgt gttcaccaac    3120
acacaataca ccaaaccccca gctgctgttt aagcgcggga ac                       3162
```

<210> SEQ ID NO 18
<211> LENGTH: 3162
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized SluCas9-1 polynucleotide

<400> SEQUENCE: 18

```
atgaaccaaa agttcattct ggggctcgat atcggcatca cctccgtggg atatggtctg     60
atcgactacg agactaagaa catcatcgac gctggagtgc gactgttccc ggaagcgaac    120
```

```
gtggagaaca acgaaggccg cagatccaag cgcgggtcca gaaggctcaa gaggcggagg    180
atccatagac tcgaaagagt gaagaagctc cttgaagatt acaatctgtt ggaccagagc    240
cagattcccc aaagcaccaa cccgtacgcc atcagagtga agggcctgtc cgaagccctg    300
tcgaaagatg aactggtcat tgccctgctg catattgcca acggcgcgg aatccataag    360 atcgacgtga tagactccaa cgatgacgtg ggcaacgaac tgtcaaccaa ggagcagctg    420
aacaagaact cgaaactgct gaaggacaag ttcgtctgcc aaattcaact ggaacggatg    480
aacgagggac aagtcagggg agagaaaaac cggttcaaga ccgcggacat catcaaggag    540
atcatccaac tcctgaatgt gcagaagaac tttcaccagc tggatgaaaa cttcattaac    600
aagtacattg aactggtgga atgcggaggg gagtacttcg agggacctgg aaagggatcc    660
ccttacggct gggaaggga ccccaaggct tggtacgaaa cgctcatggg ccattgcact    720
tactttccgg acgaactccg gtccgtgaag tacgcatact ctgccgatct gttcaatgca    780
ctcaacgacc ttaacaactt ggtgatccag cgcgatggcc tgtccaagtt ggaataccac    840
gaaaagtatc acatcatcga aacgtgttc aagcagaaaa agaagccaac tctgaagcag    900
attgccaacg aaattaacgt gaaccccgag gatatcaagg ataccggat cactaagtcc    960 ggcaaaccac agttcaccga gttcaagctg taccacgatc tgaagtcggt gctctttgac    1020
cagtccatcc tggaaaacga agatgtgctg gaccagattg ctgagatcct gaccatctac    1080
caggacaagg actcgattaa gagcaagctc acggagctgg acattctgct gaacgaagag    1140
gataaggaga acatcgcgca gctcactggt tacaccggta cccaccgctt gtcccttaag    1200
tgcatccggc tggtcctcga ggaacaatgg tactccagcc ggaaccagat ggagatcttc    1260
acgcacttga acatcaagcc gaagaagatt aacctgaccg ctgcgaacaa gatacccaag    1320
gccatgatcg acgagtttat cctctcaccg gtggtcaagc gcaccttcgg acaagccatc    1380
aacctcatca caagagattat cgagaagtac ggcgtgcctg aggatatcat catcgagctg    1440
gctcgggaga caactcaaa ggataagcag aagttcatta acgagatgca gaaaagaac    1500 gagaacactc gcaagcggat taatgagatc atcggtaaat acgggaacca gaacgccaag    1560
cggcttgtgg aaaagattcg gctccacgac gagcaggagg gaaagtgtct gtactcgctg    1620
gagagcattc ccctggagga cctcctgaac aacccaaacc actacgaagt ggatcacata    1680
atcccccgca gcgtgtcatt cgacaattcc taccataaca aggtcctcgt gaagcagtcc    1740
gagaatagca agaagtccaa cctgactccg taccagtact tcaactccgg caaatccaag    1800
ctgtcctaca accagttcaa acagcacatc ctcaacctgt caaagagcca ggacaggatc    1860
tcgaagaaga agaaggaata ccttctcgag aacgggata tcaataagtt cgaggtgcag    1920
aaggagttta tcaatagaaa cctggtggac actcgctatg ccacccgcga actgaccaac    1980
tacctgaagg cgtacttctc cgccaacaac atgaacgtga aggtcaaaac tattaacggc    2040
agcttcaccg actatctgcg caaggtctgg aagttcaaga aggaacgcaa ccacggttac    2100
aagcaccacg cggaagatgc gctgattatc gccaacgctg acttcctgtt caaggaaaac    2160
aagaagctca aggccgtgaa ctcagtgctc gagaagcctg aaatcgagac taagcagctg    2220
gacatccagg tcgattcgga agataactac tccgaaatgt tcatcatccc taagcaagtg    2280
caggacatca aggacttcag gaatttcaag tacagccatc gcgtggacaa gaagccaaac    2340
agacagctga tcaacgatac actgtattcc cccggaaga aggacaactc cacctacatc    2400
gtccaaacca ttaaggacat ctacgcaaag gacaacacca cgcttaagaa gcagttcgac    2460
```

| | |
|---|---|
| aagagccccg aaaagttcct catgtaccag cacgacccca gaaccttcga gaagcttgaa | 2520 |
| gtgatcatga agcagtacgc caacgaaaag aacccactgg ctaagtacca cgaggaaacc | 2580 |
| ggcgaatacc tgaccaagta ctccaaaaag aacaacggac cgatcgtcaa gtccctgaag | 2640 |
| tacattggga caagctcgg ctcgcacctc gatgtgaccc accagttcaa gtcctcgacc | 2700 |
| aaaaagctcg tgaagctgtc catcaagccg taccggttcg acgtgtacct gactgacaag | 2760 |
| ggatataagt tcatcaccat ttcctacctc gacgtgttga agaaggataa ctactactac | 2820 |
| attccggaac agaagtacga caagctcaag ctcggaaagg ccatcgacaa aaatgcgaag | 2880 |
| ttcatcgcga gcttctacaa gaatgacttg atcaagctgg atggcgaaat ctacaagatc | 2940 |
| atcggggtca actccgatac ccgcaacatg attgagctgg atctgcccga cattcggtac | 3000 |
| aaggaatact gcgagctgaa caacatcaag ggagaaccgc ggatcaagaa aaccatcgga | 3060 |
| aagaaagtga acagcatcga gaaactgact actgacgtcc tgggaaacgt gttcaccaac | 3120 |
| acacaataca ccaaaccccca gctgctgttt aagcgcggga ac | 3162 |

<210> SEQ ID NO 19
<211> LENGTH: 3162
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized SluCas9-2 polynucleotide

<400> SEQUENCE: 19

| | |
|---|---|
| atgaaccaga agttcatcct gggcctcgac atcggcatca cctctgttgg ctacggcctg | 60 |
| atcgactacg agacaaagaa catcatcgat gccggcgtgc ggctgttccc tgaggccaac | 120 |
| gtggaaaaca cgagggccg cagaagcaag agaggcagca aaggctgaa gcggcggaga | 180 |
| atccaccggc tggaaagagt gaagaagctg ctcgaggact acaacctgct ggaccagtct | 240 |
| cagatccctc agagcacaaa ccccctacgcc atcgagtga agggcctgtc tgaggccctg | 300 |
| agcaaggacg agctggttat cgccctgctg cacattgcca gcggagagg catccacaag | 360 |
| atcgacgtga tcgacagcaa cgacgacgtg ggcaatgagc tgagcaccaa agagcagctg | 420 |
| aacaagaaca gcaagctgct gaaggacaag ttcgtgtgcc agattcagct ggaacggatg | 480 |
| aatgagggcc aagtgcgggg cgagaagaac agattcaaga ccgccgacat catcaaagag | 540 |
| atcatccagc tgctcaacgt gcagaagaac ttccaccagc tggacgagaa cttcatcaac | 600 |
| aagtacatcg agctggtcga gatgcggcgc gagtactttg aaggccctgg aaagggcagc | 660 |
| ccttatggct gggaaggcga tcccaaggct tggtacgaga cactgatggg ccactgcacc | 720 |
| tactttcccg acgagctgag aagcgtgaag tacgcctaca cgccgacct gttcaacgcc | 780 |
| ctgaacgacc tgaacaacct cgtgatccag agagatggcc tgtccaagct ggaataccac | 840 |
| gagaagtacc acatcattga aacgtgttc aagcagaaga gaagcccac actgaagcag | 900 |
| atcgccaacg agatcaacgt gaaccccgag acatcaagg gctacagaat caccaagagc | 960 |
| ggcaagcccc agttcaccga gttcaagctg taccacgatc tgaagtccgt gctgttcgac | 1020 |
| cagagcatcc tggaaaacga ggacgtgctg gatcagatcc ccgagatcct gaccatctac | 1080 |
| caggacaagg acagcatcaa gagcaagctg accgagctgg acatcctgct gaacgaagag | 1140 |
| gacaaagaga atatcgccca gctgaccggc tacaccggca cacatagact gagcctgaag | 1200 |
| tgcatccggc tggtgctgga agaacagtgg tactccagcc ggaaccagat ggaaatcttc | 1260 |

```
acccacctga acatcaagcc caagaagatc aacctgaccg ccgccaacaa gatccccaag    1320
gccatgatcg acgagttcat tctgagcccc gtggtcaaga gaaccttcgg ccaggccatc    1380
aatctgatca acaagattat cgagaagtat ggcgtgcccg aggatatcat catcgaactg    1440
gccagagaga acaacagcaa ggacaagcaa aagttcatca acgagatgca gaaaaagaac    1500
gagaacaccc ggaagcggat caacgaaatc atcgggaagt acggcaacca gaacgccaag    1560
agactggtgg aaaagatccg gctgcacgac gagcaagagg gcaagtgtct gtacagcctg    1620
gaatctatcc ctctcgagga tctgctgaac aatcccaacc actacgaggt ggaccacatt    1680
atccccagaa gcgtgtcctt cgacaacagc taccacaaca aggtgctggt caagcagagc    1740
gagaactcca agaagtccaa tctgaccect taccagtact tcaacagcgg caagtctaag    1800
ctgagctaca accagtttaa gcagcacatc ctgaacctca gcaagagcca ggaccggatc    1860
agcaagaaga gaaagagta cctgctcgaa gagagggaca ttaacaagtt cgaggtgcag    1920
aaagagtta tcaaccggaa cctggtggac accagatacg ccaccagaga gctgaccaac    1980
tacctgaagg cctacttcag cgccaacaac atgaacgtga agtcaagac catcaacggc    2040
agcttcaccg actacctgcg gaaagtgtgg aagtttaaga agagcggaa ccacggctac    2100
aagcaccacg ccgaagatgc cctgattatc gccaatgccg acttcctgtt caagagaaac    2160
aagaaactga aggccgtgaa cagcgtgctg aaaagcccg agatcgagac aaaacagctc    2220
gacatccagg tggacagcga ggacaactac agcgagatgt tcatcatccc caacaggtg    2280
caggatatca aggacttccg gaacttcaag tacagccacc gcgtggacaa gaagcctaac    2340
cggcagctga tcaatgacac cctgtacagc cccgcaaga ggacaacag cacctacatc    2400
gtgcagacga tcaaggacat ctacgccaag gacaatacga ccctgaagaa gcagttcgac    2460
aagagccccg agaagttcct gatgtaccag cacgaccca ggaccttcga aagctggaa    2520
gtgatcatga agcagtacgc taatgagaag aacccgctgg ccaagtacca cgaggaaacc    2580
ggcgagtacc tgaccaagta ctctaagaag aacaacggcc ccatcgtgaa gtccctgaag    2640
tatatcggca acaagctggg cagccacctg gacgtgacac accagttcaa gagcagcacc    2700
aagaagctgg tcaaactgtc catcaagcca taccgcttcg acgtgtacct gacagacaag    2760
gggtacaagt ttatcaccat cagctacctc gacgtgctga gaaggataa ctactactac    2820
atccccgagc agaagtacga caagctgaag ctgggaaaag ccatcgacaa gaatgccaag    2880
ttcattgcca gcttctacaa gaacgacctc atcaagctgg acggcgagat ctacaagatc    2940
atcggcgtga actccgacac acggaacatg attgagctgg acctgcctga catccggtac    3000
aaagagtact gcgaactgaa caatatcaag ggcgagccc ggatcaaaaa gacgatcggc    3060
aagaaagtga acagcattga gaagctgacc ccgatgtgc tgggcaatgt gttcaccaac    3120
acacagtaca ccaagcctca gctgctgttc aagcggggca at                       3162
```

<210> SEQ ID NO 20
<211> LENGTH: 47
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 5 prime UTR
<400> SEQUENCE: 20

```
aggaaataag agagaaaaga agagtaagaa gaaatataag agccacc                  47
```

```
<210> SEQ ID NO 21
<211> LENGTH: 114
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 3 prime UTR

<400> SEQUENCE: 21
gcggccgctt aattaagctg ccttctgcgg ggcttgcctt ctggccatgc ccttcttctc      60
tcccttgcac ctgtacctct tggtctttga ataaagcctg agtaggaagt ctag          114

<210> SEQ ID NO 22
<211> LENGTH: 48
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: nucleoplasmin NLS, nucleotide

<400> SEQUENCE: 22
aaacggcctg ccgcgaccaa gaaagccggc caggccaaga agaagaag                   48

<210> SEQ ID NO 23
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: nucleoplasmin NLS, amino acid

<400> SEQUENCE: 23

Lys Arg Pro Ala Ala Thr Lys Lys Ala Gly Gln Ala Lys Lys Lys Lys
1               5                  10                  15

<210> SEQ ID NO 24
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SV40 NLS, nucleotide

<400> SEQUENCE: 24
cctaagaaga agcgcaaggt c                                                21

<210> SEQ ID NO 25
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: SV40 NLS, amino acid

<400> SEQUENCE: 25

Pro Lys Lys Lys Arg Lys Val
1               5
```

```
<210> SEQ ID NO 26
<211> LENGTH: 51
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: gly-ser linker 1, nucleotide

<400> SEQUENCE: 26
ggtggtggcg atcgggggg gggcggtagc gggggggggg gctctggctc g          51

<210> SEQ ID NO 27
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: gly-ser linker 1, amino acid

<400> SEQUENCE: 27

Gly Gly Gly Gly Ser Gly Gly Gly Gly Ser Gly Gly Gly Gly Ser Gly
1               5                   10                  15

Ser

<210> SEQ ID NO 28
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: gly-ser linker 2, nucleotide

<400> SEQUENCE: 28
gggggctccg gaggatccgg tggcagcggc ccc                              33

<210> SEQ ID NO 29
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: gly-ser linker 2, amino acid

<400> SEQUENCE: 29

Gly Gly Ser Gly Gly Ser Gly Gly Ser Gly Pro
1               5                   10

<210> SEQ ID NO 30
<211> LENGTH: 18
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: gly-ser linker 3, nucleotide

<400> SEQUENCE: 30
gggggcggag gaggctca                                               18
```

<210> SEQ ID NO 31
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: gly-ser linker 3, amino acid

<400> SEQUENCE: 31

Gly Gly Gly Gly Gly Ser
1               5

<210> SEQ ID NO 32
<211> LENGTH: 18
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 6xHis tag, nucleotide

<400> SEQUENCE: 32
catcaccatc accaccat                                                    18

<210> SEQ ID NO 33
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: 6xHis tag, amino acid

<400> SEQUENCE: 33

His His His His His His
1               5

<210> SEQ ID NO 34
<211> LENGTH: 3530
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: GST3, nucleotide

<400> SEQUENCE: 34
aggaaataag agagaaaaga agagtaagaa gaaatataag agccaccatg aaacggcctg      60
ccgcgaccaa gaaagccggc caggccaaga agaagaaggg tggtggcgga tcggggggggg    120 gcggtagcgg ggggggggc tctggctcga tgaaccagaa gttcattctc ggtctggaca     180
ttggcattac tagcgtggga tacggcttga ttgactacga gactaagaac atcatcgatg    240
ccggcgtccg cctgttcccg gaagccaacg tggagaacaa tgagggccgg aggtcgaaga    300
gaggctcccg ccgcctgaag cggcggcgaa tccaccggct ggagagagtg aagctgctgc    360
tcaccgaata cgacctgatc aacaaagaac agatcccgac ctccaacaac ccgtaccaga    420
tcagagtgaa gggtctgtca gaaatcctgt ccaaggacga actggcaatc gccctgctgc    480
acctggccaa gcggcgcgga atccacaacg tggatgtggc tgccgacaag gaagaaaccg    540
cttccgactc cctgagcact aaggaccaga tcaacaagaa cgccaagttc ttggagtccc    600

```
gctacgtgtg cgagctgcag aaggaacggc tggaaaacga aggtcacgtg cgcggagtgg    660
aaaaccggtt cctgacaaag gacattgtgc gcgaagcgaa gaagatcatt gatacccaaa    720
tgcagtacta ccctgaaatc gacgagactt tcaaggaaaa gtacatttcc ctggtggaaa    780
cccggcggga atacttcgaa ggccccggac agggatcgcc gttcggatgg aacggggacc    840
tcaagaagtg gtacgagatg ctgatggggc actgtaccta ctttccgcaa gaactgcgct    900
ccgtgaagta cgcgtactcc gcggatctct caacgcgtt gaatgacctg aacaacctga     960
tcattcagag agacaattcc gaaaagctcg agtaccacga aagtatcac atcatcgaga    1020 atgtgttcaa gcagaagaag aaaccgaccc tcaagcaaat cgccaaggag attggcgtca   1080
acccagagga catcaaggga tatcggatta ccaagagcgg cactcccgag tttacctctt   1140
tcaagctgtt tcatgatctg aagaaagtcg tgaaggacca tgccattctc gacgacattg   1200
atctcctgaa tcagatcgca gagatcctga ctatctacca agacaaggac tcgattgtgg   1260
cagagctggg tcagctcgaa tacctgatgt ccgaggccga caagcagtcc atctccgaac   1320
tgacagggta cacggggact catagcctgt cgctgaagtg catgaacatg atcattgatg   1380
aactgtggca cagctccatg aaccaaatgg aagtgtttac ctacctcaac atgcgcccta   1440
agaagtacga actgaaaggc taccagcgca tccccaccga catgatcgac gacgcgatct   1500
tgtcccctgt ggtcaagagg accttcattc aatccatcaa cgtgatcaac aaggtcatcg   1560
aaaagtacgg tattccagaa gatatcatca ttgagctcgc tcgggagaac aactcggatg   1620
accggaagaa gttcatcaac aatcttcaga agaagaacga agcgactcgg aaacggatca   1680
acgagatcat cggacagacc ggaaaccaga acgccaaacg gattgtcgaa aagattagac   1740
tgcacgacca gcaggaaggg aagtgcctgt actcactcga gtcaataccg ctcgaggacc   1800
tgttgaacaa ccctaaccac tatgaagtgg accacatcat ccctcggtcc gtgagcttcg   1860
acaactcgta ccacaacaaa gtgctcgtga agcagtccga aaactccaag aaatccaacc   1920
tgaccccgta ccaatacttc aattcgggaa agtcgaagct gtcgtacaac cagttcaaac   1980
aacacatact caaccttagc aaaagccagg atcgcatttc caagaagaag aaggaatacc   2040
tcctcgagga aagggacatc aacaagttcg aagtgcagaa agagttcatc aatcgcaact   2100
tggtggatac cagatatgcc acccgggaac tcaccagcta tctcaaggcc tactttccg    2160 ccaacaacat ggacgtgaag gtcaagacca tcaacgggtc cttcactaac catctgagaa   2220
aggtctggcg gtttgacaag taccgcaacc acggatacaa gcaccacgct gaagacgctc   2280
tgatcatcgc caatgccgac ttcctgttca aggaaaacaa gaagctgcag aacacgaaca   2340
agattctgga aaagcctacc attgagaaca cactaagaa ggtcaccgtg gagaaggaag    2400
aggactacaa caacgtgttc gaaactccta aactggtgga ggatatcaag caataccgcg   2460
actacaagtt ctcacaccgg gtggacaaga aaccgaatag acagctgatc aacgacacgt   2520
tgtattccac ccggatgaag gatgagcatg actacattgt gcagactatc accgatatct   2580
acggaaaaga taacactaac ctgaagaaac aattcaacaa gaacccagag aagttcctga   2640
tgtaccagaa cgaccccaag acctttgaga agctttccat catcatgaag cagtactccg   2700
acgagaagaa cccgctggcc aagtactacg aagaaaccgg agaatacctg accaagtaca   2760
gcaagaagaa caacggtccc attgtcaaga agatcaagct gctcggcaac aaggtcggaa   2820
accacctcga cgtgacaaac aagtacgaga actcgactaa gaagcttgtg aagctgtcaa   2880
tcaagaacta tagattcgac gtgtacttga ccgaaaaggg atacaagttc gtgaccatag   2940
```

```
cctatctgaa cgtgttcaag aaagataact actactacat ccccaaggac aagtaccagg   3000
agctcaaaga aaagaagaag atcaaagaca ccgaccagtt cattgcctcc ttctacaaga   3060
acgacctgat caaactgaac ggcgacctct acaagatcat tggagtgaac agcgatgaca   3120
ggaacatcat tgagctggac tactacgaca tcaagtacaa ggactactgc gagatcaaca   3180
acatcaaggg cgaaccccgg atcaagaaaa ctattggaaa gaaaaccgag tccattgaga   3240
agttcaccac tgacgtgctg ggaaacctt  acctccactc caccgagaag caccacaac   3300 tgatcttcaa gcgcggcctg gggggctccg gaggatccgg tggcagcggc ccccgaaga   3360 agaagcgcaa agtcggggc ggaggaggct cacatcacca tcaccaccat taataagcgg   3420
ccgcttaatt aagctgcctt ctgcggggct tgccttctgg ccatgccctt cttctctccc   3480
ttgcacctgt acctcttggt ctttgaataa agcctgagta ggaagtctag   3530
```

<210> SEQ ID NO 35
<211> LENGTH: 1121
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: GST3, amino acid

<400> SEQUENCE: 35

```
Met Lys Arg Pro Ala Ala Thr Lys Lys Ala Gly Gln Ala Lys Lys Lys
1               5                   10                  15

Lys Gly Gly Gly Gly Ser Gly Gly Gly Ser Gly Gly Gly Gly Ser
            20                  25                  30

Gly Ser Met Asn Gln Lys Phe Ile Leu Gly Leu Asp Ile Gly Ile Thr
        35                  40                  45

Ser Val Gly Tyr Gly Leu Ile Asp Tyr Glu Thr Lys Asn Ile Ile Asp
    50                  55                  60

Ala Gly Val Arg Leu Phe Pro Glu Ala Asn Val Glu Asn Asn Glu Gly
65                  70                  75                  80

Arg Arg Ser Lys Arg Gly Ser Arg Arg Leu Lys Arg Arg Arg Ile His
                85                  90                  95

Arg Leu Glu Arg Val Lys Leu Leu Leu Thr Glu Tyr Asp Leu Ile Asn
            100                 105                 110

Lys Glu Gln Ile Pro Thr Ser Asn Asn Pro Tyr Gln Ile Arg Val Lys
        115                 120                 125

Gly Leu Ser Glu Ile Leu Ser Lys Asp Glu Leu Ala Ile Ala Leu Leu
    130                 135                 140

His Leu Ala Lys Arg Arg Gly Ile His Asn Val Asp Val Ala Ala Asp
145                 150                 155                 160

Lys Glu Glu Thr Ala Ser Asp Ser Leu Ser Thr Lys Asp Gln Ile Asn
                165                 170                 175

Lys Asn Ala Lys Phe Leu Glu Ser Arg Tyr Val Cys Glu Leu Gln Lys
            180                 185                 190

Glu Arg Leu Glu Asn Glu Gly His Val Arg Gly Val Gly Asn Arg Phe
        195                 200                 205

Leu Thr Lys Asp Ile Val Arg Glu Ala Lys Lys Ile Ile Asp Thr Gln
    210                 215                 220

Met Gln Tyr Tyr Pro Glu Ile Asp Glu Thr Phe Lys Glu Lys Tyr Ile
225                 230                 235                 240
```

```
Ser Leu Val Glu Thr Arg Arg Glu Tyr Phe Glu Gly Pro Gly Gln Gly
                245                 250                 255

Ser Pro Phe Gly Trp Asn Gly Asp Leu Lys Lys Trp Tyr Glu Met Leu
                260                 265                 270

Met Gly His Cys Thr Tyr Phe Pro Gln Glu Leu Arg Ser Val Lys Tyr
                275                 280                 285

Ala Tyr Ser Ala Asp Leu Phe Asn Ala Leu Asn Asp Leu Asn Asn Leu
                290                 295                 300

Ile Ile Gln Arg Asp Asn Ser Glu Lys Leu Glu Tyr His Glu Lys Tyr
305                 310                 315                 320

His Ile Ile Glu Asn Val Phe Lys Gln Lys Lys Pro Thr Leu Lys
                325                 330                 335

Gln Ile Ala Lys Glu Ile Gly Val Asn Pro Glu Asp Ile Lys Gly Tyr
                340                 345                 350

Arg Ile Thr Lys Ser Gly Thr Pro Glu Phe Thr Ser Phe Lys Leu Phe
                355                 360                 365

His Asp Leu Lys Lys Val Val Lys Asp His Ala Ile Leu Asp Asp Ile
                370                 375                 380

Asp Leu Leu Asn Gln Ile Ala Glu Ile Leu Thr Ile Tyr Gln Asp Lys
385                 390                 395                 400

Asp Ser Ile Val Ala Glu Leu Gly Gln Leu Glu Tyr Leu Met Ser Glu
                405                 410                 415

Ala Asp Lys Gln Ser Ile Ser Glu Leu Thr Gly Tyr Thr Gly Thr His
                420                 425                 430

Ser Leu Ser Leu Lys Cys Met Asn Met Ile Ile Asp Glu Leu Trp His
                435                 440                 445

Ser Ser Met Asn Gln Met Glu Val Phe Thr Tyr Leu Asn Met Arg Pro
450                 455                 460

Lys Lys Tyr Glu Leu Lys Gly Tyr Gln Arg Ile Pro Thr Asp Met Ile
465                 470                 475                 480

Asp Asp Ala Ile Leu Ser Pro Val Val Lys Arg Thr Phe Ile Gln Ser
                485                 490                 495

Ile Asn Val Ile Asn Lys Val Ile Glu Lys Tyr Gly Ile Pro Glu Asp
                500                 505                 510

Ile Ile Ile Glu Leu Ala Arg Glu Asn Asn Ser Asp Asp Arg Lys Lys
                515                 520                 525

Phe Ile Asn Asn Leu Gln Lys Lys Asn Glu Ala Thr Arg Lys Arg Ile
                530                 535                 540

Asn Glu Ile Ile Gly Gln Thr Gly Asn Gln Asn Ala Lys Arg Ile Val
545                 550                 555                 560

Glu Lys Ile Arg Leu His Asp Gln Gln Glu Gly Lys Cys Leu Tyr Ser
                565                 570                 575

Leu Glu Ser Ile Pro Leu Glu Asp Leu Leu Asn Asn Pro Asn His Tyr
                580                 585                 590

Glu Val Asp His Ile Ile Pro Arg Ser Val Ser Phe Asp Asn Ser Tyr
                595                 600                 605

His Asn Lys Val Leu Val Lys Gln Ser Glu Asn Ser Lys Lys Ser Asn
                610                 615                 620

Leu Thr Pro Tyr Gln Tyr Phe Asn Ser Gly Lys Ser Lys Leu Ser Tyr
625                 630                 635                 640

Asn Gln Phe Lys Gln His Ile Leu Asn Leu Ser Lys Ser Gln Asp Arg
                645                 650                 655
```

```
Ile Ser Lys Lys Lys Lys Glu Tyr Leu Leu Glu Glu Arg Asp Ile Asn
            660                 665                 670

Lys Phe Glu Val Gln Lys Glu Phe Ile Asn Arg Asn Leu Val Asp Thr
        675                 680                 685

Arg Tyr Ala Thr Arg Glu Leu Thr Ser Tyr Leu Lys Ala Tyr Phe Ser
    690                 695                 700

Ala Asn Asn Met Asp Val Lys Val Lys Thr Ile Asn Gly Ser Phe Thr
705                 710                 715                 720

Asn His Leu Arg Lys Val Trp Arg Phe Asp Lys Tyr Arg Asn His Gly
            725                 730                 735

Tyr Lys His His Ala Glu Asp Ala Leu Ile Ile Ala Asn Ala Asp Phe
        740                 745                 750

Leu Phe Lys Glu Asn Lys Lys Leu Gln Asn Thr Asn Lys Ile Leu Glu
    755                 760                 765

Lys Pro Thr Ile Glu Asn Asn Thr Lys Val Thr Val Glu Lys Glu
770                 775                 780

Glu Asp Tyr Asn Asn Val Phe Glu Thr Pro Lys Leu Val Glu Asp Ile
785                 790                 795                 800

Lys Gln Tyr Arg Asp Tyr Lys Phe Ser His Arg Val Asp Lys Lys Pro
            805                 810                 815

Asn Arg Gln Leu Ile Asn Asp Thr Leu Tyr Ser Thr Arg Met Lys Asp
        820                 825                 830

Glu His Asp Tyr Ile Val Gln Thr Ile Thr Asp Ile Tyr Gly Lys Asp
    835                 840                 845

Asn Thr Asn Leu Lys Lys Gln Phe Asn Lys Asn Pro Glu Lys Phe Leu
850                 855                 860

Met Tyr Gln Asn Asp Pro Lys Thr Phe Glu Lys Leu Ser Ile Ile Met
865                 870                 875                 880

Lys Gln Tyr Ser Asp Glu Lys Asn Pro Leu Ala Lys Tyr Tyr Glu Glu
            885                 890                 895

Thr Gly Glu Tyr Leu Thr Lys Tyr Ser Lys Lys Asn Asn Gly Pro Ile
        900                 905                 910

Val Lys Lys Ile Lys Leu Leu Gly Asn Lys Val Gly Asn His Leu Asp
    915                 920                 925

Val Thr Asn Lys Tyr Glu Asn Ser Thr Lys Lys Leu Val Lys Leu Ser
930                 935                 940

Ile Lys Asn Tyr Arg Phe Asp Val Tyr Leu Thr Glu Lys Gly Tyr Lys
945                 950                 955                 960

Phe Val Thr Ile Ala Tyr Leu Asn Val Phe Lys Lys Asp Asn Tyr Tyr
            965                 970                 975

Tyr Ile Pro Lys Asp Lys Tyr Gln Glu Leu Lys Glu Lys Lys Lys Ile
        980                 985                 990

Lys Asp Thr Asp Gln Phe Ile Ala Ser Phe Tyr Lys Asn Asp Leu Ile
    995                 1000                1005

Lys Leu Asn Gly Asp Leu Tyr Lys Ile Ile Gly Val Asn Ser Asp
        1010                1015                1020

Asp Arg Asn Ile Ile Glu Leu Asp Tyr Tyr Asp Ile Lys Tyr Lys
        1025                1030                1035

Asp Tyr Cys Glu Ile Asn Asn Ile Lys Gly Glu Pro Arg Ile Lys
        1040                1045                1050

Lys Thr Ile Gly Lys Lys Thr Glu Ser Ile Glu Lys Phe Thr Thr
        1055                1060                1065
```

```
Asp Val Leu Gly Asn Leu Tyr Leu His Ser Thr Glu Lys Ala Pro
    1070              1075                1080

Gln Leu Ile Phe Lys Arg Gly Leu Gly Gly Ser Gly Gly Ser Gly
    1085              1090                1095

Gly Ser Gly Pro Pro Lys Lys Lys Arg Lys Val Gly Gly Gly Gly
    1100              1105                1110

Gly Ser His His His His His His
    1115              1120

<210> SEQ ID NO 36
<211> LENGTH: 3533
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: GST3-K, nucleotide

<400> SEQUENCE: 36
aggaaataag agagaaaaga agagtaagaa gaaatataag agccaccatg gcgaaacggc     60
ctgccgcgac caagaaagcc ggccaggcca agaagaagaa gggtggtggc ggatcggggg    120
ggggcggtag cggggggggg ggctctggct cgatgaacca gaagttcatt ctcggtctgg    180
acattggcat tactagcgtg ggatacggct tgattgacta cgagactaag aacatcatcg    240
atgccggcgt ccgcctgttc ccggaagcca acgtggagaa caatgagggc cggaggtcga    300
agagaggctc ccgccgcctg aagcggcggc gaatccaccg gctggagaga gtgaagctgc    360
tgctcaccga atacgacctg atcaacaaag aacagatccc gacctccaac aacccgtacc    420
agatcagagt gaagggtctg tcagaaatcc tgtccaagga cgaactggca atcgccctgc    480
tgcacctggc caagcggcgc ggaatccaca acgtggatgt ggctgccgac aaggaagaaa    540
ccgcttccga ctccctgagc actaaggacc agatcaacaa gaacgccaag ttcttggagt    600
cccgctacgt gtgcgagctg cagaaggaac ggctggaaaa cgaaggtcac gtgcgcggag    660
tggaaaaccg gttcctgaca aaggacattg tgcgcgaagc gaagaagatc attgataccc    720
aaatgcagta ctaccctgaa atcgacgaga cttttcaagga aaagtacatt tccctggtgg    780
aaacccggcg ggaatacttc gaaggccccg acagggatc gccgttcgga tggaacgggg    840
acctcaagaa gtggtacgag atgctgatgg ggcactgtac ctactttccg caagaactgc    900
gctccgtgaa gtacgcgtac tccgcggatc tcttcaacgc gttgaatgac ctgaacaacc    960
tgatcattca gagagacaat tccgaaaagc tcgagtacca cgagaagtat cacatcatcg   1020
agaatgtgtt caagcagaag aagaaaccga ccctcaagca aatcgccaag gagattggcg   1080
tcaacccaga ggacatcaag ggatatcgga ttaccaagag cggcactccc gagtttacct   1140
ctttcaagct gtttcatgat ctgaagaaag tcgtgaagga ccatgccatt ctcgacgaca   1200
ttgatctcct gaatcagatc gcagagatcc tgactatcta ccaagacaag gactcgattg   1260
tggcagagct gggtcagctc gaatacctga tgtccgaggc cgacaagcag tccatctccg   1320
aactgacagg gtacacgggg actcatagcc tgtcgctgaa gtgcatgaac atgatcattg   1380
atgaactgtg gcacagctcc atgaaccaaa tggaagtgtt tacctacctc aacatgcgcc   1440
ctaagaagta cgaactgaaa ggctaccagc gcatccccac cgacatgatc gacgacgcga   1500
tcttgtcccc tgtggtcaag aggaccttca ttcaatccat caacgtgatc aacaaggtca   1560
tcgaaaagta cggtattcca gaagatatca tcattgagct cgctcgggag aacaactcgg   1620
```

```
atgaccggaa gaagttcatc aacaatcttc agaagaagaa cgaagcgact cggaaacgga      1680
tcaacgagat catcggacag accggaaacc agaacgccaa acggattgtc gaaaagatta      1740
gactgcacga ccagcaggaa gggaagtgcc tgtactcact cgagtcaata ccgctcgagg      1800
acctgttgaa caaccctaac cactatgaag tggaccacat catccctcgg tccgtgagct      1860
tcgacaactc gtaccacaac aaagtgctcg tgaagcagtc cgaaaactcc aagaaatcca      1920
acctgacccc gtaccaatac ttcaattcgg gaaagtcgaa gctgtcgtac aaccagttca      1980
aacaacacat actcaacctt agcaaaagcc aggatcgcat ttccaagaag aagaaggaat      2040
acctcctcga ggaaagggac atcaacaagt tcgaagtgca gaaagagttc atcaatcgca      2100
acttggtgga taccagatat gccacccggg aactcaccag ctatctcaag gcctactttt      2160
ccgccaacaa catggacgtg aaggtcaaga ccatcaacgg gtccttcact aaccatctga      2220
gaaaggtctg gcggtttgac aagtaccgca accacggata caagcaccac gctgaagacg      2280
ctctgatcat cgccaatgcc gacttcctgt tcaaggaaaa caagaagctg cagaacacga      2340
acaagattct ggaaaagcct accattgaga caacactaa gaaggtcacc gtggagaagg       2400
aagaggacta caacaacgtg ttcgaaactc ctaaactggt ggaggatatc aagcaatacc      2460
gcgactacaa gttctcacac cgggtggaca gaaaaccgaa tagacagctg atcaacgaca      2520
cgttgtattc cacccggatg aaggatgagc atgactacat tgtgcagact atcaccgata      2580
tctacggaaa agataacact aacctgaaga aacaattcaa caagaaccca gagaagttcc      2640
tgatgtacca gaacgacccc aagacctttg agaagctttc catcatcatg aagcagtact      2700
ccgacgagaa gaacccgctg gccaagtact acgaagaaac cggagaatac ctgaccaagt      2760
acagcaagaa gaacaacggt cccattgtca agaagatcaa gctgctcggc aacaaggtcg      2820
gaaaccacct cgacgtgaca aacaagtacg agaactcgac taagaagctt gtgaagctgt      2880
caatcaagaa ctatagattc gacgtgtact tgaccgaaaa gggatacaag ttcgtgacca      2940
tagcctatct gaacgtgttc aagaaagata actactacta catccccaag gacaagtacc      3000
aggagctcaa agaaaagaag aagatcaaag acaccgacca gttcattgcc tccttctaca      3060
agaacgacct gatcaaactg aacggcgacc tctacaagat cattggagtg aacagcgatg      3120
acaggaacat cattgagctg gactactacg acatcaagta caaggactac tgcgagatca      3180
acaacatcaa gggcgaaccc cggatcaaga aaactattgg aaagaaaacc gagtccattg      3240
agaagttcac cactgacgtg ctgggaaacc tttacctcca ctccaccgag aaggcaccac      3300
aactgatctt caagcgcggc ctggggggct ccggaggatc cggtggcagc ggccccccga      3360
agaagaagcg caaagtcggg ggcggaggag gctcacatca ccatcaccac cattgataag      3420
cggccgctta attaagctgc cttctgcggg gcttgccttc tggccatgcc cttcttctct      3480
cccttgcacc tgtacctctt ggtctttgaa taaagcctga gtaggaagtc tag            3533
```

<210> SEQ ID NO 37
<211> LENGTH: 1122
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: GST3-K, amino acid

```
<400> SEQUENCE: 37

Met Ala Lys Arg Pro Ala Ala Thr Lys Lys Ala Gly Gln Ala Lys Lys
1               5                   10                  15

Lys Lys Gly Gly Gly Ser Gly Gly Gly Ser Gly Gly Gly
            20                  25                  30

Ser Gly Ser Met Asn Gln Lys Phe Ile Leu Gly Leu Asp Ile Gly Ile
        35                  40                  45

Thr Ser Val Gly Tyr Gly Leu Ile Asp Tyr Glu Thr Lys Asn Ile Ile
50                      55                  60

Asp Ala Gly Val Arg Leu Phe Pro Glu Ala Asn Val Glu Asn Asn Glu
65                  70                  75                  80

Gly Arg Arg Ser Lys Arg Gly Ser Arg Arg Leu Lys Arg Arg Arg Ile
                85                  90                  95

His Arg Leu Glu Arg Val Lys Leu Leu Leu Thr Glu Tyr Asp Leu Ile
                100                 105                 110

Asn Lys Glu Gln Ile Pro Thr Ser Asn Pro Tyr Gln Ile Arg Val
            115                 120                 125

Lys Gly Leu Ser Glu Ile Leu Ser Lys Asp Glu Leu Ala Ile Ala Leu
            130                 135                 140

Leu His Leu Ala Lys Arg Arg Gly Ile His Asn Val Asp Val Ala Ala
145                 150                 155                 160

Asp Lys Glu Glu Thr Ala Ser Asp Ser Leu Ser Thr Lys Asp Gln Ile
                165                 170                 175

Asn Lys Asn Ala Lys Phe Leu Glu Ser Arg Tyr Val Cys Glu Leu Gln
            180                 185                 190

Lys Glu Arg Leu Glu Asn Glu Gly His Val Arg Gly Val Glu Asn Arg
                195                 200                 205

Phe Leu Thr Lys Asp Ile Val Arg Glu Ala Lys Lys Ile Ile Asp Thr
            210                 215                 220

Gln Met Gln Tyr Tyr Pro Glu Ile Asp Glu Thr Phe Lys Glu Lys Tyr
225                 230                 235                 240

Ile Ser Leu Val Glu Thr Arg Arg Glu Tyr Phe Glu Gly Pro Gly Gln
                245                 250                 255

Gly Ser Pro Phe Gly Trp Asn Gly Asp Leu Lys Lys Trp Tyr Glu Met
            260                 265                 270

Leu Met Gly His Cys Thr Tyr Phe Pro Gln Glu Leu Arg Ser Val Lys
            275                 280                 285

Tyr Ala Tyr Ser Ala Asp Leu Phe Asn Ala Leu Asn Asp Leu Asn Asn
290                 295                 300

Leu Ile Ile Gln Arg Asp Asn Ser Glu Lys Leu Glu Tyr His Glu Lys
305                 310                 315                 320

Tyr His Ile Ile Glu Asn Val Phe Lys Gln Lys Lys Pro Thr Leu
                325                 330                 335

Lys Gln Ile Ala Lys Glu Ile Gly Val Asn Pro Glu Asp Ile Lys Gly
            340                 345                 350

Tyr Arg Ile Thr Lys Ser Gly Thr Pro Glu Phe Thr Ser Phe Lys Leu
                355                 360                 365

Phe His Asp Leu Lys Lys Val Val Lys Asp His Ala Ile Leu Asp Asp
            370                 375                 380

Ile Asp Leu Leu Asn Gln Ile Ala Glu Ile Leu Thr Ile Tyr Gln Asp
385                 390                 395                 400
```

-continued

```
Lys Asp Ser Ile Val Ala Glu Leu Gly Gln Leu Glu Tyr Leu Met Ser
            405                 410                 415
Glu Ala Asp Lys Gln Ser Ile Ser Glu Leu Thr Gly Tyr Thr Gly Thr
            420                 425                 430
His Ser Leu Ser Leu Lys Cys Met Asn Met Ile Ile Asp Glu Leu Trp
            435                 440                 445
His Ser Ser Met Asn Gln Met Glu Val Phe Thr Tyr Leu Asn Met Arg
        450                 455                 460
Pro Lys Lys Tyr Glu Leu Lys Gly Tyr Gln Arg Ile Pro Thr Asp Met
465                 470                 475                 480
Ile Asp Asp Ala Ile Leu Ser Pro Val Val Lys Arg Thr Phe Ile Gln
                485                 490                 495
Ser Ile Asn Val Ile Asn Lys Val Ile Glu Lys Tyr Gly Ile Pro Glu
                500                 505                 510
Asp Ile Ile Ile Glu Leu Ala Arg Glu Asn Asn Ser Asp Asp Arg Lys
            515                 520                 525
Lys Phe Ile Asn Asn Leu Gln Lys Lys Asn Glu Ala Thr Arg Lys Arg
            530                 535                 540
Ile Asn Glu Ile Ile Gly Gln Thr Gly Asn Gln Asn Ala Lys Arg Ile
545                 550                 555                 560
Val Glu Lys Ile Arg Leu His Asp Gln Gln Glu Gly Lys Cys Leu Tyr
                565                 570                 575
Ser Leu Glu Ser Ile Pro Leu Glu Asp Leu Leu Asn Asn Pro Asn His
            580                 585                 590
Tyr Glu Val Asp His Ile Ile Pro Arg Ser Val Ser Phe Asp Asn Ser
            595                 600                 605
Tyr His Asn Lys Val Leu Val Lys Gln Ser Glu Asn Ser Lys Lys Ser
        610                 615                 620
Asn Leu Thr Pro Tyr Gln Tyr Phe Asn Ser Gly Lys Ser Lys Leu Ser
625                 630                 635                 640
Tyr Asn Gln Phe Lys Gln His Ile Leu Asn Leu Ser Lys Ser Gln Asp
                645                 650                 655
Arg Ile Ser Lys Lys Lys Glu Tyr Leu Leu Glu Glu Arg Asp Ile
            660                 665                 670
Asn Lys Phe Glu Val Gln Lys Glu Phe Ile Asn Arg Asn Leu Val Asp
        675                 680                 685
Thr Arg Tyr Ala Thr Arg Glu Leu Thr Ser Tyr Leu Lys Ala Tyr Phe
    690                 695                 700
Ser Ala Asn Asn Met Asp Val Lys Val Lys Thr Ile Asn Gly Ser Phe
705                 710                 715                 720
Thr Asn His Leu Arg Lys Val Trp Arg Phe Asp Lys Tyr Arg Asn His
            725                 730                 735
Gly Tyr Lys His His Ala Glu Asp Ala Leu Ile Ile Ala Asn Ala Asp
            740                 745                 750
Phe Leu Phe Lys Glu Asn Lys Lys Leu Gln Asn Thr Asn Lys Ile Leu
        755                 760                 765
Glu Lys Pro Thr Ile Glu Asn Asn Thr Lys Lys Val Thr Val Glu Lys
    770                 775                 780
Glu Glu Asp Tyr Asn Asn Val Phe Glu Thr Pro Lys Leu Val Glu Asp
785                 790                 795                 800
Ile Lys Gln Tyr Arg Asp Tyr Lys Phe Ser His Arg Val Asp Lys Lys
                805                 810                 815
```

Pro Asn Arg Gln Leu Ile Asn Asp Thr Leu Tyr Ser Thr Arg Met Lys
            820                 825                 830

Asp Glu His Asp Tyr Ile Val Gln Thr Ile Thr Asp Ile Tyr Gly Lys
        835                 840                 845

Asp Asn Thr Asn Leu Lys Lys Gln Phe Asn Lys Asn Pro Glu Lys Phe
    850                 855                 860

Leu Met Tyr Gln Asn Asp Pro Lys Thr Phe Glu Lys Leu Ser Ile Ile
865                 870                 875                 880

Met Lys Gln Tyr Ser Asp Glu Lys Asn Pro Leu Ala Lys Tyr Tyr Glu
                885                 890                 895

Glu Thr Gly Glu Tyr Leu Thr Lys Tyr Ser Lys Lys Asn Asn Gly Pro
            900                 905                 910

Ile Val Lys Lys Ile Lys Leu Leu Gly Asn Lys Val Gly Asn His Leu
        915                 920                 925

Asp Val Thr Asn Lys Tyr Glu Asn Ser Thr Lys Lys Leu Val Lys Leu
    930                 935                 940

Ser Ile Lys Asn Tyr Arg Phe Asp Val Tyr Leu Thr Glu Lys Gly Tyr
945                 950                 955                 960

Lys Phe Val Thr Ile Ala Tyr Leu Asn Val Phe Lys Lys Asp Asn Tyr
                965                 970                 975

Tyr Tyr Ile Pro Lys Asp Lys Tyr Gln Glu Leu Lys Glu Lys Lys
            980                 985                 990

Ile Lys Asp Thr Asp Gln Phe Ile Ala Ser Phe Tyr Lys Asn Asp Leu
            995                 1000                1005

Ile Lys Leu Asn Gly Asp Leu Tyr Lys Ile Ile Gly Val Asn Ser
    1010                1015                1020

Asp Asp Arg Asn Ile Ile Glu Leu Asp Tyr Tyr Asp Ile Lys Tyr
    1025                1030                1035

Lys Asp Tyr Cys Glu Ile Asn Asn Ile Lys Gly Glu Pro Arg Ile
    1040                1045                1050

Lys Lys Thr Ile Gly Lys Lys Thr Glu Ser Ile Glu Lys Phe Thr
    1055                1060                1065

Thr Asp Val Leu Gly Asn Leu Tyr Leu His Ser Thr Glu Lys Ala
    1070                1075                1080

Pro Gln Leu Ile Phe Lys Arg Gly Leu Gly Gly Ser Gly Gly Ser
    1085                1090                1095

Gly Gly Ser Gly Pro Pro Lys Lys Lys Arg Lys Val Gly Gly Gly
    1100                1105                1110

Gly Gly Ser His His His His His His
    1115                1120

<210> SEQ ID NO 38
<211> LENGTH: 3410
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: GST3-v1, nucleotide

<400> SEQUENCE: 38
aggaaataag agagaaaaga agagtaagaa gaaatataag agccaccatg gcccctaaga      60
agaagcgcaa ggtcatgaac cagaagttca ttctcggtct ggacattggc attactagcg     120
tgggatacgg cttgattgac tacgagacta agaacatcat cgatgccggc gtccgcctgt     180

```
tcccggaagc caacgtggag aacaatgagg gccggaggtc gaagagaggc tcccgccgcc    240
tgaagcggcg gcgaatccac cggctggaga gagtgaagct gctgctcacc gaatacgacc    300
tgatcaacaa agaacagatc ccgacctcca acaacccgta ccagatcaga gtgaagggtc    360
tgtcagaaat cctgtccaag gacgaactgg caatcgccct gctgcacctg gccaagcggc    420
gcggaatcca caacgtggat gtggctgccg acaaggaaga aaccgcttcc gactccctga    480
gcactaagga ccagatcaac aagaacgcca agttcttgga gtcccgctac gtgtgcgagc    540
tgcagaagga acggctggaa aacgaaggtc acgtgcgcgg agtggaaaac cggttcctga    600
caaaggacat tgtgcgcgaa gcgaagaaga tcattgatac ccaaatgcag tactaccctg    660
aaatcgacga gactttcaag gaaaagtaca tttccctggt ggaaacccgg cgggaatact    720
tcgaaggccc cggacaggga tcgccgttcg gatggaacgg ggacctcaag aagtggtacg    780
agatgctgat ggggcactgt acctactttc gcaagaact gcgctccgtg aagtacgcgt    840
actccgcgga tctcttcaac gcgttgaatg acctgaacaa cctgatcatt cagagagaca    900
attccgaaaa gctcgagtac cacgagaagt atcacatcat cgagaatgtg ttcaagcaga    960
agaagaaacc gaccctcaag caaatcgcca aggagattgg cgtcaaccca gaggacatca   1020
agggatatcg gattaccaag agcggcactc ccgagtttac ctctttcaag ctgtttcatg   1080
atctgaagaa agtcgtgaag gaccatgcca ttctcgacga cattgatctc ctgaatcaga   1140
tcgcagagat cctgactatc taccaagaca aggactcgat tgtggcagag ctgggtcagc   1200
tcgaatacct gatgtccgag gccgacaagc agtccatctc cgaactgaca gggtacacgg   1260
ggactcatag cctgtcgctg aagtgcatga acatgatcat tgatgaactg tggcacagct   1320
ccatgaacca aatggaagtg tttacctacc tcaacatgcg ccctaagaag tacgaactga   1380
aaggctacca gcgcatcccc accgacatga tcgacgacgc gatcttgtcc cctgtggtca   1440
agaggacctt cattcaatcc atcaacgtga tcaacaaggt catcgaaaag tacggaatac   1500
cagaagatat catcattgag ctcgctcggg agaacaactc ggatgaccgg aagaagttca   1560
tcaacaatct tcagaagaag aacgaagcga ctcggaaacg gatcaacgag atcatcggac   1620
agaccggaaa ccagaacgcc aaacggattg tcgaaaagat tagactgcac gaccagcagg   1680
aagggaagtg cctgtactca ctcgagtcaa taccgctcga ggaccgttg aacaaccta    1740 accactatga agtggaccac atcatccctc ggtcgtgag cttcgacaac tcgtaccaca   1800
acaaagtgct cgtgaagcag tccgaaaact ccaagaaatc caacctgacc ccgtaccaat   1860
acttcaattc gggaaagtcg aagctgtcgt acaaccagtt caaacaacac atactcaacc   1920
ttagcaaaag ccaggatcgc atttccaaga agaagaagga ataccctcctc gaggaaaggg   1980 acatcaacaa gttcgaagtg cagaaagagt tcatcaatcg caacttggtg gataccagat   2040
atgccacccg ggaactcacc agctatctca aggcctactt ttccgccaac aacatggacg   2100
tgaaggtcaa gaccatcaac gggtccttca ctaaccatct gagaaaggtc tggcggtttg   2160
acaagtaccg caaccacgga tacaagcacc acgctgagga cgctctgatc atcgccaatg   2220
ccgacttcct gttcaaggaa aacaagaagc tgcagaacac gaacaagatt ctggaaaagc   2280
ctaccattga gaacaacact aagaaggtca ccgtggagaa ggaagaggac tacaacaacg   2340
tgttcgaaac tcctaaactg gtggaggata tcaagcaata ccgcgactac aagttctcac   2400
accgggtgga caagaaaccg aatagacagc tgatcaacga cacgttgtat tccacccgga   2460
tgaaggatga gcatgactac attgtgcaga ctatcaccga tatctacgga aaagataaca   2520
ctaacctgaa gaaacaattc aacaagaacc cagagaagtt cctgatgtac cagaacgacc   2580
```

-continued

```
ccaagacctt tgagaagctt tccatcatca tgaagcagta ctccgacgag aagaacccgc    2640
tggccaagta ctacgaagaa accggagaat acctgaccaa gtacagcaag aagaacaacg    2700
gtcccattgt caagaagatc aagctgctcg gcaacaaggt cggaaaccac ctcgacgtga    2760
caaacaagta cgagaactcg actaagaagc ttgtgaagct gtcaatcaag aactatagat    2820
tcgacgtgta cttgaccgaa aagggataca agttcgtgac catagcctat ctgaacgtgt    2880
tcaagaaaga taactactac tacatcccca aggacaagta ccaggagctc aaagaaaaga    2940
agaagatcaa agacaccgac cagttcattg cctccttcta caagaacgac ctgatcaaac    3000
tgaacggcga cctctacaag atcattggag tgaacagcga tgacaggaac atcattgagc    3060
tggactacta cgacatcaag tacaaggact actgcgagat caacaacatc aagggcgaac    3120
cccggatcaa gaaaactatt ggaaagaaaa ccgagtccat tgagaagttc accactgacg    3180
tgctgggaaa cctttacctc cactccaccg agaaggcacc acaactgatc ttcaagcgcg    3240
gcctgaaacg gcccgccgca accaagaagg ccggccaggc gaagaagaag aaatgagcgg    3300
ccgcttaatt aagctgcctt ctgcggggct tgccttctgg ccatgccctt cttctctccc    3360
ttgcacctgt acctcttggt ctttgaataa agcctgagta ggaagtctag                3410
```

<210> SEQ ID NO 39
<211> LENGTH: 1082
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: GST3-v1, amino acid

<400> SEQUENCE: 39

```
Met Ala Pro Lys Lys Arg Lys Val Met Asn Gln Lys Phe Ile Leu
1               5                   10                  15

Gly Leu Asp Ile Gly Ile Thr Ser Val Gly Tyr Gly Leu Ile Asp Tyr
                20                  25                  30

Glu Thr Lys Asn Ile Ile Asp Ala Gly Val Arg Leu Phe Pro Glu Ala
            35                  40                  45

Asn Val Glu Asn Asn Glu Gly Arg Arg Ser Lys Arg Gly Ser Arg Arg
        50                  55                  60

Leu Lys Arg Arg Arg Ile His Arg Leu Glu Arg Val Lys Leu Leu Leu
65                  70                  75                  80

Thr Glu Tyr Asp Leu Ile Asn Lys Glu Gln Ile Pro Thr Ser Asn Asn
                85                  90                  95

Pro Tyr Gln Ile Arg Val Lys Gly Leu Ser Glu Ile Leu Ser Lys Asp
                100                 105                 110

Glu Leu Ala Ile Ala Leu Leu His Leu Ala Lys Arg Arg Gly Ile His
            115                 120                 125

Asn Val Asp Val Ala Ala Asp Lys Glu Glu Thr Ala Ser Asp Ser Leu
        130                 135                 140

Ser Thr Lys Asp Gln Ile Asn Lys Asn Ala Lys Phe Leu Glu Ser Arg
145                 150                 155                 160

Tyr Val Cys Glu Leu Gln Lys Glu Arg Leu Glu Asn Glu Gly His Val
                165                 170                 175

Arg Gly Val Glu Asn Arg Phe Leu Thr Lys Asp Ile Val Arg Glu Ala
                180                 185                 190
```

-continued

```
Lys Lys Ile Ile Asp Thr Gln Met Gln Tyr Tyr Pro Glu Ile Asp Glu
            195                 200                 205

Thr Phe Lys Glu Lys Tyr Ile Ser Leu Val Glu Thr Arg Arg Glu Tyr
    210                 215                 220

Phe Glu Gly Pro Gly Gln Gly Ser Pro Phe Gly Trp Asn Gly Asp Leu
225                 230                 235                 240

Lys Lys Trp Tyr Glu Met Leu Met Gly His Cys Thr Tyr Phe Pro Gln
                245                 250                 255

Glu Leu Arg Ser Val Lys Tyr Ala Tyr Ser Ala Asp Leu Phe Asn Ala
                260                 265                 270

Leu Asn Asp Leu Asn Asn Leu Ile Ile Gln Arg Asp Asn Ser Glu Lys
                275                 280                 285

Leu Glu Tyr His Glu Lys Tyr His Ile Ile Glu Asn Val Phe Lys Gln
                290                 295                 300

Lys Lys Lys Pro Thr Leu Lys Gln Ile Ala Lys Glu Ile Gly Val Asn
305                 310                 315                 320

Pro Glu Asp Ile Lys Gly Tyr Arg Ile Thr Lys Ser Gly Thr Pro Glu
                325                 330                 335

Phe Thr Ser Phe Lys Leu Phe His Asp Leu Lys Val Val Lys Asp
                340                 345                 350

His Ala Ile Leu Asp Asp Ile Asp Leu Leu Asn Gln Ile Ala Glu Ile
                355                 360                 365

Leu Thr Ile Tyr Gln Asp Lys Asp Ser Ile Val Ala Glu Leu Gly Gln
                370                 375                 380

Leu Glu Tyr Leu Met Ser Glu Ala Asp Lys Gln Ser Ile Ser Glu Leu
385                 390                 395                 400

Thr Gly Tyr Thr Gly Thr His Ser Leu Ser Leu Lys Cys Met Asn Met
                405                 410                 415

Ile Ile Asp Glu Leu Trp His Ser Ser Met Asn Gln Met Glu Val Phe
                420                 425                 430

Thr Tyr Leu Asn Met Arg Pro Lys Lys Tyr Glu Leu Lys Gly Tyr Gln
                435                 440                 445

Arg Ile Pro Thr Asp Met Ile Asp Asp Ala Ile Leu Ser Pro Val Val
                450                 455                 460

Lys Arg Thr Phe Ile Gln Ser Ile Asn Val Ile Asn Lys Val Ile Glu
465                 470                 475                 480

Lys Tyr Gly Ile Pro Glu Asp Ile Ile Ile Glu Leu Ala Arg Glu Asn
                485                 490                 495

Asn Ser Asp Asp Arg Lys Lys Phe Ile Asn Asn Leu Gln Lys Lys Asn
                500                 505                 510

Glu Ala Thr Arg Lys Arg Ile Asn Glu Ile Ile Gly Gln Thr Gly Asn
                515                 520                 525

Gln Asn Ala Lys Arg Ile Val Glu Lys Ile Arg Leu His Asp Gln Gln
                530                 535                 540

Glu Gly Lys Cys Leu Tyr Ser Leu Glu Ser Ile Pro Leu Glu Asp Leu
545                 550                 555                 560

Leu Asn Asn Pro Asn His Tyr Glu Val Asp His Ile Ile Pro Arg Ser
                565                 570                 575

Val Ser Phe Asp Asn Ser Tyr His Asn Lys Val Leu Val Lys Gln Ser
                580                 585                 590

Glu Asn Ser Lys Lys Ser Asn Leu Thr Pro Tyr Gln Tyr Phe Asn Ser
                595                 600                 605
```

```
Gly Lys Ser Lys Leu Ser Tyr Asn Gln Phe Lys Gln His Ile Leu Asn
610                 615                 620
Leu Ser Lys Ser Gln Asp Arg Ile Ser Lys Lys Lys Glu Tyr Leu
625                 630                 635                 640
Leu Glu Glu Arg Asp Ile Asn Lys Phe Glu Val Gln Lys Glu Phe Ile
                    645                 650                 655
Asn Arg Asn Leu Val Asp Thr Arg Tyr Ala Thr Arg Glu Leu Thr Ser
                660                 665                 670
Tyr Leu Lys Ala Tyr Phe Ser Ala Asn Asn Met Asp Val Lys Val Lys
            675                 680                 685
Thr Ile Asn Gly Ser Phe Thr Asn His Leu Arg Lys Val Trp Arg Phe
690                 695                 700
Asp Lys Tyr Arg Asn His Gly Tyr Lys His His Ala Glu Asp Ala Leu
705                 710                 715                 720
Ile Ile Ala Asn Ala Asp Phe Leu Phe Lys Glu Asn Lys Lys Leu Gln
                725                 730                 735
Asn Thr Asn Lys Ile Leu Glu Lys Pro Thr Ile Glu Asn Asn Thr Lys
                740                 745                 750
Lys Val Thr Val Glu Lys Glu Glu Asp Tyr Asn Asn Val Phe Glu Thr
            755                 760                 765
Pro Lys Leu Val Glu Asp Ile Lys Gln Tyr Arg Asp Tyr Lys Phe Ser
770                 775                 780
His Arg Val Asp Lys Lys Pro Asn Arg Gln Leu Ile Asn Asp Thr Leu
785                 790                 795                 800
Tyr Ser Thr Arg Met Lys Asp Glu His Asp Tyr Ile Val Gln Thr Ile
                805                 810                 815
Thr Asp Ile Tyr Gly Lys Asp Asn Thr Asn Leu Lys Lys Gln Phe Asn
            820                 825                 830
Lys Asn Pro Glu Lys Phe Leu Met Tyr Gln Asn Asp Pro Lys Thr Phe
            835                 840                 845
Glu Lys Leu Ser Ile Ile Met Lys Gln Tyr Ser Asp Glu Lys Asn Pro
850                 855                 860
Leu Ala Lys Tyr Tyr Glu Glu Thr Gly Glu Tyr Leu Thr Lys Tyr Ser
865                 870                 875                 880
Lys Lys Asn Asn Gly Pro Ile Val Lys Lys Ile Lys Leu Leu Gly Asn
                885                 890                 895
Lys Val Gly Asn His Leu Asp Val Thr Asn Lys Tyr Glu Asn Ser Thr
            900                 905                 910
Lys Lys Leu Val Lys Leu Ser Ile Lys Asn Tyr Arg Phe Asp Val Tyr
            915                 920                 925
Leu Thr Glu Lys Gly Tyr Lys Phe Val Thr Ile Ala Tyr Leu Asn Val
930                 935                 940
Phe Lys Lys Asp Asn Tyr Tyr Ile Pro Lys Asp Lys Tyr Gln Glu
945                 950                 955                 960
Leu Lys Glu Lys Lys Ile Lys Asp Thr Asp Gln Phe Ile Ala Ser
                965                 970                 975
Phe Tyr Lys Asn Asp Leu Ile Leu Asn Gly Asp Leu Tyr Lys Ile
                980                 985                 990
Ile Gly Val Asn Ser Asp Asp Arg Asn Ile Ile Glu Leu Asp Tyr Tyr
            995                 1000                1005
Asp Ile Lys Tyr Lys Asp Tyr Cys Glu Ile Asn Asn Ile Lys Gly
        1010                1015                1020
```

```
Glu Pro Arg Ile Lys Lys Thr Ile Gly Lys Lys Thr Glu Ser Ile
    1025                1030                1035

Glu Lys Phe Thr Thr Asp Val Leu Gly Asn Leu Tyr Leu His Ser
    1040                1045                1050

Thr Glu Lys Ala Pro Gln Leu Ile Phe Lys Arg Gly Leu Lys Arg
    1055                1060                1065

Pro Ala Ala Thr Lys Lys Ala Gly Gln Ala Lys Lys     Lys Lys
    1070                1075                1080
```

<210> SEQ ID NO 40
<211> LENGTH: 3410
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: GST1-v1, nucleotide

<400> SEQUENCE: 40

```
aggaaataag agagaaaaga agagtaagaa gaaatataag agccaccatg gcccctaaga    60
agaagcgcaa ggtcatgaac cagaagttca ttctcggtct ggacattggc attactagcg   120
tgggatacgg cttgattgac tacgagacta agaacatcat cgatgccggc gtccgcctgt   180
tcccggaagc caacgtggag aacaatgagg gccggaggtc gaagagaggc tcccgccgcc   240
tgaagcggcg gcgaatccac cggctggaga gagtgaagct gctgctcacc gaatacgacc   300
tgatcaacaa agaacagatc ccgacctcca acaacccgta ccagatcaga gtgaagggtc   360
tgtcagaaat cctgtccaag gacgaactgg caatcgccct gctgcacctg ccaagcggc    420
gcggaatcca aacgtggat gtggctgccg acaaggaaga aaccgcttcc gactccctga    480
gcactaagga ccagatcaac aagaacgcca agttcttgga gtcccgctac gtgtgcgagc   540
tgcagaagga acggctggaa aacgaaggtc acgtgcgcgg agtggaaaac cggttcctga   600
caaaggacat tgtgcgcgaa gcgaagaaga tcattgatac ccaaatgcag tactaccctg   660
aaatcgacga gactttcaag gaaaagtaca tttcccctgg tggaaacccg gcgggaatact  720
tcgaaggccc cggacaggga tcgccgttcg gatggaacgg ggacctcaag aagtggtacg   780
agatgctgat ggggcactgt acctactttc gcaagaact gcgctccgtg aagtacgcgt   840
actccgcgga tctcttcaac gcgttgaatg acctgaacaa cctgatcatt cagagagaca   900
attccgaaaa gctcgagtac cacgagaagt atcacatcat cgagaatgtg ttcaagcaga   960
agaagaaacc gaccctcaag caaatcgcca aggagattgg cgtcaaccca gaggacatca   1020
agggatatcg gattaccaag agcggcactc ccgagtttac ctctttcaag ctgtttcatg   1080
atctgaagaa agtcgtgaag gaccatgcca ttctcgacga cattgatctc ctgaatcaga   1140
tcgcagagat cctgactatc taccaagaca aggactcgat tgtggcagag ctgggtcagc   1200
tcgaatacct gatgtccgag gccgacaagc agtccatctc cgaactgaca gggtacacgg   1260
ggactcatag cctgtcgctg aagtgcatga acatgatcat tgatgaactg tggcacagct   1320
ccatgaacca aatggaagtg tttacctacc tcaacatgcg ccctaagaag tacgaactga   1380
aaggctacca gcgcatcccc accgacatga tcgacgacgc gatcttgtcc cctgtggtca   1440
agaggacctt cattcaatcc atcaacgtga tcaacaaggt catcgaaaag tacggaatac   1500
cagaagatat catcattgag ctcgctcggg agaacaactc ggatgaccgg aagaagttca   1560
tcaacaatct tcagaagaag aacgaagcga ctcggaaacg gatcaacgag atcatcggac   1620
```

| | |
|---|---|
| agaccggaaa ccagaacgcc aaacggattg tcgaaaagat tagactgcac gaccagcagg | 1680 |
| aagggaagtg cctgtactca ctcgagtcaa taccgctcga ggacctgttg aacaacccta | 1740 |
| accactatga agtggaccac atcatccctc ggtccgtgag cttcgacaac tcgtaccaca | 1800 |
| acaaagtgct cgtgaagcag tccgaaaact ccaagaaatc caacctgacc ccgtaccaat | 1860 |
| acttcaattc gggaaagtcg aagctgtcgt acaaccagtt caaacaacac atactcaacc | 1920 |
| ttagcaaaag ccaggatcgc atttccaaga agaagaagga ataccctcc gaggaaaggg | 1980 |
| acatcaacaa gttcgaagtg cagaaagagt tcatcaatcg caacttggtg gataccagat | 2040 |
| atgccacccg ggaactcacc aactatctca aggcctactt tccgccaac aacatgaacg | 2100 |
| tgaaggtcaa gaccatcaac gggtccttca ctgactacct gagaaaggtc tggaagttca | 2160 |
| agaaggaacg caaccacgga tacaagcacc acgctgagga cgctctgatc atcgccaatg | 2220 |
| ccgacttcct gttcaaggaa acaagaagc tgaaagctgt caactcagtg ctggaaaagc | 2280 |
| ctgaaatcga gactaagcag ctggatatcc aagtggactc tgaggacaac tacagcgaga | 2340 |
| tgttcatcat ccctaaacaa gtgcaggata tcaaggactt tcgcaacttc aagtactcac | 2400 |
| accgggtgga caagaaaccg aatagacagc tgatcaacga cacgttgtat tccacccgga | 2460 |
| agaaggataa ctcaacctac attgtgcaga ctatcaagga tatctacgcc aaagataaca | 2520 |
| ctactctgaa gaaacaattc gacaagtccc cagagaagtt cctgatgtac cagcacgacc | 2580 |
| cccgaacctt tgagaagctt gaagtgatca tgaagcagta cgccaacgag aagaacccgc | 2640 |
| tggccaagta ccatgaagaa accggagaat acctgaccaa gtacagcaag aagaacaacg | 2700 |
| gtcccattgt caagagcctg aagtacatcg gcaacaagct gggatccac ctcgacgtga | 2760 |
| cacatcagtt caagtcgtcg actaagaagc ttgtgaagct gtcaatcaag aactatagat | 2820 |
| tcgacgtgta cttgaccgaa aagggataca agttcgtgac catagcctat ctgaacgtgt | 2880 |
| tcaagaaaga taactactac tacatcccca aggacaagta ccaggagctc aaagaaaaga | 2940 |
| agaagatcaa agacaccgac cagttcattg cctccttcta caagaacgac ctgatcaaac | 3000 |
| tgaacgccga cctctacaag atcattggag tgaacagcga tgacaggaac atcattgagc | 3060 |
| tggactacta cgacatcaag tacaaggact actgcgagat caacaacatc aagggcgaac | 3120 |
| cccggatcaa gaaaactatt ggaaagaaaa ccgagtccat tgagaagttc accactgacg | 3180 |
| tgctgggaaa cctttacctc cactccaccg agaaggcacc acaactgatc ttcaagcgcg | 3240 |
| gcctgaaacg gcccgccgca accaagaagg ccggccaggc gaagaagaag aaatgagcgg | 3300 |
| ccgcttaatt aagctgcctt ctgcggggct tgccttctgg ccatgccctt cttctctccc | 3360 |
| ttgcacctgt acctcttggt ctttgaataa agcctgagta ggaagtctag | 3410 |

<210> SEQ ID NO 41
<211> LENGTH: 1082
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: GST1-v1, amino acid

<400> SEQUENCE: 41

Met Ala Pro Lys Lys Lys Arg Lys Val Met Asn Gln Lys Phe Ile Leu
1               5                   10                  15

Gly Leu Asp Ile Gly Ile Thr Ser Val Gly Tyr Gly Leu Ile Asp Tyr
            20                  25                  30

```
Glu Thr Lys Asn Ile Ile Asp Ala Gly Val Arg Leu Phe Pro Glu Ala
         35                  40                  45

Asn Val Glu Asn Asn Glu Gly Arg Arg Ser Lys Arg Gly Ser Arg Arg
 50                  55                  60

Leu Lys Arg Arg Ile His Arg Leu Glu Arg Val Lys Leu Leu Leu
 65                  70                  75                  80

Thr Glu Tyr Asp Leu Ile Asn Lys Glu Gln Ile Pro Thr Ser Asn Asn
                 85                  90                  95

Pro Tyr Gln Ile Arg Val Lys Gly Leu Ser Glu Ile Leu Ser Lys Asp
             100                 105                 110

Glu Leu Ala Ile Ala Leu Leu His Leu Ala Lys Arg Arg Gly Ile His
             115                 120                 125

Asn Val Asp Val Ala Ala Asp Lys Glu Thr Ala Ser Asp Ser Leu
 130                 135                 140

Ser Thr Lys Asp Gln Ile Asn Lys Asn Ala Lys Phe Leu Glu Ser Arg
145                 150                 155                 160

Tyr Val Cys Glu Leu Gln Lys Glu Arg Leu Glu Asn Glu Gly His Val
                 165                 170                 175

Arg Gly Val Glu Asn Arg Phe Leu Thr Lys Asp Ile Val Arg Glu Ala
             180                 185                 190

Lys Lys Ile Ile Asp Thr Gln Met Gln Tyr Tyr Pro Glu Ile Asp Glu
             195                 200                 205

Thr Phe Lys Glu Lys Tyr Ile Ser Leu Val Glu Thr Arg Arg Glu Tyr
     210                 215                 220

Phe Glu Gly Pro Gly Gln Gly Ser Pro Phe Gly Trp Asn Gly Asp Leu
225                 230                 235                 240

Lys Lys Trp Tyr Glu Met Leu Met Gly His Cys Thr Tyr Phe Pro Gln
             245                 250                 255

Glu Leu Arg Ser Val Lys Tyr Ala Tyr Ser Ala Asp Leu Phe Asn Ala
             260                 265                 270

Leu Asn Asp Leu Asn Asn Leu Ile Ile Gln Arg Asp Asn Ser Glu Lys
         275                 280                 285

Leu Glu Tyr His Glu Lys Tyr His Ile Ile Glu Asn Val Phe Lys Gln
         290                 295                 300

Lys Lys Lys Pro Thr Leu Lys Gln Ile Ala Lys Glu Ile Gly Val Asn
305                 310                 315                 320

Pro Glu Asp Ile Lys Gly Tyr Arg Ile Thr Lys Ser Gly Thr Pro Glu
             325                 330                 335

Phe Thr Ser Phe Lys Leu Phe His Asp Leu Lys Lys Val Val Lys Asp
             340                 345                 350

His Ala Ile Leu Asp Asp Ile Asp Leu Leu Asn Gln Ile Ala Glu Ile
         355                 360                 365

Leu Thr Ile Tyr Gln Asp Lys Asp Ser Ile Val Ala Glu Leu Gly Gln
     370                 375                 380

Leu Glu Tyr Leu Met Ser Glu Ala Asp Lys Gln Ser Ile Ser Glu Leu
385                 390                 395                 400

Thr Gly Tyr Thr Gly Thr His Ser Leu Ser Leu Lys Cys Met Asn Met
                 405                 410                 415

Ile Ile Asp Glu Leu Trp His Ser Ser Met Asn Gln Met Glu Val Phe
             420                 425                 430

Thr Tyr Leu Asn Met Arg Pro Lys Lys Tyr Glu Leu Lys Gly Tyr Gln
     435                 440                 445
```

```
Arg Ile Pro Thr Asp Met Ile Asp Asp Ala Ile Leu Ser Pro Val Val
    450                 455                 460

Lys Arg Thr Phe Ile Gln Ser Ile Asn Val Ile Asn Lys Val Ile Glu
465                 470                 475                 480

Lys Tyr Gly Ile Pro Glu Asp Ile Ile Ile Glu Leu Ala Arg Glu Asn
                485                 490                 495

Asn Ser Asp Asp Arg Lys Lys Phe Ile Asn Asn Leu Gln Lys Lys Asn
                500                 505                 510

Glu Ala Thr Arg Lys Arg Ile Asn Glu Ile Ile Gly Gln Thr Gly Asn
                515                 520                 525

Gln Asn Ala Lys Arg Ile Val Glu Lys Ile Arg Leu His Asp Gln Gln
530                 535                 540

Glu Gly Lys Cys Leu Tyr Ser Leu Glu Ser Ile Pro Leu Glu Asp Leu
545                 550                 555                 560

Leu Asn Asn Pro Asn His Tyr Glu Val Asp His Ile Ile Pro Arg Ser
                565                 570                 575

Val Ser Phe Asp Asn Ser Tyr His Asn Lys Val Leu Val Lys Gln Ser
                580                 585                 590

Glu Asn Ser Lys Lys Ser Asn Leu Thr Pro Tyr Gln Tyr Phe Asn Ser
                595                 600                 605

Gly Lys Ser Lys Leu Ser Tyr Asn Gln Phe Lys Gln His Ile Leu Asn
                610                 615                 620

Leu Ser Lys Ser Gln Asp Arg Ile Ser Lys Lys Lys Glu Tyr Leu
625                 630                 635                 640

Leu Glu Glu Arg Asp Ile Asn Lys Phe Glu Val Gln Lys Glu Phe Ile
                645                 650                 655

Asn Arg Asn Leu Val Asp Thr Arg Tyr Ala Thr Arg Glu Leu Thr Asn
                660                 665                 670

Tyr Leu Lys Ala Tyr Phe Ser Ala Asn Asn Met Asn Val Lys Val Lys
                675                 680                 685

Thr Ile Asn Gly Ser Phe Thr Asp Tyr Leu Arg Lys Val Trp Lys Phe
690                 695                 700

Lys Lys Glu Arg Asn His Gly Tyr Lys His His Ala Gly Asp Ala Leu
705                 710                 715                 720

Ile Ile Ala Asn Ala Asp Phe Leu Phe Lys Glu Asn Lys Lys Leu Lys
                725                 730                 735

Ala Val Asn Ser Val Leu Glu Lys Pro Glu Ile Glu Thr Lys Gln Leu
                740                 745                 750

Asp Ile Gln Val Asp Ser Glu Asp Asn Tyr Ser Glu Met Phe Ile Ile
                755                 760                 765

Pro Lys Gln Val Gln Asp Ile Lys Asp Phe Arg Asn Phe Lys Tyr Ser
                770                 775                 780

His Arg Val Asp Lys Lys Pro Asn Arg Gln Leu Ile Asn Asp Thr Leu
785                 790                 795                 800

Tyr Ser Thr Arg Lys Lys Asp Asn Ser Thr Tyr Ile Val Gln Thr Ile
                805                 810                 815

Lys Asp Ile Tyr Ala Lys Asp Asn Thr Thr Leu Lys Lys Gln Phe Asp
                820                 825                 830

Lys Ser Pro Glu Lys Phe Leu Met Tyr Gln His Asp Pro Arg Thr Phe
                835                 840                 845

Glu Lys Leu Glu Val Ile Met Lys Gln Tyr Ala Asn Glu Lys Asn Pro
850                 855                 860
```

| Leu | Ala | Lys | Tyr | His | Glu | Glu | Thr | Gly | Glu | Tyr | Leu | Thr | Lys | Tyr | Ser |
|-----|-----|-----|-----|-----|-----|-----|-----|-----|-----|-----|-----|-----|-----|-----|-----|
| 865 |     |     |     |     | 870 |     |     |     |     | 875 |     |     |     |     | 880 |

Lys Lys Asn Asn Gly Pro Ile Val Lys Ser Leu Lys Tyr Ile Gly Asn
               885             890                 895

Lys Leu Gly Ser His Leu Asp Val Thr His Gln Phe Lys Ser Ser Thr
           900             905             910

Lys Lys Leu Val Lys Leu Ser Ile Lys Asn Tyr Arg Phe Asp Val Tyr
           915             920             925

Leu Thr Glu Lys Gly Tyr Lys Phe Val Thr Ile Ala Tyr Leu Asn Val
       930             935             940

Phe Lys Lys Asp Asn Tyr Tyr Tyr Ile Pro Lys Asp Lys Tyr Gln Glu
945             950             955             960

Leu Lys Glu Lys Lys Lys Ile Lys Asp Thr Asp Gln Phe Ile Ala Ser
               965             970             975

Phe Tyr Lys Asn Asp Leu Ile Lys Leu Asn Gly Asp Leu Tyr Lys Ile
                   980             985             990

Ile Gly Val Asn Ser Asp Asp Arg Asn Ile Ile Glu Leu Asp Tyr Tyr
           995             1000            1005

Asp Ile Lys Tyr Lys Asp Tyr Cys Glu Ile Asn Asn Ile Lys Gly
1010            1015                1020

Glu Pro Arg Ile Lys Lys Thr Ile Gly Lys Lys Thr Glu Ser Ile
1025                1030                1035

Glu Lys Phe Thr Thr Asp Val Leu Gly Asn Leu Tyr Leu His Ser
1040                1045                1050

Thr Glu Lys Ala Pro Gln Leu Ile Phe Lys Arg Gly Leu Lys Arg
1055                1060                1065

Pro Ala Ala Thr Lys Lys Ala Gly Gln Ala Lys Lys Lys Lys
1070                1075                1080

<210> SEQ ID NO 42
<211> LENGTH: 3396
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Slu, nucleotide

<400> SEQUENCE: 42

| aggaaataag agagaaaaga agagtaagaa gaaatataag agccaccatg gcccccaaga | 60 |
| agaaacgcaa agtcatgaac caaaagttca ttctggggct cgatatcggc atcacctccg | 120 |
| tgggatatgg tctgatcgac tacgagacta agaacatcat cgacgctgga gtgcgactgt | 180 |
| tcccggaagc gaacgtggag aacaacgaag gccgcagatc caagcgcggg tccagaaggc | 240 |
| tcaagaggcg gaggatccat agactcgaaa gagtgaagaa gctccttgaa gattacaatc | 300 |
| tgttggacca gagccagatt ccccaaagca ccaacccgta cgccatcaga gtgaagggcc | 360 |
| tgtccgaagc cctgtcgaaa gatgaactgg tcattgccct gctgcatatt gccaaacggc | 420 |
| gcggaatcca taagatcgac gtgatagact ccaacgatga cgtgggcaac gaactgtcaa | 480 |
| ccaaggagca gctgaacaag aactcgaaac tgctgaagga caagttcgtc tgccaaattc | 540 |
| aactggaacg gatgaacgag ggacaagtca ggggagagaa aaaccggttc aagaccgcgg | 600 |
| acatcatcaa ggagatcatc caactcctga atgtgcagaa gaactttcac cagctggatg | 660 |
| aaaacttcat taacaagtac attgaactgg tggaaatgcg gagggagtac ttcgagggac | 720 |

```
ctggaaaggg atcccctttac ggctggaag gggaccccaa ggcttggtac gaaacgctca    780
tgggccattg cacttacttt ccggacgaac tccggtccgt gaagtacgca tactctgccg    840
atctgttcaa tgcactcaac gaccttaaca acttggtgat ccagcgcgat ggcctgtcca    900
agttggaata ccacgaaaag tatcacatca tcgagaacgt gttcaagcag aaaaagaagc    960
caactctgaa gcagattgcc aacgaaatta acgtgaaccc cgaggatatc aagggatacc   1020
ggatcactaa gtccggcaaa ccacagttca ccgagttcaa gctgtaccac gatctgaagt   1080
cggtgctctt tgaccagtcc atcctggaaa acgaagatgt gctggaccag attgctgaga   1140
tcctgaccat ctaccaggac aaggactcga ttaagagcaa gctcacggag ctggacattc   1200
tgctgaacga agaggataag gagaacatcg cgcagctcac tggttacacc ggtacccacc   1260
gcttgtccct taagtgcatc cggctggtcc tcgaggaaca atggtactcc agccggaacc   1320
agatggagat cttcacgcac ttgaacatca agccgaagaa gattaacctg accgctgcga   1380
acaagatacc caaggccatg atcgacgagt ttatcctctc accggtggtc aagcgcacct   1440
tcggacaagc catcaacctc atcaacaaga ttatcgagaa gtacggcgtg cctgaggata   1500
tcatcatcga gctggctcgg gagaacaact caaaggataa gcagaagttc attaacgaga   1560
tgcagaaaaa gaacgagaac actcgcaagc ggattaatga gatcatcggt aaatacggga   1620
accagaacgc caagcggctt gtggaaaaga ttcggctcca cgacgagcag gagggaaagt   1680
gtctgtactc gctggagagc attccctgg aggacctcct gaacaaccca aaccactacg   1740
aagtggatca cataatcccc cgcagcgtgt cattcgacaa ttcctaccat aacaaggtcc   1800
tcgtgaagca gtccgagaat agcaagaagt ccaacctgac tccgtaccag tacttcaact   1860
ccggcaaatc caagctgtcc tacaaccagt tcaaacagca catcctcaac ctgtcaaaga   1920
gccaggacag gatctcgaag aagaagaagg aataccttct cgaggaacgg gatatcaata   1980
agttcgaggt gcagaaggag tttatcaata gaaacctggt ggacactcgc tatgccaccc   2040
gcgaactgac caactacctg aaggcgtact tctccgccaa caacatgaac gtgaaggtca   2100
aaactattaa cggcagcttc accgactatc tgcgcaaggt ctggaagttc aagaaggaac   2160
gcaaccacgg ttacaagcac cacgcggaag atgcgctgat tatcgccaac gctgacttcc   2220
tgttcaagga aaacaagaag ctcaaggccg tgaactcagt gctcgagaag cctgaaatcg   2280
agactaagca gctggacatc caggtcgatt cggaagataa ctactccgaa atgttcatca   2340
tccctaagca agtgcaggac atcaaggact tcaggaattt caagtacagc catcgcgtgg   2400
acaagaagcc aaacagacag ctgatcaacg atacactgta ttccacccgg aagaggaca   2460 actccaccta catcgtccaa accattaagg acatctacgc aaaggacaac accacgctta   2520
agaagcagtt cgacaagagc cccgaaaagt tcctcatgta ccagcacgac cccagaacct   2580
tcgagaagct tgaagtgatc atgaagcagt acgccaacga aaagaaccca ctggctaagt   2640
accacgagga aacggcgaa tacctgacca agtactccaa aaagaacaac ggaccgatcg   2700
tcaagtccct gaagtacatt gggaacaagc tcggctcgca cctcgatgtg acccaccagt   2760
tcaagtcctc gaccaaaaag ctcgtgaagc tgtccatcaa gccgtaccgg ttcgacgtgt   2820
acctgactga caagggatat aagttcatca ccatttccta cctcgacgtg ttgaagaagg   2880
ataactacta ctacattccg gaacagaagt acgacaagct caagctcgga aaggccatcg   2940
acaaaaatgc gaagttcatc gcgagcttct acaagaatga cttgatcaag ctggatggcg   3000
aaatctacaa gatcatcggg gtcaactccg ataccgcaa catgattgag ctggatctgc   3060
```

-continued

```
ccgacattcg gtacaaggaa tactgcgagc tgaacaacat caagggagaa ccgcggatca    3120
agaaaaccat cggaaagaaa gtgaacagca tcgagaaact gactactgac gtcctgggaa    3180
acgtgttcac caacacacaa tacaccaaac cccagctgct gtttaagcgc gggaacaagc    3240
gccctgccgc aactaagaag gccggacagg ccaaaaagaa gaaatgagcg gccgcttaat    3300
taagctgcct tctgcggggc ttgccttctg gccatgccct tcttctctcc cttgcacctg    3360
tacctcttgg tctttgaata aagcctgagt aggaag                              3396
```

<210> SEQ ID NO 43
<211> LENGTH: 1079
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: S1u, amino acid

<400> SEQUENCE: 43

```
Met Ala Pro Lys Lys Lys Arg Lys Val Met Asn Gln Lys Phe Ile Leu
1               5                   10                  15

Gly Leu Asp Ile Gly Ile Thr Ser Val Gly Tyr Gly Leu Ile Asp Tyr
            20                  25                  30

Glu Thr Lys Asn Ile Ile Asp Ala Gly Val Arg Leu Phe Pro Glu Ala
        35                  40                  45

Asn Val Glu Asn Asn Glu Gly Arg Arg Ser Lys Arg Gly Ser Arg Arg
    50                  55                  60

Leu Lys Arg Arg Arg Ile His Arg Leu Glu Arg Val Lys Lys Leu Leu
65                  70                  75                  80

Glu Asp Tyr Asn Leu Leu Asp Gln Ser Gln Ile Pro Gln Ser Thr Asn
                85                  90                  95

Pro Tyr Ala Ile Arg Val Lys Gly Leu Ser Glu Ala Leu Ser Lys Asp
            100                 105                 110

Glu Leu Val Ile Ala Leu Leu His Ile Ala Lys Arg Arg Gly Ile His
        115                 120                 125

Lys Ile Asp Val Ile Asp Ser Asn Asp Val Gly Asn Glu Leu Ser
130                 135                 140

Thr Lys Glu Gln Leu Asn Lys Asn Ser Lys Leu Leu Lys Asp Lys Phe
145                 150                 155                 160

Val Cys Gln Ile Gln Leu Glu Arg Met Asn Glu Gly Gln Val Arg Gly
                165                 170                 175

Glu Lys Asn Arg Phe Lys Thr Ala Asp Ile Ile Lys Glu Ile Ile Gln
            180                 185                 190

Leu Leu Asn Val Gln Lys Asn Phe His Gln Leu Asp Glu Asn Phe Ile
        195                 200                 205

Asn Lys Tyr Ile Glu Leu Val Glu Met Arg Arg Glu Tyr Phe Glu Gly
    210                 215                 220

Pro Gly Lys Gly Ser Pro Tyr Gly Trp Glu Gly Asp Pro Lys Ala Trp
225                 230                 235                 240

Tyr Glu Thr Leu Met Gly His Cys Thr Tyr Phe Pro Asp Glu Leu Arg
                245                 250                 255

Ser Val Lys Tyr Ala Tyr Ser Ala Asp Leu Phe Asn Ala Leu Asn Asp
            260                 265                 270

Leu Asn Asn Leu Val Ile Gln Arg Asp Gly Leu Ser Lys Leu Glu Tyr
        275                 280                 285
```

```
His Glu Lys Tyr His Ile Ile Glu Asn Val Phe Lys Gln Lys Lys
    290                 295                 300

Pro Thr Leu Lys Gln Ile Ala Asn Glu Ile Asn Val Asn Pro Glu Asp
305                 310                 315                 320

Ile Lys Gly Tyr Arg Ile Thr Lys Ser Gly Lys Pro Gln Phe Thr Glu
                325                 330                 335

Phe Lys Leu Tyr His Asp Leu Lys Ser Val Leu Phe Asp Gln Ser Ile
                340                 345                 350

Leu Glu Asn Glu Asp Val Leu Asp Gln Ile Ala Glu Ile Leu Thr Ile
                355                 360                 365

Tyr Gln Asp Lys Asp Ser Ile Lys Ser Lys Leu Thr Glu Leu Asp Ile
370                 375                 380

Leu Leu Asn Glu Glu Asp Lys Glu Asn Ile Ala Gln Leu Thr Gly Tyr
385                 390                 395                 400

Thr Gly Thr His Arg Leu Ser Leu Lys Cys Ile Arg Leu Val Leu Glu
                405                 410                 415

Glu Gln Trp Tyr Ser Ser Arg Asn Gln Met Glu Ile Phe Thr His Leu
                420                 425                 430

Asn Ile Lys Pro Lys Lys Ile Asn Leu Thr Ala Ala Asn Lys Ile Pro
                435                 440                 445

Lys Ala Met Ile Asp Glu Phe Ile Leu Ser Pro Val Val Lys Arg Thr
450                 455                 460

Phe Gly Gln Ala Ile Asn Leu Ile Asn Lys Ile Ile Glu Lys Tyr Gly
465                 470                 475                 480

Val Pro Glu Asp Ile Ile Ile Glu Leu Ala Arg Glu Asn Asn Ser Lys
                485                 490                 495

Asp Lys Gln Lys Phe Ile Asn Glu Met Gln Lys Lys Asn Glu Asn Thr
                500                 505                 510

Arg Lys Arg Ile Asn Glu Ile Ile Gly Lys Tyr Gly Asn Gln Asn Ala
                515                 520                 525

Lys Arg Leu Val Glu Lys Ile Arg Leu His Asp Glu Gln Glu Gly Lys
530                 535                 540

Cys Leu Tyr Ser Leu Glu Ser Ile Pro Leu Glu Asp Leu Leu Asn Asn
545                 550                 555                 560

Pro Asn His Tyr Glu Val Asp His Ile Ile Pro Arg Ser Val Ser Phe
                565                 570                 575

Asp Asn Ser Tyr His Asn Lys Val Leu Val Lys Gln Ser Glu Asn Ser
                580                 585                 590

Lys Lys Ser Asn Leu Thr Pro Tyr Gln Tyr Phe Asn Ser Gly Lys Ser
                595                 600                 605

Lys Leu Ser Tyr Asn Gln Phe Lys Gln His Ile Leu Asn Leu Ser Lys
                610                 615                 620

Ser Gln Asp Arg Ile Ser Lys Lys Lys Glu Tyr Leu Leu Glu Glu
625                 630                 635                 640

Arg Asp Ile Asn Lys Phe Glu Val Gln Lys Glu Phe Ile Asn Arg Asn
                645                 650                 655

Leu Val Asp Thr Arg Tyr Ala Thr Arg Glu Leu Thr Asn Tyr Leu Lys
                660                 665                 670

Ala Tyr Phe Ser Ala Asn Asn Met Asn Val Lys Val Lys Thr Ile Asn
                675                 680                 685

Gly Ser Phe Thr Asp Tyr Leu Arg Lys Val Trp Lys Phe Lys Lys Glu
690                 695                 700
```

Arg Asn His Gly Tyr Lys His His Ala Glu Asp Ala Leu Ile Ile Ala
705                 710                 715                 720

Asn Ala Asp Phe Leu Phe Lys Glu Asn Lys Lys Leu Lys Ala Val Asn
            725                 730                 735

Ser Val Leu Glu Lys Pro Glu Ile Glu Thr Lys Gln Leu Asp Ile Gln
        740                 745                 750

Val Asp Ser Glu Asp Asn Tyr Ser Glu Met Phe Ile Ile Pro Lys Gln
        755                 760                 765

Val Gln Asp Ile Lys Asp Phe Arg Asn Phe Lys Tyr Ser His Arg Val
        770                 775                 780

Asp Lys Lys Pro Asn Arg Gln Leu Ile Asn Asp Thr Leu Tyr Ser Thr
785                 790                 795                 800

Arg Lys Lys Asp Asn Ser Thr Tyr Ile Val Gln Thr Ile Lys Asp Ile
                805                 810                 815

Tyr Ala Lys Asp Asn Thr Thr Leu Lys Lys Gln Phe Asp Lys Ser Pro
            820                 825                 830

Glu Lys Phe Leu Met Tyr Gln His Asp Pro Arg Thr Phe Glu Lys Leu
        835                 840                 845

Glu Val Ile Met Lys Gln Tyr Ala Asn Glu Lys Asn Pro Leu Ala Lys
        850                 855                 860

Tyr His Glu Glu Thr Gly Glu Tyr Leu Thr Lys Tyr Ser Lys Lys Asn
865                 870                 875                 880

Asn Gly Pro Ile Val Lys Ser Leu Lys Tyr Ile Gly Asn Lys Leu Gly
                885                 890                 895

Ser His Leu Asp Val Thr His Gln Phe Lys Ser Ser Thr Lys Lys Leu
            900                 905                 910

Val Lys Leu Ser Ile Lys Pro Tyr Arg Phe Asp Val Tyr Leu Thr Asp
        915                 920                 925

Lys Gly Tyr Lys Phe Ile Thr Ile Ser Tyr Leu Asp Val Leu Lys Lys
930                 935                 940

Asp Asn Tyr Tyr Tyr Ile Pro Glu Gln Lys Tyr Asp Lys Leu Lys Leu
945                 950                 955                 960

Gly Lys Ala Ile Asp Lys Asn Ala Lys Phe Ile Ala Ser Phe Tyr Lys
                965                 970                 975

Asn Asp Leu Ile Lys Leu Asp Gly Glu Ile Tyr Lys Ile Ile Gly Val
            980                 985                 990

Asn Ser Asp Thr Arg Asn Met Ile Glu Leu Asp Leu Pro Asp Ile Arg
        995                 1000                1005

Tyr Lys Glu Tyr Cys Glu Leu Asn Asn Ile Lys Gly Glu Pro Arg
        1010                1015                1020

Ile Lys Lys Thr Ile Gly Lys Val Asn Ser Ile Glu Lys Leu
        1025                1030                1035

Thr Thr Asp Val Leu Gly Asn Val Phe Thr Asn Thr Gln Tyr Thr
        1040                1045                1050

Lys Pro Gln Leu Leu Phe Lys Arg Gly Asn Lys Arg Pro Ala Ala
        1055                1060                1065

Thr Lys Lys Ala Gly Gln Ala Lys Lys Lys Lys
        1070                1075

<210> SEQ ID NO 44
<211> LENGTH: 3393
<212> TYPE: DNA
<213> ORGANISM: Artificial sequence
<220> FEATURE:

<223> OTHER INFORMATION: Synthetic polynucleotide
<220> FEATURE:
<221> NAME/KEY: misc_feature
<223> OTHER INFORMATION: F8 nucleotide

<400> SEQUENCE: 44

| | | | | | |
|---|---|---|---|---|---|
| aggaaataag | agagaaaaga | agagtaagaa | gaaatataag | agccaccatg gcccccaaga | 60 |
| agaaacgcaa | agtcatgaac | caaaagttca | ttctggggct | cgatatcggc atcacctccg | 120 |
| tgggatatgg | tctgatcgac | tacgagacta | agaacatcat | cgacgctgga gtgcgactgt | 180 |
| tcccggaagc | gaacgtggag | aacaacgaag | gccgcagatc | caagcgcggg tccagaaggc | 240 |
| tcaagaggcg | gaggatccat | agactcgaga | gagtgaagtc | gctcctttcg aatacaaga | 300 |
| ttatcagcgg | tcttgccccc | accaacaacc | aaccgtacaa | catcagagtg aagggcctga | 360 |
| ccgaacagct | gaccaaagat | gaactggccg | tcgccctgct | gcatattgcc aaacggcgcg | 420 |
| gaatccataa | gatcgacgtg | attgacagca | acgatgacgt | gggaaacgag ctgtcaacca | 480 |
| aggaacagct | taacaagaac | agcaaattgc | tgaaggacaa | gtttgtctgc caaattcaac | 540 |
| tggaacggat | gaacgaggga | caagtcaggg | gagagaaaaa | ccggttcaag accgccgaca | 600 |
| tcatcaagga | gatcatccaa | ctgctgaacg | tgcagaagaa | cttccaccaa ctggatgaaa | 660 |
| acttcattaa | caagtacatt | gaactggtgg | aaatgcggag | ggagtacttc gagggacctg | 720 |
| gacagggatc | ccctttcggc | tggaatgggg | accttaagaa | gtggtacgaa atgttgatgg | 780 |
| gccattgcac | ttactttccg | caagaactcc | ggtccgtgaa | gtacgcatac tctgccgacc | 840 |
| tgttcaatgc | actcaacgac | cttaacaact | tgatcatcca | gcgcgataac tcggaaaagt | 900 |
| tggaatacca | cgaaaagtat | cacatcatcg | agaacgtgtt | caagcagaaa aagaagccaa | 960 |
| ctctgaagca | gattgccaag | gaaattggcg | tgaatccgga | ggatatcaag ggataccgga | 1020 |
| tcactaagtc | cggcacgcca | gagttcaccg | agttcaagct | gtaccacgat ctgaagtcgg | 1080 |
| tgctctttga | ccagtccatc | ctggaaaacg | aagatgtgct | ggaccagatt gctgagatcc | 1140 |
| tgaccatcta | ccaggacaag | gactcgatta | agtccaagct | caccgagctg acattctgc | 1200 |
| tgaacgaaga | agataaggag | aacatcgcgc | agctcaccgg | ttacaatggt acccaccgct | 1260 |
| tgtcccttaa | gtgcatccgc | ctggtgctgg | aggaacagtg | gtactcgagc cggaaccaga | 1320 |
| tggagatctt | cactcacttg | aacatcaagc | cgaaaaagat | taacctgact gccgccaaca | 1380 |
| agatacccaa | ggccatgatc | gacgagttta | tcctctcacc | ggtggtcaag cgcaccttca | 1440 |
| ttcaatctat | caacgtgatc | aacaaggtca | tcgagaagta | cggcattcct gaggatatca | 1500 |
| tcatcgagct | ggctcgggag | aacaactcag | acgataggaa | gaagttcatt aacaacctcc | 1560 |
| agaaaaagaa | cgaggccact | cgcaagcgga | ttaatgagat | catcggtcag accgggaacc | 1620 |
| agaacgccaa | gcggatcgtg | gaaaagattc | ggctccacga | ccaacaggag ggaaagtgtc | 1680 |
| tgtactcgct | ggagtcgatt | gcactgatgg | acctcctgaa | caacccacag aactacgaag | 1740 |
| tcgatcacat | aatcccccgc | agcgtggcat | tcgacaactc | catccataac aaggtcctcg | 1800 |
| tgaagcagat | cgagaatagc | aagaagggga | accggactcc | gtaccagtac ctgaactcct | 1860 |
| ccgacgccaa | gctgtcatac | aatcagttca | acagcacat | tctcaacctg tccaagtcaa | 1920 |
| aggacaggat | ctccaagaag | aagaaggact | accttctcga | ggaacgggat atcaataagt | 1980 |
| tcgaggtgca | gaaggagttt | atcaatagaa | acctggtgga | cactcgctat gccacccgcg | 2040 |
| aactgaccag | ctacctgaag | gcgtacttct | ccgccaacaa | catggacgtg aaggtcaaaa | 2100 |
| ctattaacgg | cagcttcacc | aaccatctgc | gcaaggtctg | gaggttcgac aagtaccgca | 2160 |

```
accacggtta caagcaccac gcggaagatg cgctgattat cgccaacgct gacttcctgt    2220
tcaaggaaaa caagaagctc aaggccgtga actcagtgct cgagaagcct gaaatcgaga    2280
ctaagcagct ggacatccag gtcgattcgg aagataacta ctccgaaatg ttcatcatcc    2340
ctaagcaagt gcaggacatc aaggacttca ggaatttcaa gtacagccat cgcgtggaca    2400
agaagccaaa cagacagctg atcaacgata cactgtattc cacccggaag aaggacaact    2460
ccacctacat cgtccaaacc attaaggaca tctacgcaaa ggacaacacc acgcttaaga    2520
agcagttcga caagagcccc gaaaagttcc tcatgtacca gcacgacccc agaaccttcg    2580
agaagcttga agtgatcatg aagcagtacg ccaacgaaaa gaacccactg gctaagtacc    2640
acgaggaaac cggcgaatac ctgaccaagt actccaaaaa gaacaacgga ccgatcgtca    2700
agtccctgaa gtacattggg aacaagctcg gctcgcacct cgatgtgacc caccagttca    2760
agtcctcgac caaaaagctc gtgaagctgt ccatcaagcc gtaccggttc gacgtgtacc    2820
tgactgacaa gggatataag ttcatcacca tttcctacct cgacgtgttg aagaaggata    2880
actactacta cattccggaa cagaagtacg acaagctcaa gctcggaaag gccatcgaca    2940
aaaatgcgaa gttcatcgcg agcttctaca agaatgactt gatcaagctg gatggcgaaa    3000
tctacaagat catcggggtc aactccgata cccgcaacat gattgagctg gatctgcccg    3060
acattcggta caaggaatac tgcgagctga caacatcaa gggagaaccg cggatcaaga    3120 aaccatcgg aaagaaagtg aacagcatcg agaaactgac tactgacgtc ctgggaaacg    3180
tgttcaccaa cacacaatac accaaacccc agctgctgtt taagcgcggg aacaagcgcc    3240
ctgccgcaac taagaaggcc ggacaggcca aaaagaagaa atgagcggcc gcttaattaa    3300
gctgccttct gcgggcttg ccttctggcc atgcccttct tctctcccett gcacctgtac    3360 ctcttggtct ttgaataaag cctgagtagg aag    3393
```

<210> SEQ ID NO 45
<211> LENGTH: 1078
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: F8, amino acid

<400> SEQUENCE: 45

```
Met Ala Pro Lys Lys Lys Arg Lys Val Met Asn Gln Lys Phe Ile Leu
1               5                   10                  15

Gly Leu Asp Ile Gly Ile Thr Ser Val Gly Tyr Gly Leu Ile Asp Tyr
            20                  25                  30

Glu Thr Lys Asn Ile Ile Asp Ala Gly Val Arg Leu Phe Pro Glu Ala
        35                  40                  45

Asn Val Glu Asn Asn Glu Gly Arg Arg Ser Lys Arg Gly Ser Arg Arg
    50                  55                  60

Leu Lys Arg Arg Arg Ile His Arg Leu Glu Arg Val Lys Ser Leu Leu
65                  70                  75                  80

Ser Glu Tyr Lys Ile Ile Ser Gly Leu Ala Pro Thr Asn Asn Gln Pro
                85                  90                  95

Tyr Asn Ile Arg Val Lys Gly Leu Thr Glu Gln Leu Thr Lys Asp Glu
            100                 105                 110

Leu Ala Val Ala Leu Leu His Ile Ala Lys Arg Arg Gly Ile His Lys
        115                 120                 125
```

```
Ile Asp Val Ile Asp Ser Asn Asp Val Gly Asn Glu Leu Ser Thr
130                 135                 140
Lys Glu Gln Leu Asn Lys Asn Ser Lys Leu Leu Lys Asp Lys Phe Val
145                 150                 155                 160
Cys Gln Ile Gln Leu Glu Arg Met Asn Glu Gly Gln Val Arg Gly Glu
                165                 170                 175
Lys Asn Arg Phe Lys Thr Ala Asp Ile Ile Lys Glu Ile Ile Gln Leu
            180                 185                 190
Leu Asn Val Gln Lys Asn Phe His Gln Leu Asp Glu Asn Phe Ile Asn
        195                 200                 205
Lys Tyr Ile Glu Leu Val Glu Met Arg Arg Glu Tyr Phe Glu Gly Pro
210                 215                 220
Gly Gln Gly Ser Pro Phe Gly Trp Asn Gly Asp Leu Lys Lys Trp Tyr
225                 230                 235                 240
Glu Met Leu Met Gly His Cys Thr Tyr Phe Pro Gln Glu Leu Arg Ser
                245                 250                 255
Val Lys Tyr Ala Tyr Ser Ala Asp Leu Phe Asn Ala Leu Asn Asp Leu
            260                 265                 270
Asn Asn Leu Ile Ile Gln Arg Asp Asn Ser Glu Lys Leu Glu Tyr His
        275                 280                 285
Glu Lys Tyr His Ile Ile Glu Asn Val Phe Lys Gln Lys Lys Lys Pro
290                 295                 300
Thr Leu Lys Gln Ile Ala Lys Glu Ile Gly Val Asn Pro Glu Asp Ile
305                 310                 315                 320
Lys Gly Tyr Arg Ile Thr Lys Ser Gly Thr Pro Glu Phe Thr Glu Phe
                325                 330                 335
Lys Leu Tyr His Asp Leu Lys Ser Val Leu Phe Asp Gln Ser Ile Leu
            340                 345                 350
Glu Asn Glu Asp Val Leu Asp Gln Ile Ala Glu Ile Leu Thr Ile Tyr
        355                 360                 365
Gln Asp Lys Asp Ser Ile Lys Ser Lys Leu Thr Glu Leu Asp Ile Leu
370                 375                 380
Leu Asn Glu Glu Asp Lys Glu Asn Ile Ala Gln Leu Thr Gly Tyr Asn
385                 390                 395                 400
Gly Thr His Arg Leu Ser Leu Lys Cys Ile Arg Leu Val Leu Glu Glu
                405                 410                 415
Gln Trp Tyr Ser Ser Arg Asn Gln Met Glu Ile Phe Thr His Leu Asn
            420                 425                 430
Ile Lys Pro Lys Lys Ile Asn Leu Thr Ala Ala Asn Lys Ile Pro Lys
        435                 440                 445
Ala Met Ile Asp Glu Phe Ile Leu Ser Pro Val Val Lys Arg Thr Phe
450                 455                 460
Ile Gln Ser Ile Asn Val Ile Asn Lys Val Ile Glu Lys Tyr Gly Ile
465                 470                 475                 480
Pro Glu Asp Ile Ile Ile Glu Leu Ala Arg Glu Asn Asn Ser Asp Asp
                485                 490                 495
Arg Lys Lys Phe Ile Asn Asn Leu Gln Lys Lys Asn Glu Ala Thr Arg
            500                 505                 510
Lys Arg Ile Asn Glu Ile Ile Gly Gln Thr Gly Asn Gln Asn Ala Lys
        515                 520                 525
Arg Ile Val Glu Lys Ile Arg Leu His Asp Gln Gln Glu Gly Lys Cys
530                 535                 540
```

```
Leu Tyr Ser Leu Glu Ser Ile Ala Leu Met Asp Leu Leu Asn Asn Pro
545                 550                 555                 560

Gln Asn Tyr Glu Val Asp His Ile Ile Pro Arg Ser Val Ala Phe Asp
            565                 570                 575

Asn Ser Ile His Asn Lys Val Leu Val Lys Gln Ile Glu Asn Ser Lys
        580                 585                 590

Lys Gly Asn Arg Thr Pro Tyr Gln Tyr Leu Asn Ser Asp Ala Lys
    595                 600                 605

Leu Ser Tyr Asn Gln Phe Lys Gln His Ile Leu Asn Leu Ser Lys Ser
610                 615                 620

Lys Asp Arg Ile Ser Lys Lys Lys Asp Tyr Leu Leu Glu Glu Arg
625                 630                 635                 640

Asp Ile Asn Lys Phe Glu Val Gln Lys Glu Phe Ile Asn Arg Asn Leu
                645                 650                 655

Val Asp Thr Arg Tyr Ala Thr Arg Glu Leu Thr Ser Tyr Leu Lys Ala
            660                 665                 670

Tyr Phe Ser Ala Asn Asn Met Asp Val Lys Val Lys Thr Ile Asn Gly
        675                 680                 685

Ser Phe Thr Asn His Leu Arg Lys Val Trp Arg Phe Asp Lys Tyr Arg
690                 695                 700

Asn His Gly Tyr Lys His His Ala Glu Asp Ala Leu Ile Ile Ala Asn
705                 710                 715                 720

Ala Asp Phe Leu Phe Lys Glu Asn Lys Lys Leu Lys Ala Val Asn Ser
                725                 730                 735

Val Leu Glu Lys Pro Glu Ile Glu Thr Lys Gln Leu Asp Ile Gln Val
            740                 745                 750

Asp Ser Glu Asp Asn Tyr Ser Glu Met Phe Ile Ile Pro Lys Gln Val
        755                 760                 765

Gln Asp Ile Lys Asp Phe Arg Asn Phe Lys Tyr Ser His Arg Val Asp
    770                 775                 780

Lys Lys Pro Asn Arg Gln Leu Ile Asn Asp Thr Leu Tyr Ser Thr Arg
785                 790                 795                 800

Lys Lys Asp Asn Ser Thr Tyr Ile Val Gln Thr Ile Lys Asp Ile Tyr
                805                 810                 815

Ala Lys Asp Asn Thr Thr Leu Lys Lys Gln Phe Asp Lys Ser Pro Glu
            820                 825                 830

Lys Phe Leu Met Tyr Gln His Asp Pro Arg Thr Phe Glu Lys Leu Glu
        835                 840                 845

Val Ile Met Lys Gln Tyr Ala Asn Glu Lys Asn Pro Leu Ala Lys Tyr
    850                 855                 860

His Glu Glu Thr Gly Glu Tyr Leu Thr Lys Tyr Ser Lys Asn Asn
865                 870                 875                 880

Gly Pro Ile Val Lys Ser Leu Lys Tyr Ile Gly Asn Lys Leu Gly Ser
                885                 890                 895

His Leu Asp Val Thr His Gln Phe Lys Ser Ser Thr Lys Lys Leu Val
            900                 905                 910

Lys Leu Ser Ile Lys Pro Tyr Arg Phe Asp Val Tyr Leu Thr Asp Lys
        915                 920                 925

Gly Tyr Lys Phe Ile Thr Ile Ser Tyr Leu Asp Val Leu Lys Lys Asp
    930                 935                 940

Asn Tyr Tyr Tyr Ile Pro Glu Gln Lys Tyr Asp Lys Leu Lys Leu Gly
945                 950                 955                 960
```

| | | | | | | |
|---|---|---|---|---|---|---|
| Lys | Ala | Ile | Asp Lys Asn 965 | Ala | Lys Phe Ile 970 | Ala Ser Phe Tyr Lys Asn 975 |

Asp Leu Ile Lys Leu Asp Gly Glu Ile Tyr Lys Ile Ile Gly Val Asn
            980              985              990

Ser Asp Thr Arg Asn Met Ile Glu Leu Asp Leu Pro Asp Ile Arg Tyr
         995            1000             1005

Lys Glu Tyr Cys Glu Leu Asn Asn Ile Lys Gly Glu Pro Arg Ile
    1010              1015              1020

Lys Lys Thr Ile Gly Lys Lys Val Asn Ser Ile Glu Lys Leu Thr
    1025              1030              1035

Thr Asp Val Leu Gly Asn Val Phe Thr Asn Thr Gln Tyr Thr Lys
    1040              1045              1050

Pro Gln Leu Leu Phe Lys Arg Gly Asn Lys Arg Pro Ala Ala Thr
    1055              1060              1065

Lys Lys Ala Gly Gln Ala Lys Lys Lys Lys
    1070              1075

<210> SEQ ID NO 46
<211> LENGTH: 3405
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: E2, nucleotide

<400> SEQUENCE: 46

```
aggaaataag agagaaaaga agagtaagaa gaaatataag agccaccatg gccccaaga      60 agaaacgcaa agtcatgaac caaaagttca ttctggggct cgatatcggc atcacctccg    120
tgggatatgg tctgatcgac tacgagacta agaacatcat cgacgctgga gtgcgactgt    180
tcccggaagc gaacgtggag aacaacgaag gccgcagatc caagcgcggg tccagaaggc    240
tcaagaggcg gaggatccat agactcgaca gagtgaagca cctccttgcc gaatacgatc    300
tgttggacct taccaacatt cccaagagca ccaacccgta ccaaaccaga gtgaagggcc    360
tgaacgaaaa gctgtcgaaa gatgaactgg tcattgccct gctgcatatt gccaaacggc    420
gcggaatcca taacgtggac gtggccgctg acaaggaaga gactgcgtcc gactcgctgt    480
caaccaagga ccagatcaac aagaacgcca aattcctgga aagccgctac gtctgcgagc    540
ttcaaaaaga acggctggag aacgagggac acgtcagggg agtggagaac cggttcctga    600
ccaaggacat cgtgcgggaa gccaagaaga tcatcgacac ccaaatgcag tattatccgg    660
aaattgatga aactttaag gagaagtaca tttccctggt ggaaactcgg agggagtact    720
tcgagggacc tggaaaggga tccccttcg gctgggaagg gaacattaag aagtggtttg    780
aacagatgat gggccattgc acttactttc ggaagaact ccggtccgtg aagtactcat    840
actctgccga gctgttcaat gcactcaacg accttaacaa cttggtgatc acccgcgatg    900
aagatgccaa gttgaactac ggagaaaagt tccagatcat cgagaacgtg ttcaagcaga    960
aaaagacccc aaatctgaag cagattgcca tcgaaattgg cgtgcacgag actgagatca   1020
agggataccg ggtcaacaag tccggcacgc cagagttcac cgagttcaag ctgtaccacg   1080
atctgaagtc gatcgtgttt gacaagtcca ccctggaaaa cgaagccatt ctggaccaga   1140
ttgctgagat cctgaccatc taccaggacg agcaatcgat taaggaagaa ctgaacaagc   1200
tccccgagat tctgaacgaa caggataagg ccgagatcgc gaagctcatt ggttacaatg   1260
```

```
gtacccaccg cttgtccctt aagtgcatcc atctgatcaa tgaggaactg tggcagacca    1320
gccggaacca gatggagatc ttcaattact tgaacatcaa gccgaacaag gtggacctgt    1380
ccgaacagaa caagataccc aaggacatgg tcaacgactt tatcctctca ccggtggtca    1440
agcgcacctt cattcaatct atcaacgtga tcaacaaggt catcgagaag tacggcattc    1500
ctgaggatat catcatcgag ctggctcggg agaacaactc agacgatagg aagaagttca    1560
ttaacaacct ccagaaaaag aacgaggcca ctcgcaagcg gattaatgag atcatcggtc    1620
agaccgggaa ccagaacgcc aagcggatcg tggaaaagat tcggctccac gaccaacagg    1680
agggaaagtg tctgtactcg ctgaaggaca ttccccctgga ggacctcctg aggaacccaa    1740
acaactacga catcgatcac ataatccccc gcagcgtgtc attcgacgat ccatgcata     1800 acaaggtcct cgtgcggaga gagcagaatg ccaagaagaa caaccagact ccgtaccagt    1860
acctgacgtc cggctacgca gacatcaagt actcagtgtt caaacagcac gtgctcaacc    1920
tggccgagaa caaggacagg atgaccaaga agaagcgcga ataccttctc gaggaacggg    1980
atatcaataa gttcgaggtg cagaaggagt ttatcaatag aaacctggtg gacactcgct    2040
atgccacccg cgaactgacc aactacctga aggcgtactt ctccgccaac aacatgaacg    2100
tgaaggtcaa aactattaac ggcagcttca ccgactatct gcgcaaggtc tggaagttca    2160
agaaggaacg caaccacggt tacaagcacc acgcggaaga tgcgctgatt atcgccaacg    2220
ctgacttcct gttcaaggaa aacaagaagc tcaaggccgt gaactcagtg ctcgagaagc    2280
ctgaaatcga gactaagcag ctggacatcc aggtcgattc ggaagataac tactccgaaa    2340
tgttcatcat ccctaagcaa gtgcaggaca tcaaggactt caggaatttc aagtacagcc    2400
atcgcgtgga caagaagcca acagacagc tgatcaacga tacactgtat ccacccgga    2460 agaaggacaa ctccacctac atcgtccaaa ccattaagga catctacgca aaggacaaca    2520
ccacgcttaa gaagcagttc gacaagagcc ccgaaaagtt cctcatgtac cagcacgacc    2580
ccagaacctt cgagaagctt gaagtgatca tgaagcagta cgccaacgaa aagaacccac    2640
tggctaagta ccacgaggaa accggcgaat acctgaccaa gtactccaaa agaacaacg    2700 gaccgatcgt caagtccctg aagtacattg ggaacaagct cggctcgcac ctcgatgtga    2760
cccaccagtt caagtcctcg accaaaaagc tcgtgaagct gtccatcaag ccgtaccggt    2820
tcgacgtgta cctgactgac aagggatata agttcatcac catttcctac ctcgacgtgt    2880
tgaagaagga taactactac tacattccgg aacagaagta cgacaagctc aagctcggaa    2940
aggccatcga caaaaatgcg aagttcatcg cgagcttcta caagaatgac ttgatcaagc    3000
tggatggcga aatctacaag atcatcgggg tcaactccga tacccgcaac atgattgagc    3060
tggatctgcc cgacattcgg tacaaggaat actgcgagct gaacaacatc aagggagaac    3120
cgcggatcaa gaaaaccatc ggaaagaaag tgaacagcat cgagaaactg actactgacg    3180
tcctgggaaa cgtgttcacc aacacacaat acaccaaacc ccagctgctg tttaagcgcg    3240
ggaacaagcg ccctgccgca actaagaagg ccggacaggc caaaaagaag aaatgagcgg    3300
ccgcttaatt aagctgcctt ctgcggggct tgccttctgg ccatgccctt cttctctccc    3360
ttgcacctgt acctcttggt ctttgaataa agcctgagta ggaag                   3405
```

<210> SEQ ID NO 47  
<211> LENGTH: 1082  
<212> TYPE: PRT  
<213> ORGANISM: Artificial sequence  
<220> FEATURE:  
<223> OTHER INFORMATION: Synthetic polypeptide -continued

```
<220> FEATURE:
<221> NAME/KEY: misc_feature
<223> OTHER INFORMATION: E2, amino acid

<400> SEQUENCE: 47

Met Ala Pro Lys Lys Arg Lys Val Met Asn Gln Lys Phe Ile Leu
1               5                   10                  15

Gly Leu Asp Ile Gly Ile Thr Ser Val Gly Tyr Gly Leu Ile Asp Tyr
                20                  25                  30

Glu Thr Lys Asn Ile Ile Asp Ala Gly Val Arg Leu Phe Pro Glu Ala
                35                  40                  45

Asn Val Glu Asn Asn Glu Gly Arg Arg Ser Lys Arg Gly Ser Arg Arg
50                  55                  60

Leu Lys Arg Arg Arg Ile His Arg Leu Asp Arg Val Lys His Leu Leu
65                  70                  75                  80

Ala Glu Tyr Asp Leu Leu Asp Leu Thr Asn Ile Pro Lys Ser Thr Asn
                85                  90                  95

Pro Tyr Gln Thr Arg Val Lys Gly Leu Asn Glu Lys Leu Ser Lys Asp
                100                 105                 110

Glu Leu Val Ile Ala Leu Leu His Ile Ala Lys Arg Arg Gly Ile His
                115                 120                 125

Asn Val Asp Val Ala Ala Asp Lys Glu Glu Thr Ala Ser Asp Ser Leu
130                 135                 140

Ser Thr Lys Asp Gln Ile Asn Lys Asn Ala Lys Phe Leu Glu Ser Arg
145                 150                 155                 160

Tyr Val Cys Glu Leu Gln Lys Glu Arg Leu Glu Asn Glu Gly His Val
                165                 170                 175

Arg Gly Val Glu Asn Arg Phe Leu Thr Lys Asp Ile Val Arg Glu Ala
                180                 185                 190

Lys Lys Ile Ile Asp Thr Gln Met Gln Tyr Tyr Pro Glu Ile Asp Glu
                195                 200                 205

Thr Phe Lys Glu Lys Tyr Ile Ser Leu Val Glu Thr Arg Arg Glu Tyr
210                 215                 220

Phe Glu Gly Pro Gly Lys Gly Ser Pro Phe Gly Trp Glu Gly Asn Ile
225                 230                 235                 240

Lys Lys Trp Phe Glu Gln Met Met Gly His Cys Thr Tyr Phe Pro Glu
                245                 250                 255

Glu Leu Arg Ser Val Lys Tyr Ser Tyr Ser Ala Glu Leu Phe Asn Ala
                260                 265                 270

Leu Asn Asp Leu Asn Asn Leu Val Ile Thr Arg Asp Glu Asp Ala Lys
                275                 280                 285

Leu Asn Tyr Gly Glu Lys Phe Gln Ile Ile Glu Asn Val Phe Lys Gln
                290                 295                 300

Lys Lys Thr Pro Asn Leu Lys Gln Ile Ala Ile Glu Ile Gly Val His
305                 310                 315                 320

Glu Thr Glu Ile Lys Gly Tyr Arg Val Asn Lys Ser Gly Thr Pro Glu
                325                 330                 335

Phe Thr Glu Phe Lys Leu Tyr His Asp Leu Lys Ser Ile Val Phe Asp
                340                 345                 350

Lys Ser Ile Leu Glu Asn Glu Ala Ile Leu Asp Gln Ile Ala Glu Ile
                355                 360                 365

Leu Thr Ile Tyr Gln Asp Glu Gln Ser Ile Lys Glu Glu Leu Asn Lys
                370                 375                 380
```

```
Leu Pro Glu Ile Leu Asn Glu Gln Asp Lys Ala Glu Ile Ala Lys Leu
385                 390                 395                 400

Ile Gly Tyr Asn Gly Thr His Arg Leu Ser Leu Lys Cys Ile His Leu
            405                 410                 415

Ile Asn Glu Glu Leu Trp Gln Thr Ser Arg Asn Gln Met Glu Ile Phe
        420                 425                 430

Asn Tyr Leu Asn Ile Lys Pro Asn Lys Val Asp Leu Ser Glu Gln Asn
            435                 440                 445

Lys Ile Pro Lys Asp Met Val Asn Asp Phe Ile Leu Ser Pro Val Val
        450                 455                 460

Lys Arg Thr Phe Ile Gln Ser Ile Asn Val Ile Asn Lys Val Ile Glu
465                 470                 475                 480

Lys Tyr Gly Ile Pro Glu Asp Ile Ile Ile Glu Leu Ala Arg Glu Asn
                485                 490                 495

Asn Ser Asp Asp Arg Lys Lys Phe Ile Asn Asn Leu Gln Lys Lys Asn
            500                 505                 510

Glu Ala Thr Arg Lys Arg Ile Asn Glu Ile Ile Gly Gln Thr Gly Asn
        515                 520                 525

Gln Asn Ala Lys Arg Ile Val Glu Lys Ile Arg Leu His Asp Gln Gln
            530                 535                 540

Glu Gly Lys Cys Leu Tyr Ser Leu Lys Asp Ile Pro Leu Glu Asp Leu
545                 550                 555                 560

Leu Arg Asn Pro Asn Asn Tyr Asp Ile Asp His Ile Ile Pro Arg Ser
                565                 570                 575

Val Ser Phe Asp Asp Ser Met His Asn Lys Val Leu Val Arg Arg Glu
            580                 585                 590

Gln Asn Ala Lys Lys Asn Asn Gln Thr Pro Tyr Gln Tyr Leu Thr Ser
            595                 600                 605

Gly Tyr Ala Asp Ile Lys Tyr Ser Val Phe Lys Gln His Val Leu Asn
        610                 615                 620

Leu Ala Glu Asn Lys Asp Arg Met Thr Lys Lys Arg Glu Tyr Leu
625                 630                 635                 640

Leu Glu Glu Arg Asp Ile Asn Lys Phe Glu Val Gln Lys Glu Phe Ile
                645                 650                 655

Asn Arg Asn Leu Val Asp Thr Arg Tyr Ala Thr Arg Glu Leu Thr Asn
            660                 665                 670

Tyr Leu Lys Ala Tyr Phe Ser Ala Asn Asn Met Asn Val Lys Val Lys
        675                 680                 685

Thr Ile Asn Gly Ser Phe Thr Asp Tyr Leu Arg Lys Val Trp Lys Phe
        690                 695                 700

Lys Lys Glu Arg Asn His Gly Tyr Lys His His Ala Glu Asp Ala Leu
705                 710                 715                 720

Ile Ile Ala Asn Ala Asp Phe Leu Phe Lys Glu Asn Lys Lys Leu Lys
                725                 730                 735

Ala Val Asn Ser Val Leu Glu Lys Pro Glu Ile Glu Thr Lys Gln Leu
            740                 745                 750

Asp Ile Gln Val Asp Ser Glu Asp Asn Tyr Ser Glu Met Phe Ile Ile
        755                 760                 765

Pro Lys Gln Val Gln Asp Ile Lys Asp Phe Arg Asn Phe Lys Tyr Ser
        770                 775                 780

His Arg Val Asp Lys Lys Pro Asn Arg Gln Leu Ile Asn Asp Thr Leu
785                 790                 795                 800
```

Tyr Ser Thr Arg Lys Lys Asp Asn Ser Thr Tyr Ile Val Gln Thr Ile
            805                 810                 815

Lys Asp Ile Tyr Ala Lys Asp Asn Thr Thr Leu Lys Lys Gln Phe Asp
        820                 825                 830

Lys Ser Pro Glu Lys Phe Leu Met Tyr Gln His Asp Pro Arg Thr Phe
        835                 840                 845

Glu Lys Leu Glu Val Ile Met Lys Gln Tyr Ala Asn Glu Lys Asn Pro
    850                 855                 860

Leu Ala Lys Tyr His Glu Thr Gly Glu Tyr Leu Thr Lys Tyr Ser
865                 870                 875                 880

Lys Lys Asn Asn Gly Pro Ile Val Lys Ser Leu Lys Tyr Ile Gly Asn
                885                 890                 895

Lys Leu Gly Ser His Leu Asp Val Thr His Gln Phe Lys Ser Ser Thr
            900                 905                 910

Lys Lys Leu Val Lys Leu Ser Ile Lys Pro Tyr Arg Phe Asp Val Tyr
        915                 920                 925

Leu Thr Asp Lys Gly Tyr Lys Phe Ile Thr Ile Ser Tyr Leu Asp Val
        930                 935                 940

Leu Lys Lys Asp Asn Tyr Tyr Tyr Ile Pro Glu Gln Lys Tyr Asp Lys
945                 950                 955                 960

Leu Lys Leu Gly Lys Ala Ile Asp Lys Asn Ala Lys Phe Ile Ala Ser
                965                 970                 975

Phe Tyr Lys Asn Asp Leu Ile Lys Leu Asp Gly Glu Ile Tyr Lys Ile
            980                 985                 990

Ile Gly Val Asn Ser Asp Thr Arg  Asn Met Ile Glu Leu  Asp Leu Pro
        995                 1000                1005

Asp Ile Arg Tyr Lys Glu Tyr  Cys Glu Leu Asn Asn  Ile Lys Gly
    1010                1015                1020

Glu Pro Arg Ile Lys Lys Thr  Ile Gly Lys Lys Val  Asn Ser Ile
    1025                1030                1035

Glu Lys Leu Thr Thr Asp Val  Leu Gly Asn Val Phe  Thr Asn Thr
    1040                1045                1050

Gln Tyr Thr Lys Pro Gln Leu  Leu Phe Lys Arg Gly  Asn Lys Arg
    1055                1060                1065

Pro Ala Ala Thr Lys Lys Ala  Gly Gln Ala Lys Lys  Lys Lys
    1070                1075                1080

<210> SEQ ID NO 48
<211> LENGTH: 3396
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P2H12, nucleotide

<400> SEQUENCE: 48
aggaaataag agagaaaaga agagtaagaa gaaatataag agccaccatg gcccccaaga      60
agaaacgcaa agtcatgaac caaaagttca ttctggggct cgatatcggc atcacctccg     120
tgggatatgg tctgatcgac tacgagacta agaacatcat cgacgctgga gtgcgactgt     180
tcccggaagc gaacgtggag aacaacgaag gccgcagatc caagcgcggg tccagaaggc     240
tcaagaggcg gaggatccat agactcgaga gagtgaagaa gctccttgaa gattacaatc     300
tgttggacca gtcacagatt ccccaaagca ccaacccgta cgccatcaga gtgaagggcc     360

```
tgtcagaagc actgtcgaaa gatgaactgg tcattgccct gctgcatatt gccaaacggc    420
gcggaatcca taacatcaac gtgtcgagcg aagatgagga cgcgtccaac gaactgtcaa    480
ccaaggaaca gatcaaccgg aacaacaaac tgctgaagga caaatacgtc tgcgaggtgc    540
agcttcaacg gctgaaagag ggacagatca ggggagagaa aaaccggttc aagaccaccg    600
acatccttaa ggagatcgac caactcctga agtgcagaa ggactatcac aacctcgaca    660
ttgattttat caaccagtac aaggagattg tggaaactcg agggagtac ttcgagggac    720 ctggaaaggg atcccttat ggctgggaag gggaccccaa ggcttggtac gaaaccctga    780
tgggccattg cacttacttt ccggatgaac tccggtccgt gaagtacgct tactctgccg    840
acctgttcaa tgcactcaac gaccttaaca acttggtgat ccaacgcgat ggtctttcca    900
agttggagta ccacgaaaag taccacatca tcgagaacgt gttcaagcag aaaaagaagc    960
caactctgaa gcagattgcc aacgaaatta acgtgaaccc cgaggatatc aagggatacc   1020
ggattaccaa gtccggcaaa ccagagttca cctcattcaa gctgtttcac gatctgaaga   1080
aggtcgtgaa ggaccacgcc atcctggatg acattgatct tctgaaccag attgctgaga   1140
tcctgaccat ctaccaggac aaggactcga ttgtggccga actgggacag ctcgagtacc   1200
tgatgtccga agccgataag cagtccatca gcgaactcac cggttacacc ggtacccact   1260
ccttgtccct taagtgcatg aacatgatca ttgacgaact gtggcactcc agcatgaacc   1320
agatggaggt gttcacctac ttgaacatgc gcccgaagaa gtacgagctg aagggctacc   1380
agcgcatacc cacggacatg atcgacgacg ccatcctctc accggtggtc aagcgcacct   1440
tcattcaatc tatcaacgtg atcaacaagg tcatcgagaa gtacggcatt cctgaggata   1500
tcatcatcga gctggctcgg gagaacaact cagacgatag gaagaagttc attaacaacc   1560
tccagaaaaa gaacgaggcc actcgcaagc ggattaatga gatcatcggt cagaccggga   1620
accagaacgc caagcggatc gtggaaaaga ttcggctcca cgaccaacag gagggaaagt   1680
gtctgtactc gctggagtcc attccctgg aggacctcct gaacaaccca aaccactacg   1740
aggtcgatca cataatcccc cgcagcgtgt cattcgacaa ctcctaccat aacaaggtcc   1800
tcgtgaagca gtcggagaat agcaagaagt cgaacctgac tccgtaccag tacttcaact   1860
ccggcaaatc caagctgtcc tacaatcagt tcaaacagca cattctcaac ctgtccaaga   1920
gccaggacag gatttcgaag aagaagaagg aatacttct cgaggaacgg gatatcaata   1980
agttcgaggt gcagaaggag tttatcaata gaaacctggt ggacactcgc tatgccaccc   2040
gcgaactgac caactacctg aaggcgtact tctccgccaa caacatgaac gtgaaggtca   2100
aaactattaa cggcagcttc accgactatc tgcgcaaggt ctggaagttc aagaaggaac   2160
gcaaccacgg ttacaagcac cacgcggaag atgcgctgat tatcgccaac gctgacttcc   2220
tgttcaagga aaacaagaag ctcaaggccg tgaactcagt gctcgagaag cctgaaatcg   2280
agactaagca gctggacatc caggtcgatt cggaagataa ctactccgaa atgttcatca   2340
tccctaagca agtgcaggac atcaaggact tcaggaattt caagtacagc catcgcgtgg   2400
acaagaagcc aaacagacag ctgatcaacg atacactgta ttccacccgg aagaaggaca   2460
actccaccta tcgtccaa accattaagg acatctacgc aaaggacaac accacgctta   2520
agaagcagtt cgacaagagc cccgaaaagt tcctcatgta ccagcacgac cccagaacct   2580
tcgagaagct tgaagtgatc atgaagcagt acgccaacga aaagaaccca ctggctaagt   2640
accacgagga aaccggcgaa tacctgacca agtactccaa aaagaacaac ggaccgatcg   2700
tcaagtccct gaagtacatt gggaacaagc tcggctcgca cctcgatgtg acccaccagt   2760
```

```
tcaagtcctc gaccaaaaag ctcgtgaagc tgtccatcaa gccgtaccgg ttcgacgtgt    2820
acctgactga caagggatat aagttcatca ccatttccta cctcgacgtg ttgaagaagg    2880
ataactacta ctacattccg gaacagaagt acgacaagct caagctcgga aaggccatcg    2940
acaaaaatgc gaagttcatc gcgagcttct acaagaatga cttgatcaag ctggatggcg    3000
aaatctacaa gatcatcggg gtcaactccg atacccgcaa catgattgag ctggatctgc    3060
ccgacattcg gtacaaggaa tactgcgagc tgaacaacat caaggagaa ccgcggatca    3120 agaaaaccat cggaaagaaa gtgaacagca tcgagaaact gactactgac gtcctgggaa    3180
acgtgttcac caacacacaa taccacaaac cccagctgct gtttaagcgc gggaacaagc    3240
gccctgccgc aactaagaag gccggacagg ccaaaaagaa gaaatgagcg gccgcttaat    3300
taagctgcct tctgcgggc ttgccttctg gccatgccct tcttctctcc cttgcacctg    3360
tacctcttgg tctttgaata aagcctgagt aggaag                              3396
```

<210> SEQ ID NO 49
<211> LENGTH: 1079
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: P2H12, amino acid

<400> SEQUENCE: 49

```
Met Ala Pro Lys Lys Arg Lys Val Met Asn Gln Lys Phe Ile Leu
1               5                   10                  15

Gly Leu Asp Ile Gly Ile Thr Ser Val Gly Tyr Gly Leu Ile Asp Tyr
                20                  25                  30

Glu Thr Lys Asn Ile Ile Asp Ala Gly Val Arg Leu Phe Pro Glu Ala
            35                  40                  45

Asn Val Glu Asn Asn Glu Gly Arg Arg Ser Lys Arg Gly Ser Arg Arg
        50                  55                  60

Leu Lys Arg Arg Arg Ile His Arg Leu Glu Arg Val Lys Lys Leu Leu
65                  70                  75                  80

Glu Asp Tyr Asn Leu Leu Asp Gln Ser Gln Ile Pro Gln Ser Thr Asn
                85                  90                  95

Pro Tyr Ala Ile Arg Val Lys Gly Leu Ser Glu Ala Leu Ser Lys Asp
                100                 105                 110

Glu Leu Val Ile Ala Leu Leu His Ile Ala Lys Arg Arg Gly Ile His
            115                 120                 125

Asn Ile Asn Val Ser Ser Glu Asp Glu Asp Ala Ser Asn Glu Leu Ser
        130                 135                 140

Thr Lys Glu Gln Ile Asn Arg Asn Asn Lys Leu Leu Lys Asp Lys Tyr
145                 150                 155                 160

Val Cys Glu Val Gln Leu Gln Arg Leu Lys Glu Gly Gln Ile Arg Gly
                165                 170                 175

Glu Lys Asn Arg Phe Lys Thr Thr Asp Ile Leu Lys Glu Ile Asp Gln
            180                 185                 190

Leu Leu Lys Val Gln Lys Asp Tyr His Asn Leu Asp Ile Asp Phe Ile
        195                 200                 205

Asn Gln Tyr Lys Glu Ile Val Glu Thr Arg Arg Glu Tyr Phe Glu Gly
        210                 215                 220
```

Pro Gly Lys Gly Ser Pro Tyr Gly Trp Glu Gly Asp Pro Lys Ala Trp
225                 230                 235                 240

Tyr Glu Thr Leu Met Gly His Cys Thr Tyr Phe Pro Asp Glu Leu Arg
            245                 250                 255

Ser Val Lys Tyr Ala Tyr Ser Ala Asp Leu Phe Asn Ala Leu Asn Asp
                260                 265                 270

Leu Asn Asn Leu Val Ile Gln Arg Asp Gly Leu Ser Lys Leu Glu Tyr
            275                 280                 285

His Glu Lys Tyr His Ile Ile Glu Asn Val Phe Lys Gln Lys Lys Lys
            290                 295                 300

Pro Thr Leu Lys Gln Ile Ala Asn Glu Ile Asn Val Asn Pro Glu Asp
305                 310                 315                 320

Ile Lys Gly Tyr Arg Ile Thr Lys Ser Gly Lys Pro Glu Phe Thr Ser
                325                 330                 335

Phe Lys Leu Phe His Asp Leu Lys Lys Val Lys Asp His Ala Ile
            340                 345                 350

Leu Asp Asp Ile Asp Leu Leu Asn Gln Ile Ala Glu Ile Leu Thr Ile
            355                 360                 365

Tyr Gln Asp Lys Asp Ser Ile Val Ala Glu Leu Gly Gln Leu Glu Tyr
370                 375                 380

Leu Met Ser Glu Ala Asp Lys Gln Ser Ile Ser Glu Leu Thr Gly Tyr
385                 390                 395                 400

Thr Gly Thr His Ser Leu Ser Leu Lys Cys Met Asn Met Ile Ile Asp
                405                 410                 415

Glu Leu Trp His Ser Ser Met Asn Gln Met Glu Val Phe Thr Tyr Leu
            420                 425                 430

Asn Met Arg Pro Lys Lys Tyr Glu Leu Lys Gly Tyr Gln Arg Ile Pro
            435                 440                 445

Thr Asp Met Ile Asp Asp Ala Ile Leu Ser Pro Val Val Lys Arg Thr
450                 455                 460

Phe Ile Gln Ser Ile Asn Val Ile Asn Lys Val Ile Glu Lys Tyr Gly
465                 470                 475                 480

Ile Pro Glu Asp Ile Ile Ile Glu Leu Ala Arg Glu Asn Asn Ser Asp
                485                 490                 495

Asp Arg Lys Lys Phe Ile Asn Asn Leu Gln Lys Lys Asn Glu Ala Thr
            500                 505                 510

Arg Lys Arg Ile Asn Glu Ile Ile Gly Gln Thr Gly Asn Gln Asn Ala
            515                 520                 525

Lys Arg Ile Val Glu Lys Ile Arg Leu His Asp Gln Gln Glu Gly Lys
530                 535                 540

Cys Leu Tyr Ser Leu Glu Ser Ile Pro Leu Glu Asp Leu Leu Asn Asn
545                 550                 555                 560

Pro Asn His Tyr Glu Val Asp His Ile Ile Pro Arg Ser Val Ser Phe
                565                 570                 575

Asp Asn Ser Tyr His Asn Lys Val Leu Val Lys Gln Ser Glu Asn Ser
            580                 585                 590

Lys Lys Ser Asn Leu Thr Pro Tyr Gln Tyr Phe Asn Ser Gly Lys Ser
            595                 600                 605

Lys Leu Ser Tyr Asn Gln Phe Lys Gln His Ile Leu Asn Leu Ser Lys
            610                 615                 620

Ser Gln Asp Arg Ile Ser Lys Lys Lys Glu Tyr Leu Leu Glu Glu
625                 630                 635                 640

```
Arg Asp Ile Asn Lys Phe Glu Val Gln Lys Glu Phe Ile Asn Arg Asn
            645                 650                 655

Leu Val Asp Thr Arg Tyr Ala Thr Arg Glu Leu Thr Asn Tyr Leu Lys
            660                 665                 670

Ala Tyr Phe Ser Ala Asn Asn Met Asn Val Lys Val Lys Thr Ile Asn
            675                 680                 685

Gly Ser Phe Thr Asp Tyr Leu Arg Lys Val Trp Lys Phe Lys Lys Glu
            690                 695                 700

Arg Asn His Gly Tyr Lys His His Ala Glu Asp Ala Leu Ile Ile Ala
705                 710                 715                 720

Asn Ala Asp Phe Leu Phe Lys Glu Asn Lys Lys Leu Lys Ala Val Asn
            725                 730                 735

Ser Val Leu Glu Lys Pro Glu Ile Glu Thr Lys Gln Leu Asp Ile Gln
            740                 745                 750

Val Asp Ser Glu Asp Asn Tyr Ser Glu Met Phe Ile Ile Pro Lys Gln
            755                 760                 765

Val Gln Asp Ile Lys Asp Phe Arg Asn Phe Lys Tyr Ser His Arg Val
            770                 775                 780

Asp Lys Lys Pro Asn Arg Gln Leu Ile Asn Asp Thr Leu Tyr Ser Thr
785                 790                 795                 800

Arg Lys Lys Asp Asn Ser Thr Tyr Ile Val Gln Thr Ile Lys Asp Ile
            805                 810                 815

Tyr Ala Lys Asp Asn Thr Thr Leu Lys Lys Gln Phe Asp Lys Ser Pro
            820                 825                 830

Glu Lys Phe Leu Met Tyr Gln His Asp Pro Arg Thr Phe Glu Lys Leu
            835                 840                 845

Glu Val Ile Met Lys Gln Tyr Ala Asn Glu Lys Asn Pro Leu Ala Lys
            850                 855                 860

Tyr His Glu Glu Thr Gly Glu Tyr Leu Thr Lys Tyr Ser Lys Lys Asn
865                 870                 875                 880

Asn Gly Pro Ile Val Lys Ser Leu Lys Tyr Ile Gly Asn Lys Leu Gly
            885                 890                 895

Ser His Leu Asp Val Thr His Gln Phe Lys Ser Ser Thr Lys Lys Leu
            900                 905                 910

Val Lys Leu Ser Ile Lys Pro Tyr Arg Phe Asp Val Tyr Leu Thr Asp
            915                 920                 925

Lys Gly Tyr Lys Phe Ile Thr Ile Ser Tyr Leu Asp Val Leu Lys Lys
            930                 935                 940

Asp Asn Tyr Tyr Tyr Ile Pro Glu Gln Lys Tyr Asp Lys Leu Lys Leu
945                 950                 955                 960

Gly Lys Ala Ile Asp Lys Asn Ala Lys Phe Ile Ala Ser Phe Tyr Lys
            965                 970                 975

Asn Asp Leu Ile Lys Leu Asp Gly Glu Ile Tyr Lys Ile Ile Gly Val
            980                 985                 990

Asn Ser Asp Thr Arg Asn Met Ile  Glu Leu Asp Leu Pro  Asp Ile Arg
            995                 1000                1005

Tyr Lys Glu Tyr Cys Glu Leu  Asn Asn Ile Lys Gly  Glu Pro Arg
            1010                1015                1020

Ile Lys Lys Thr Ile Gly Lys  Lys Val Asn Ser Ile  Glu Lys Leu
            1025                1030                1035

Thr Thr Asp Val Leu Gly Asn  Val Phe Thr Asn Thr  Gln Tyr Thr
            1040                1045                1050
```

```
Lys Pro Gln Leu Leu Phe Lys  Arg Gly Asn Lys Arg  Pro Ala Ala
    1055                1060               1065

Thr Lys  Lys Ala Gly Gln Ala  Lys Lys Lys Lys
    1070                 1075

<210> SEQ ID NO 50
<211> LENGTH: 100
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: gRNA targeting albumin gene
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: phosphorothioate linkage
<220> FEATURE:
<221> NAME/KEY: misc_feature
<222> LOCATION: (98)..(99)
<223> OTHER INFORMATION: phosphorothioate linkage
<220> FEATURE:
<221> NAME/KEY: misc_feature
<222> LOCATION: (99)..(100)
<223> OTHER INFORMATION: phosphorothioate linkage

<400> SEQUENCE: 50
ugccaguucc cgaucguuac guuuuaguac ucuggaaaca gaaucuacug aaacaagaca         60
auaugucgug uuuaucccau caauuuauug gugggauuuu                              100
```